US008841455B2

United States Patent
Boys et al.

(10) Patent No.: US 8,841,455 B2
(45) Date of Patent: Sep. 23, 2014

(54) SUBSTITUTED N-(1H-INDAZOL-4-YL)IMIDAZO[1,2-A] PYRIDINE-3-CARBOXAMIDE COMPOUNDS AS CFMS INHIBITORS

(75) Inventors: Mark Laurence Boys, Boulder, CO (US); Michael F. Bradley, Boulder, CO (US); Robert Kirk DeLisle, Boulder, CO (US); D. David Hennings, Boulder, CO (US); April L. Kennedy, Denver, CO (US); Fredrik P. Marmsater, Boulder, CO (US); Matthew David Medina, Boulder, CO (US); Mark C. Munson, Acton, MA (US); Bryson Rast, Westminster, CO (US); James P. Rizzi, Addison, TX (US); Martha E. Rodriguez, Lafayette, CO (US); George T. Topalov, Pittsburgh, PA (US); Qian Zhao, Louisville, CO (US)

(73) Assignee: Array BioPharma Inc., Boulder, CO (US)

( * ) Notice: Subject to any disclaimer, the term of this patent is extended or adjusted under 35 U.S.C. 154(b) by 264 days.

(21) Appl. No.: 13/517,938

(22) PCT Filed: Dec. 20, 2010

(86) PCT No.: PCT/US2010/061341
§ 371 (c)(1),
(2), (4) Date: Jun. 20, 2012

(87) PCT Pub. No.: WO2011/079076
PCT Pub. Date: Jun. 30, 2011

(65) Prior Publication Data
US 2012/0258952 A1   Oct. 11, 2012

Related U.S. Application Data

(60) Provisional application No. 61/288,729, filed on Dec. 21, 2009.

(51) Int. Cl.
C07D 491/02  (2006.01)
C07D 231/56  (2006.01)

(52) U.S. Cl.
USPC ......................... 546/121; 548/361.1

(58) Field of Classification Search
USPC ......................... 546/121; 548/361.1
See application file for complete search history.

(56) References Cited

FOREIGN PATENT DOCUMENTS

| WO | WO 2006/081230 A2 | 8/2006 |
| WO | WO 2007/076360 A1 | 7/2007 |
| WO | WO 2008/124323 A1 | 10/2008 |
| WO | WO 2009/071483 A1 | 6/2009 |

OTHER PUBLICATIONS

Burns et al., "c-FMS inhibitors: a patent review", *Expert Opin. Ther. Patents* [Early Online], pp. 1-19 (2011).
Patent Cooperation Treaty, International Search Report and Written Opinion for PCT/US2010/061341, 9 pages, dated Feb. 24, 2011.

*Primary Examiner* — Nizal Chandrakumar
(74) *Attorney, Agent, or Firm* — Viksnins Harris & Padys PLLP; Sarah S. Mastous

(57) ABSTRACT

Compounds of Formula (I): and pharmaceutically acceptable salts thereof in which $R^1$, $R^2$, $R^3$, $R^4$ and $R^5$ have the meanings given in the specification, are inhibitors of cFMS and are useful in the treatment of bone-related diseases, cancer, autoimmune disorders, inflammatory diseases, cardiovascular diseases and pain.

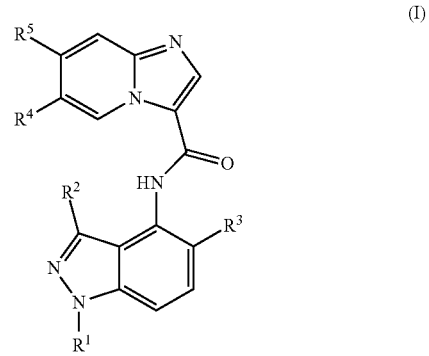

41 Claims, No Drawings

SUBSTITUTED N-(1H-INDAZOL-4-YL)IMIDAZO[1,2-A] PYRIDINE-3-CARBOXAMIDE COMPOUNDS AS CFMS INHIBITORS

The present invention relates to novel compounds, to pharmaceutical compositions comprising the compounds, to processes for making the compounds, and to the use of the compounds in therapy. More particularly, it relates to certain substituted N-(1H-indazol-4-yl)imidazo[1,2-a]pyridine-3-carboxamide compounds which are inhibitors of cFMS, a type III receptor tyrosine kinases, which are useful in the treatment of bone-related diseases, cancer, autoimmune disorders, inflammatory diseases, cardiovascular diseases and pain.

Macrophage colony-stimulating factor-1 receptor (CSF-1R), a tyrosine receptor kinase also known as cFMS, is the receptor for colony stimulating factor-1 (CSF-1), also known as M-CSF. CSF-1 is an important growth factor for bone progenitor cells, monocytes, macrophages, and cells of macrophage lineage such as osteoclasts and dendritic cells. Binding of CSF-1 to the cFMS extracellular domain induces cFMS dimerization and trans-autophosphorylation of the intracellular cFMS kinase domain. Once phosphorylated, cFMS serves as a docking site for several cytoplasmic signaling molecules, the activation of which leads to de novo gene expression and proliferation. Robust expression of cFMS is restricted to monocytes, tissue macrophages, and osteoclasts, and therefore cFMS inhibitors may be useful in treating diseases where osteoclasts, dendritic cells and macrophages are pathogenic, such as autoimmune/inflammatory diseases, cancer and bone-related diseases.

Bone is a dynamic tissue, subject to a constant remodeling process that operates to maintain skeletal strength and health. This remodeling process entails two phases: an osteolysis phase and an osteogenesis phase. In osteolysis, osteoclast cells invade bone and erode it by releasing acids and enzymes that dissolve collagen and minerals. This creates a small cavity in the bone. In osteogenesis, osteoblast cells deposit new collagen and minerals into the cavity. When osteolysis and osteogenesis are in balance, no net change in bone mass results. However, in certain disease states, osteolysis is more active than osteogenesis, resulting in a net loss of bone.

One particularly serious cause of localized excessive osteolysis is cancer metastasis to bone. Cancer cells often secrete factors, such as M-CSF, that promote osteoclast development and activity. When such cancers establish themselves in bone, they promote extensive osteolytic damage and can result in, for example, bone fracture and spinal compression. Such tumor-associated osteolysis coincides with many types of malignancies, including hematological malignancies (e.g., myeloma and lymphoma) and solid tumors (e.g., breast, prostate, lung, renal and thyroid). Accordingly, there remains a need for therapies that reduce or delay complications which arise from the spread of cancer to the bone.

When excessive osteolysis occurs throughout broad areas of the skeleton, it falls under the generic description osteoporosis. Common types of osteoporosis include age-related, post-menopausal, treatment-induced bone loss (e.g., as a result of treatment with glucocorticoids, aromatase inhibitors, or anti-androgen therapy), diabetes-associated and disuse osteoporosis. In the United States alone, millions of individuals suffer from the disease and its attendant pain, deformities and debilitating fractures.

Osteoclasts are multinucleated cells that are derived from monocytic precursors and operate under the control of numerous cytokines and growth factors. Differentiation of the monocytic precursors into osteoclasts is a complex process that requires both M-CSF and RANKL (receptor activator of the NF-kappa B ligand). Inhibiting osteoclast development and function is a desirable approach to treating excessive osteolysis. However, the currently available substances that do so have limited utility, and often cause significant side effects. Thus, a continuing need exists for effective and practical treatments for excessive osteolytic conditions.

Macrophages, which are related to osteoclasts, play an important role in inflammatory disease, cancer and bone disorders. For example, macrophages, which are related to osteoclasts, are a major component of the host cellular response to cancers, and can contribute to tumor growth. In particular, macrophages, as well as tumor cells, secrete M-CSF, a key cytokine for development of osteoclasts from monocyte precursors. Macrophages, as well as monocytes and some tumor cells, also express M-CSF receptors.

Solid tumors comprise a number of cell types, including macrophages. These tumor-associated macrophages (TAMs) are believed to play a number of roles to promote tumor progression and metastasis (Pollard, J. W., Nat. Rev. Cancer, 2004, 4:71; Lewis, C. E. and Pollard, J. W., Cancer Res., 2006, 66:605). Upon recruitment to the tumor environment, macrophages release factors involved in the growth and motility of tumor cells. Monocyte/macrophage development and proliferation depends upon the signaling pathway of CSF-1R and its ligand CSF-1. Recent depletion studies in cancer models showed a role for M-CSF in promoting tumor growth and progression to metastasis (Chitu, V. and Stanley, E. R., Curr. Opin. Immunol., 2006, 18:39-48; Pollard., J. W., Nature Rev. Cancer, 2004, 80:59-65; Paulus, P., et al., Cancer Res. 2006, 66:4349-4356). Inhibition of this pathway therefore could reduce TAM levels, leading to multiple effects on tumor types in which macrophages have a significant presence.

Macrophages are also a predominant source of tumor necrosis factor (TNF) and interleukin-1 (IL-1) in the destructive pannus of rheumatoid arthritis. TNF and IL-1 activate stromal expression of hematopoietic factors including CSF-1. In turn, CSF-1 recruits monocytes and promotes macrophage survival, functional activation, and in some settings, proliferation. Thus, TNF and CSF-1 interact in a perpetuating cycle that leads to inflammation and joint destruction.

Macrophage numbers are also elevated in atherosclerotic plaque (Arch. Pathol. Lab. Med. 1985, 109: 445-449) where they are thought to contribute to disease progression.

Inflammatory mechanisms are also believed to play an important role in hyperalgesia resulting from nerve injury. Nerve damage can stimulate macrophage infiltration and increase the number of activated T cells (Abbadie, C., 2005, Trends Immunol. 26(1):529-534). Under these conditions, neuroinflammatory and immune responses contribute as much to the development and maintenance of pain as the initial damage itself. The role of circulating monocytes/macrophages in the development of neuropathic hyperalgesia and Wallerian degeneration due to partial nerve injury was confirmed in an animal model (Liu et al., Pain, 2000, 86: 25-32) in which macrophages were depleted following sciatic nerve ligation. In this study, treatment of nerve-injured rats with liposome-encapsulated Cl$_2$MDP (dichloromethylene diphosphonate), which is reported to effectively reduce the number of macrophages at the site of nerve transaction, alleviated thermal hyperalgesia and reduced degeneration of both myelinated and unmyelinated axons. In addition, in many instances neuropathic pain is associated with nerve inflammation (neuritis) in the absence of nerve injury. Based on an animal model of neuritis (Tal M., Curr. Rev. Pain 1999, 3(6): 440-446), it has been suggested that there is a role for some cytokines in nocicoption and hyperalgesia by evoking peripheral sensitization, in which trauma and classical tissue inflammation are not seen. Thus, macrophage depletion by administration of a cFMS inhibitor could have clinical potential in treatment or prevention of neuropathic pain, either as a result of nerve injury or in the absence of nerve injury.

Several classes of small molecule inhibitors of cFMS said to be useful for treating cancer, autoimmune and inflammatory diseases are known (Huang, H. et al., J. Med. Chem., 2009, 52, 1081-1099; Scott, D. A. et al., Bioorg. & Med. Chem. Lett., 2009, 19, 697-700).

SUMMARY OF THE INVENTION

It has now been found that certain substituted N-(1H-indazol-4-yl)imidazo[1,2-a]pyridine-3-carboxamide compounds are inhibitors of cFMS and are useful for treating disorders and diseases sensitive to inhibition of type III receptor tyrosine kinases such as cFMS.

Accordingly, one embodiment of this invention provides a compound of the general Formula I:

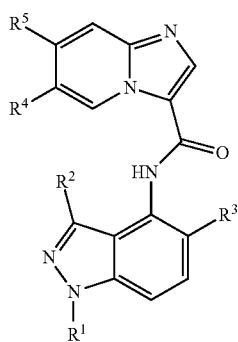

I or a pharmaceutically acceptable salt thereof, wherein $R^1$, $R^2$, $R^3$, $R^4$ and $R^5$ are as defined herein.

In another aspect of the invention, there are provided pharmaceutical compositions comprising compounds of Formula I and a carrier, diluent or excipient.

In another aspect of the invention, there is provided a method of inhibiting type III receptor tyrosine kinases such as cFMS in a mammal comprising administering to said mammal an effective amount of a compound of Formula I.

In another aspect of the invention, there is provided a method for treating bone-related diseases, cancer, autoimmune disorders, inflammatory diseases, cardiovascular diseases or pain in a mammal, which comprises administering to said mammal a therapeutically effective amount of a compound of Formula I or a pharmaceutically acceptable salt thereof.

In another aspect of the invention, there is provided a use of a compound of Formula I in the manufacture of a medicament for the treatment of bone-related diseases, cancer, autoimmune disorders, inflammatory diseases, cardiovascular diseases or pain in a mammal, which comprises administering to said mammal a therapeutically effective amount of a compound of Formula I or a pharmaceutically acceptable salt thereof.

In another aspect of the invention, there is provided a use of a compound of Formula I in the treatment of bone-related diseases, cancer, autoimmune disorders, inflammatory diseases, cardiovascular diseases or pain in a mammal, which comprises administering to said mammal a therapeutically effective amount of a compound of Formula I or a pharmaceutically acceptable salt thereof.

Another aspect provides intermediates for preparing compounds of Formula I. In one embodiment, certain compounds of Formula I may be used as intermediates for the preparation of other compounds of Formula I.

Another aspect includes processes for preparing, methods of separation, and methods of purification of the compounds described herein.

DETAILED DESCRIPTION OF THE INVENTION

Accordingly, one embodiment of this invention provides a compound of the general Formula I:

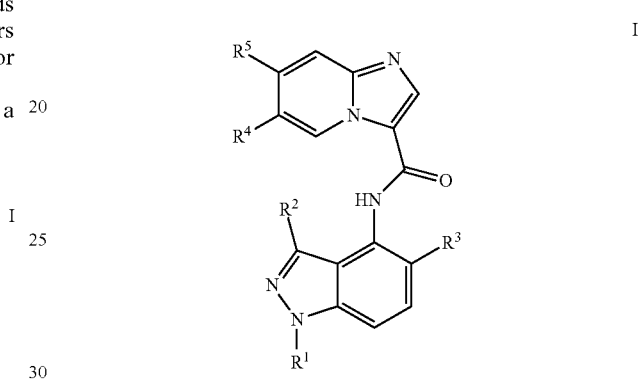

I or a pharmaceutically acceptable salt thereof, wherein:

$R^1$ is hetAr$^1$CH$_2$—, hetAr$^2$CH$_2$—, (3-6C cycloalkyl)-CH$_2$—, tetrahydropyranylCH$_2$—, benzyl which is optionally substituted with (1-4C)alkoxy, or (N-1-3C alkyl)pyridinonyl-CH$_2$— which is optionally substituted with one or more substituents independently selected from (1-6C)alkyl;

hetAr$^1$ is pyridyl optionally substituted with one or more substituents independently selected from (1-6C)alkyl, (1-4C) alkoxy, halogen, hetCyc$^1$, hetCyc$^1$-CH$_2$—, amino(2-4C) alkoxy, [di(1-3C alkyl)amino](2-4C)alkoxy, dihydroxy(3-4C)alkoxy, hetCyc$^2$O—, hetCyc$^{2a}$(1-2C)alkoxy and OH;

hetCyc$^1$ is a 6-membered heterocycle having 1-2 ring N atoms and optionally substituted with NH$_2$;

hetCyc$^2$ and hetCyc$^{2a}$ are independently a 5-6 membered heterocycle having 1-2 ring N atoms and optionally substituted with one or more substituents independently selected from (1-6C)alkyl, OH, and halogen;

hetAr$^2$ is a 5-membered heteroaryl ring having 2-3 ring heteroatoms independently selected from N, S and O whereat least one of said heteroatoms is N, wherein said ring is optionally substituted with one or more substituents independently selected from (1-6C)alkyl, (2-4C)hydroxyalkyl, (3-4C)dihydroxyalkyl, (3-6C cycloalkyl)CH$_2$—, hetCyc$^3$, hetCyc$^{3a}$(1-2C)alkyl, and benzyl optionally substituted with (1-4C) alkoxy;

hetCyc$^3$ and hetCyc$^{3a}$ are independently a 6-membered heterocyclic ring having 1-2 ring N atoms and optionally substituted with a halogen;

$R^2$ is (2-4C)alkyl, cyclopropyl, OMe, I or Br;

$R^3$ is H or Cl;

$R^4$ is H or CN;

$R^5$ is H, halogen, OH, hetAr$^3$, hetAr$^4$, N-(1-3C alkyl)pyridinone, hetAr$^5$, hetCyc$^4$, hetCyc$^5$C(=O)—, hetCyc$^6$(1-4C alkyl)-, hetCyc$^7$ (1-4C)alkoxy, (hetCyc$^8$)—O—, hetCyc$^9$ (1-4C)alkoxy, (1-3C alkoxy)(1-4C)alkoxy, hydroxy(1-4C) alkoxy, dihydroxy(2-4C)alkoxy, difluoroamino(1-4C)

alkoxy, [di(1-3C alkyl)amino](1-4C)alkoxy, [(1-4C alkoxy)carbonylamide]difluoro (1-4C)alkoxy, (1-4C alkyl)C(=O)NH(2-4C)alkylthio-, (1-4Calkyl)OC(=O)—, (1-4C alkyl)C(=O)—, hydroxy(1-4C)alkyl, [hydroxy(2-4C)alkyl)amino]-(1-4C)alkyl, [(1-4C alkoxy)(1-4C alkyl)amino](1-4C)alkyl, [di(1-4C alkyl)amino](1-4C)alkyl, R'R"NC(=O)—, 1-6 Calkylthio, benzyloxy, [hydroxy(1-4C)alkoxy](1-4C)alkoxy or [(2-4Calkenyloxy)(1-4C)alkoxy](1-4C)alkoxy;

hetAr$^3$ is a 5-membered heteroaryl ring having 1-3 ring heteroatoms independently selected from N, O and S, wherein said ring is optionally substituted with one or more substituents independently selected from (1-6C)alkyl and [di(1-3C alkyl)amino]CH$_2$—;

hetAr$^4$ is a 6-membered heteroaryl ring having 1-2 ring N atoms and optionally substituted with one or more substituents independently selected from (1-6C)alkyl;

hetAr$^5$ is a 9-membered partially unsaturated bicyclic heterocyclic ring having 3 ring N atoms and optionally substituted with one or more substituents independently selected from (1-6C)alkyl;

hetCyc$^4$ is a 5-7 membered saturated or partially unsaturated heterocyclic ring having 1-2 ring heteroatoms selected from N and O and at least one of said heteroatoms is N, wherein said ring is optionally substituted with one or more substituents independently selected from (1-6C)alkyl, hydroxy(1-4C)alkyl, OH and oxo;

hetCyc$^5$ is a 6 membered heterocyclic ring having 1-2 ring N atoms and optionally substituted with one or more substituents independently selected from (1-6C)alkyl;

hetCyc$^6$ is a 4-6 membered heterocyclic ring having 1-2 ring N atoms and optionally substituted with one or more substituents independently selected from (1-6C)alkyl, (1-4C)alkoxy and halogen;

hetCyc$^7$ is a 4-6 membered heterocycle having 1-2 ring heteroatoms independently selected from N, O and S, wherein one of said ring nitrogen atoms is optionally oxidized to N(O) and wherein said S ring atom is optionally oxidized to SO or SO$_2$, wherein hetCyc$^7$ is optionally substituted with one or more substituents independently selected from (1-6C)alkyl, (1-4C)alkylOC(=O)—, (1-4C)alkoxy, OH and halogen;

hetCyc$^8$ is a 4-6 membered heterocycle having one or two ring N atoms and optionally substituted with one or more substituents independently selected from (1-6C)alkyl and OH;

hetCyc$^9$ is a bridged 8-membered heterocyclic ring having 2 ring atoms selected from N and O wherein at least one of said heteroatoms is N, wherein said ring is optionally substituted with (1-6C)alkyl;

R' is H or (1-4C)alkyl;

R" is (1-4C)alkyl, hetCyc$^{10}$-, amino(1-4C)alkyl, or [di(1-4C alkyl)amino](1-4C alkyl); and hetCyc$^{10}$ is a 5 membered heterocycle having a ring N atom and optionally substituted with one or more substituents independently selected from (1-6C)alkyl.

In one embodiment, a compound Formula I includes compounds wherein:

R$^1$ is hetAr$^1$CH$_2$—, hetAr$^2$CH$_2$—, (3-6C cyclo alkyl)-CH$_2$—, tetrahydropyranylCH$_2$—, benzyl which is optionally substituted with (1-4C)alkoxy, or (N-1-3C alkyl)pyridinonyl-CH$_2$— which is optionally substituted with one or more substituents independently selected from (1-6C)alkyl;

hetAr$^1$ is pyridyl optionally substituted with one or more substituents independently selected from (1-6C)alkyl, (1-4C)alkoxy, halogen, hetCyc$^1$, hetCyc$^1$-CH$_2$—, amino(2-4C)alkoxy, [di(1-3C alkyl)amino](2-4C)alkoxy, dihydroxy(3-4C)alkoxy, hetCyc$^2$O— and hetCyc$^{2a}$(1-2C)alkoxy;

hetCyc$^1$ is a 6-membered heterocycle having 1-2 ring N atoms and optionally substituted with NH$_2$;

hetCyc$^2$ and hetCyc$^{2a}$ are independently a 5-6 membered heterocycle having 1-2 ring N atoms and optionally substituted with one or more substituents independently selected from (1-6C)alkyl, OH, and halogen;

hetAr$^2$ is a 5-membered heteroaryl ring having 2-3 ring heteroatoms independently selected from N, S and O where at least one of said heteroatoms is N, wherein said ring is optionally substituted with one or more substituents independently selected from (1-6C)alkyl, (2-4C)hydroxyalkyl, (3-4C)dihydroxyalkyl, (3-6C cycloalkyl)CH$_2$—, hetCyc$^3$, hetCyc$^{3a}$(1-2C)alkyl, and benzyl optionally substituted with (1-4C)alkoxy;

hetCyc$^3$ and hetCyc$^{3a}$ are independently a 6-membered heterocyclic ring having 1-2 ring N atoms and optionally substituted with a halogen;

R$^2$ is (2-4C)alkyl, cyclopropyl, OMe, I or Br;

R$^3$ is H or Cl;

R$^4$ is H or CN;

R$^5$ is H, F, OH, hetAr$^3$, hetAr$^4$, N-(1-3C alkyl)pyridinone, hetAr$^5$, hetCyc$^4$, hetCyc$^5$C(=O)—, hetCyc$^6$(1-4C alkyl)-, hetCyc$^7$(1-4C)alkoxy, (hetCyc$^8$)—O—, hetCyc$^9$(1-4C)alkoxy, (1-3C alkoxy)(1-4C)alkoxy, hydroxy(1-4C)alkoxy, dihydroxy(2-4C)alkoxy, difluoroamino(1-4C)alkoxy, [di(1-3C alkyl)amino](1-4C)alkoxy, [(1-4C alkoxy)carbonylamide]difluoro (1-4C)alkoxy, (1-4C alkyl)C(=O)NH(2-4C)alkylthio-, (1-4Calkyl)OC(=O)—, (1-4C alkyl)C(=O)—, hydroxy(1-4C)alkyl, [hydroxy(2-4C)alkyl)amino]-(1-4C)alkyl, [(1-4C alkoxy)(1-4C alkyl)amino](1-4C)alkyl, [di(1-4C alkyl)amino](1-4C)alkyl, or R'R"NC(=O)—;

hetAr$^3$ is a 5-membered heteroaryl ring having 1-3 ring heteroatoms independently selected from N, O and S, wherein said ring is optionally substituted with one or more substituents independently selected from (1-6C)alkyl and [di(1-3C alkyl)amino]CH$_2$—;

hetAr$^4$ is a 6-membered heteroaryl ring having 1-2 ring N atoms and optionally substituted with one or more substituents independently selected from (1-6C)alkyl;

hetAr$^5$ is a 9-membered partially unsaturated bicyclic heterocyclic ring having 3 ring N atoms and optionally substituted with one or more substituents independently selected from (1-6C)alkyl;

hetCyc$^4$ is a 5-7 membered saturated or partially unsaturated heterocyclic ring having 1-2 ring heteroatoms selected from N and O and at least one of said heteroatoms is N, wherein said ring is optionally substituted with one or more substituents independently selected from (1-6C)alkyl, hydroxy(1-4C)alkyl, OH and oxo;

hetCyc$^5$ is a 6 membered heterocyclic ring having 1-2 ring N atoms and optionally substituted with one or more substituents independently selected from (1-6C)alkyl;

hetCyc$^6$ is a 4-6 membered heterocyclic ring having 1-2 ring N atoms and optionally substituted with one or more substituents independently selected from (1-6C)alkyl, (1-4C)alkoxy and halogen;

hetCyc$^7$ is a 4-6 membered heterocycle having 1-2 ring heteroatoms independently selected from N, O and S, wherein one of said ring nitrogen atoms is optionally oxidized to N(O) and wherein said S ring atom is optionally oxidized to SO or SO$_2$, wherein hetCyc$^7$ is optionally substituted with one or more substituents independently selected from (1-6C)alkyl, (1-4C)alkylOC(=O)—, (1-4C)alkoxy, OH and F;

hetCyc$^8$ is a 4-6 membered heterocycle having one or two ring N atoms and optionally substituted with one or more substituents independently selected from (1-6C)alkyl and OH;

hetCyc⁹ is a bridged 8-membered heterocyclic ring having 2 ring atoms selected from N and O wherein at least one of said heteroatoms is N, wherein said ring is optionally substituted with (1-6C)alkyl;

R' is H or (1-4C)alkyl;

R" is (1-4C)alkyl, hetCyc¹⁰-, amino(1-4C)alkyl, or [di(1-4C alkyl)amino](1-4C alkyl); and hetCyc¹⁰ is a 5 membered heterocycle having a ring N atom and optionally substituted with one or more substituents independently selected from (1-6C)alkyl.

Compounds of Formula I are inhibitors of the type III receptor tyrosine kinases such as cFMS, and are useful for treating bone-related diseases involving bone resorption, cancer, autoimmune disorders, inflammatory diseases, and cardiovascular diseases.

In one embodiment, R¹ is hetAr¹CH₂— or hetAr²CH₂—.

In one embodiment, R¹ is hetAr¹CH₂—, wherein hetAr¹ is pyridyl optionally substituted with one or more substituents independently selected from (1-6C)alkyl, (1-4C)alkoxy, halogen, hetCyc¹, hetCyc¹-CH₂—, amino(2-4C)alkoxy, [di(1-3C alkyl)amino](2-4C)alkoxy, dihydroxy(3-4C)alkoxy, hetCyc²O—, hetCyc²(1-2C)alkoxy and OH.

In one embodiment, R¹ is hetAr¹CH₂—, wherein hetAr¹ is pyridyl optionally substituted with one or more substituents independently selected from (1-6C)alkyl, (1-4C)alkoxy, halogen, hetCyc¹, hetCyc¹-CH₂—, amino(2-4C)alkoxy, [di(1-3C alkyl)amino](2-4C)alkoxy, dihydroxy(3-4C)alkoxy, hetCyc²O— and hetCyc²ᵃ(1-2C)alkoxy.

Particular examples of (1-6C)alkyl substituents for hetAr¹ include (1-4C)alkyl substituents such as methyl, ethyl, propyl, isopropyl, butyl, and isobutyl.

Particular examples of (1-4C)alkoxy substituents for hetAr¹ include methoxy and ethoxy.

A particular example of a halogen substituent for hetAr¹ is fluoro.

Examples of hetCyc¹ and hetCyc¹CH₂— substituents for hetAr¹ include piperidinyl, piperazinyl, piperidinylmethyl and piperazinylmethyl substituents which are optionally substituted with NH₂. Particular examples include piperazin-1-yl, 4-aminopiperidin-1-yl and piperazin-1-ylmethyl.

Examples of amino(2-4C)alkoxy substituents for hetAr¹ include groups wherein one of the carbon atoms of the (2-4C) alkoxy portion is substituted with an amino group. Particular examples include NH₂CH₂CH₂O— and NH₂CH₂CH₂CH₂O—.

Examples of [di(1-3C alkyl)amino](2-4C)alkoxy substituents for hetAr¹ include groups wherein one of the carbon atoms of the (2-4C)alkoxy portion is substituted with a di(1-3C alkyl)amino group, such as a dimethylamino group. Particular examples include Me₂NCH₂CH₂O— and Me₂NCH₂CH₂CH₂O—.

Examples of dihydroxy(3-4C)alkoxy substituents for hetAr¹ include saturated linear or branched-chain monovalent alkoxy radicals of three to four carbon atoms, respectively, wherein two of the hydrogen atoms are replaced with an OH group, provided that two OH groups are not on the same carbon. A particular example includes HOCH₂CH(OH)CH₂O—.

Examples of hetCyc²O— and hetCyc²ᵃ(1-2C)alkoxy substituents for hetAr¹ include pyrrolidinyloxy, piperidinyloxy, pyrrolidinylmethoxy, piperidinylmethoxy, piperazinylmethoxy, pyrrolidinylethoxy, piperidinylethoxy and piperazinylethoxy groups, wherein the hetCyc² and hetCyc²ᵃ portions are optionally substituted with one or more substituents independently selected from (1-6C)alkyl, halogen, and OH. In certain embodiments hetCyc² and hetCyc²ᵃ are optionally substituted with one or more substituents independently selected from methyl, fluoro and OH, for example one or two of said substituents. Particular examples of hetCyc²O— and hetCyc²ᵃ(1-2C)alkoxy include piperidin-4-yloxy, (4-methylpiperazin-1-yl)ethoxy, 2-(piperazin-1-yl)ethoxy, pyrrolidine-3-yloxy, (N-methyl-3-hydroxy-pyrrolidin-2-yl)methoxy, (3-hydroxypyrrolidin-2-yl)methoxy and 3-fluoropiperidin-4-yloxy.

In certain embodiments, R¹ is hetAr¹CH₂— wherein hetAr¹ is pyridyl optionally substituted with one or more substituents independently selected from methyl, ethyl, isopropyl, methoxy, ethoxy, fluoro, piperazinyl, piperazinylmethyl, aminopiperidinyl, aminopropoxy, aminoethoxy, dimethylaminopropoxy, 2,3-dihydroxypropoxy, piperidin-4-yloxy, (4-methylpiperazin-1-yl)ethoxy, 2-(piperazin-1-yl)ethoxy, pyrrolidine-3-yloxy, (N-methyl-3-hydroxy-pyrrolidin-2-yl)methoxy, (3-hydroxypyrrolidin-2-yl)methoxy, 3-fluoropiperidin-4-yloxy and hydroxy. In certain embodiments, hetAr¹ is optionally substituted with one or two of said substituents.

In certain embodiments, R¹ is hetAr¹CH₂— wherein hetAr¹ is pyridyl optionally substituted with one or more substituents independently selected from methyl, ethyl, isopropyl, methoxy, ethoxy, fluoro, piperazinyl, piperazinylmethyl, aminopiperidinyl, aminopropoxy, aminoethoxy, dimethylaminopropoxy, 2,3-dihydroxypropoxy, piperidin-4-yloxy, (4-methylpiperazin-1-yl)ethoxy, 2-(piperazin-1-yl)ethoxy, pyrrolidine-3-yloxy, (N-methyl-3-hydroxy-pyrrolidin-2-yl)methoxy, (3-hydroxypyrrolidin-2-yl)methoxy and 3-fluoropiperidin-4-yloxy. In certain embodiments, hetAr¹ is optionally substituted with one or two of said substituents.

Particular values for R¹ when represented by hetAr¹CH₂— include the structures:

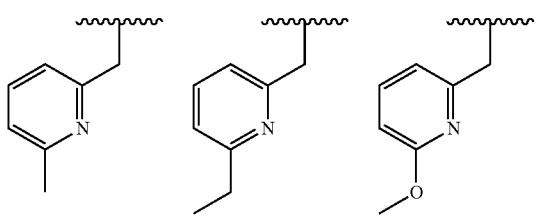

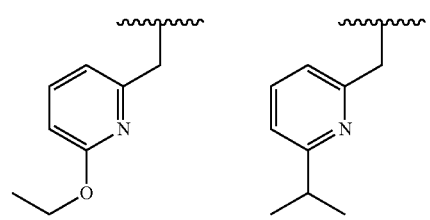

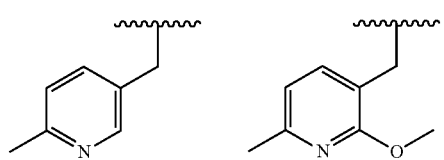

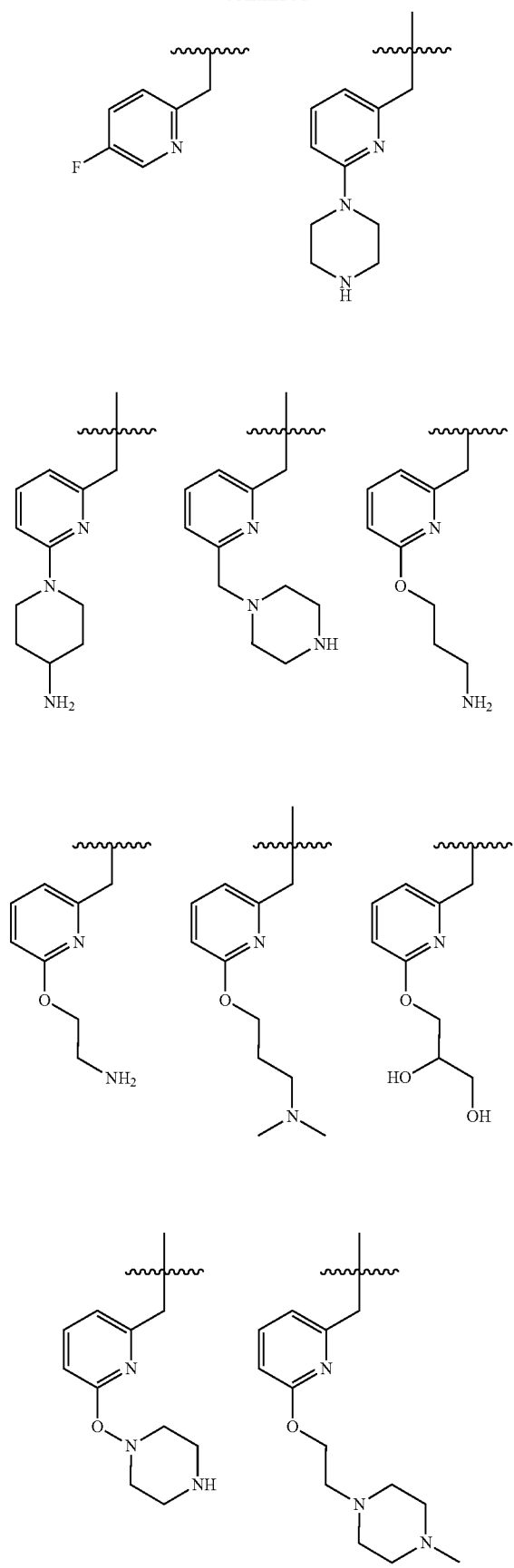
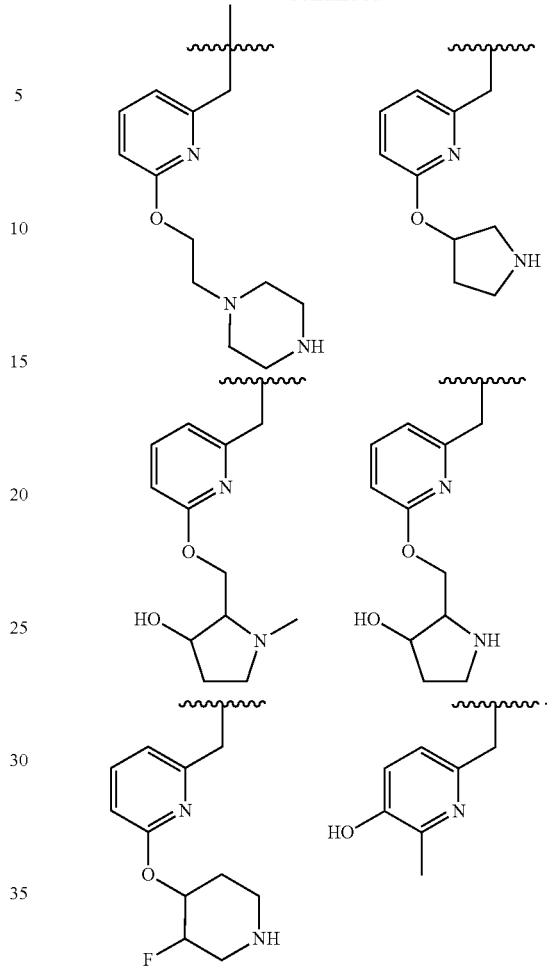

In one embodiment, R¹ is hetAr²CH₂—, where hetAr² is a 5-membered heteroaryl ring having 2-3 ring heteroatoms independently selected from N, S and O where at least one of said heteroatoms is N, wherein said ring is optionally substituted with one or more substituents independently selected from (1-6C)alkyl, (2-4C)hydroxyalkyl, (3-4C)dihydroxyalkyl, (3-6C cycloalkyl)CH₂—, hetCyc³, hetCyc³(1-2C)alkyl, and benzyl optionally substituted with (1-4C)alkoxy.

Particular examples of hetAr² rings include thiazolyl, pyrazolyl, thiadiazolyl and oxazolyl.

Examples of (1-6C)alkyl substituents for hetAr² include (1-4C)alkyl groups, for example methyl, ethyl, propyl and isopropyl.

An example of a (2-4C)hydroxyalkyl substituent for hetAr² is HOCH₂CH₂—.

An example of a (3-4C)dihydroxyalkyl substituent for hetAr² is HOCH₂CH(OH)CH₂—.

An example of a (3-6C cycloalkyl)CH₂— substituent for hetAr² is cyclopropylmethyl.

Examples of hetCyc³ and hetCyc³ᵃ(1-2C)alkyl substituents for hetAr² include piperidinyl, piperidinylethyl and piperazinylethyl, wherein the heterocyclic portion is optionally substituted with halogen, for example fluoro. Particular examples include 2-piperazinylethyl and 3-fluoropiperidin-4-yl.

Examples of benzyl substituents optionally substituted with (1-4C)alkoxy include methoxy-substituted benzyl groups, such as 4-methoxybenzyl.

In one embodiment, hetAr² is optionally substituted with one or two substituents independently selected from methyl, ethyl, isopropyl, 2-hydroxyethyl, 2,3-dihydroxypropyl, 2-piperazinylethyl, cyclopropylmethyl, 2-hydroxyethyl, 3-fluoropiperidin-4-yl and 4-methoxybenzyl.

Particular examples of $R^1$ when represented by hetAr²CH₂— include the structures:

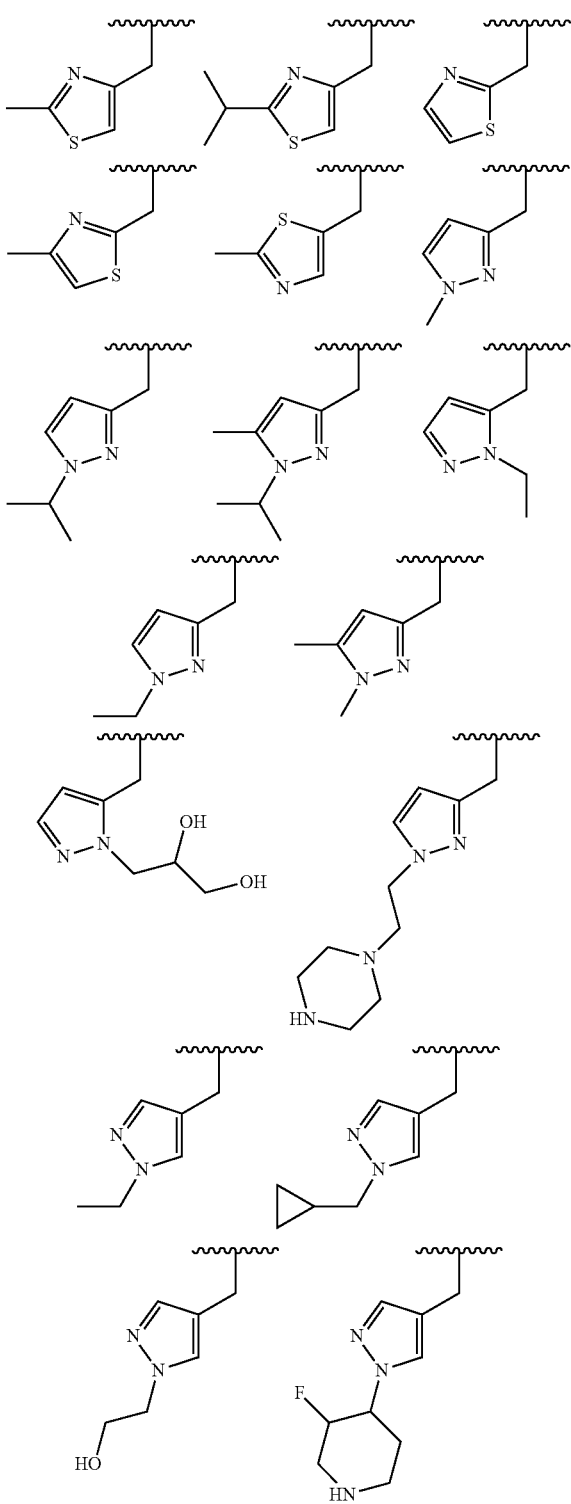

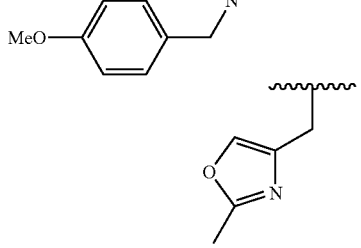

In one embodiment, $R^1$ is (3-6C cycloalkyl)-CH₂—, tetrahydropyranylCH₂—, or benzyl which is optionally substituted with (1-4C)alkoxy.

In one embodiment, $R^1$ is (3-6C cycloalkyl)-CH₂—. A particular example includes cyclopropylmethyl.

In one embodiment, $R^1$ is tetrahydropyranyl-CH₂—. Examples include the structures:

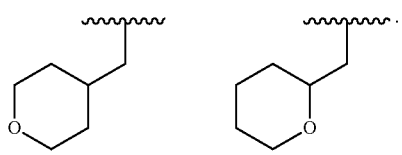 [SMILES: *CC1CCOCC1 ; *CC1CCCCO1]

In one embodiment, $R^1$ is benzyl optionally substituted with (1-4C alkoxy). Examples of alkoxy groups include methoxy and ethoxy. Particular examples of $R^1$ include benzyl and 4-methoxybenzyl.

In one embodiment, $R^1$ is N-(1-3C alkyl)pyridinonyl-CH₂— optionally substituted with a substituent selected from (1-6C)alkyl. Examples of substituents include (1-4C)alkyl groups such as methyl and ethyl. Particular examples of $R^1$ include the structures:

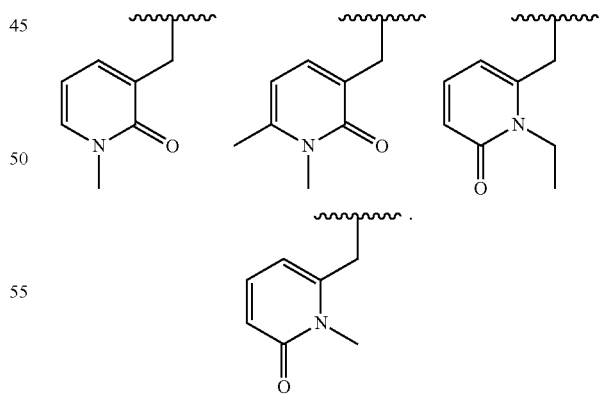

In one embodiment, $R^5$ is halogen.
In one embodiment, $R^5$ is F, Cl or Br.
In one embodiment, $R^5$ is selected from H, F, Cl, Br and OH.
In one embodiment, $R^5$ is selected from H, F and OH.
In one embodiment, $R^5$ is H.
In one embodiment, $R^5$ is F.

In one embodiment, $R^5$ is OH.

In one embodiment, $R^5$ is selected from hetAr$^3$, hetAr$^4$, N-(1-3C alkyl)pyridinone and hetAr$^5$.

In one embodiment, $R^5$ is hetAr$^3$, wherein hetAr$^3$ is a 5-membered heteroaryl ring having 1-3 ring heteroatoms independently selected from N, O and S, wherein said ring is optionally substituted with one or more substituents independently selected from (1-6C)alkyl and [di(1-3C alkyl)amino]CH$_2$. In one embodiment, at least one of said ring heteroatoms is nitrogen. In embodiments wherein at least one of said ring heteroatoms is nitrogen, hetAr$^3$ can be a nitrogen radical (wherein hetAr$^3$ is linked to the imidazopyridine ring of Formula I through a ring nitrogen atom of hetAr$^3$) or a carbon radical (wherein hetAr$^3$ is linked to the imidazopyridine ring of Formula I through a ring carbon atom of hetAr$^3$). Examples of hetAr$^3$ include pyrazolyl, triazolyl, thiadiazolyl, oxadiazolyl and furanyl rings optionally substituted with one or more substituents independently selected from (1-6C)alkyl and [di(1-3C alkyl)amino]CH$_2$—. In certain embodiments hetCyc$^3$ is optionally substituted with one or two of said substituents. In certain embodiments hetAr$^3$ is optionally substituted with one or two substituents independently selected from methyl, ethyl, and Me$_2$NCH$_2$. Particular examples of $R^5$ when represented by hetAr$^3$ include the structures:

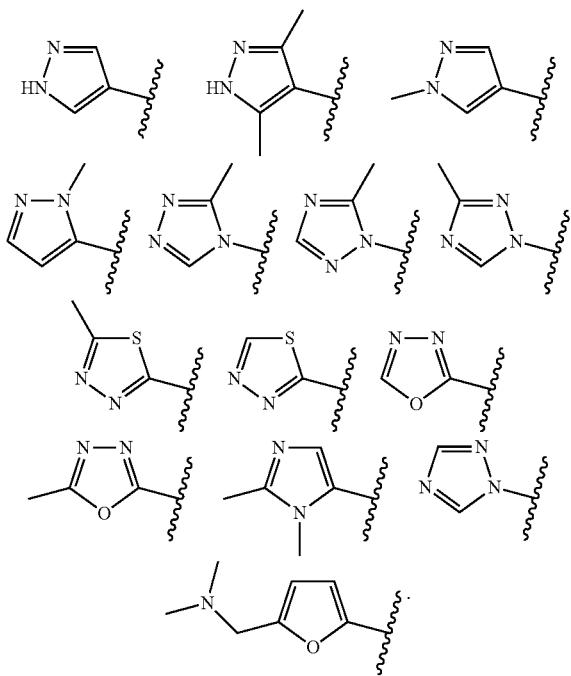

In one embodiment, $R^5$ is hetAr$^4$. Example of hetAr$^4$ include pyrimidyl and pyridyl rings optionally substituted with a substituent selected from (1-6C alkyl), for example (1-4C)alkyl, for example methyl or ethyl. Particular examples of $R^5$ when represented by hetAr$^4$ include the structures:

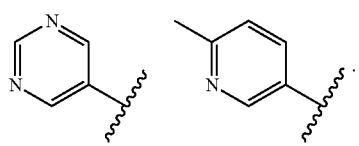

In one embodiment, $R^5$ is N-(1-3C alkyl)pyridinone. A particular example is N-methylpyridinone which can be represented by the structure:

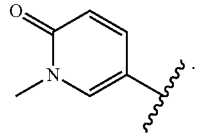 [SMILES: *c1ccc(=O)n(C)c1]

In one embodiment, $R^5$ is hetAr$^5$. Examples of hetAr$^5$ include a 5 membered heteroaryl ring fused to a 6-membered heterocycle ring, wherein one or both of said rings are optionally substituted with a group independently selected from (1-6C alkyl). Particular examples include 5,6,7,8-tetrahydroimidazopyrazine rings optionally substituted with a substituent selected from (1-6C alkyl), for example (1-4C)alkyl, for example methyl or ethyl. Particular values for $R^5$ when represented by hetAr$^5$ include the structures:

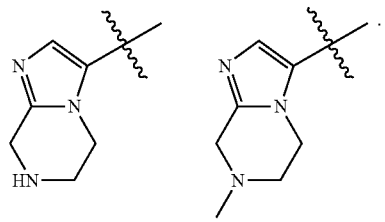 [SMILES: *c1cnc2n1CCNC2 ; *c1cnc2n1CCN(C)C2]

In one embodiment, $R^5$ is pyrazolyl, triazolyl, thiadiazolyl, oxadiazolyl or furanyl optionally substituted with one or more substituents independently selected from (1-6C)alkyl and [di(1-3C alkyl)amino]CH$_2$—; pyrimidyl or pyridyl optionally substituted with a substituent selected from (1-6C alkyl); N-methylpyridinone; or 5,6,7,8-tetrahydroimidazopyrazinyl optionally substituted with a substituent selected from (1-6C alkyl).

In one embodiment, $R^5$ is hetCyc$^4$. Examples of hetCyc$^4$ include piperidinyl, piperazinyl, pyrrolidinyl, diazepanyl, morpholinyl, and tetrahydropyridinyl rings optionally substituted with one or more substituents independently selected from (1-6C)alkyl, hydroxy(1-4C)alkyl, OH and oxo (provided that the oxo is on a ring carbon atom). In certain embodiments, hetCyc$^4$ is substituted with one or more substituents independently selected from methyl, ethyl, OH, HOCH$_2$CH$_2$— and oxo. In one embodiment, hetCyc$^4$ is optionally substituted with one or two of said substituents. In one embodiment, hetCyc$^4$ is a nitrogen radical, that is, hetCyc$^4$ is linked to the imidazopyridine ring of Formula I through a ring nitrogen atom of hetCyc$^4$. In one embodiment, hetCyc$^4$ is a carbon radical, that is, hetCyc$^4$ is linked to the imidazopyridine ring of Formula I through a ring carbon atom of hetCyc$^4$.

Particular examples of $R^5$ when represented by hetCyc$^4$ include the structures:

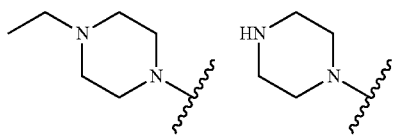

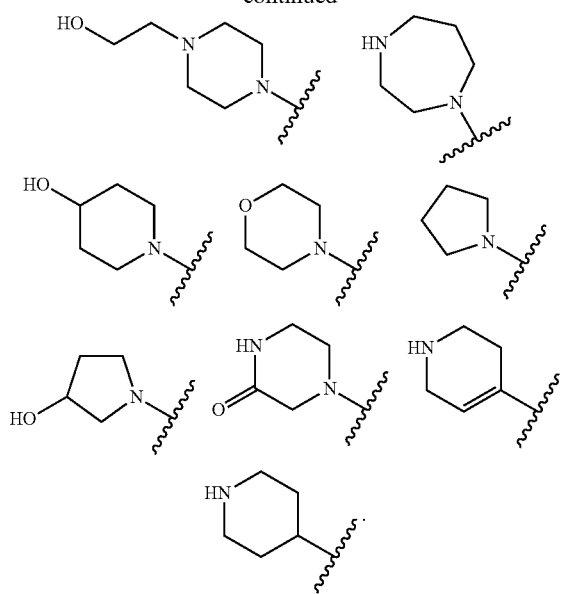

In one embodiment, $R^5$ is hetCyc$^5$C(=O)—. Examples of hetCyc$^5$ include piperidinyl and piperazinyl rings optionally substituted with (1-6C)alkyl, for example (1-4C)alkyl, for example methyl or ethyl. Particular examples of $R^5$ when represented by hetCyc$^5$C(=O)— include the structures:

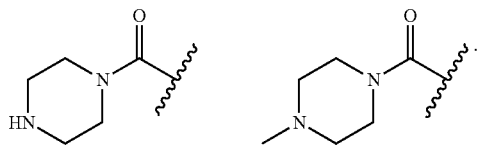

In one embodiment, $R^5$ is hetCyc$^6$(1-4Calkyl)-. Examples of hetCyc$^6$ include azetidinyl, pyrrolidinyl, piperidinyl and piperazinyl rings optionally substituted with one or more substituents independently selected from (1-6C)alkyl, (1-4C)alkoxy and halogen. In certain embodiments hetCyc$^6$ is optionally substituted with one or more substituents independently selected from methyl, ethyl, fluoro and methoxy. In certain embodiments, hetCyc$^6$ is optionally substituted with one or two of said substituents. In certain embodiments, $R^5$ is hetCyc$^6$(1-3C)alkyl. Particular examples of $R^5$ when represented by hetCyc$^6$(1-4Calkyl)- include the structures:

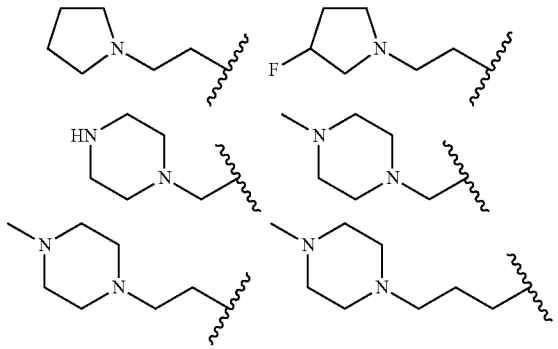

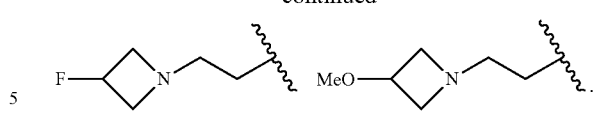

In one embodiment, $R^5$ is hetCyc$^7$(1-4C)alkoxy. Examples of hetCyc$^7$ groups include azetidinyl, pyrrolidinyl, piperidinyl, piperazinyl, morpholinyl, 1-methyl-piperazinyl-1-oxide, and thiomorpholinyl-1,1-dioxide, each of which is optionally substituted with one or more substituents independently selected from (1-6C)alkyl, (1-4C)alkylOC(=O)—, (1-4C)alkoxy, OH and halogen. In certain embodiments, hetCyc$^7$ is azetidinyl, pyrrolidinyl, piperidinyl, piperazinyl, morpholinyl, 1-methyl-piperazinyl-1-oxide, or thiomorpholinyl-1,1-dioxide, each of which is optionally substituted with one or more substituents independently selected from (1-6C)alkyl, (1-4C)alkylOC(=O)—, (1-4C)alkoxy, OH and F. In certain embodiments, hetCyc$^7$ is azetidinyl, pyrrolidinyl, piperidinyl, piperazinyl, morpholinyl, 1-methyl-piperazinyl-1-oxide, or thiomorpholinyl-1,1-dioxide, each of which is optionally substituted with one or more substituents independently selected form methyl, ethyl, isopropyl, fluoro, methoxy, OH, and (CH$_3$)$_3$C(=O)—. In certain embodiments hetCyc$^7$ is optionally substituted with one or two of said substituents. In certain embodiments, $R^5$ is hetCyc$^7$(1-2C)alkoxy.

Particular examples of $R^5$ when represented by hetCyc$^7$(1-4C)alkoxy include the structures:

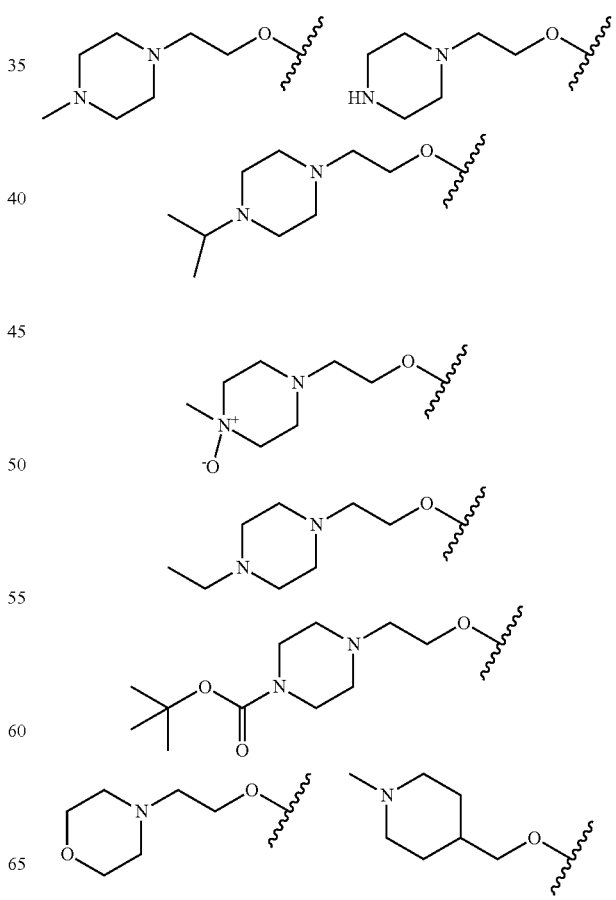

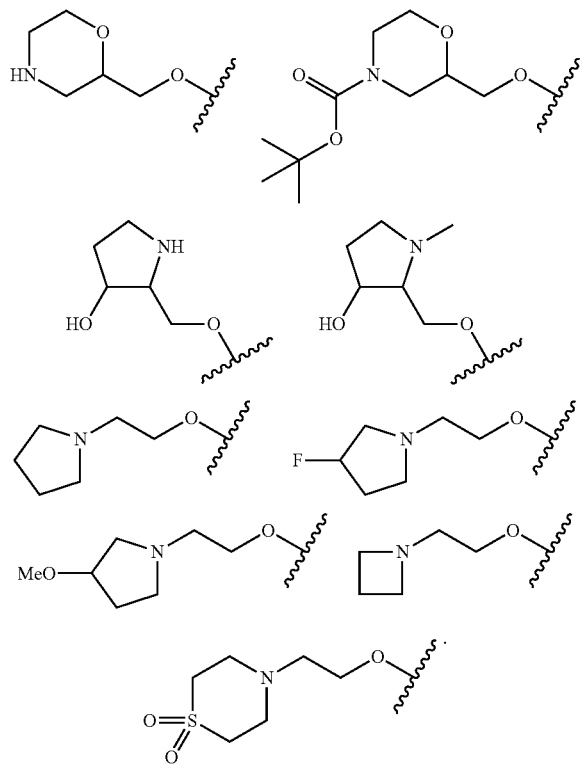

In one embodiment, $R^5$ is hetCyc$^8$O—. Examples of hetCyc$^8$O— include azetidinyloxy, pyrrolidinyloxy, piperidinyloxy and piperazinyloxy rings optionally substituted with one or more substituents independently selected from (1-6C) alkyl and OH. In certain embodiments hetCyc$^8$O— is azetidinyloxy, pyrrolidinyloxy or piperidinyloxy optionally substituted with one or more substituents independently selected from methyl and OH, for example one or two of said substituents. Particular examples of $R^5$ when represented by (hetCyc$^8$)—O— include the structures:

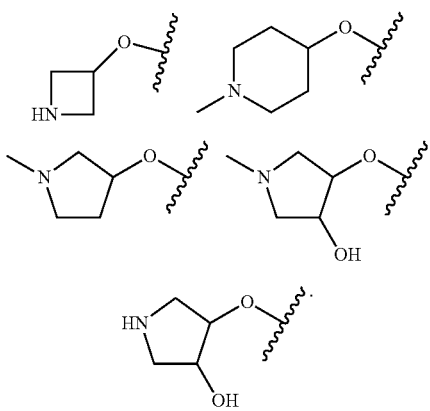

In one embodiment, $R^5$ is hetCyc$^9$(1-4C)alkoxy. Examples of hetCyc$^9$ rings include 3,8-diazabicyclo[3.2.1]octane and 8-oxa-3-azabicyclo[3.2.1]octane rings optionally substituted with (1-6C)alkyl. Particular examples of $R^5$ when represented by hetCyc$^9$(1-4C)alkoxy include the structures:

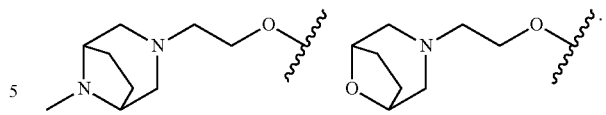

In one embodiment, $R^5$ is selected from hetCyc$^4$, hetCyc$^5$C(=O)—, hetCyc$^6$(1-4Calkyl)-, hetCyc$^7$(1-4C)alkoxy, (hetCyc$^8$)—O— and hetCyc$^9$(1-4C)alkoxy.

In one embodiment, $R^5$ is selected from hetCyc$^7$(1-4C)alkoxy, (hetCyc$^8$)—O— and hetCyc$^9$(1-4C)alkoxy.

In one embodiment, $R^5$ is selected from hetCyc$^7$(1-4C)alkoxy and hetCyc$^8$(1-4C)alkoxy.

In one embodiment, $R^5$ is (1-3C alkoxy)(1-4C)alkoxy, that is, a (1-4C)alkoxy group wherein one of the carbon atoms is substituted with (1-3C alkoxy), for example a methoxy group. A particular example of $R^5$ when represented by (1-3C alkoxy)(1-4C)alkoxy includes the structure:

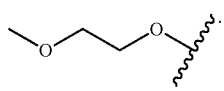 [SMILES: *OCCOC]

In one embodiment, $R^5$ is hydroxy(1-4C)alkoxy, that is, a (1-4C)alkoxy group wherein one of the carbon atoms is substituted with hydroxy. A particular example of $R^5$ when represented by hydroxy(1-4C)alkoxy includes the structure:

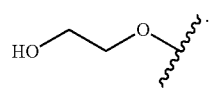 [SMILES: *OCCO]

In one embodiment, $R^5$ is dihydroxy(2-4C)alkoxy, that is, a (2-4C)alkoxy group wherein two of the carbon atoms are substituted with a hydroxy group, provided the hydroxy groups are not on the same carbon atom. A particular example of $R^5$ when represented by dihydroxy(2-4C)alkoxy includes the structure:

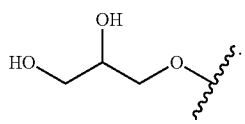 [SMILES: *OCC(O)CO]

In one embodiment, $R^5$ is difluoroamino(1-4C)alkoxy, that is, a (1-4C)alkoxy group wherein one of the hydrogen atoms of the alkoxy portion as defined herein is replaced with an amino group and two of the hydrogen atoms of the alkoxy portion as defined herein are each replaced with a fluorine atom. A particular example of $R^5$ when represented by difluoroamino(1-4C)alkoxy includes the structure:

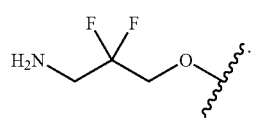 [SMILES: *OCC(F)(F)CN]

In one embodiment, $R^5$ is [di(1-3C alkyl)amino](1-4C) alkoxy, that is, a (1-4C)alkoxy group wherein one of the carbon atoms is substituted with a di(1-3C alkyl)amino, for example a dimethylamino group. A particular example of $R^5$ when represented by [di(1-3C alkyl)amino](1-4C)alkoxy includes the structure:

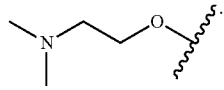 [SMILES: *OCCN(C)C]

In one embodiment, $R^5$ is [(1-4C alkoxy)carbonylamide]difluoro(1-4C)alkoxy, that is, a (1-4C)alkoxy group wherein two of the carbon atoms are each substituted with a fluorine atom and one of the carbon atoms is substituted with a (1-4C alkoxy)carbonylamide, for example a $(CH_3)_3C(=O)NH-$ group. A particular example of $R^5$ when represented by [(1-4C alkoxy)carbonylamide]difluoro(1-4C)alkoxy includes the structure:

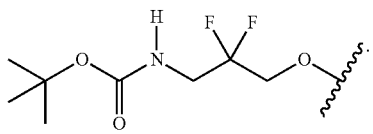 [SMILES: *OCC(F)(F)CNC(=O)OC(C)(C)C]

In one embodiment, $R^5$ is (1-4C alkyl)C(=O)NH(2-4C)alkylthio-, that is, a (2-4C)alkylthio group in which the radical is on the sulfur atom, wherein one of the carbon atoms is substituted with a (1-4C alkyl)C(=O)NH— group. A particular example of $R^5$ when represented by (1-4C alkyl)C(=O)NH(2-4C)alkylthio includes the structure:

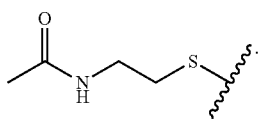 [SMILES: *SCCNC(C)=O]

In one embodiment, $R^5$ is (1-4Calkyl)OC(=O)—. A particular example of $R^5$ includes the structure:

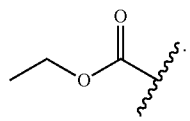

In one embodiment, $R^5$ is (1-4C alkyl)C(=O)—. A particular example of $R^5$ includes the structure:

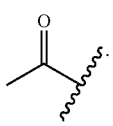

In one embodiment, $R^5$ is hydroxy(1-4C)alkyl. Particular examples of $R^5$ include the structures:

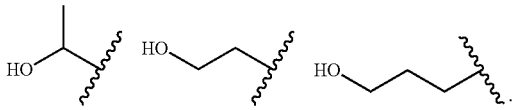

In one embodiment, $R^5$ is [(2-4C)hydroxyalkyl)amino]-(1-4C)alkyl, that is, a (1-4C)alkyl group wherein one of the carbon atoms is substituted with a [hydroxy(2-4C alkyl)] amino group, for example a $HOCH_2CH_2NH-$ group. A particular example of $R^5$ includes the structure:

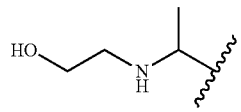

In one embodiment, $R^5$ is [(1-4C alkoxy)(1-4C alkyl)amino](1-4C)alkyl, that is, a (1-4C)alkyl group wherein one of the carbon atoms is substituted with a [(1-4C alkoxy)(1-4C alkyl)]amino group, for example a methoxy(1-4C alkyl) NH— group.

A particular example of $R^5$ when represented by [(1-4C alkoxy)(1-4C alkyl)]amino(1-4C)alkyl includes the structure:

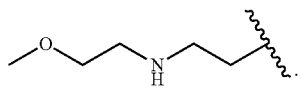 [SMILES: *CCNCCOC]

In one embodiment, $R^5$ is [di(1-4C alkyl)amino](1-4C) alkyl, that is, a (1-4C)alkyl group wherein one of the carbon atoms is substituted with a di(1-4C alkyl)amino.

In one embodiment, $R^5$ is dimethylamino(1-4C alkyl). Particular examples when $R^5$ is [di(1-4C alkyl)amino](1-4C) alkyl include the structures:

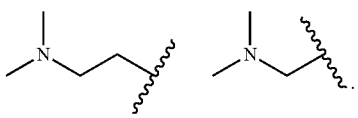

In one embodiment, $R^5$ is selected from (1-3C alkoxy)(1-4C)alkoxy, hydroxy(1-4C)alkoxyl, dihydroxy(1-4C)alkoxy, difluoroamino(1-4C)alkoxy, [di(1-3C alkyl)amino](1-4C) alkoxy, [(1-4C alkoxy)carbonylamide]difluoro (1-4C)alkoxy and (1-4C alkyl)C(=O)NH(2-4C)alkylthio-.

In one embodiment, $R^5$ is selected from (1-4Calkyl)OC(=O)— and (1-4C alkyl)C(=O)—.

In one embodiment, $R^5$ is selected from hydroxy(1-4C) alkyl, [(2-4C)hydroxyalkyl)]amino-(1-4C)alkyl, [(1-4C alkoxy)(1-4C alkyl)]amino(1-4C)alkyl and [di(1-4C alkyl) amino](1-4C)alkyl.

In one embodiment, $R^5$ is R'R"NC(=O)—, where R' is H or methyl and R" is (1-4C)alkyl, $hetCyc^{10}$-, [amino(1-4C alkyl)] or [di(1-4C alkyl)amino](1-4C alkyl). In one embodiment, R' is H. In one embodiment, R' is methyl.

In one embodiment, $R^5$ is $hetCyc^{10}$-NR'C(=O). Examples of $hetCyc^{10}$ groups include pyrrolidinyl rings optionally substituted with (1-6C alkyl), for example (1-4C alkyl), for example methyl or ethyl. Particular examples of R⁵ when represented by hetCyc¹⁰-NR'C(=O) include the structures:

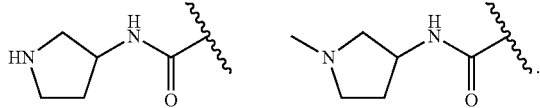

In one embodiment, R⁵ is [amino(1-4C)alkyl)]NR'C(=O)—. A particular example of R⁵ includes the structure:

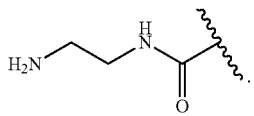

In one embodiment, R⁵ is [di(1-4C alkyl)amino](1-4C alkyl)NHC(=O)—. In one embodiment R⁵ is dimethylamino (1-4C alkyl)NR'C(=O)—. A particular example of R⁵ includes the structure:

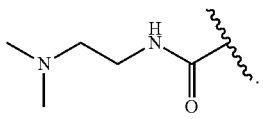 [SMILES: *C(=O)NCCN(C)C]

In one embodiment, R⁵ is (1-4C alkyl)NR'C(=O). A particular example of R⁵ includes the structures:

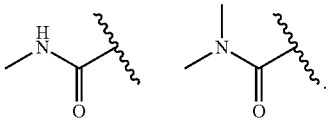

In one embodiment, R⁵ is 1-6Calkylthio. In one embodiment, R⁵ is CH₃S—.

In one embodiment, R⁵ is selected from benzyloxy, [hydroxy(1-4C)alkoxy](1-4C)alkoxy and [(2-4Calkenyloxy)(1-4C)alkoxy](1-4C)alkoxy.

In one embodiment, R⁵ is benzyloxy, which can be represented by the structure:

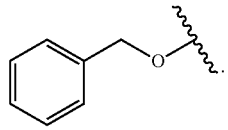 [SMILES: *OCc1ccccc1]

In one embodiment, R⁵ is [hydroxy(1-4C)alkoxy](1-4C) alkoxy, that is, a (1-4C)alkoxy group wherein one of the carbon atoms is substituted with a hydroxy(1-4C)alkoxy substituent, such as a hydroxyethoxy group. A particular example is the structure:

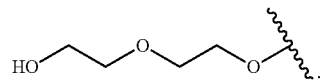 [SMILES: *OCCOCCO]

In one embodiment, R⁵ is [(2-4Calkenyloxy)(1-4C) alkoxy](1-4C)alkoxy, that is, a (1-4C)alkoxy group wherein one of the carbon atoms is substituted with a [(2-4Calkenyloxy)(1-4C)alkoxy]substituent. A particular example is the structure:

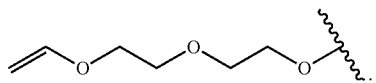 [SMILES: *OCCOCCOC=C]

In certain embodiments, R² is cyclopropyl or (2-4C)alkyl.
In certain embodiments, R² is (2-4C)alkyl. Examples include ethyl, propyl, isopropyl, butyl, isobutyl and tert-butyl.
In certain embodiments of Formula I, R² is ethyl.
In certain embodiments of Formula I, R² is cyclopropyl.
In certain embodiments of Formula I, R² is OMe, I or Br.
In certain embodiments of Formula I, R² is OMe.
In certain embodiments of Formula I, R² is I or Br.
In certain embodiments of Formula I, R³ is H.
In certain embodiments of Formula I, R³ is Cl.
In certain embodiments of Formula I, R⁴ is H.
In certain embodiments of Formula I, R⁴ is CN.
In certain embodiments of Formula I, R² is ethyl, cyclopropyl, OMe, I or Br.
In certain embodiments of Formula I, R² is ethyl or cyclopropyl.
In one embodiment of Formula I, R¹ is hetAr¹CH₂— or hetAr²CH₂—; R² is cyclopropyl or (2-4C)alkyl; R³ is hydrogen; R⁴ is hydrogen; and R⁵ is hetCyc⁴, hetCyc⁵C(=O)—, hetCyc⁶(1-4Calkyl)-, hetCyc⁷(1-4C)alkoxy, (hetCyc⁸)—O— and hetCyc⁹(1-4C)alkoxy.
In one embodiment of Formula I, R¹ is hetAr¹CH₂— or hetAr²CH₂—; R² is cyclopropyl or (2-4C)alkyl; R³ is hydrogen; R⁴ is hydrogen; and R⁵ is hetCyc⁷(1-4C)alkoxy, (hetCyc⁸)—O— or hetCyc⁹(1-4C)alkoxy.
In one embodiment of Formula I, R¹ is hetAr¹CH₂—; R² is cyclopropyl or (2-4C)alkyl; R³ is hydrogen; R⁴ is hydrogen; and R⁵ is hetCyc⁷(1-4C)alkoxy, (hetCyc⁸)—O— or hetCyc⁹(1-4C)alkoxy.
In one embodiment of Formula I, R¹ is hetAr¹CH₂—; R² is cyclopropyl or (2-4C)alkyl; R³ is hydrogen; R⁴ is hydrogen; and R⁵ is hetCyc⁷(1-4C)alkoxy.
In one embodiment of Formula I, R¹ is hetAr¹CH₂—; R² is cyclopropyl or (2-4C)alkyl; R³ is hydrogen; R⁴ is hydrogen; and R⁵ is azetidinyl, pyrrolidinyl, piperidinyl, piperazinyl, morpholinyl, 1-methyl-piperazinyl-1-oxide, or thiomorpholinyl-1,1-dioxide, each of which is optionally substituted with one or more substituents independently selected from (1-6C)alkyl, (1-4C)alkylOC(=O)—, (1-4C)alkoxy, OH and F.
In one embodiment of Formula I, R¹ is hetAr¹CH₂—; R² is cyclopropyl or ethyl; R³ is hydrogen; R⁴ is hydrogen; and R⁵ is azetidinyl, pyrrolidinyl, piperidinyl, piperazinyl, morpholinyl, 1-methyl-piperazinyl-1-oxide, or thiomorpholinyl-1,1-dioxide, each of which is optionally substituted with one or more substituents independently selected form methyl, ethyl, isopropyl, fluoro, methoxy, OH, and (CH₃)₃C(=O)—.
In one embodiment of Formula I, R¹ is pyridyl optionally substituted with one or more substituents independently selected from methyl, ethyl, isopropyl, methoxy, ethoxy, fluoro, piperazinyl, piperazinylmethyl, aminopiperidinyl, aminopropoxy, aminoethoxy, dimethylaminopropoxy, 2,3-dihydroxypropoxy, piperidin-4-yloxy, (4-methylpiperazin-1-yl)ethoxy, 2-(piperazin-1-yl)ethoxy, pyrrolidine-3-yloxy, (N-methyl-3-hydroxy-pyrrolidin-2-yl)methoxy, (3-hydroxy-pyrrolidin-2-yl)methoxy, 3-fluoropiperidin-4-yloxy and hydroxy; $R^2$ is cyclopropyl or ethyl; $R^3$ is hydrogen; $R^4$ is hydrogen; and $R^5$ is azetidinyl, pyrrolidinyl, piperidinyl, piperazinyl, morpholinyl, 1-methyl-piperazinyl-1-oxide, or thiomorpholinyl-1,1-dioxide, each of which is optionally substituted with one or more substituents independently selected form methyl, ethyl, isopropyl, fluoro, methoxy, OH, and $(CH_3)_3C(=O)-$.

In one embodiment of Formula I, $R^1$ is (3-6C cycloalkyl)-$CH_2-$, tetrahydropyranyl$CH_2-$, or benzyl which is optionally substituted with (1-4C)alkoxy; $R^2$ is cyclopropyl or (2-4C)alkyl; $R^3$ is hydrogen; $R^4$ is hydrogen; and $R^5$ is selected from hetCyc$^4$, hetCyc$^5$C(=O)—, hetCyc$^6$(1-4Calkyl)-, hetCyc$^7$(1-4C)alkoxy, (hetCyc$^8$)—O— and hetCyc$^9$(1-4C)alkoxy.

In one embodiment of Formula I, $R^1$ is (3-6C cycloalkyl)-$CH_2-$, tetrahydropyranyl$CH_2-$, or benzyl which is optionally substituted with (1-4C)alkoxy; $R^2$ is cyclopropyl or ethyl; $R^3$ is hydrogen; $R^4$ is hydrogen; and $R^5$ is hetCyc$^7$(1-4C)alkoxy, (hetCyc$^8$)—O— or hetCyc$^9$(1-4C)alkoxy.

In one embodiment of Formula I, $R^1$ is (3-6C cycloalkyl)-$CH_2-$, tetrahydropyranyl$CH_2-$, or benzyl which is optionally substituted with (1-4C)alkoxy; $R^2$ is cyclopropyl or (2-4C)alkyl; $R^3$ is hydrogen; $R^4$ is hydrogen; and $R^5$ is hetCyc$^7$(1-4C)alkoxy, (hetCyc$^8$)—O— or hetCyc$^9$(1-4C)alkoxy.

In one embodiment of Formula I, $R^1$ is (3-6C cycloalkyl)-$CH_2-$, tetrahydropyranyl$CH_2-$, or benzyl which is optionally substituted with (1-4C)alkoxy; $R^2$ is cyclopropyl or (2-4C)alkyl; $R^3$ is hydrogen; $R^4$ is hydrogen; and $R^5$ is hetCyc$^7$(1-4C)alkoxy.

In one embodiment of Formula I, $R^1$ is (3-6C cycloalkyl)-$CH_2-$, tetrahydropyranyl$CH_2-$, or benzyl which is optionally substituted with (1-4C)alkoxy; $R^2$ is cyclopropyl or ethyl; $R^3$ is hydrogen; $R^4$ is hydrogen; and $R^5$ is hetCyc$^7$(1-4C)alkoxy.

In one embodiment of Formula I, $R^1$ is hetAr$^1$CH$_2$— or hetAr$^2$CH$_2$—; $R^2$ is cyclopropyl or (2-4C)alkyl; $R^3$ is hydrogen; $R^4$ is hydrogen; and $R^5$ is hetAr$^3$, hetAr$^4$, N-(1-3C alkyl) pyridinone or hetAr$^5$.

In one embodiment of Formula I, $R^1$ is hetAr$^1$CH$_2$— or hetAr$^2$CH$_2$—; $R^2$ is cyclopropyl or ethyl; $R^3$ is hydrogen; $R^4$ is hydrogen; and $R^5$ is pyrazolyl, triazolyl, thiadiazolyl, oxadiazolyl or furanyl optionally substituted with one or more substituents independently selected from (1-6C)alkyl and [di(1-3C alkyl)amino]CH$_2$—; pyrimidyl or pyridyl optionally substituted with a substituent selected from (1-6C alkyl); N-methylpyridinone; or 5,6,7,8-tetrahydroimidazopyrazinyl optionally substituted with a substituent selected from (1-6C alkyl).

In one embodiment of Formula I, $R^1$ is hetAr$^1$CH$_2$— or hetAr$^2$CH$_2$—; $R^2$ is cyclopropyl or (2-4C)alkyl; $R^3$ is hydrogen; $R^4$ is hydrogen; and $R^5$ is (1-3C alkoxy)(1-4C)alkoxy, hydroxy(1-4C)alkoxyl, dihydroxy(2-4C)alkoxy, difluoroamino(1-4C)alkoxy, [di(1-3C alkyl)amino](1-4C)alkoxy, [(1-4C alkoxy)carbonylamide]difluoro (1-4C)alkoxy or (1-4C alkyl)C(=O)NH(2-4C)alkylthio-.

In one embodiment of Formula I, $R^1$ is hetAr$^1$CH$_2$— or hetAr$^2$CH$_2$—; $R^2$ is cyclopropyl or ethyl; $R^3$ is hydrogen; $R^4$ is hydrogen; and $R^5$ is (1-3C alkoxy)(1-4C)alkoxy, hydroxy(1-4C)alkoxyl, dihydroxy(2-4C)alkoxy, difluoroamino(1-4C)alkoxy, [di(1-3C alkyl)amino](1-4C)alkoxy, [(1-4C alkoxy)carbonyl amide]difluoro (1-4C)alkoxy or (1-4C alkyl)C(=O)NH(2-4C)alkylthio-.

In one embodiment of Formula I, $R^1$ is hetAr$^1$CH$_2$— or hetAr$^2$CH$_2$—; $R^2$ is cyclopropyl or (2-4C)alkyl; $R^3$ is hydrogen; $R^4$ is hydrogen; and $R^5$ is (1-4Calkyl)OC(=O)— or (1-4C alkyl)C(=O)—.

In one embodiment of Formula I, $R^1$ is hetAr$^1$CH$_2$— or hetAr$^2$CH$_2$—; $R^2$ is cyclopropyl or ethyl; $R^3$ is hydrogen; $R^4$ is hydrogen; and $R^5$ is (1-4Calkyl)OC(=O)— or (1-4C alkyl)C(=O)—.

In one embodiment of Formula I, $R^1$ is hetAr$^1$CH$_2$— or hetAr$^2$CH$_2$—; $R^2$ is cyclopropyl or (2-4C)alkyl; $R^3$ is hydrogen; $R^4$ is hydrogen; and $R^5$ is selected from hydroxy(1-4C)alkyl, [(2-4C)hydroxyalkyl)]amino-(1-4C)alkyl, [1-4C alkoxy)(1-4C alkyl)]amino(1-4C)alkyl and [di(1-4C alkyl)amino](1-4C)alkyl.

In one embodiment of Formula I, $R^1$ is hetAr$^1$CH$_2$— or hetAr$^2$CH$_2$—; $R^2$ is cyclopropyl or ethyl; $R^3$ is hydrogen; $R^4$ is hydrogen; and $R^5$ is selected from hydroxy(1-4C)alkyl, [(2-4C)hydroxyalkyl)]amino-(1-4C)alkyl, [1-4C alkoxy)(1-4C alkyl)]amino(1-4C)alkyl and [di(1-4C alkyl)amino](1-4C)alkyl.

The terms "(1-6C)alkyl" and "(1-4C)alkyl" as used herein refer to saturated linear or branched-chain monovalent hydrocarbon radicals of one to six carbon atoms, or one to four carbon atoms, respectively. Examples include, but are not limited to, methyl, ethyl, 1-propyl, isopropyl, 1-butyl, isobutyl, sec-butyl, tert-butyl, 2-methyl-2-propyl, pentyl, and hexyl.

The terms "(1-4C)alkoxy" and "(2-4C)alkoxy" as used herein refer to saturated linear or branched-chain monovalent alkoxy radicals of one to four carbon atoms or two to four carbon atoms, respectively, wherein the radical is on the oxygen atom. Examples include methoxy, ethoxy, propoxy, isopropoxy, and butoxy.

The term "hydroxy(1-4C)alkyl" as used herein refers to saturated linear or branched-chain monovalent radicals of one to four carbon atoms, wherein one of the carbon atoms is substituted with a hydroxy group.

The term "(3-4C)dihydroxyalkyl" as used herein refers to saturated linear or branched-chain monovalent radicals of three to four carbon atoms, wherein two of the carbon atoms are substituted with a hydroxy group, provided both hydroxy groups are not on the same carbon atom.

The term "amino(1-4C)alkyl" as used herein refers to saturated linear or branched-chain monovalent radicals of one to four carbon atoms, wherein one of the carbon atoms is substituted with an amino (NH$_2$) group The term "halogen" includes fluoro, chloro, bromo and iodo.

When a chemical formula is used to describe a substituent, the dash on the right side of the formula indicates the portion of the substituent that has the free valence.

When terms are used to describe a multi-component substituent, the rightmost portion of the substituent that has the free valence. To illustrate, the term [(1-4C alkoxy)(1-4C alkyl)amino](1-4C)alkyl contains three components: (1-4C alkoxy), (1-4C alkyl)amino and (1-4C alkyl). As written, the free valence is on the (1-4C alkyl) portion of this substituent.

A prefix attached to a multi-component substituent only applies to the first component. To illustrate, the term "alkylcycloalkyl" contains two components: alkyl and cycloalkyl. Thus, the prefix "halo" on haloalkoxyalkyl indicates that only the alkoxy component of the alkoxyalkyl substituent is substituted with one or more halogen radicals. Alternatively, if the halogen substitution may only occur on the alkyl component, the substituent would instead be described as "alkoxyhaloalkyl."

It will be appreciated that certain compounds according to the invention may contain one or more centers of asymmetry and may therefore be prepared and isolated as a mixture of isomers such as a racemic or diastereomeric mixture, or in an enantiomerically or diastereomerically pure form. It is intended that all stereoisomeric forms of the compounds of the invention, including but not limited to, diastereomers, enantiomers and atropisomers, as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

It will also be appreciated that certain compounds of Formula I may be used as intermediates for the preparation of further compounds of Formula I.

The compounds of Formula I include salts thereof. In certain embodiments, the salts are pharmaceutically acceptable salts. In addition, the compounds of Formula I include other salts of such compounds which are not necessarily pharmaceutically acceptable salts, and which may be useful as intermediates for preparing and/or purifying compounds of Formula I and/or for separating enantiomers of compounds of Formula I.

It will further be appreciated that the compounds of Formula I and their salts may be isolated in the form of solvates, and accordingly that any such solvate is included within the scope of the present invention. For example, compounds of Formula I can exist in unsolvated as well as solvated forms with pharmaceutically acceptable solvents such as water, ethanol, and the like. The use of a drying agent to remove trace amounts of solvent in the preparation of a compound of Formula I does not preclude the existence of a solvated form of a compound of Formula I made by that process.

Compounds of the invention may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1H$, $^2H$, $^3H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof when oxygen is mentioned, it is understood to refer to $^{14}O$, $^{15}O$, $^{16}O$, $^{17}O$, $^{18}O$ or mixtures thereof and when fluoro is mentioned, it is understood to refer to $^{18}F$, $^{19}F$ or mixtures thereof. The compounds according to the invention therefore also comprise compounds with one or more isotopes of one or more atom, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds of the present invention, whether radioactive or not, are intended to be encompassed within the scope of the present invention.

The present invention further provides a process for the preparation of a compound of Formula I or a salt thereof as defined herein which comprises:

(a) coupling a corresponding compound of formula II

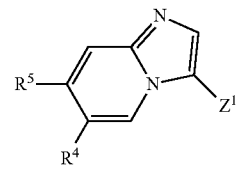

II where $Z^1$ is —COOH or a reactive derivative thereof with a corresponding compound of formula III

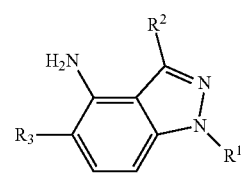

III in the presence of a coupling reagent; or (b) coupling a corresponding compound of formula IV

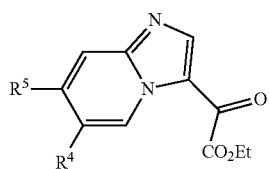

IV with a compound of formula III

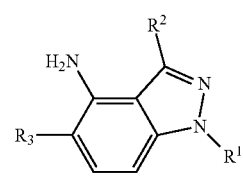

III in the presence of a base; or (c) for a compound of Formula I where $R^5$ is hetCyc$^7$(1-4C)alkoxy, (hetCyc$^8$)—O—, hetCyc$^9$(1-4C)alkoxy, hydroxy(1-4C)alkoxy, difluoroamino(1-4C)alkoxy, or [(1-4C alkoxy)carbonylamide]difluoro(1-4C)alkoxy, reacting a corresponding compound of formula V

V

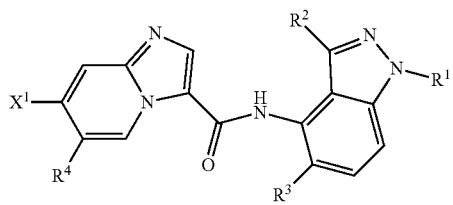

where X$^1$ is F or Cl, with a compound having the formula R$^{5a}$—O— where R$^{5a}$ is hetCyc$^7$ (1-4C)alkyl-OH, hetCyc$^8$-OH, hetCyc$^9$ (1-4C)alkyl-OH, P$^1$O-(1-4C)alkyl-OH, difluoroamino(1-4C)alkyl-OH or [(1-4C alkoxy)carbonylamide] difluoro (1-4C)alkyl-OH, respectively, in the presence of a base, where P$^1$ is a hydroxyl protecting group; or (d) for a compound of Formula I where R$^5$ is hetCyc$^4$ where hetCyc$^4$ is a nitrogen radical, reacting a corresponding compound of formula V-a V-a

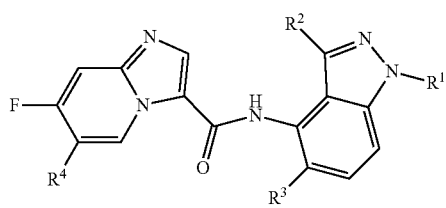

with a compound having the formula hetCyc$^4$-H; or (e) for a compound of Formula I where R$^5$ is hetAr$^3$ and hetAr$^3$ is a nitrogen radical, reacting a corresponding compound of formula V-a V-a

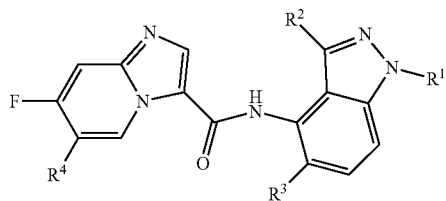

with a compound having the formula hetAr$^3$—H in the presence of a base; or (f) for a compound of Formula I where R$^5$ is a carbon linked substituent selected from hetAr$^3$, hetAr$^4$, and N-(1-3C alkyl)pyridinone, reacting a corresponding compound of formula V-b V-b

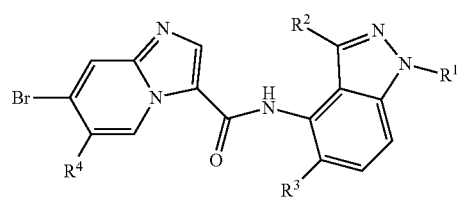

with a compound having the formula VI

VI

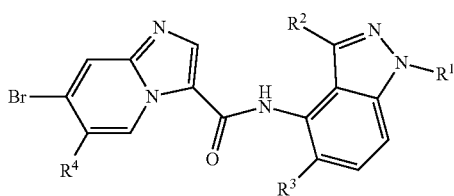

where Ring E is a carbon-linked radical selected from hetAr$^3$—, hetAr$^4$—, and N-(1-3C alkyl)pyridinonyl, respectively, in the presence of a palladium catalyst and a base; or (g) for a compound of Formula I where R$^5$ is hetAr$^3$— or hetAr$^5$— where hetAr$^3$ and hetAr$^5$ are carbon radicals, reacting a corresponding compound of formula V-b with a compound having the formula hetAr$^3$—H or hetAr$^5$—H, respectively, in the presence of a palladium catalyst and a base and optionally in the presence of a ligand; or (h) for a compound of Formula I where R$^5$ is hetCyc$^5$C(=O)—, reacting a corresponding compound having the formula VII

VII

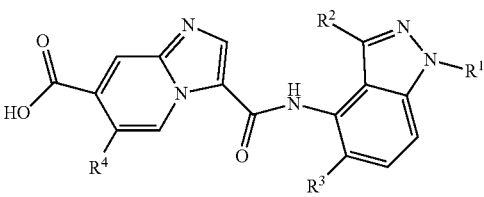

with a compound having the formula hetCyc$^5$-H in the presence of a coupling reagent; or (i) for a compound of Formula I where $R^5$ has the structure:

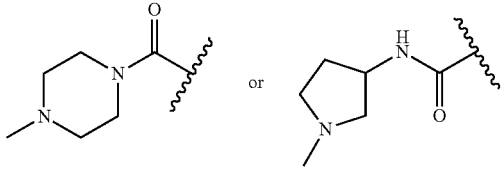

reacting a corresponding compound having the formula VIII

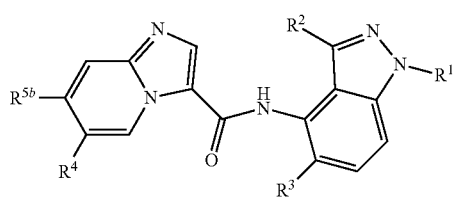

where $R^{5b}$ is

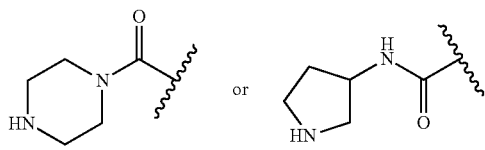 [SMILES: *C(=O)N1CCNCC1 ; *C(=O)NC1CCNC1]

respectively, with formaldehyde in the presence of a reducing agent; or (j) for a compound of Formula I where $R^5$ is R'R"NC(=O)—, reacting a corresponding compound of formula IX

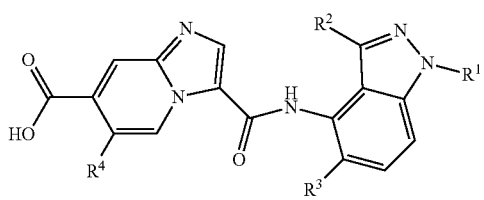

with a compound having the formula R'R"NH in the presence of a coupling agent; or (k) for a compound of Formula I wherein $R^5$ is an oxadiazole substituent having the formula:

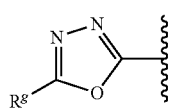

where $R^g$ is H or Me, cyclizing a corresponding compound having the formula X

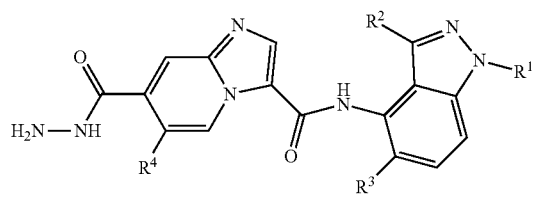

in the presence of trimethoxymethane or triethoxyethane, respectively; or (l) for a compound of Formula I wherein $R^5$ is 1,3,4-thiadiazol-2-yl, cyclizing a corresponding compound having the formula XI

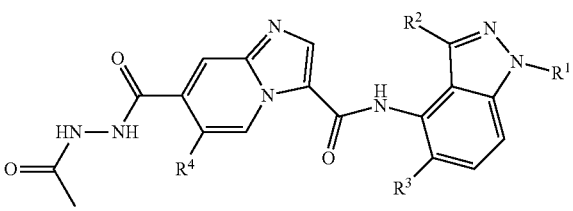

in the presence of $P_2S_5$; or (m) for a compound of Formula I wherein $R^5$ is hetCyc$^6$(1-2Calkyl)- (where hetCyc$^6$ is a nitrogen radical), [(1-4C alkoxy)(1-4C alkyl)]amino(1-2C)alkyl, or [hydroxy(2-4C)alkyl)]amino-(1-2C)alkyl, reacting a corresponding compound of formula XII

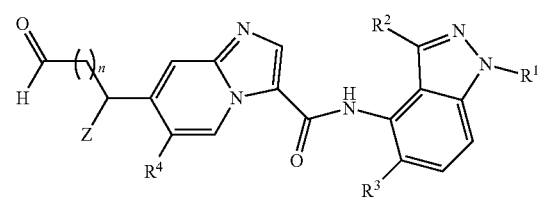

where n is 0 or 1 and Z is H or Me, with hetCyc$^6$-H, [(1-4C alkoxy)(1-4C alkyl)]NH$_2$ or [hydroxy(2-4C)alkyl)]NH$_2$, respectively, in the presence of a reducing agent; or (n) for a compound of Formula I wherein $R^1$ is hetAr$^1$CH$_2$— wherein hetAr$^1$ is substituted with hetCyc$^1$ where hetCyc$^1$ is a nitrogen radical, reacting a compound having the formula XIII

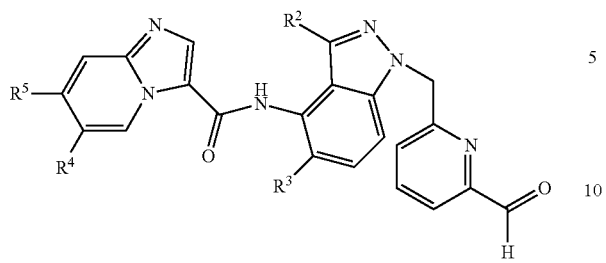

with a compound having the formula hetCyc¹-H in the presence of a reducing agent; or (o) for a compound of Formula I wherein $R^2$ is ethyl, coupling a corresponding compound having the formula XIV

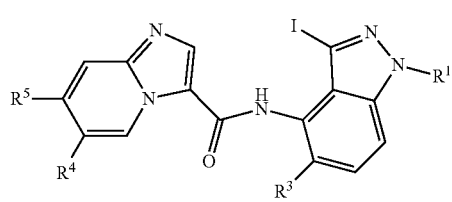

with a compound having the formula $(CH_2=CH)BF_3K$ in the presence of a palladium catalyst and a base, followed by reduction of the 3-vinyl-1H-indazolyl intermediate; or (p) for a compound of Formula I wherein $R^1$ is hetAr²CH₂— and hetAr² is a pyrazolyl ring having a ring N atom substituted with a substituent selected from hetCyc³(1-2Calkyl)- or (1-6C)alkyl-, reacting a corresponding compound having the formula XV

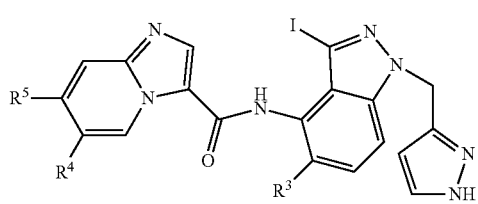

with a compound having the formula hetCyc³(1-2Calkyl)-$X^2$ or (1-6C)alkyl-$X^2$, respectively, wherein $X^2$ is a leaving group or atom, in the presence of a base; or (q) for a compound of Formula I wherein $R^1$ is hetAr¹CH₂, wherein hetAr¹ is pyridyl substituted with amino(2-4C)alkoxy, [di(1-3C alkyl)amino](2-4C)alkoxy, dihydroxy(3-4C)alkoxy, hetCyc²O— or hetCyc²ᵃ(1-2C)alkoxy, reacting a corresponding compound having the formula XVI

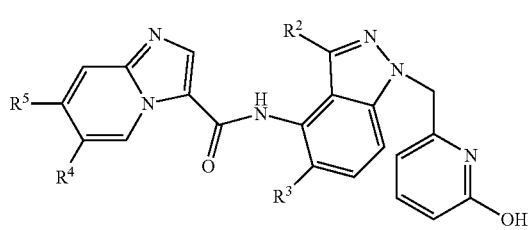

with a compound having the formula amino(2-4C)—$X^3$, [di(1-3C alkyl)amino](2-4C)—$X^3$, dihydroxy(3-4C)—$X^3$, hetCyc²-$X^3$, or hetCyc²ᵃ(1-2C)—$X^3$, respectively, where $X^3$ is a leaving atom or group in the presence of a base; or (r) for a compound of Formula I wherein $R^1$ is hetAr¹CH₂—, wherein hetAr¹ is pyridyl substituted with —CH₂NMe₂ or ethyl, coupling a corresponding compound having the formula XVI-a

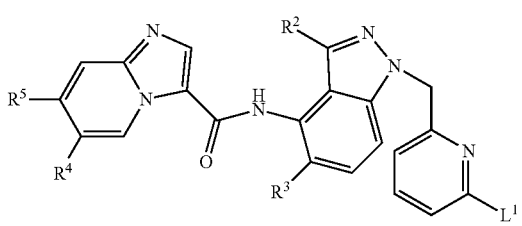

where $L^1$ is a leaving group or atom, with a compound having the formula Me₂NCH₂BF₃K or $(CH_2=CH)BF_3K$, respectively, in the presence of a palladium catalyst (and a base when coupling with $(CH_2=CH)BF_3K$), followed by reduction of the vinyl group when compound XVI-a is coupled with $(CH_2=CH)BF_3K$; or (s) for a compound of Formula I wherein $R^1$ is N-(1-3C alkyl)pyridinonyl-CH₂-optionally substituted with one or more substituted independently selected from (1-6C)alkyl, coupling a corresponding compound having the formula XVI

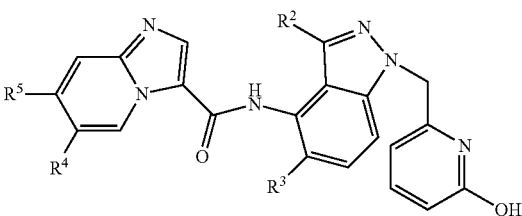

with (1-6C alkyl)-$L^2$ where $L^2$ is a leaving group or atom in the presence of a base; or (t) for a compound of Formula I wherein $R^1$ is hetAr¹CH₂—, wherein hetAr¹ is pyridyl substituted with hetCyc²ᵃ(1-2C)alkoxy, coupling a corresponding compound having the formula XVI

XVI

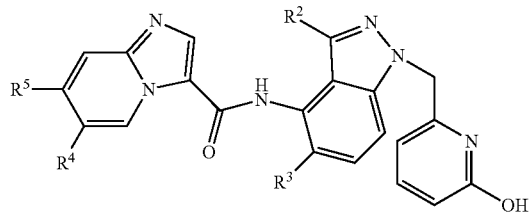

with a compound having the formula hetCyc$^{2a}$(1-2C)OH in the presence of a coupling reagent; or (u) for a compound of Formula I wherein $R^1$ is hetAr$^1$CH$_2$—, wherein hetAr$^1$ is pyridyl substituted with het-Cyc$^1$- where hetCyc$^1$- is a nitrogen radical, coupling a corresponding compound having the formula XVI-a XVI-a

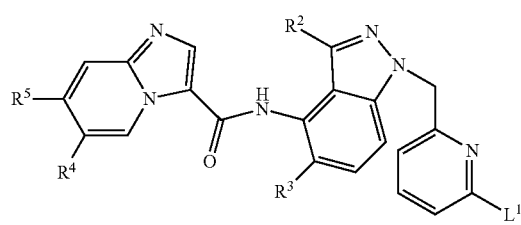

where L$^1$ is a leaving group or atom, with a corresponding compound having the formula hetCyc$^1$-H in the presence of a palladium catalyst, a ligand and a base; or (v) for a compound of Formula I wherein $R^1$ is hetAr$^1$CH$_2$—, wherein hetAr$^1$ is pyridyl substituted with dimethylamino(2-4C)alkoxy, reacting a compound having the formula XVI-b XVI-b

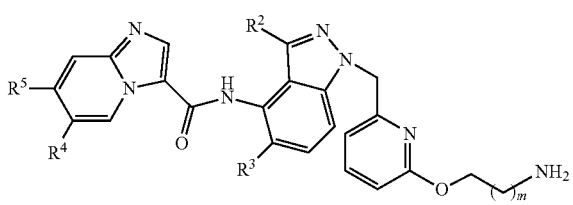

where m is 1, 2 or 3, with formaldehyde in the presence of a base; or (w) for a compound of Formula I wherein $R^1$ is hetAr$^1$CH$_2$—, wherein hetAr$^1$ is pyridyl substituted with hetCyc$^{2a}$(1-2C)alkoxy and hetCyc$^{2a}$ has an N-methyl substituted ring N atom, reacting a corresponding compound having the formula XVI-c XVI-c

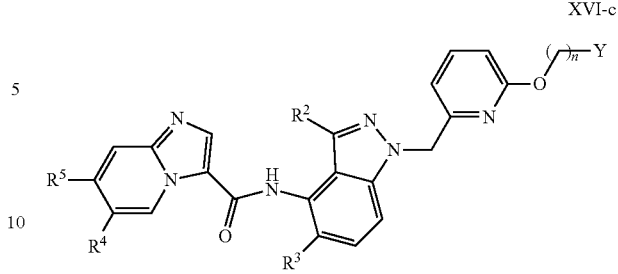

where n is 1 or 2 and Y is a hetCyc$^{2a}$ having a ring NH group, with formaldehyde in the presence of a reducing agent; or (x) for a compound of Formula I wherein $R^5$ is hetCyc$^6$CH$_2$— where hetCyc$^6$ is a nitrogen radical, coupling a corresponding compound having the formula XVII

XVII

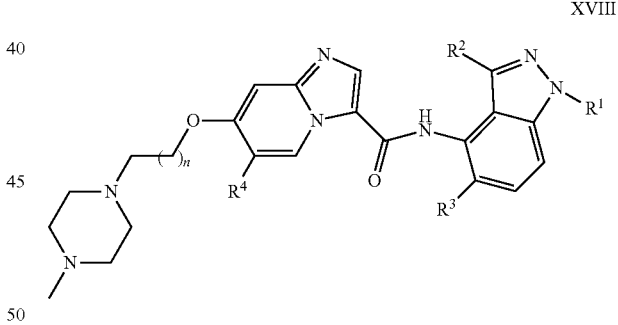

where L$^2$ is a leaving group with a compound having the formula hetCyc$^6$-H in the presence of a base; or (y) for a compound of Formula I where $R^5$ is hetCyc$^7$(1-4C)alkoxy and hetCyc$^7$ is N-methylpiperazine-1-oxide, reacting a corresponding compound of formula XVIII

XVIII

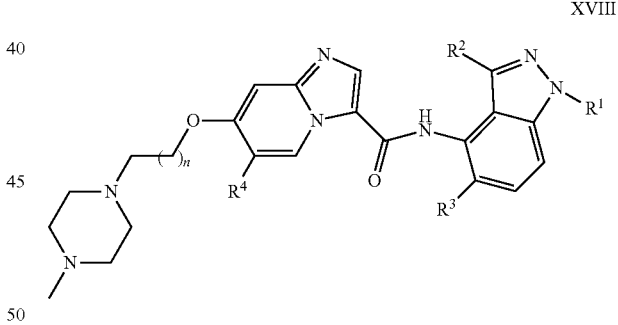

where n is 0, 1, 2 or 3, with an oxidizing agent; or (z) for a compound of Formula I wherein $R^5$ is hetCyc$^6$(1-4Calkyl)- where hetCyc$^6$ a nitrogen radical, reacting a corresponding compound having the formula XIX

XIX

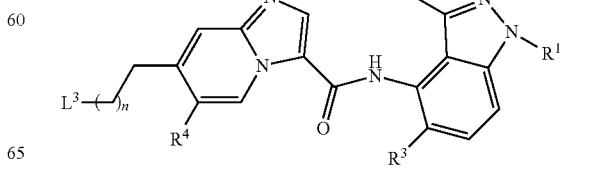

where n is 0, 1, 2 or 3, and $L^3$ is a leaving group, with a corresponding compound having the formula hetCyc$^6$H in the presence of a base; or (aa) for compound of Formula I where $R^5$ is (1-4C alkyl)C(=O)NH(2-4C)alkylthio-, coupling a corresponding compound having the formula V

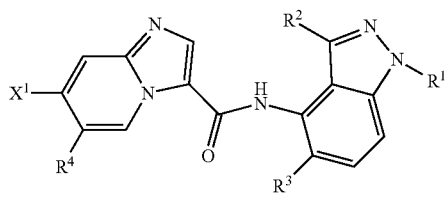

where $X^1$ is F or Cl, with a compound having the formula (I-4C alkyl)C(=O)NH(2-4C)alkyl-SH in the presence of a base; or (bb) for a compound of Formula I wherein $R^5$ is CH$_3$C(=O)—, coupling a corresponding compound having the formula V-b

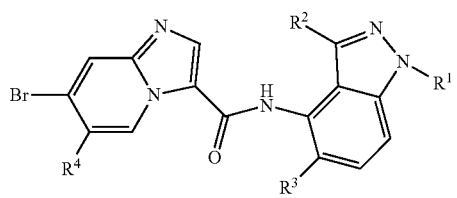

with a compound having the formula

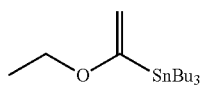

in the presence of a palladium catalyst and a ligand, followed by treatment with acid; or (cc) for a compound of Formula I wherein $R^5$ is HO(CH$_2$CH$_2$)—, treating a corresponding compound having the formula XX

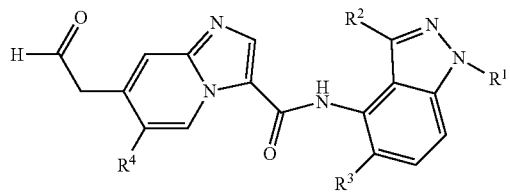

with a reducing agent; and removing any protecting groups if desired and forming a salt thereof if desired.

Referring to method (a), the coupling of the compound of formula II with a compound of formula III may be performed using conventional amide bond formation conditions, for example by treating the carboxylic acid with an activating agent, followed by addition of the amine in the presence of a base. Suitable activating agents include oxalyl chloride, thionyl chloride, EDCI, HATU, and HOBt. Suitable bases include amine bases, for example triethylamine, diisopropylethylamine, pyridine, or excess ammonia. Suitable solvents include DCM, DCE, THF, and DMF.

Alternatively, the amide bond formation can be performed by coupling a reactive derivative of a carboxylic acid of formula II, for example an acid halide such as an acid chloride, or a lithium salt thereof.

Referring to method (b), suitable bases include alkali metal hydrides such as NaH, alkali metal amine bases such as lithium diisopropylamide and silicon-containing alkali metal amides (e.g., sodium hexamethyldisilazide or lithium hexamethyldisilazide).

Referring to method (c), suitable bases include alkali metal carbonates or alkoxides, such as for example cesium carbonate or sodium tert-butoxide.

Referring to method (d), suitable solvents include toluene and THF. The reaction is conveniently performed at elevated temperatures for example at temperatures between 110-120° C.

Referring to method (e), suitable bases include alkali metal hydrides, such as sodium hydride or potassium hydride. Convenient solvents include aprotic solvents such as ethers (for example tetrahydrofuran or p-dioxane), DMF, or acetone. The reaction can be conveniently performed at elevated temperatures, for example temperatures ranging from 90 to 110° C.

Referring to method (f), suitable palladium catalysts include Pd$_2$(dba)$_3$, Pd(PPh$_3$)$_4$, and Pd(OAc)$_2$. Convenient solvents include aprotic solvents such as ethers (for example tetrahydrofuran or p-dioxane), toluene or DMF. The reaction can be conveniently performed at elevated temperatures, for example temperatures ranging from 70 to 90° C.

Referring to method (g), suitable palladium catalysts include Pd$_2$(dba)$_3$, Pd(PPh$_3$)$_4$, and Pd(OAc)$_2$. Suitable ligands include trifuran-2-ylphosphine, rac-BINAP, DIPHOS and the like. The base may be, for example, an alkali metal carbonate or alkoxide, such as for example cesium carbonate or sodium tert-butoxide. Convenient solvents include aprotic solvents such as ethers (for example tetrahydrofuran or p-dioxane), toluene or DMF.

Referring to method (h), suitable coupling reagents include 1-(3-dimethylaminopropyl)-3-ethylcarbodiimide (EDCI), DCC, 1,1'-carbonyldiimidazole (CDI) and the like.

Referring to method (i), suitable reducing agents include Na(OAc)$_3$BH and NaCNBH$_3$. Suitable solvents include neutral solvents such as acetonitrile, THF, and dichloroethane.

Referring to method (j), examples of suitable coupling agents include CDI, EDCI, phosgene, and bis(trichloromethyl) carbonate. Suitable solvents include dichloromethane, dichloroethane, THF, and DMF. The reaction is conveniently performed at ambient temperature or at elevated temperatures, e.g., at about 60-80° C.

Referring to method (k), the reaction is conveniently performed with excess trimethoxymethane or triethoxyethane at elevated temperatures, for example at 100-120° C.

Referring to method (l), suitable solvents include aprotic solvents such as ethers (for example tetrahydrofuran or p-dioxane), toluene and/or DMF. The reaction is conveniently performed at elevated temperatures, for example at 100-120° C.

Referring to methods (m), (n), (v), (w) and (cc), suitable reducing agents include Na(OAc)$_3$BH and NaCNBH$_3$. Suitable solvents include methanol, ethanol, and dichloromethane or mixtures thereof. The reaction is conveniently performed at ambient temperature.

Referring to method (O), suitable palladium catalysts include Pd(PPh$_3$)$_4$, Pd$_2$(dba)$_3$, Pd(OAc)$_2$, Pd(PPh$_3$)$_2$Cl$_2$ and 1,1'-bis(diphenylphosphino)ferrocene-PdCl$_2$-dichloromethane complex. Convenient solvents include aprotic solvents such as ethers (for example tetrahydrofuran or p-dioxane), toluene, DMF, DME, IPA, or mixtures thereof. The reaction can be conveniently performed at a temperature ranging from ambient temperature to 120° C., for example from 80 to 110° C.

Referring to method (p), the leaving group $X^2$ may be an alkylsulfonyl or arylsulfonyl group, for example, a triflate group, or an arylsulfonyloxy group or an alkylsulfonyloxy group, such as a mesylate or a tosylate group. Alternatively, $X^2$ may be a leaving atom such as Cl or Br. The base may be, for example, an alkali metal carbonate, hydroxide or alkoxide, such as for example cesium carbonates, sodium carbonate, potassium carbonate, sodium hydroxide, cesium hydroxide or potassium tert-butoxide. Convenient solvents include aprotic solvents such as ethers (for example tetrahydrofuran or p-dioxane), toluene, DMF or DME. The reaction can be conveniently performed at ambient temperature.

Referring to method (q), the leaving atom $X^3$ may be, for example, a halide such as Br or I. Alternatively, $X^3$ may be a leaving group, such as an arylsulfonyloxy group or an alkylsulfonyloxy group, such as a tosylate or a mesylate group. The base may be, for example, an alkali metal hydride or carbonate, such as sodium hydride, potassium hydride, sodium carbonate, potassium carbonate or cesium carbonate. Convenient solvents include aprotic solvents such as ethers (for example tetrahydrofuran or p-dioxane), DMF, DMA, or acetone. The reaction can be conveniently performed at a temperature ranging from ambient temperature to 100° C.

Referring to method (r), suitable palladium catalysts include Pd(PPh$_3$)$_4$, Pd$_2$(dba)$_3$, Pd(OAc)$_2$, Pd(PPh$_3$)$_2$Cl$_2$ and 1,1'-bis(diphenylphosphino)ferrocene-PdCl$_2$-dichloromethane complex. Suitable bases include tertiary amine bases such as diisopropylethylamine (DIEA) and triethylamine. The reaction can be performed neat or in a solvent mixture such as dioxane/water. The reaction can be conveniently performed at elevated temperatures, for example 80 to 110° C. The reduction of the vinyl intermediate can be carried out using standard hydrogenation conditions known to those skilled in the art, for example in the presence of palladium on carbon.

Referring to method (s), the base may be, for example, an alkali metal hydride or carbonate, such as sodium hydride, potassium hydride, sodium carbonate, potassium carbonate or cesium carbonate. Convenient solvents include aprotic solvents such as ethers (for example tetrahydrofuran or p-dioxane), DMF, or acetone.

Referring to method (t), the coupling reagent may be any suitable reagent(s) known to those skilled in the art, for example, DEAD and PPh$_3$. Convenient solvents include aprotic solvents such as ethers (for example tetrahydrofuran). The reaction can be conveniently performed at a temperature ranging from −78 to 100° C.

Referring to method (u), the leaving atom $L^1$ may be, for example, a halide such as Br or I. Alternatively, $L^1$ may be a leaving group, for example, a triflate group or an arylsulfonyloxy group or an alkylsulfonyloxy group, such as a tosylate or a mesylate group. Suitable palladium catalysts include Pd$_2$(dba)$_3$ and Pd(OAc)$_2$. Suitable ligands include (rac-2,2'-bis(diphenylphosphino)-1,1'-binaphthyl (rac-BINAP) or DIPHOS. The base may be, for example, an alkali metal carbonate or alkoxide, such as for example cesium carbonate or sodium tert-butoxide. Convenient solvents include aprotic solvents such as ethers (for example tetrahydrofuran or p-dioxane) or toluene.

Referring to method (x), the leaving group $L^2$ may be an alkylsulfonyloxy group, such as a tosylate or a mesylate group. The base may be an alkali metal carbonate or bicarbonate, such as sodium or potassium carbonate or bicarbonate. Convenient solvents include aprotic solvents such as ethers (for example tetrahydrofuran or p-dioxane) and DMF. The reaction can be conveniently performed at a temperature ranging from ambient temperature to 50° C.

Referring to method (y), suitable oxidizing agents include organic perbenzoic acids such as metachloroperbenzoic acid. Convenient solvents include aprotic solvents such as DCM, ethers (for example tetrahydrofuran or p-dioxane) and DMF. The reaction temperature for this oxidizing step is typically in the range from −25° C. to ambient temperature, for example between −20° C. and 0° C.

Referring to method (z), the leaving group $L^3$ may be an alkylsulfonyloxy group, such as a tosylate or a mesylate group. Convenient solvents include aprotic solvents such as ethers (for example tetrahydrofuran or p-dioxane) and DMF.

Referring to method (aa), suitable bases include an alkali metal carbonate or alkoxide, such as for example cesium carbonate or sodium tert-butoxide. Convenient solvents include aprotic solvents such as ethers (for example tetrahydrofuran or p-dioxane) and DMF.

Referring to method (bb), suitable palladium catalysts include Pd(PPh$_3$)$_4$, Pd$_2$(dba)$_3$, Pd(OAc)$_2$, Pd(PPh$_3$)$_2$Cl$_2$ and 1,1'-bis(diphenylphosphino)ferrocene-PdCl$_2$-dichloromethane complex.

Amine groups in compounds described in any of the above methods may be protected with any convenient amine protecting group, for example as described in Greene & Wuts, eds., "Protecting Groups in Organic Synthesis", John Wiley & Sons, Inc. Examples of amine protecting groups include acyl and alkoxycarbonyl groups, such as t-butoxycarbonyl (BOC), and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", John Wiley & Sons, Inc. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", John Wiley & Sons, Inc. Examples of alcohol protecting groups include benzyl, trityl, silyl ethers, and the like.

The compounds of the formulas V, V-a, V-b, VII, VIII, IX, X, XI, XII, XIII, XIV, XV, XVI, XVI-a, XVI-b, XVI-c, XVII, XVIII, XIX and XX are also believed to be novel and are provided as further aspects of the invention.

The compounds of Formula I represent novel potent inhibitors of protein tyrosine kinases, such as cFMS, and may be useful in the prevention and treatment of disorders resulting from actions of these kinases. The ability of compounds of the invention to act as inhibitors of cFMS may be demonstrated by the enzyme assay described in Example A or the cellular assay described in Example D.

In addition, representative compounds of the invention have been shown to be selective for the cFMS kinase over type III receptor tyrosine kinases. For example, representative compounds of Formula I where $R^2$ is ethyl or cyclopropyl in general show an increased selectivity for cFMS versus PDGFR and cKit when compared to compounds where $R^2$ is H, methyl, F or Cl. In particular, representative compounds of Formula I where $R^2$ is ethyl or cyclopropyl in general show an increased selectivity for cFMS versus PDGFR and cKit when compared to compounds where $R^2$ is H or F.

As used herein, "increased selectivity" means that a compound of Formula I is at least 10 fold more potent in inhibiting cFMS relative to inhibiting PDGFR or cKit when tested in an appropriate cell assay such as the assays described in Examples D, E and F.

Compounds of Formula I may be of therapeutic value in the treatment of bone-related diseases, cancer, autoimmune disorders, inflammatory diseases, cardiovascular diseases and pain.

In one embodiment, the compounds of Formula I are useful for the treatment of bone-related diseases.

Examples of bone-related diseases include metastatic bone disease, treatment-induced bone loss, osteoporosis, rheumatoid arthritis, ankylosing spondylitis, Paget's disease, and periodontal disease. The osteoporosis may be attributed to (1) menopause in women, (2) aging in men or women, (3) suboptimal bone growth during childhood and adolescence that resulted in failure to reach peak bone mass, and/or (4) bone loss secondary to other disease conditions, eating disorders, medications and/or medical treatments (for example, as a result of treatment with glucocorticoids, aromatase inhibition therapy, or anti-androgen therapy).

Other osteolytic diseases that can be treated according to the present invention are more localized. A particular example is metastatic tumor-induced osteolysis. In this condition, bone cancers or bone metastases induce localized osteolysis that causes pain, bone weakness and fractures. Such localized osteolysis also permits tumors to grow larger by creating more space for them in the bone and releasing growth factors from the bone matrix. Cancers presently known to cause tumor-induced osteolysis include hematological malignancies (e.g., myeloma and lymphoma) and solid tumors (e.g., breast, prostate, lung, renal and thyroid), all of which the present invention contemplates treating.

In one embodiment, the compounds of Formula I are useful for the treatment of cancers and proliferative disorders. Examples include multiple myeloma, acute myeloid leukemia (AML), chronic myeloid leukemia (CML), prostate cancer, breast cancer, ovarian cancer, melanoma, glioblastoma multiforme, giant cell tumor of bone (also known as osteoclastome), giant cell tumor of the tendon sheath (also known as tenosynovial giant cell tumor or TGCT), metastasis of tumors to other tissues, other chronic myeloproliferative diseases such as myelofibrosis, and pigmented villonodular synovitis (PVNS).

In one embodiment, the compounds of Formula I are useful for the treatment of autoimmune disorders and inflammatory diseases.

Examples of autoimmune disorders and inflammatory diseases include but are not limited to, rheumatoid arthritis, osteoarthritis, psoriatic arthritis, ankylosing spondylitis, Adult Still's, glomerulonephritis, osteoporosis, Sjogren's syndrome, inflammatory bowel disease, ulcerative colitis, Crohn's disease, Langerhans cell histiocytosis, hemophagocytic syndrome, multicentric reticulohistiocytosis, and Paget's disease.

In one embodiment, the compounds of Formula I are useful for the treatment of cardiovascular diseases. Examples of cardiovascular diseases include atherosclerosis, peripheral vascular disease, coronary artery disease, ischemia/reperfusion, hypertension, restenosis and arterial inflammation.

In one embodiment, the compounds of Formula I are useful for the treatment of pain. In one embodiment, the compounds of Formula I are useful for the treatment of pain as a result of nerve injury. In one embodiment, the compounds of Formula I are useful for the treatment of neuropathic pain associated with nerve inflammation (neuritis) in the absence of nerve injury. Such pain syndromes include back pain, temporomandibular joint (TMJ) disorder, and rheumatoid arthritis.

Compounds of Formula I may be administered alone as a sole therapy or can be administered in addition with one or more other substances and/or treatments that work by the same or a different mechanism of action. Such conjoint treatment may be achieved by way of the simultaneous, sequential or separate administration of the individual components of the treatment.

Accordingly, the invention further provides methods of treating bone-related diseases in mammals, including humans, by administration of a therapeutically effective amount of at least one compound of Formula I or a pharmaceutically acceptable salt thereof. The compounds may be administered alone or may be administered in combination with one or more drugs for the treatment of bone-related diseases that work by the same or a different mechanism of action.

The invention further provides methods of treating cancer in mammals, including humans, by administration of a therapeutically effective amount of at least one compound of Formula I or a pharmaceutically acceptable salt thereof.

In the field of medical oncology it is normal practice to use a combination of different forms of treatment to treat each patient with cancer. In medical oncology the other component(s) of such conjoint treatment in addition to compositions of the present invention may be, for example, surgery, radiotherapy, chemotherapy, signal transduction inhibitors and/or monoclonal antibodies.

Accordingly, the compounds of Formula I may be administered in combination with one or more agents selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, cytostatic agents anti-androgens, targeted antibodies, HMG-CoA reductase inhibitors, and prenyl-protein transferase inhibitors.

The invention also provides methods of treating cardiovascular diseases in mammals, including humans, by administration of at least one compound of Formula I or a pharmaceutically acceptable salt thereof. The compounds may be administered alone or may be administered in combination with one or more drugs for the treatment of cardiovascular diseases that work by the same or a different mechanism of action.

The invention also provides methods of treating inflammatory diseases in mammals, including humans, by administration of at least one compound of Formula I or a pharmaceutically acceptable salt thereof. The compounds may be administered alone for the treatment of inflammatory disease or may be administered in combination with one or more drugs for treating inflammatory diseases that work by the same or a different mechanism of action, such as gold salts or methotrexate.

The invention also provides methods of treating pain in mammals, including humans, by administration of at least one compound of Formula I or a pharmaceutically acceptable salt thereof. The compounds may be administered alone for the treatment of pain or may be administered in combination with one or more drugs for treating pain that work by the same or a different mechanism of action.

In one embodiment, as used herein, the term treatment includes prophylaxis as well as treatment of a preexisting condition.

In one embodiment, the terms "treatment" or "treating" as used herein, mean an alleviation, in whole or in part, of symptoms associated with a disorder or condition (e.g., bone-related diseases, cancer, autoimmune disorders, inflammatory diseases, cardiovascular diseases and pain, as described herein), or slowing, or halting of further progression or worsening of those symptoms.

In one embodiment, the term "preventing" as used herein means the prevention of the onset, recurrence or spread, in whole or in part, of the disease or condition (e.g., bone-related diseases, cancer, autoimmune disorders, inflammatory diseases, cardiovascular diseases and pain as described herein), or a symptom thereof.

The phrase "effective amount" means an amount of compound that, when administered to a mammal in need of such treatment, is sufficient to (i) treat or prevent a particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

The present invention further provides a pharmaceutical composition, which comprises a compound of Formula I or a pharmaceutically acceptable salt thereof, as defined hereinabove. In one embodiment, the pharmaceutical composition includes the compound of Formula I together with a pharmaceutically acceptable diluent or carrier.

The present invention further provides a compound of Formula I or a pharmaceutically acceptable salt thereof, for use in therapy. In one embodiment, the invention provides a compound of Formula I or a pharmaceutically acceptable salt thereof, for use in the treatment of bone-related diseases, cancer, autoimmune disorders, inflammatory diseases, cardiovascular diseases and pain in a mammal.

According to a further aspect, the present invention provides the use of a compound of Formula I or a pharmaceutically acceptable salt thereof, in the treatment of bone-related diseases, cancer, autoimmune disorders, inflammatory diseases, cardiovascular diseases and pain in a mammal.

Particular compounds of the invention include one or more compounds independently selected from:

N-(1-Benzyl-3-iodo-1H-indazol-4-yl)-7-(2-methoxyethoxy) imidazo[1,2-a]pyridine-3-carboxamide;

N-(1-Benzyl-3-ethyl-1H-indazol-4-yl)-7-(2-methoxyethoxy)imidazo[1,2-a]pyridine-3-carboxamide;

N-(1-Benzyl-3-cyclopropyl-1H-indazol-4-yl)-7-(2-methoxyethoxy)imidazo[1,2-a]pyridine-3-carboxamide;

N-(1-Benzyl-5-chloro-3-ethyl-1H-indazol-4-yl)-7-(2-methoxyethoxy)imidazo[1,2-a]pyridine-3-carboxamide;

N-(3-Ethyl-1-((6-methylpyridin-2-yl)methyl)-1H-indazol-4-yl)imidazo[1,2-a]pyridine-3-carboxamide;

N-(3-ethyl-1-((2-methoxy-6-methylpyridin-3-yl)methyl)-1H-indazol-4-yl)imidazo[1,2-a]pyridine-3-carboxamide;

N-(3-ethyl-1-((1-(2-(piperazin-1-yl)ethyl)-1H-pyrazol-3-yl)methyl)-1H-indazol-4-yl)imidazo[1,2-a]pyridine-3-carboxamide;

N-(1-((1-(2,3-dihydroxypropyl)-1H-pyrazol-5-yl)methyl)-3-ethyl-1H-indazol-4-yl)imidazo[1,2-a]pyridine-3-carboxamide;

N-(1-((6-(2-aminoethoxy)pyridin-2-yl)methyl)-3-ethyl-1H-indazol-4-yl)imidazo[1,2-a]pyridine-3-carboxamide;

N-(1-((6-(3-aminopropoxy)pyridin-2-yl)methyl)-3-ethyl-1H-indazol-4-yl)imidazo[1,2-a]pyridine-3-carboxamide;

N-(1-((6-(3-(dimethylamino)propoxy)pyridin-2-yl)methyl)-3-ethyl-1H-indazol-4-yl)imidazo[1,2-a]pyridine-3-carboxamide;

N-(3-ethyl-1-((6-methylpyridin-2-yl)methyl)-1H-indazol-4-yl)-7-(piperazine-1-carbonyl)imidazo[1,2-a]pyridine-3-carboxamide;

N-(3-ethyl-1-((6-methylpyridin-2-yl)methyl)-1H-indazol-4-yl)-7-(4-methylpiperazine-1-carbonyl)imidazo[1,2-a]pyridine-3-carboxamide;

N-(3-ethyl-1-((6-(piperazin-1-ylmethyl)pyridin-2-yl)methyl)-1H-indazol-4-yl)imidazo[1,2-a]pyridine-3-carboxamide;

N-(3-ethyl-1-((6-methoxypyridin-2-yl)methyl)-1H-indazol-4-yl)imidazo[1,2-a]pyridine-3-carboxamide;

N-(3-ethyl-1-((6-methylpyridin-2-yl)methyl)-1H-indazol-4-yl)-7-(2-morpholinoethoxy)imidazo[1,2-a]pyridine-3-carboxamide;

(S)—N-(3-ethyl-1-((6-(pyrrolidin-3-yloxy)pyridin-2-yl)methyl)-1H-indazol-4-yl)imidazo[1,2-a]pyridine-3-carboxamide;

N-(3-ethyl-1-((6-((3R,4R)-3-fluoropiperidin-4-yloxy)pyridin-2-yl)methyl)-1H-indazol-4-yl)imidazo[1,2-a]pyridine-3-carboxamide;

N-(3-ethyl-1-((6-(piperidin-4-yloxy)pyridin-2-yl)methyl)-1H-indazol-4-yl)imidazo[1,2-a]pyridine-3-carboxamide;

N-(3-ethyl-1-((1-(4-methoxybenzyl)-1H-pyrazol-4-yl)methyl)-1H-indazol-4-yl)imidazo[1,2-a]pyridine-3-carboxamide;

N-(3-ethyl-1-((1-(2-hydroxyethyl)-1H-pyrazol-4-yl)methyl)-1H-indazol-4-yl)imidazo[1,2-a]pyridine-3-carboxamide;

N-(3-ethyl-1-((1-((3R,4R)-3-fluoropiperidin-4-yl)-1H-pyrazol-4-yl)methyl)-1H-indazol-4-yl)imidazo[1,2-a]pyridine-3-carboxamide;

Ethyl 3-(3-ethyl-1-((6-methylpyridin-2-yl)methyl)-1H-indazol-4-ylcarbamoyl)imidazo[1,2-a]pyridine-7-carboxylate;

N-(3-ethyl-1-((6-ethylpyridin-2-yl)methyl)-1H-indazol-4-yl)imidazo[1,2-a]pyridine-3-carboxamide;

N-(3-ethyl-1-((1-methyl-6-oxo-1,6-dihydropyridin-2-yl) methyl)-1H-indazol-4-yl)imidazo[1,2-a]pyridine-3-carboxamide;

N-(3-ethyl-1-((1-ethyl-6-oxo-1,6-dihydropyridin-2-yl)methyl)-1H-indazol-4-yl)imidazo[1,2-a]pyridine-3-carboxamide;

N-(1-((6-ethoxypyridin-2-yl)methyl)-3-ethyl-1H-indazol-4-yl)imidazo[1,2-a]pyridine-3-carboxamide;

N-(3-ethyl-1-((6-methylpyridin-2-yl)methyl)-1H-indazol-4-yl)-7-(1,3,4-oxadiazol-2-yl)imidazo[1,2-a]pyridine-3-carboxamide;

N-(3-ethyl-1-((6-methylpyridin-2-yl)methyl)-1H-indazol-4-yl)-7-(5-methyl-1,3,4-oxadiazol-2-yl)imidazo[1,2-a]pyridine-3-carboxamide;

N-(3-ethyl-1-((6-methylpyridin-2-yl)methyl)-1H-indazol-4-yl)-7-(piperazin-1-ylmethyl)imidazo[1,2-a]pyridine-3-carboxamide;

N-(3-ethyl-1-((6-methylpyridin-2-yl)methyl)-1H-indazol-4-yl)-7-((4-methylpiperazin-1-yl)methyl)imidazo[1,2-a]pyridine-3-carboxamide;

N-(3-ethyl-1-((6-methylpyridin-2-yl)methyl)-1H-indazol-4-yl)-7-((3S,4S)-4-hydroxypyrrolidin-3-yloxy)imidazo[1,2-a]pyridine-3-carboxamide;

N-(3-ethyl-1-((6-methylpyridin-2-yl)methyl)-1H-indazol-4-yl)-7-((3R,4R)-4-hydroxypyrrolidin-3-yloxy)imidazo[1,2-a]pyridine-3-carboxamide;

N-(3-ethyl-1-((6-methylpyridin-2-yl)methyl)-1H-indazol-4-yl)-7-((3S,4S)-4-hydroxy-1-methylpyrrolidin-3-yloxy)imidazo[1,2-a]pyridine-3-carboxamide;

N-(3-ethyl-1-((6-methylpyridin-2-yl)methyl)-1H-indazol-4-yl)-7-((3R,4R)-4-hydroxy-1-methylpyrrolidin-3-yloxy)imidazo[1,2-a]pyridine-3-carboxamide;

N-(3-ethyl-1-((6-(((2R,3S)-3-hydroxypyrrolidin-2-yl)methoxy)pyridin-2-yl)methyl)-1H-indazol-4-yl)imidazo[1,2-a]pyridine-3-carboxamide;

4-(2-(3-(3-ethyl-1-((6-methylpyridin-2-yl)methyl)-1H-indazol-4-ylcarbamoyl)imidazo[1,2-a]pyridin-7-yloxy)ethyl)-1-methylpiperazine 1-oxide;

N-(3-ethyl-1-((6-methylpyridin-2-yl)methyl)-1H-indazol-4-yl)-7-(((2R,3S)-3-hydroxypyrrolidin-2-ylmethoxy)imidazo[1,2-a]pyridine-3-carboxamide;

N-(3-ethyl-1-((1-ethyl-1H-pyrazol-5-yl)methyl)-1H-indazol-4-yl)imidazo[1,2-a]pyridine-3-carboxamide;

N-(3-ethyl-1-((1-ethyl-1H-pyrazol-3-yl)methyl)-1H-indazol-4-yl)imidazo[1,2-a]pyridine-3-carboxamide;

N-(3-ethyl-1-((6-(((2R,3S)-3-hydroxy-1-methylpyrrolidin-2-yl)methoxy)pyridin-2-yl)methyl)-1H-indazol-4-yl)imidazo[1,2-a]pyridine-3-carboxamide;

N-(3-ethyl-1-((6-methylpyridin-2-yl)methyl)-1H-indazol-4-yl)-7-(((2R,3S)-3-hydroxy-1-methylpyrrolidin-2-yl)methoxy)imidazo[1,2-a]pyridine-3-carboxamide;

N-(3-ethyl-1-((6-(2-(piperazin-1-yl)ethoxy)pyridin-2-yl)methyl)-1H-indazol-4-yl)imidazo[1,2-a]pyridine-3-carboxamide;

N-(3-ethyl-1-((6-methylpyridin-2-yl)methyl)-1H-indazol-4-yl)-7-(((1,3,4-thiadiazol-2-yl)imidazo[1,2-a]pyridine-3-carboxamide;

N-(3-ethyl-1-((6-methylpyridin-2-yl)methyl)-1H-indazol-4-yl)-7-(2-(4-methylpiperazin-1-yl)ethoxy)imidazo[1,2-a]pyridine-3-carboxamide;

N3-(3-ethyl-1-((6-methylpyridin-2-yl)methyl)-1H-indazol-4-yl)-N7-(pyrrolidin-3-yl)imidazo[1,2-a]pyridine-3,7-dicarboxamide;

N7-(2-aminoethyl)-N3-(3-ethyl-1-((6-methylpyridin-2-yl)methyl)-1H-indazol-4-yl)imidazo[1,2-a]pyridine-3,7-dicarboxamide;

N3-(3-ethyl-1-((6-methylpyridin-2-yl)methyl)-1H-indazol-4-yl)-N7-methylimidazo[1,2-a]pyridine-3,7-dicarboxamide;

N3-(3-ethyl-1-((6-methylpyridin-2-yl)methyl)-1H-indazol-4-yl)-N7,N7-dimethylimidazo[1,2-a]pyridine-3,7-dicarboxamide;

N3-(3-ethyl-1-((6-methylpyridin-2-yl)methyl)-1H-indazol-4-yl)-N7-(1-methylpyrrolidin-3-yl)imidazo[1,2-a]pyridine-3,7-dicarboxamide;

N-(2-(dimethylamino)ethyl)-N3-(3-ethyl-1-((6-methylpyridin-2-yl)methyl)-1H-indazol-4-yl)imidazo[1,2-a]pyridine-3,7-dicarboxamide;

7-(1,2-dimethyl-1H-imidazol-5-yl)-N-(3-ethyl-1-((6-methylpyridin-2-yl)methyl)-1H-indazol-4-yl)imidazo[1,2-a]pyridine-3-carboxamide;

N-(1-((1,6-dimethyl-2-oxo-1,2-dihydropyridin-3-yl)methyl)-3-ethyl-1H-indazol-4-yl)imidazo[1,2-a]pyridine-3-carboxamide;

N-(3-ethyl-1-((6-(2-(4-methylpiperazin-1-yl)ethoxy)pyridin-2-yl)methyl)-1H-indazol-4-yl)imidazo[1,2-a]pyridine-3-carboxamide;

N-(1-((1,5-dimethyl-1H-pyrazol-3-yl)methyl)-3-ethyl-1H-indazol-4-yl)imidazo[1,2-a]pyridine-3-carboxamide;

N-(1-((1,5-dimethyl-1H-pyrazol-3-yl)methyl)-3-ethyl-1H-indazol-4-yl)-7-(2-(4-methylpiperazin-1-yl)ethoxy)imidazo[1,2-a]pyridine-3-carboxamide;

N-(3-ethyl-1-((1-methyl-1H-pyrazol-3-yl)methyl)-1H-indazol-4-yl)imidazo[1,2-a]pyridine-3-carboxamide;

N-(3-ethyl-1-((1-methyl-1H-pyrazol-3-yl)methyl)-1H-indazol-4-yl)-7-(2-(4-methylpiperazin-1-yl)ethoxy)imidazo[1,2-a]pyridine-3-carboxamide;

N-(3-ethyl-1-((6-methylpyridin-2-yl)methyl)-1H-indazol-4-yl)-7-(5,6,7,8-tetrahydroimidazo[1,2-a]pyrazin-3-yl)imidazo[1,2-a]pyridine-3-carboxamide;

N-(3-ethyl-1-((6-methylpyridin-2-yl)methyl)-1H-indazol-4-yl)-7-(7-methyl-5,6,7,8-tetrahydroimidazo[1,2-a]pyrazin-3-yl)imidazo[1,2-a]pyridine-3-carboxamide;

N-(3-cyclopropyl-1-((1-ethyl-1H-pyrazol-3-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((1-ethyl-1H-pyrazol-3-yl)methyl)-1H-indazol-4-yl)-7-(2-(4-isopropylpiperazin-1-yl)ethoxy)imidazo[1,2-a]pyridine-3-carboxamide;

N-(3-cyclopropyl-1-((1-isopropyl-1H-pyrazol-3-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((1-isopropyl-1H-pyrazol-3-yl)methyl)-1H-indazol-4-yl)-7-(2-(4-isopropylpiperazin-1-yl)ethoxy)imidazo[1,2-a]pyridine-3-carboxamide;

N-(3-cyclopropyl-1-((6-methylpyridin-2-yl)methyl)-1H-indazol-4-yl)-7-(2-(4-methylpiperazin-1-yl)ethoxy)imidazo[1,2-a]pyridine-3-carboxamide;

7-chloro-N-(3-cyclopropyl-1-((6-methylpyridin-2-yl)methyl)-1H-indazol-4-yl)imidazo[1,2-a]pyridine-3-carboxamide;

N-(1-((6-(2,3-dihydroxypropoxy)pyridin-2-yl)methyl)-3-ethyl-1H-indazol-4-yl)imidazo[1,2-a]pyridine-3-carboxamide;

N-(3-ethyl-1-((6-(piperazin-1-yl)pyridin-2-yl)methyl)-1H-indazol-4-yl)imidazo[1,2-a]pyridine-3-carboxamide;

N-(1-((6-(4-aminopiperidin-1-yl)pyridin-2-yl)methyl)-3-ethyl-1H-indazol-4-yl)imidazo[1,2-a]pyridine-3-carboxamide;

N-(3-ethyl-1-((1-ethyl-1H-pyrazol-4-yl)methyl)-1H-indazol-4-yl)imidazo[1,2-a]pyridine-3-carboxamide;

N-(1-((1-(cyclopropylmethyl)-1H-pyrazol-4-yl)methyl)-3-ethyl-1H-indazol-4-yl)imidazo[1,2-a]pyridine-3-carboxamide;

4-(2-(3-(3-cyclopropyl-1-((6-methylpyridin-2-yl)methyl)-1H-indazol-4-ylcarbamoyl)imidazo[1,2-a]pyridin-7-yloxy)ethyl)-1-methylpiperazine 1-oxide;
N-(3-cyclopropyl-1-((6-methylpyridin-2-yl)methyl)-1H-indazol-4-yl)-7-(2-(piperazin-1-yl)ethoxy)imidazo[1,2-a]pyridine-3-carboxamide;
6-cyano-N-(3-ethyl-1-((6-methylpyridin-2-yl)methyl)-1H-indazol-4-yl)imidazo[1,2-a]pyridine-3-carboxamide;
N-(3-ethyl-1-((6-methylpyridin-2-yl)methyl)-1H-indazol-4-yl)-7-(2-(4-isopropylpiperazin-1-yl)ethoxy)imidazo[1,2-a]pyridine-3-carboxamide;
N-(3-cyclopropyl-1-((6-methylpyridin-2-yl)methyl)-1H-indazol-4-yl)-7-(2-(4-isopropylpiperazin-1-yl)ethoxy)imidazo[1,2-a]pyridine-3-carboxamide;
N-(3-cyclopropyl-1-((1-methyl-2-oxo-1,2-dihydropyridin-3-yl)methyl)-1H-indazol-4-yl)-7-(2-(4-methylpiperazin-1-yl)ethoxy)imidazo[1,2-a]pyridine-3-carboxamide;
7-(2-(azetidin-1-yl)ethoxy)-N-(3-cyclopropyl-1-((6-methylpyridin-2-yl)methyl)-1H-indazol-4-yl)imidazo[1,2-a]pyridine-3-carboxamide;
7-fluoro-N-(3-cyclopropyl-1-((6-methylpyridin-2-yl)methyl)-1H-indazol-4-yl)imidazo[1,2-a]pyridine-3-carboxamide;
N-(3-ethyl-1-((6-methylpyridin-2-yl)methyl)-1H-indazol-4-yl)-7-((1-methylpiperidin-4-yl)methoxy)imidazo[1,2-a]pyridine-3-carboxamide;
N-(3-ethyl-1-((6-methylpyridin-2-yl)methyl)-1H-indazol-4-yl)-7-(2-(4-ethylpiperazin-1-yl)ethoxy)imidazo[1,2-a]pyridine-3-carboxamide;
(R)—N-(3-ethyl-1-((6-methylpyridin-2-yl)methyl)-1H-indazol-4-yl)-7-(1-methylpyrrolidin-3-yloxy)imidazo[1,2-a]pyridine-3-carboxamide;
N-(3-ethyl-1-((6-methylpyridin-2-yl)methyl)-1H-indazol-4-yl)-7-(1-methylpiperidin-4-yloxy)imidazo[1,2-a]pyridine-3-carboxamide;
N-(3-ethyl-1-((6-methylpyridin-2-yl)methyl)-1H-indazol-4-yl)-7-(2-(pyrrolidin-1-yl)ethoxy)imidazo[1,2-a]pyridine-3-carboxamide;
N-(3-cyclopropyl-1-((6-methylpyridin-2-yl)methyl)-1H-indazol-4-yl)-7-(2-morpholinoethoxy)imidazo[1,2-a]pyridine-3-carboxamide;
(S)—N-(3-ethyl-1-((6-methylpyridin-2-yl)methyl)-1H-indazol-4-yl)-7-(1-methylpyrrolidin-3-yloxy)imidazo[1,2-a]pyridine-3-carboxamide;
tert-butyl 2-((3-(3-ethyl-1-((6-methylpyridin-2-yl)methyl)-1H-indazol-4-ylcarbamoyl)imidazo[1,2-a]pyridin-7-yloxy)methyl)morpholine-4-carboxylate;
tert-butyl 3-(3-(3-ethyl-1-((6-methylpyridin-2-yl)methyl)-1H-indazol-4-ylcarbamoyl)imidazo[1,2-a]pyridin-7-yloxy)-2,2-difluoropropylcarbamate;
N-(3-ethyl-1-((1-ethyl-1H-pyrazol-3-yl)methyl)-1H-indazol-4-yl)-7-(2-(4-isopropylpiperazin-1-yl)ethoxy)imidazo[1,2-a]pyridine-3-carboxamide;
N-(3-cyclopropyl-1-((6-methylpyridin-2-yl)methyl)-1H-indazol-4-yl)-7-(2-(pyrrolidin-1-yl)ethoxy)imidazo[1,2-a]pyridine-3-carboxamide;
(R)—N-(3-ethyl-1-((6-methylpyridin-2-yl)methyl)-1H-indazol-4-yl)-7-(2-(3-methoxypyrrolidin-1-yl)ethoxy)imidazo[1,2-a]pyridine-3-carboxamide;
N-(3-ethyl-1-((6-methylpyridin-2-yl)methyl)-1H-indazol-4-yl)-7-(2-(8-methyl-3,8-diazabicyclo[3.2.1]octan-3-yl)ethoxy)imidazo[1,2-a]pyridine-3-carboxamide;
(S)—N-(3-ethyl-1-((6-methylpyridin-2-yl)methyl)-1H-indazol-4-yl)-7-(2-(3-methoxypyrrolidin-1-yl)ethoxy)imidazo[1,2-a]pyridine-3-carboxamide;
N-(3-ethyl-1-((1-ethyl-1H-pyrazol-3-yl)methyl)-1H-indazol-4-yl)-7-(2-(pyrrolidin-1-yl)ethoxy)imidazo[1,2-a]pyridine-3-carboxamide;
N-(3-cyclopropyl-1-((6-methylpyridin-2-yl)methyl)-1H-indazol-4-yl)-7-(1-methylpiperidin-4-yloxy)imidazo[1,2-a]pyridine-3-carboxamide;
(S)—N-(3-ethyl-1-((6-methylpyridin-2-yl)methyl)-1H-indazol-4-yl)-7-(2-(3-fluoropyrrolidin-1-yl)ethoxy)imidazo[1,2-a]pyridine-3-carboxamide;
N-(3-cyclopropyl-1-((6-methylpyridin-2-yl)methyl)-1H-indazol-4-yl)-7-(2-thiomorpholine 1,1-dioxide ethoxy)imidazo[1,2-a]pyridine-3-carboxamide;
N-(3-ethyl-1-((1-ethyl-1H-pyrazol-3-yl)methyl)-1H-indazol-4-yl)-7-(1-methylpiperidin-4-yloxy)imidazo[1,2-a]pyridine-3-carboxamide;
N-(3-ethyl-1-((6-methylpyridin-2-yl)methyl)-1H-indazol-4-yl)-7-(2-(8-Oxa-3-azabicyclo[3.2.1]octane)ethoxy)imidazo[1,2-a]pyridine-3-carboxamide;
N-(3-cyclopropyl-1-((1-methyl-2-oxo-1,2-dihydropyridin-3-yl)methyl)-1H-indazol-4-yl)-7-(2-(pyrrolidin-1-yl)ethoxy)imidazo[1,2-a]pyridine-3-carboxamide;
N-(3-ethyl-1-((1-ethyl-1H-pyrazol-3-yl)methyl)-1H-indazol-4-yl)-7-(2-morpholinoethoxy)imidazo[1,2-a]pyridine-3-carboxamide;
N-(3-cyclopropyl-1-((1-methyl-2-oxo-1,2-dihydropyridin-3-yl)methyl)-1H-indazol-4-yl)-7-(2-morpholinoethoxy)imidazo[1,2-a]pyridine-3-carboxamide;
7-(2-(azetidin-1-yl)ethoxy)-N-(3-cyclopropyl-1-((1-methyl-2-oxo-1,2-dihydropyridin-3-yl)methyl)-1H-indazol-4-yl)imidazo[1,2-a]pyridine-3-carboxamide;
N-(3-ethyl-1-((6-methylpyridin-2-yl)methyl)-1H-indazol-4-yl)-7-(2-(piperazin-1-yl)ethoxy)imidazo[1,2-a]pyridine-3-carboxamide;
N-(3-ethyl-1-((6-methylpyridin-2-yl)methyl)-1H-indazol-4-yl)-7-(2-hydroxyethoxy)imidazo[1,2-a]pyridine-3-carboxamide;
7-(3-amino-2,2-difluoropropoxy)-N-(3-ethyl-1-((6-methylpyridin-2-yl)methyl)-1H-indazol-4-yl)imidazo[1,2-a]pyridine-3-carboxamide;
7-(azetidin-3-yloxy)-N-(3-ethyl-1-((6-methylpyridin-2-yl)methyl)-1H-indazol-4-yl)imidazo[1,2-a]pyridine-3-carboxamide;
N-(3-ethyl-1-((6-methylpyridin-2-yl)methyl)-1H-indazol-4-yl)-7-(morpholin-2-ylmethoxy)imidazo[1,2-a]pyridine-3-carboxamide;
(R)—N-(3-ethyl-1-((6-methylpyridin-2-yl)methyl)-1H-indazol-4-yl)-7-(2-(3-fluoropyrrolidin-1-yl)ethoxy)imidazo[1,2-a]pyridine-3-carboxamide;
N-(3-ethyl-1-((6-methylpyridin-2-yl)methyl)-1H-indazol-4-yl)-7-(piperazin-1-yl)imidazo[1,2-a]pyridine-3-carboxamide;
N-(3-ethyl-1-((6-methylpyridin-2-yl)methyl)-1H-indazol-4-yl)-7-morpholinoimidazo[1,2-a]pyridine-3-carboxamide;
(R)—N-(3-ethyl-1-((6-methylpyridin-2-yl)methyl)-1H-indazol-4-yl)-7-(3-hydroxypyrrolidin-1-yl)imidazo[1,2-a]pyridine-3-carboxamide;
N-(3-ethyl-1-((6-methylpyridin-2-yl)methyl)-1H-indazol-4-yl)-7-(4-(2-hydroxyethyl)piperazin-1-yl)imidazo[1,2-a]pyridine-3-carboxamide;
N-(3-ethyl-1-((6-methylpyridin-2-yl)methyl)-1H-indazol-4-yl)-7-(4-hydroxypiperidin-1-yl)imidazo[1,2-a]pyridine-3-carboxamide;
(S)—N-(3-ethyl-1-((6-methylpyridin-2-yl)methyl)-1H-indazol-4-yl)-7-(3-hydroxypyrrolidin-1-yl)imidazo[1,2-a]pyridine-3-carboxamide;

N-(3-ethyl-1-((6-methylpyridin-2-yl)methyl)-1H-indazol-4-yl)-7-(4-ethylpiperazin-1-yl)imidazo[1,2-a]pyridine-3-carboxamide;

N-(3-ethyl-1-((6-methylpyridin-2-yl)methyl)-1H-indazol-4-yl)-7-(3-oxopiperazin-1-yl)imidazo[1,2-a]pyridine-3-carboxamide;

7-(1,4-diazepan-1-yl)-N-(3-ethyl-1-((6-methylpyridin-2-yl)methyl)-1H-indazol-4-yl)imidazo[1,2-a]pyridine-3-carboxamide;

N-(3-ethyl-1-((1-ethyl-1H-pyrazol-3-yl)methyl)-1H-indazol-4-yl)-7-(1H-1,2,4-triazol-1-yl)imidazo[1,2-a]pyridine-3-carboxamide;

N-(3-ethyl-1-((1-ethyl-1H-pyrazol-3-yl)methyl)-1H-indazol-4-yl)-7-fluoroimidazo[1,2-a]pyridine-3-carboxamide;

N-(3-ethyl-1-((6-methylpyridin-2-yl)methyl)-1H-indazol-4-yl)-7-(1H-1,2,4-triazol-1-yl)imidazo[1,2-a]pyridine-3-carboxamide;

N-(3-ethyl-1-((6-methylpyridin-2-yl)methyl)-1H-indazol-4-yl)-7-(3-methyl-1H-1,2,4-triazol-1-yl)imidazo[1,2-a]pyridine-3-carboxamide;

N-(3-ethyl-1-((6-methylpyridin-2-yl)methyl)-1H-indazol-4-yl)-7-(5-methyl-1H-1,2,4-triazol-1-yl)imidazo[1,2-a]pyridine-3-carboxamide;

N-(3-ethyl-1-((6-methylpyridin-2-yl)methyl)-1H-indazol-4-yl)-7-(3-methyl-4H-1,2,4-triazol-4-yl)imidazo[1,2-a]pyridine-3-carboxamide;

7-(2,3-dihydroxypropoxy)-N-(3-ethyl-1-((6-methylpyridin-2-yl)methyl)-1H-indazol-4-yl)imidazo[1,2-a]pyridine-3-carboxamide;

N-(3-ethyl-1-((1-ethyl-1H-pyrazol-3-yl)methyl)-1H-indazol-4-yl)-7-(1-methyl-1H-pyrazol-4-yl)imidazo[1,2-a]pyridine-3-carboxamide;

N-(3-ethyl-1-((1-ethyl-1H-pyrazol-3-yl)methyl)-1H-indazol-4-yl)-7-(1-methyl-1H-pyrazol-4-yl)imidazo[1,2-a]pyridine-3-carboxamide;

N-(1-((1,5-dimethyl-1H-pyrazol-3-yl)methyl)-3-ethyl-1H-indazol-4-yl)-7-(5-((dimethylamino)methyl)furan-2-yl)imidazo[1,2-a]pyridine-3-carboxamide;

(R)—N-(3-ethyl-1-((6-methylpyridin-2-yl)methyl)-1H-indazol-4-yl)-7-(2-(3-fluoropyrrolidin-1-yl)ethyl)imidazo[1,2-a]pyridine-3-carboxamide;

N-(3-ethyl-1-((6-methylpyridin-2-yl)methyl)-1H-indazol-4-yl)-7-(2-(4-methylpiperazin-1-yl)ethyl)imidazo[1,2-a]pyridine-3-carboxamide;

N-(3-ethyl-1-((6-methylpyridin-2-yl)methyl)-1H-indazol-4-yl)-7-(2-(3-fluoroazetidin-1-yl)ethyl)imidazo[1,2-a]pyridine-3-carboxamide;

7-(2-(dimethylamino)ethyl)-N-(3-ethyl-1-((6-methylpyridin-2-yl)methyl)-1H-indazol-4-yl)imidazo[1,2-a]pyridine-3-carboxamide;

N-(3-ethyl-1-((6-methylpyridin-2-yl)methyl)-1H-indazol-4-yl)-7-(2-(3-methoxyazetidin-1-yl)ethyl)imidazo[1,2-a]pyridine-3-carboxamide;

7-((Dimethylamino)methyl)-N-(3-ethyl-1-((6-methylpyridin-2-yl)methyl)-1H-indazol-4-yl)imidazo[1,2-a]pyridine-3-carboxamide;

7-((dimethylamino)methyl)-N-(3-ethyl-1-((1-ethyl-1H-pyrazol-3-yl)methyl)-1H-indazol-4-yl)imidazo[1,2-a]pyridine-3-carboxamide;

N-(3-iodo-1-((2-methylthiazol-5-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((5-methyl-1,3,4-thiadiazol-2-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((2-methyloxazol-4-yl)methyl)-1H-indazol-4-yl)-7-(2-(4-methylpiperazin-1-yl)ethoxy)imidazo[1,2-a]pyridine-3-carboxamide;

N-(3-ethyl-1-((6-methylpyridin-2-yl)methyl)-1H-indazol-4-yl)-7-(pyrimidin-5-yl)imidazo[1,2-a]pyridine-3-carboxamide;

N-(3-ethyl-1-((6-methylpyridin-2-yl)methyl)-1H-indazol-4-yl)-7-(6-methylpyridin-3-yl)imidazo[1,2-a]pyridine-3-carboxamide;

N-(3-ethyl-1-((6-methylpyridin-2-yl)methyl)-1H-indazol-4-yl)-7-(3-(4-methylpiperazin-1-yl)propyl)imidazo[1,2-a]pyridine-3-carboxamide;

N-(3-methoxy-1-((6-methylpyridin-3-yl)methyl)-1H-indazol-4-yl)-7-(2-methoxyethoxy)imidazo[1,2-a]pyridine-3-carboxamide;

N-(3-bromo-1-((6-methylpyridin-3-yl)methyl)-1H-indazol-4-yl)-7-(2-methoxyethoxy)imidazo[1,2-a]pyridine-3-carboxamide;

N-(3-methoxy-1-((6-methylpyridin-2-yl)methyl)-1H-indazol-4-yl)-7-(2-(4-methylpiperazin-1-yl)ethoxy)imidazo[1,2-a]pyridine-3-carboxamide;

N-(3-ethyl-1-(thiazol-2-ylmethyl)-1H-indazol-4-yl)imidazo[1,2-a]pyridine-3-carboxamide;

N-(3-ethyl-1-((6-methylpyridin-3-yl)methyl)-1H-indazol-4-yl)imidazo[1,2-a]pyridine-3-carboxamide;

N-(3-ethyl-1-((6-methylpyridin-3-yl)methyl)-1H-indazol-4-yl)-7-(2-(4-methylpiperazin-1-yl)ethoxy)imidazo[1,2-a]pyridine-3-carboxamide;

N-(3-ethyl-1-(thiazol-2-ylmethyl)-1H-indazol-4-yl)-7-(2-(4-methylpiperazin-1-yl)ethoxy)imidazo[1,2-a]pyridine-3-carboxamide;

N-(3-ethyl-1-((4-methylthiazol-2-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((6-methylpyridin-3-yl)methyl)-1H-indazol-4-yl)-7-(2-(4-methylpiperazin-1-yl)ethoxy)imidazo[1,2-a]pyridine-3-carboxamide;

N-(3-ethyl-1-((2-methylthiazol-4-yl)methyl)-1H-indazol-4-yl)-7-(2-(4-methylpiperazin-1-yl)ethoxy)imidazo[1,2-a]pyridine-3-carboxamide;

N-(3-ethyl-1-((5-fluoropyridin-2-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((5-fluoropyridin-2-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((2-methylthiazol-4-yl)methyl)-1H-indazol-4-yl)-7-(2-(4-methylpiperazin-1-yl)ethoxy)imidazo[1,2-a]pyridine-3-carboxamide;

N-(3-ethyl-1-((2-isopropylthiazol-4-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((2-isopropylthiazol-4-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((5-fluoropyridin-2-yl)methyl)-1H-indazol-4-yl)-7-(2-(4-isopropylpiperazin-1-yl)ethoxy)imidazo[1,2-a]pyridine-3-carboxamide;

7-(2-acetamidoethylthio)-N-(3-ethyl-1-((6-methylpyridin-2-yl)methyl)-1H-indazol-4-yl)imidazo[1,2-a]pyridine-3-carboxamide;

N-(3-cyclopropyl-1-((5-hydroxy-6-methylpyridin-2-yl)methyl)-1H-indazol-4-yl)-7-(2-(4-methylpiperazin-1-yl)ethoxy)imidazo[1,2-a]pyridine-3-carboxamide;

7-(Benzyloxy)-N-(3-cyclopropyl-1-((6-methylpyridin-2-yl)methyl)-1H-indazol-4-yl)imidazo[1,2-a]pyridine-3-carboxamide;

N-(3-cyclopropyl-1-((6-methylpyridin-2-yl)methyl)-1H-indazol-4-yl)-7-hydroxyimidazo[1,2-a]pyridine-3-carboxamide;

N-(3-cyclopropyl-1-((6-methylpyridin-2-yl)methyl)-1H-indazol-4-yl)-7-(methylthio)imidazo[1,2-a]pyridine-3-carboxamide;

N-(3-cyclopropyl-1-((6-methylpyridin-2-yl)methyl)-1H-indazol-4-yl)-7-(2-(2-(vinyloxy)ethoxy)ethoxy)imidazo[1,2-a]pyridine-3-carboxamide;

N-(3-cyclopropyl-1-((6-methylpyridin-2-yl)methyl)-1H-indazol-4-yl)-7-(2-(2-hydroxyethoxy)ethoxy)imidazo[1,2-a]pyridine-3-carboxamide;

7-bromo-N-(3-cyclopropyl-1-((6-methylpyridin-2-yl)methyl)-1H-indazol-4-yl)imidazo[1,2-a]pyridine-3-carboxamide; and pharmaceutically acceptable salts thereof. Particular mention is made of hydrochloride salts (including hydrochloride, dihydrochloride and trihydrochloride salts) of the aforementioned compounds.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, Alfa, Aesar, TCI, Maybridge, or other suitable suppliers, and were used without further purification unless otherwise indicated. Tetrahydrofuran (THF), dichloromethane (DCM, methylene chloride), toluene, dimethylformamide (DMF) and dioxane were purchased from Aldrich in Sure/Seal™ bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried or dried under a stream of dry nitrogen.

Column chromatography was done on a Biotage system (Manufacturer: Dyax Corporation) having a silica gel or C-18 reverse phase column, or on a silica SepPak cartridge (Waters), or using conventional flash column chromatography on silica gel.

Abbreviations used in the Examples have the following meanings

| AcOH | Acetic acid |
|---|---|
| $Ag_2CO_3$ | Silver carbonate |
| APCI | Atmospheric Pressure Chemical Ionization |
| Boc | tert-butoxycarbonyl |
| $CBr_4$ | Carbon tetrabromide |
| $CH_3CN$ | Acetonitrile |
| $CHCl_3$ | Chloroform |
| $Cs_2CO_3$ | Cesium Carbonate |
| DCE | 1,2-Dichloroethane |
| DCM | Dichloromethane |
| DMA | N,N-Dimethylacetamide |
| DMF | N,N-Dimethylformamide |
| DMSO | dimethylsulfoxide |
| $Et_2O$ | Diethyl ether |
| $Et_3N$ | Triethylamine |
| $Et_3SiH$ | Triethyl silane |
| EtOAc | Ethyl acetate |
| EtOH | Ethanol |
| GF/F | Glass Fiber Filter |
| HATU | (2-(7-Aza-1H-benzotriazole-1-yl)-1,1,3,3-tetramethyluronium hexafluorophosphate) |
| HCHO | Formaldehyde |
| HCl | Hydrogen chloride or hydrochloric acid |
| IPA | Isopropyl alcohol |
| $K_2CO_3$ | Potassium carbonate |
| LAH | Lithium Aluminum Hydride |
| LHMDS | Lithium bis(trimethylsilyl)amide (also known as lithium hexamethyldisilazide) |
| MeOH | Methanol |
| MTBE | tert-butyl-methylether |
| $Na_2SO_4$ | Sodium sulfate |
| $Na_2SO_4 \cdot 10H_2O$ | Sodium sulfate decahydrate |
| $NaBH(OAc)_3$ | Sodium triacetoxyborohydride |
| $NaHCO_3$ | Sodium bicarbonate |
| NaOH | Sodium Hydroxide |
| NaOH | Sodium hydroxide |
| $NH_4Cl$ | Ammonium Chloride |
| $NH_4OH$ | Ammonium hydroxide |
| NMP | N-Methylpyrrolidone |
| $P_2S_5$ | Phosphorus pentasulfide |
| $Pd(PPh_3)_4$: | Tetrakis(triphenylphosphine)palladium(0) |
| $PdCl_2(dppf) \cdot dcm$ | 1,1'-Bis(diphenylphosphino)ferrocene-palladium(II)dichloride dichloromethane complex |
| PMB | 4-methoxybenzyl |
| t-BuOH | tert-Butanol |
| TEA | triethylamine |
| TFA | Trifluoroacetic acid |
| THF | Tetrahydrofuran |

Example A cFMS Kinase Assay

The ability of compounds of Formula I to inhibit cFMS was determined by the following assay. cFMS enzymatic activity was measured using the LANCE® Ultra TR-FRET assay technology from PerkinElmer (Waltham, Mass.). Incubation mixtures contained the following: 50 mM NaHEPES, pH 7.3, 10 mM $MgCl_2$, 0.5 mM $MnCl_2$, 0.01% Triton X-100, 1 mM DTT, 1% DMSO, 10 µM ATP, 25 nM LANCE® Ultra ULight™-poly GAT and 0.5 nM cFMS in a total volume of 10 µL. The concentration of compounds of Formula I was varied over 10-point, 3-fold dilution series with 10,000 nM typically being the highest dose. Incubations were carried out in white ProxyPlate™-384 Plus plates (PerkinElmer) at 22° C. for 20 minutes, after which 10 µL of a quench/detection solution was added containing 1× LANCE® Detection Buffer, 2 nM LANCE® Eu—W1024 Anti-phosphotyrosine (PY20) and 36 mM EDTA. After an additional 60 minutes incubation at 22° C., the assay plate was read on an EnVision™ 2103 Multilabel Reader (PerkinElmer) using an excitation wavelength of 340 nm and emission wavelengths of 615 nm and 665 nm. Percent of control (POC) was calculated using the following equation:

$$POC = 100 \left[ \frac{Em665_{Sample} - AvgEm665_{Background}}{AvgEm665_{Unihibited} - AvgEm665_{Background}} \right]$$

A standard 4-parameter logistic model was fit to the inhibitor dose response curves, with the $IC_{50}$ being defined as the concentration of inhibitor giving 50 POC.

Table A provides averaged $IC_{50}$ values for compounds of the invention when tested in this assay.

TABLE A

| Ex. # | cFMS enzyme IC$_{50}$ (nM) |
|---|---|
| 1 | 112.0 |
| 2 | 117.9 |
| 3 | 57.9 |
| 4 | 42.0 |
| 5 | 137.0 |
| 6 | 515.8 |
| 7 | 3066.9 |
| 8 | 3002.7 |
| 9 | 454.9 |
| 10 | 395.4 |
| 11 | 4876.5 |
| 12 | 903.2 |
| 13 | 2558.8 |
| 14 | 3844.8 |
| 15 | 138.2 |
| 16 | 145.1 |
| 17 | 1396.9 |
| 18 | 1136.4 |
| 19 | 860.1 |
| 20 | 1037.9 |
| 21 | 2907.5 |
| 22 | 2256.2 |
| 23 | 141.2 |
| 24 | 409.9 |
| 25 | 1973.5 |
| 26 | 4910.5 |
| 27 | 100.8 |
| 28 | 176.2 |
| 29 | 555.6 |
| 30 | 191.3 |
| 31 | 333.1 |
| 32 | 341.5 |
| 33 | 286.8 |
| 34 | 688.5 |
| 35 | 488.2 |
| 36 | 554.6 |
| 37 | 725.3 |
| 38 | 98.3 |
| 39 | 331.8 |
| 40 | 358.5 |
| 41 | 931.9 |
| 42 | 275.1 |
| 43 | 395.7 |
| 44 | 232.6 |
| 45 | 172.1 |
| 46 | 264.6 |
| 47 | 310.6 |
| 48 | 426.4 |
| 49 | 738.2 |
| 50 | 348.1 |
| 51 | 430.1 |
| 52 | 134.6 |
| 53 | 1617.8 |
| 54 | 1253.3 |
| 55 | 936.5 |
| 56 | 313.5 |
| 57 | 1611.6 |
| 58 | 492.1 |
| 59 | 250.1 |
| 60 | 391.2 |
| 61 | 95.1 |
| 62 | 92.8 |
| 63 | 94.7 |
| 64 | 121.9 |
| 65 | 283.7 |
| Step C | |
| 65 | 93.6 |
| Step D | |
| 66 | 591.8 |
| 67 | 1721.2 |
| 68 | 1215.7 |
| 69 | 1718.9 |
| 70 | 977.1 |
| 71 | 621.2 |
| 72 | 102.3 |
| 73 | 1229.0 |
| 74 | 157.6 |
| 75 | 106.8 |
| 76 | 266.9 |
| 77 | 497 |
| Step B | |
| 77 | 149.8 |
| Step C | |
| 78 | 82.5 |
| 79 | 120.4 |
| 80 | 184.6 |
| 81 | 163.7 |
| 82 | 172.6 |
| 83 | 305.2 |
| 84 | 188.2 |
| 85 | 379.9 |
| 86 | 876.7 |
| 87 | 167.7 |
| 88 | 141.0 |
| 89 | 155.9 |
| 90 | 163.5 |
| 91 | 183.3 |
| 92 | 193.5 |
| 93 | 198.2 |
| 94 | 219.3 |
| 95 | 238.7 |
| 96 | 267.7 |
| 97 | 271.3 |
| 98 | 497.2 |
| 99 | 325.9 |
| 100 | 558.4 |
| 101 | 703.3 |
| 102 | 276.2 |
| 103 | 192.4 |
| 104 | 380.0 |
| 105 | 187.4 |
| 106 | 141.2 |
| 107 | 371.1 |
| 108 | 87.9 |
| 109 | 96.6 |
| 110 | 184.6 |
| 111 | 152.3 |
| 112 | 170.5 |
| 113 | 218.7 |
| 114 | 91.4 |
| 115 | 204.9 |
| 116 | 173.7 |
| 117 | 633 |
| Step A | |
| 117 | 462.7 |
| Step B | |
| 118 | 235.8 |
| 119 | 232.2 |
| 120 | 522.6 |
| 121 | 929.2 |
| 122 | 280.0 |
| 123 | 72.8 |
| 124 | 155.8 |
| 125 | 141.1 |
| 126 | 278.4 |
| 127 | 157.4 |
| 128 | 217.3 |
| 129 | 6551.3 |
| 130 | 2135.6 |
| 131 | 1893.7 |
| 132 | 4121.9 |
| 133 | 183.3 |
| 134 | 449.3 |
| 135 | 1171.4 |
| 136 | 400.6 |
| 137 | 54.6 |
| 138 | 274.8 |
| 139 | 137.5 |
| 140 | 108.4 |
| 141 | 32.7 |
| 142 | 1563.4 |
| 143 | 711.3 |
| 144 | 276.2 |
| 145 | 178.8 |

TABLE A-continued

| Ex. # | cFMS enzyme IC$_{50}$ (nM) |
|---|---|
| 146 | 102.4 |
| 147 | 123.0 |
| 148 | 259.5 |
| 149 | 200.7 |
| 150 | 136.1 |
| 151 | 148.5 |
| 152 | 79.5 |
| 153 | 118.3 |
| 154 | 131.7 |
| 155 | 217.8 |
| 156 | 86.75 |
| 157 | 493.5 |
| 158 | 227.05 |
| 159 | 18.5 |
| 160 | 90.4 |
| 161 | 753.2 |
| 162 | 74.4 |

Example B

Osteolytic Bone Model

Bone metastases from carcinomas are the most common malignancies of the bone. This model was developed to screen compounds of Formula I in a model of osteolytic bone to determine the ability of compounds of Formula I to inhibit osteolysis. Briefly, rat mammary carcinoma cells were resuspended in PBS (Ca$^+$, Mg$^+$) at 3.0×10$^6$ cells/mL. Sprague Dawley rats were placed under isofluorane and a small incision in the skin was made near the knee joint. To ensure minimal tissue damage, blunt dissection of the tibia was performed using sterile, cotton-tipped applicators. A bone drill was used to pierce the proximal tibia and to expose the marrow. Cells were injected (10 µL/animal) into the marrow using a 25 µL Hamilton Syringe and the injection site was sealed using bone wax. The incision site was closed using sterile wound clips and animals were placed back in bedded cages for recovery. Animals were dosed and monitored once daily for 14 days. Mechanical allodynia was assessed on day 0 and 14. Fifteen days following tibial injections, animals were euthanized and the injected limb amputated and placed in 10% NBF. Radiographic analysis of formalin fixed tibias was performed to assess osteolysis.

Compounds described herein were shown or will be shown to be effective in this model.

Example C

Adjuvant-Induced Arthritis (AIA) Model

Rheumatoid arthritis is a disabling chronic inflammatory disease that progressively destroys peripheral joints. The rat adjuvant-induced arthritis model was used to examine the ability of compounds of Formula I to inhibit inflammation of the joint, as measured by ankle swelling and histology, and bone resorption.

Animals

Male Lewis rats (7-9 weeks of age; 8 per group for arthritis, 4 per group for normal control) were acclimated for 7 days after arrival.

Experimental Protocol

Acclimated animals were randomized into groups by body weight and then anesthetized with Isoflurane and given lipoidal amine (LA) in Freund's complete adjuvant (100 µL injection of 6.5 mg LA, intradermal administration at the base of the tail, Day 0). Caliper measurements of normal (pre-disease) right and left ankle joints were taken on day 7 post-adjuvant injection. On day 8, dosing began for vehicle and compound treatment groups. Methotrexate treatment (0.075 mg/kg) began on day 0 prior to adjuvant injection. Animals received treatment with once daily oral doses on days 1-18 of the test compound (10, 30 or 100 mg/kg) and was well tolerated at all doses administered. Rats were weighed on days 0, 4, and 8-14 and caliper measurements of ankles were taken on days 7 and 9-18. Final body weights and caliper measurements of ankles and paws were taken on day 18. On day 18, animals were euthanized, both hind paws were removed, and the hind paws weighed. Paws were analyzed by micro-computed tomography (µCt) and then placed in formalin for histopathologic analyses. Spleens were also removed, weighed and placed in formalin for histopathologic analyses.

Compounds described herein were shown or will be shown to be effective in this model.

Example D cFMS Cell-Based Assay

The ability of compounds of Formula I to inhibit cFMS activation in cells was determined by the following assay. THP-1 cells (human acute monocytic leukemia cell line) were serum-starved for 4 hours prior to treatment with compounds of Formula I for 1 hour. The concentration of compounds of Formula I was varied over a 9-point, 3-fold dilution series with 5,000 nM typically being the highest dose. Cell culture and treatment were carried out in a humidified 37° C., 5% CO$_2$ incubator. Treated cells were stimulated with 250 ng/mL recombinant human MCSF for 1 minute to induce activation of cFMS. Cells were lysed in a manner which preserves phosphoproteins, and the lysate was analyzed by ELISA (R&D Systems, Human Phospho-M-CSF R DuoSet IC DYC3268), in which total cFMS protein in the lysate is captured and phosphotyrosine residues of cFMS are detected. A standard curve, made using purified phospho-M-CSF R protein, was used to quantify phospho-c-FMS in compound-treated wells. A standard 4-parameter logistic model was fit to the inhibitor dose response curves, with the IC$_{50}$ being defined as the concentration of inhibitor giving 50 POC.

Example E

Phospho PDGFR LICOR Cell Assay

Compounds were screened for inhibition of PDGFR beta phosphorylation in the HS27 human fibroblast cell line. Cells were seeded into a 96 well tissue culture plate, then incubated overnight in a 37° C./5% CO$_2$ incubator. The following day, cells were treated for one hour with test compound dilutions. After stimulation with PDGF-BB ligand for 10 minutes, cells were washed with PBS and fixed in 3.7% formaldehyde in PBS for 10 minutes. This was followed by washing in PBS/0.2% Triton X-100 and permeabilizing in 100% MeOH for 10 minutes. Cells were incubated in blocking buffer for 1 hour. Antibodies to phosphorylated PDGFRβ and total ERK were added to the cells and incubated for 3 hours. After washing with PBS/0.2% Triton X-100, the cells were incubated with fluorescently-labeled secondary antibodies for an additional hour. Cells were then washed with PBS and analyzed for fluorescence at both wavelengths using the Odyssey Infrared Imaging System (LI-COR Biosciences). Phosphorylated PDGFR signal was normalized to total ERK signal. A standard 4-parameter logistic model was fit to the inhibitor dose response curves, with the $IC_{50}$ being defined as the concentration of inhibitor giving 50 POC.

Example F c-Kit Cell-Based Assay

The ability of compounds of Formula I to inhibit c-Kit activation in cells was determined by the following assay. M-07e cells (human acute megakaryoblastic leukemia cell line) were serum-starved for 4 hours prior to treatment with compounds of Formula I for 1 hour. The concentration of compounds of Formula I was varied over a 9-point, 3-fold dilution series with 5,000 nM typically being the highest dose. Cell culture and treatment were carried out in a humidified 37° C., 5% $CO_2$ incubator. Treated cells were stimulated with 150 ng/ml recombinant human SCF for 4 minutes to induce activation of c-Kit. Cells were lysed in a manner which preserves phosphoproteins, and the lysate was analyzed by ELISA (R&D Systems, Human Phospho-SCF R DuoSet IC DYC3527), in which total c-Kit protein in the lysate is captured and phosphotyrosine residues of c-Kit are detected. A standard curve, made using purified phospho-SCF R protein, was used to quantify phospho-c-Kit in compound-treated wells. A standard 4-parameter logistic model was fit to the inhibitor dose response curves, with the $IC_{50}$ being defined as the concentration of inhibitor giving 50 POC.

Preparation of Synthetic Intermediates Utilized in the Examples

Preparation A

7-Bromoimidazo[1,2-a]pyridine-3-carboxylic acid

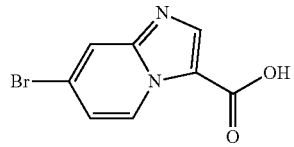 [SMILES: O=C(O)c1cnc2cc(Br)ccn12]

Step A: Preparation of ethyl 7-bromoimidazo[1,2-a]pyridine-3-carboxylate: 4-Bromopyridin-2-amine (10.0 g, 0.06 mol) was mixed with ethanol (50 mL) in a reaction flask, under an atmosphere of dry nitrogen. A solution of ethyl 2-chloro-3-oxopropanoate (5% in benzene; 222 mL; Commercial solution from Toronto Research Chemicals Inc.) was added. The mixture was heated to 60° C. under nitrogen for 5 hours. After allowing the mixture to cool the solvent was removed under vacuum to give a brown solid. The solid was mixed with ethyl acetate (500 mL) and sodium bicarbonate solution (200 mL) and stirred to dissolve. The phases were separated and the bicarbonate solution was extracted further with ethyl acetate (100 mL). The combined ethyl acetate extracts were dried over sodium sulfate, filtered and concentrated under vacuum to give a solid. The crude material was dissolved in ethyl acetate and passed through a short column of silica, eluting with ethyl acetate. Fractions containing the product were concentrated under reduced pressure to give ethyl 7-bromoimidazo[1,2-a]pyridine-3-carboxylate (15 g) as a pale yellow solid.

Step B: Preparation of 7-bromoimidazo[1,2-a]pyridine-3-carboxylic acid: Ethyl 7-bromoimidazo[1,2-a]pyridine-3-carboxylate (15 g, 56 mmol) and lithium hydroxide monohydrate (3 g, 71.4 mmol) were mixed with a 1:2:1 mixture of tetrahydrofuran/ethanol/water (560 mL). The mixture was stirred at ambient temperature for 16 hours. The solvent was removed under vacuum to give a yellow gum. Water (300 mL) and dichloromethane were added and the phases were separated. The aqueous phase was cooled in an ice-water bath before adjusting the pH to 3 using 2N sulfuric acid. The product precipitated, was collected by filtration and was washed with a small amount of water (50 mL) then dried under vacuum to give 7-bromoimidazo[1,2-a]pyridine-3-carboxylic acid (8.3 g) as an off-white solid.

Preparation B

3-Bromo-4-nitro-1H-indazole

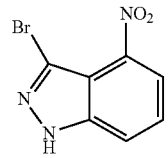 [SMILES: O=[N+]([O-])c1cccc2[nH]nc(Br)c12]

Sodium acetate (52.8 g, 644 mmol) and 4-nitro-1H-indazole (100 g, 613 mmol) were mixed with acetic acid (1000 mL) and chloroform (1000 mL) in a 5 L 4-neck flask with mechanical stirring. A solution of bromine (103 g, 644 mmol) in acetic acid (120 mL) was added over approximately 3.5 hours, while keeping the temperature below 21° C. After the addition was completed, the reaction mixture was stirred for an additional 2 hours. The reaction mixture was concentrated under reduced pressure. Water (2000 mL) was added to the residue. The yellow solids were collected by filtration and washed with water (3×1000 mL). The solids were air-dried on the filter and then under vacuum at 40° C. to give the desired product (129 g) as a yellow solid.

Preparation C

3-Bromo-1-((6-methylpyridin-2-yl)methyl)-4-nitro-1H-indazole

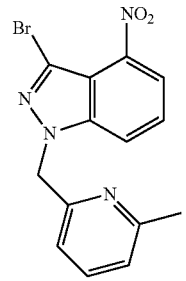 [SMILES: Cc1cccc(Cn2nc(Br)c3c([N+](=O)[O-])cccc32)n1]

To a stirred solution of 3-bromo-4-nitro-1H-indazole (Preparation B; 40 g, 165 mmol) in anhydrous DMF (320 mL) was added at ambient temperature potassium carbonate (45.7 g, 331 mmol). 2-(Chloromethyl)-6-methylpyridine hydrochloride (31 g, 174 mmol) was added in portions, and the reaction mixture was stirred at ambient temperature for 16 hours. The reaction mixture was concentrated under reduced pressure. The residue was partitioned between water (800 mL) and methylene chloride (1000 mL). The phases were separated and the aqueous phase was extracted further with methylene chloride (200 mL). The combined organic extracts were dried (MgSO$_4$) and concentrated under reduced pressure to give a brown solid. The crude product was triturated with ether (400 mL) and the solids were collected by filtration, washed with ether, and dried under vacuum to afford the desired product as brown solid (46 g).

Preparation D

Ethyl 7-(2-(4-methylpiperazin-1-yl)ethoxy)imidazo[1,2-a]pyridine-3-carboxylate

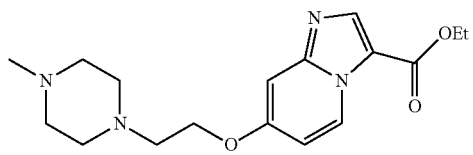 [SMILES: CCOC(=O)c1cnc2cc(OCCN3CCN(C)CC3)ccn12]

Potassium 2-chloro-3-ethoxy-3-oxoprop-1-en-1-olate (120 g, 635 mmol) was suspended (through vigorous magnetic stirring) in 1800 mL of ether and 6N sulfuric acid (53 mL, 317 mmol) was added slowly. The lower aqueous suspension was sampled periodically for acidity. Additional water (100 mL) was added to aid in phase separation. When the pH of the lower (aqueous) phase dropped below 3, the ether phase was separated. The aqueous phase was further extracted with ether (200 mL). The combined ether phases were dried over sodium sulfate and magnesium sulfate for 10 minutes. The solution was filtered and concentrated under reduced pressure, with the temperature not exceeding 20° C. An off-white semi-solid (100 g) was obtained. This was dissolved in absolute ethanol (800 mL). 4-(2-(4-Methylpiperazin-1-yl)ethoxy)pyridin-2-amine (Preparation F; 75 g, 317 mmol) was added, and the mixture was heated under nitrogen at 65° C. for 18 hours. The mixture was cooled to ambient temperature and the resulting suspension was evaporated to dryness under reduced pressure. The resulting solids were triturated with THF, collected by filtration and then dried under vacuum. The material (an HCl salt) was mixed with water (1 L) and ethanol (500 mL). Sodium bicarbonate (50 g) was added and the mixture was stirred for 18 hours. The suspension was evaporated to dryness under vacuum. The solids were extracted with a large volume of ethyl acetate (4 L) and THF (1 L) until no further product was extracted. The organic solution was further dried with sodium sulfate and magnesium sulfate, filtered and concentrated under vacuum to give a solid. The material was triturated with ether (500 mL) and the solids were collected by filtration and dried under vacuum to afford the desired product (86.2 g) as an off-white solid.

Preparation E

Potassium (E)-2-chloro-3-ethoxy-3-oxoprop-1-en-1-olate

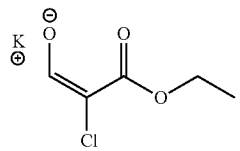

A mixture of ethyl 2-chloroacetate (220.8 g; 1802 mmol) and ethyl formate (133.5 g; 1802 mmol) was added slowly to a suspension of potassium t-butoxide (202.2 g; 1802 mmol) in diisopropyl ether (2000 mL) at 0° C. (maintaining the temperature<20° C.) with mechanical stirring. The mixture was stirred at ambient temperature for 24 hours. The solids were collected by filtration and washed with diisopropyl ether (500 mL) and acetonitrile (2×1500 mL). The material was dried under vacuum to give the product (270 g) which was used without further purification.

Preparation F 4-(2-(4-Methylpiperazin-1-yl)ethoxy)pyridin-2-amine

Sodium hydride (60% in mineral oil; 43.56 g; 1089 mmol) was added to a 3 L reaction flask under nitrogen. A mechanical stirrer and thermocouple was attached. Dry diglyme (400 mL) was added. A solution of 2-(4-methylpiperazin-1-yl)ethanol (157 g; 1089 mmol) in diglyme (450 mL) was added slowly with stirring. The mixture was stirred with warming to 40° C. for 1 hour. 4-Chloropyridin-2-amine (70.0 g; 544.5 mmol) was added as a solid. The mixture was heated to 80° C. with stirring until effervescence had ceased. The temperature was increased to 157° C. for 16 hours. The mixture was allowed to cool and diluted with water (500 mL). THF (1000 mL) was added followed by sodium chloride (sufficient to saturate the aqueous phase). The phases were separated and the aqueous phase was further extracted with THF (3×800 mL). Additional water was added as required to aid in phase separation. The combined organic phases were dried with sodium sulfate (1000 g) for 16 hours and filtered. The solvent was removed under vacuum to remove the majority of the THF. The solution was filtered through Celite® to remove fine particulates rinsing with diglyme. The diglyme was removed under vacuum (10 mm Hg vacuum, with the bath temperature increased to 60° C.). The residue was placed under high vacuum for 1 hour and then triturated with ether (400 mL). The resulting solids were collected by filtration, washed with ether and dried under vacuum to give the product (100.4 g) as an off white solid.

Preparation G 4-(2-(4-Isopropylpiperazin-1-yl)ethoxy)pyridin-2-amine

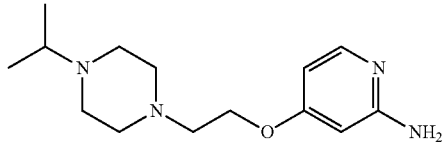 [SMILES: CC(C)N1CCN(CCOc2ccnc(N)c2)CC1]

Sodium hydride (60% in mineral oil; 21.00 g; 525 mmol) was added to a 4-neck (2 L) flask under nitrogen with mechanical stirrer, condenser, thermocouple and addition funnel attached. Dry diglyme (450 mL) was added. A solution of 2-(4-isopropylpiperazin-1-yl)ethanol (90.45 g; 525 mmol) in diglyme (150 mL) was added slowly with stirring. The temperature was slowly increased to 40° C. until effervescence had ceased. The mixture was allowed to cool and 4-chloropyridin-2-amine (45.00 g; 350 mmol) was added. The mixture was heated at 157° C. for 16 hours and allowed to cool. Water (300 mL) was added followed by THF (750 mL). Sodium chloride was added (sufficient to saturate the aqueous phase). The phases were separated and the aqueous phase was further extracted with THF (3×600 mL). The combined organic phases were dried with sodium sulfate (600 g) for 16 hours and then filtered. The solvent was removed under vacuum (8 mm Hg, bath temperature at 60° C., to remove the diglyme). The residue was dissolved in THF (1000 mL) and filtered (Celite) to remove some fine particulates. The solvent was removed under vacuum to give a pale brown oil. The material was placed under high vacuum. A solid slowly formed (about 130 g). Ether (200 mL) was added and the material was physically broken up. Hexane (about 200 mL) was added, and the resulting solids were mechanically stirred to break them up. The solids were collected by filtration and washed (hexane/ether 1:1). The material was dried under vacuum to give the desired product (38.4 g) as a cream colored solid.

Preparation H 7-bromo-N(1-((1,5-dimethyl-1H-pyrazol-3-yl)-3-ethyl-1H-indazol-4-yl)imidazo[1,2-a]pyridine-3-carboxamide

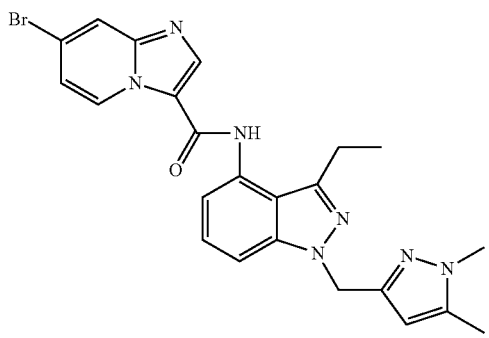 [SMILES: CCc1nn(Cc2cc(C)n(C)n2)c2cccc(NC(=O)c3cnc4cc(Br)ccn34)c12]

To a cooled (ice/water bath) solution of 1-((1,5-dimethyl-1H-pyrazol-3-yl)methyl)-3-ethyl-1H-indazol-4-amine (1.16 g; 4.31 mmol) in anhydrous THF (15 mL), under nitrogen, was added LHMDS (1.0 M in THF; 4.22 mmol). A solution of methyl 7-bromoimidazo[1,2-a]pyridine-3-carboxylate (0.50 g; 1.96 mmol) in DMA (5 mL) was added drop wise. The mixture was stirred with cooling for 2 hours and then added to an excess of water. The mixture was extracted multiple times with DCM and EtOAc. The combined organic extracts were dried over sodium sulfate and then concentrated under reduced pressure. The residue was purified by chromatography on silica gel, eluting with methanol/DCM (3:97) to give the desired product as a white solid.

Preparation I 7-fluoroimidazo[1,2-a]pyridine-3-carboxylic acid

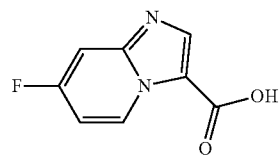

Step A: Preparation of tert-butyl 4-fluoropyridin-2-ylcarbamate: To a 2 L flask was charged 2-chloro-4-fluoropyridine (20 g, 152 mmol), tert-butyl carbamate (89 g, 760 mmol), tris(dibenzylideneacetone) dipalladium (1.39 g, 1.52 mmol), X-PHOS (2-(dicyclohexylphosphino)-2',4',6'-triisopropyl-1,1'-biphenyl) (1.48 g, 3.10 mmol), cesium carbonate (99 g, 588 mmol), and tetrahydrofuran (500 mL) under an atmosphere of dry nitrogen. This mixture was heated at reflux under nitrogen for 7 hours. A further 1 equivalent of cesium carbonate was added to drive the reaction to completion (heated a further 7 hours). The mixture was cooled to ambient temperature, filtered through Celite and washed with ethyl acetate. The filtrate was partitioned between saturated sodium bicarbonate and ethyl acetate. The aqueous phase was extracted with ethyl acetate twice. The combined organic phases were washed with brine and dried with sodium sulfate, concentrated under vacuum, and purified by column chromatography to give tert-butyl 4-fluoropyridin-2-ylcarbamate as a pale yellow solid (22.6 g).

Step B: Preparation of 4-fluoropyridin-2-amine: To a 1 L flask was added tert-butyl 4-fluoropyridin-2-ylcarbamate (3.5 g, 16.5 mmol) and dichloromethane (100 mL). The mixture was cooled to 0-5° C. using an ice/water bath. Trifluoroacetic acid (75 mL) was added slowly with continued stirring. The mixture was stirred at ambient temperature for 16 hours. The mixture was concentrated under vacuum before partitioning between saturated sodium bicarbonate and ethyl acetate. The aqueous layer was washed with ethyl acetate twice. The combined organic phases were washed with brine and dried with sodium sulfate before concentrating under vacuum to give 4-fluoropyridin-2-amine as a pale yellow solid (1.76 g).

Step C: Preparation of ethyl 7-fluoroimidazo[1,2-a]pyridine-3-carboxylate: 4-Fluoropyridin-2-amine (10.0 g, 48.0 mmol) was mixed with ethanol (40 mL) in a reaction flask, under an atmosphere of dry nitrogen. A solution of ethyl 2-chloro-3-oxopropanoate (5% in benzene, 178 mL, Commercial solution from Toronto Research Chemicals Inc.) was added. The mixture was heated to 60° C. under nitrogen for 4 hours. After allowing the mixture to cool the solvent was removed under vacuum to give a brown solid. The solid was mixed with ethyl acetate (300 mL) and sodium bicarbonate solution (75 mL) and stirred to dissolve. The phases were separated and the bicarbonate solution was extracted further with ethyl acetate (75 mL). The combined ethyl acetate extracts were dried over sodium sulfate, filtered and concentrated under vacuum to give a solid. The crude material was dissolved in ethyl acetate and passed through a short column of silica, eluting with ethyl acetate. Fractions containing the product were concentrated to give ethyl 7-fluoroimidazo[1,2-a]pyridine-3-carboxylate as a white solid (13 g).

Step D: Preparation of 7-fluoroimidazo[1,2-a]pyridine-3-carboxylic acid: Ethyl 7-fluoroimidazo[1,2-a]pyridine-3-carboxylate (8 g; 44.4 mmol) was mixed with tetrahydrofuran (225 mL), ethanol (110 mL) and water (55 mL). Lithium hydroxide monohydrate (0.962 g; 22.9 mmol) was added. The mixture was stirred at ambient temperature for 16 hours. The mixture was concentrated under reduced pressure to remove tetrahydrofuran and ethanol. 2 N hydrochloric acid was added to the mixture to adjust to pH 3. A white precipitate formed which was collected by filtration and dried under high vacuum to give 7-fluoroimidazo[1,2-a]pyridine-3-carboxylic acid as a white solid (6.3 g).

Preparation J 7-fluoro-N-(3-methyl-1-((6-methylpyridin-2-yl)methyl)-1H-indazol-4-yl)imidazo[1,2-a]pyridine-3-carboxamide

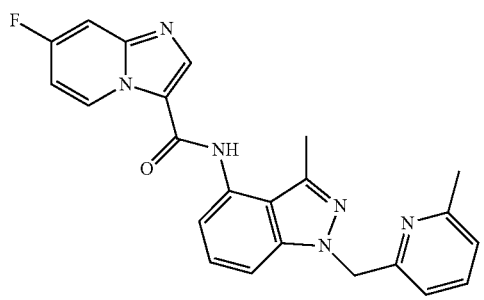 [SMILES: Cc1cccc(Cn2nc(C)c3c(NC(=O)c4cnc5cc(F)ccn45)cccc32)n1]

Step A: Preparation of 3-methyl-1-((6-methylpyridin-2-yl)methyl)-4-nitro-1H-indazole: A dry, 100 mL round bottom flask equipped with a reflux condenser and a nitrogen line was charged with 3-iodo-1-((6-methylpyridin-2-yl)methyl)-4-nitro-1H-indazole (Example 142, Step B; 100 mg, 0.254 mmol), tri-o-tolylphosphine (15.4 mg, 0.051 mmol), and tris(dibenzylideneacetone)dipalladium (0) (23 mg, 0.025 mmol). The flask was purged with nitrogen and anhydrous N,N-dimethylformamide (30 mL), and tetramethylstannane (0.04 mL, 0.28 mmol) were added, followed by triethylamine (0.04 mL, 0.30 mmol). The flask was thoroughly degassed under nitrogen and heated at 80° C. for 6 hours. The reaction mixture was cooled to ambient temperature, diluted with water, and extracted multiple times with DCM and EtOAc. The combined organic extracts were dried over anhydrous sodium sulfate, and concentrated under reduced pressure. The crude product was subjected to preparative thin-layer chromatography on silica with 2% MeOH-DCM as eluent to afford 56.8 mg of desired product as a yellow solid.

Step B: Preparation of 3-methyl-1-((6-methylpyridin-2-yl)methyl)-1H-indazol-4-amine: A suspension of 3-methyl-1-((6-methylpyridin-2-yl)methyl)-4-nitro-1H-indazole (54 mg, 0.19 mmol) in absolute EtOH (1.5 mL) was treated at ambient temperature with 10% palladium hydroxide on carbon (27 mg, 0.019 mmol). The mixture was stirred at ambient temperature under a hydrogen atmosphere for 16 hours, and then filtered through a Celite pad, washing with EtOH. The filtrate was concentrated under reduced pressure to afford the product (36 mg) as a yellow oil.

Step C: Preparation of 7-fluoro-N-(3-methyl-1-((6-methylpyridin-2-yl)methyl)-1H-indazol-4-yl)imidazo[1,2-a]pyridine-3-carboxamide: A solution of 7-fluoroimidazo[1,2-a]pyridine-3-carboxylic acid (Preparation I; 0.15 g, 0.84 mmol) in anhydrous 1-methyl-2-pyrrolidinone (4 mL) was treated with anhydrous triethylamine (0.3 mL, 2.11 mmol). The mixture was stirred until the reaction became homogeneous. 2,4,6-Trichlorobenzoyl chloride (0.22 g, 0.89 mmol) was added dropwise and the reaction mixture was allowed to stir for 30 minutes at ambient temperature. Within 5 minutes, the anhydride precipitate formed and vigorous stirring was required. 3-Methyl-1-((6-methylpyridin-2-yl)methyl)-1H-indazol-4-amine (0.19 g, 0.75 mmol) was added as a 0.5 M solution in anhydrous 1-methyl-2-pyrrolidinone. The reaction mixture was heated at 80° C. and stirred for 16 hours. The mixture was cooled to ambient temperature and solids were removed by filtration, washing the filter cake with ethyl acetate. The filtrate was concentrated under vacuum to remove ethyl acetate. The remaining solution was diluted with saturated sodium bicarbonate and a dark brown precipitate formed which was isolated by filtration to give 7-fluoro-N-(3-methyl-1-((6-methylpyridin-2-yl)methyl)-1H-indazol-4-yl)imidazo[1,2-a]pyridine-3-carboxamide as a brown solid (170 mg).

EXAMPLES

Example 1

N-(1-Benzyl-3-iodo-1H-indazol-4-yl)-7-(2-methoxyethoxy)imidazo[1,2-a]pyridine-3-carboxamide

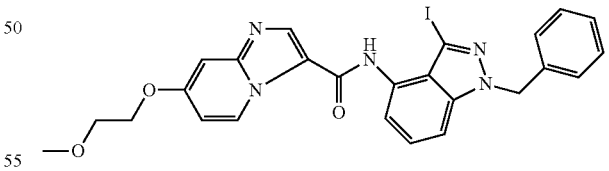

Step A: Preparation of 2-chloro-4-(2-methoxyethoxy)pyridine: To a 1 L flask was charged 2-chloro-4-nitropyridine (100 g, 630.7 mmol) and 2-methoxyethanol (746.8 mL, 9461 mmol) under an atmosphere of dry nitrogen. The mixture was cooled, with stirring, to 0° C. utilizing an ice/water bath. Potassium tert-butoxide (81.95 g, 693.8 mmol) was added and the mixture was stirred for 30 minutes. The ice/water bath was removed and the mixture was stirred for an additional 2 hours at ambient temperature. The mixture was concentrated under vacuum. Water (500 mL) was added and the mixture was extracted with dichloromethane. The combined extracts were dried over sodium sulfate, filtered and concentrated under vacuum to give 2-chloro-4-(2-methoxyethoxy)pyridine as a gold colored oil (115 g).

Step B: Preparation of 4-(2-methoxyethoxy)pyridin-2-amine: 2-Chloro-4-(2-methoxyethoxy)pyridine (30.0 g; 159.9 mmol), X-PHOS (dicyclohexyl[2',4',6'-tris(1-methylethyl)[1,1'-biphenyl]-2-yl]-phosphine) (3.03 g, 6.356 mmol), and Tris(dibenzylideneacetone)dipalladium (2.26 g; 2.468 mmol) were combined in a reaction flask under an atmosphere of dry nitrogen. Anhydrous tetrahydrofuran (150 mL) was added. The mixture was degassed by alternately evacuating the flask followed by filling with dry nitrogen (three times). The mixture was cooled to 0-5° C. using an ice/water bath. Lithium hexamethyldisilazide (LHMDS) (325 mL, 325.0 mmol) was added via addition funnel maintaining the temperature below 5° C. The ice/water bath was removed and the mixture was heated to reflux (60-65° C.) for 1.5 hours. After allowing the mixture to cool an ice/water bath was put in place. Hydrochloric acid (2N; 300 mL) was added with stirring, maintaining the temperature below 30° C. After stirring for 15 minutes the mixture was transferred to a separatory funnel with the addition of methyl t-butyl ether (MTBE) (300 mL) and water (20 mL). The phases were separated. The aqueous phase was basified by the addition of sodium hydroxide (50%; 10 mL) and then extracted with dichloromethane. The combined dichloromethane extracts were dried over sodium sulfate and filtered. Heptane (300 mL) was added. The solution was concentrated under vacuum to about one third the initial volume. Heptane (200 mL) was added. Further concentration resulted in solids precipitating. The solids were collected by filtration and washed with heptane (100 mL). The solids were dried under vacuum at 55° C. to give 4-(2-methoxyethoxy)pyridin-2-amine as an off white solid (23.62 g).

Step C: Preparation of ethyl 7-(2-methoxyethoxy)imidazo[1,2-a]pyridine-3-carboxylate: 4-(2-Methoxyethoxy)pyridin-2-amine (5.00 g; 29.7 mmol) was mixed with ethanol (20 mL) in a reaction flask, under an atmosphere of dry nitrogen. A solution of ethyl 2-chloro-3-oxopropanoate (5% in benzene; 110 mL; Commercial solution from Toronto Research Chemicals Inc.) was added. The mixture was heated to 60° C. under nitrogen for 4 hours. After allowing the mixture to cool the solvent was removed under vacuum to give a give a brown solid (9 g). The solid was mixed with ethyl acetate (200 mL) and sodium bicarbonate solution (50 mL) and stirred to dissolve. The phases were separated and the bicarbonate solution was extracted with additional ethyl acetate (50 mL). The combined ethyl acetate extracts were dried over sodium sulfate, filtered and concentrated under vacuum to give a brown solid (7.0 g). The material was dissolved in ethyl acetate and passed through a short column of silica, eluting with ethyl acetate. Fractions containing product were concentrated to give ethyl 7-(2-methoxyethoxy)imidazo[1,2-a]pyridine-3-carboxylate as a cream colored solid (3.77 g).

Step D: Preparation of 7-(2-methoxyethoxy)imidazo[1,2-a]pyridine-3-carboxylic acid: Ethyl 7-(2-methoxyethoxy)imidazo[1,2-a]pyridine-3-carboxylate (6.0 6 g; 22.9 mmol) was mixed with tetrahydrofuran (225 mL), ethanol (110 mL) and water (55 mL). Lithium hydroxide monohydrate (0.962 g; 22.9 mmol) was added. The mixture was stirred under an atmosphere of nitrogen and heated at 40° C. for 22 hours. The mixture was allowed to cool and then concentrated under reduced pressure to give a yellow gum. Water (50 mL) was added and the mixture was stirred until homogeneous. Hydrochloric acid (2N) was added with stirring to adjust to pH3. The mixture was cooled with an ice/water bath. The resulting precipitate was collected by filtration and washed with a small amount of water (10 mL). The material was dried under vacuum to give 7-(2-methoxyethoxy)imidazo[1,2-a]pyridine-3-carboxylic acid as a white solid (4.90 g).

Step E: Preparation of 3-iodo-4-nitro-1H-indazole: A solution of 4-nitro-1H-indazole (50.0 g; 306 mmol) in N,N-dimethylformamide (600 mL) was cooled to 5° C. under a nitrogen atmosphere with stirring. Powdered potassium hydroxide (68.8 g; 1226 mmol) was added. A solution of iodine (156 g; 613 mmol) in DMF (200 mL) was added slowly to the reaction mixture over 2 hours maintaining the temperature between 5 and 10° C. The mixture was stirred at 25° C. for 24 hours. Additional iodine (39.0 g; 153.2 mmol) and potassium hydroxide (17.2 g; 306.5 mmol) was added. The mixture was stirred at 25° C. for a further 12 hours. The reaction mixture was added to an aqueous solution of sodium bisulfite (10% solution; 3300 mL) with stirring. The resulting precipitate was collected by filtration and washed with water. The material was dried in a vacuum oven at 40° C. The material was dissolved in methylene chloride/methanol (10:1; 1.5 L) and filtered through Celite® to remove inorganic impurities. Concentration of the solution under vacuum gave 3-iodo-4-nitro-1H-indazole as a yellow solid (75 g).

Step F: Preparation of 1-benzyl-3-iodo-4-nitro-1H-indazole: 3-Iodo-4-nitro-1H-indazole (0.50 g; 1.73 mmol) was dissolved with stirring in dimethylformamide (15 mL) under an atmosphere of nitrogen. Potassium carbonate (0.478 g; 3.46 mmol) was added followed by benzyl bromide (0.325 g; 1.90 mmol). The mixture was stirred for 16 hours at 25° C. The mixture was added to water (50 mL) and ethyl acetate (50 mL) with stirring. The mixture was transferred to a reparatory funnel and the phases were separated. The ethyl acetate phase was dried over sodium sulfate, filtered and concentrated under vacuum. The crude product was purified by silica gel chromatography, eluting with hexane/ethyl acetate (5:1). The fractions containing product were concentrated under vacuum to give the 1-benzyl-3-iodo-4-nitro-1H-indazole as a yellow oil (456 mg).

Step G: Preparation of 1-benzyl-3-iodo-1H-indazol-4-amine: 1-Benzyl-3-iodo-4-nitro-1H-indazole (340 mg; 0.897 mmol) was dissolved in a mixture of ethanol (8 mL) and water (2 mL). Ammonium chloride (24 mg; 0.45 mmol) and iron powder (501 mg; 8.97 mmol) were added and the mixture was stirred with heating to 75° C. under a nitrogen atmosphere for 4 hours. The mixture was allowed to cool, diluted with ethyl acetate (50 mL) and filtered through a pad of Celite. The solution was concentrated under reduced pressure to give 1-benzyl-3-iodo-1H-indazol-4-amine (313 mg) as a pale yellow oil.

Step H: Preparation of N-(1-benzyl-3-iodo-1H-indazol-4-yl)-7-(2-methoxyethoxy)imidazo[1,2-a]pyridine-3-carboxamide: 7-(2-M ethoxyethoxy)imidazo[1,2-a]pyridine-3-carboxylic acid (150 mg; 0.635 mmol) was suspended in methylene chloride (2 mL), with stirring, under an atmosphere of dry nitrogen. Oxalyl chloride (0.698 mmol) was added as a 2N solution in dichloromethane (0.35 mL). A catalytic amount of dimethylformamide (1 drop) was added. The mixture was stirred until effervescence had ceased (30 minutes). 1-Benzyl-3-iodo-1H-indazol-4-amine (product of step G) (222 mg; 0.635 mmol) was added as a solution in dichloromethane (2 mL). Diisopropylethylamine (213 mg; 0.29 mL; 1.65 mmol) was added and the mixture was stirred under nitrogen in a sealed vessel for 24 hours. A thick suspension formed. The mixture was diluted with diethyl ether (20 mL) and the solids were collected by filtration. The solids were washed with ether and water and then dried under vacuum. This gave the desired product, N-(1-Benzyl-3-iodo-1H-indazol-4-yl)-7-(2-methoxyethoxy)imidazo[1,2-a]pyri-

Example 2

N-(1-Benzyl-3-ethyl-1H-indazol-4-yl)-7-(2-methoxyethoxy)imidazo[1,2-a]pyridine-3-carboxamide

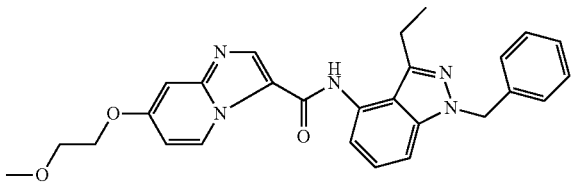 [SMILES: CCc1nn(Cc2ccccc2)c2cccc(NC(=O)c3cnc4cc(OCCOC)ccn34)c12]

Step A: Preparation of 1-benzyl-3-ethyl-4-nitro-1H-indazole: To a mixture of 1-benzyl-3-iodo-4-nitro-1H-indazole (304 mg, 0.802 mmol) (prepared as in Example 1, steps E-F) and 1,1'-Bis(diphenylphosphino)ferrocene-palladium(II) dichloride dichloromethane complex (196 mg, 0.241 mmol) in dioxane (4.0 mL) under an atmosphere of dry nitrogen was added a solution of diethylzinc (1.6 mL, 1.60 mmol; 1 molar in hexane) with magnetic stirring. The mixture was heated at reflux for 2 hours. After allowing to cool methanol (1 mL) was added followed by dichloromethane (30 mL) and the mixture was stirred for 30 minutes. The mixture was transferred to a separatory funnel and washed with water (30 mL). The organic phase was dried over magnesium sulfate, filtered and concentrated under vacuum. The crude product was purified by column chromatography on silica, eluting with 15-20% ethyl acetate in hexanes. Fractions containing product were concentrated under reduced pressure to give 1-benzyl-3-ethyl-4-nitro-1H-indazole (46 mg).

Step B: Preparation of 1-benzyl-3-ethyl-1H-indazol-4-amine: A mixture of 1-benzyl-3-ethyl-4-nitro-1H-indazole (46.0 mg, 0.164 mmol), iron powder (91.3 mg, 1.64 mmol) and ammonium chloride (4.4 mg, 0.082 mmol) was stirred in a 4:1 mixture of ethanol and water (5 mL) with heating to 85° C. for 60 minutes. The solvent was removed under reduced pressure. Ethyl acetate (4 mL) and triethylamine (1 mL) was added and the mixture was heated for 15 minutes at 85° C. After cooling, the mixture was filtered through glass fiber filter paper, rinsing with methanol, dichloromethane and ethyl acetate. The filtrate was concentrated under reduced pressure to provide 1-benzyl-3-ethyl-1H-indazol-4-amine as an oil (40 mg).

Step C: Preparation of N-(1-benzyl-3-ethyl-1H-indazol-4-yl)-7-(2-methoxyethoxy)imidazo[1,2-a]pyridine-3-carboxamide: To a magnetically stirred suspension of 7-(2-methoxyethoxy)imidazo[1,2-a]pyridine-3-carboxylic acid (32.1 mg, 0.136 mmol) (prepared as in Example 1, steps A-D) in dry dichloromethane (1.5 mL), in a sealed vial, was added dry N,N-dimethylformamide (5 µL). The stirred mixture was cooled to 5° C. using ice bath. A solution of oxalyl chloride (86.8 µL, 0.174 mmol; 2M in dichloromethane) was added and the mixture was stirred for 10 minutes, occasionally allowing the resulting gases to vent. To the resulting solution was added 1-benzyl-3-ethyl-1H-indazol-4-amine (40 mg, 0.159 mmol) and triethylamine (30.2 µL, 0.217 mmol). The mixture was allowed to warm to ambient temperature and stirred for 16 hours. The mixture was evaporated to dryness under a stream of nitrogen. The resulting residue was purified using preparative thin layer chromatography, eluting with 5% methanol in dichloromethane. The material was further purified with a second preparative thin layer chromatography, eluting with 8% methanol in chloroform containing 0.5% ammonium hydroxide solution to provide N-(1-benzyl-3-ethyl-1H-indazol-4-yl)-7-(2-methoxyethoxy)imidazo[1,2-a]pyridine-3-carboxamide (12 mg). MS (APCI), positive scan, m/z=470.3 (M+H).

Example 3

N-(1-Benzyl-3-cyclopropyl-1H-indazol-4-yl)-7-(2-methoxyethoxy)imidazo[1,2-a]pyridine-3-carboxamide

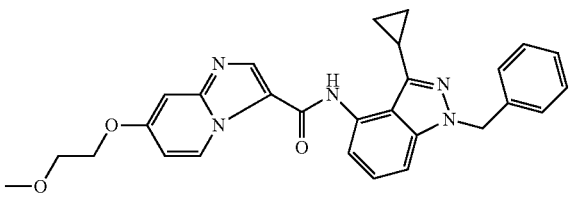 [SMILES: COCCOc1ccn2c(C(=O)Nc3cccc4c3c(C3CC3)nn4Cc3ccccc3)cnc2c1]

Step A: Preparation of 1-benzyl-4-nitro-1H-indazole: To a solution of 4-nitro-1H-indazole (1.00 g; 6.13 mmol) in dry DMF (15 mL) under an atmosphere of dry nitrogen was added potassium carbonate (1.69 g; 12.3 mmol) and benzyl bromide (1.15 g; 6.74 mmol). The mixture was stirred at ambient temperature for 24 hours. Water (50 mL) was added and the mixture was extracted with ethyl acetate. The combined organic extracts were dried over sodium sulfate and filtered. The solvent was removed under reduced pressure to give a brown solid which was a mixture of two regioisomers. The desired isomer was separated by chromatography on silica (Biotage SNAP column, 100 g), eluting with hexane/ethyl acetate (20:1 to 10:1 to 5:1). The desired (N1) regioisomer was the first to elute. The fractions containing the desired product were evaporated under reduced pressure to give 1-benzyl-4-nitro-1H-indazole (730 mg) as a yellow solid.

Step B: Preparation of 1-benzyl-3-bromo-4-nitro-1H-indazole: To a solution of 1-benzyl-4-nitro-1H-indazole (350 mg, 1.38 mmol) in acetic acid (5 mL), in a reaction vial was added bromine (265 mg, 1.66 mmol). The reaction vial was sealed and heated to 80° C., with magnetic stirring, for 2 hours. The mixture was allowed to cool. Saturated aqueous sodium bicarbonate solution was added (sufficient for the mixture to reach pH 8). The resulting solids were collected by filtration and washed with water. The material was dried under vacuum to give 1-benzyl-3-bromo-4-nitro-1H-indazole (455 mg).

Step C: Preparation of 1-benzyl-3-cyclopropyl-4-nitro-1H-indazole: To a reaction vial was added 1-benzyl-3-bromo-4-nitro-1H-indazole (100 mg, 0.301 mmol), cyclopropylboronic acid (33.6 mg, 0.391 mmol) and potassium phosphate (192 mg, 0.903 mmol). Toluene (1.5 mL) and water (0.1 mL) were added. The mixture was purged with argon for 30 minutes. Palladium (II) acetate (3.38 mg, 0.0151 mmol) and tri-cyclohexyl phosphine (8.44 mg, 0.0301 mmol) were added. The reaction vessel was purged with argon and sealed. The mixture was heated at 100° C. for 24 hours. The mixture was filtered through glass fiber filter paper, washing with ethyl acetate and methanol followed by concentration under reduced pressure. The material was purified by preparative chromatography on silica, eluting with hexane/ethyl acetate (5:1). The band containing the desired product was isolated and concentrated under reduced pressure to give 1-benzyl-3-cyclopropyl-4-nitro-1H-indazole (60.5 mg).

Step D: Preparation of 1-benzyl-3-cyclopropyl-1H-indazol-4-amine: To a reaction flask was added 1-benzyl-3-cyclopropyl-4-nitro-1H-indazole (60.0 mg, 0.205 mmol), iron powder (114 mg, 2.05 mmol) and ammonium chloride (10.9 mg, 0.205 mmol). Ethanol (0.8 mL) and water (0.2 mL) were added and the mixture was heated at 85° C. with stirring for 60 minutes. The solvent was removed under reduced pressure. Ethyl acetate (0.8 mL) and triethylamine (0.2 mL) was added and the mixture was heated at 60° C. for 10 minutes. The mixture was filtered through glass fiber filter paper, washing with methanol and ethyl acetate. The filtrate was concentrated under reduced pressure. The material was purified by preparative chromatography, eluting with 3% methanol in dichloromethane, containing 0.5% ammonium hydroxide solution to give 1-benzyl-3-cyclopropyl-1H-indazol-4-amine (36 mg).

Step E: Preparation of N-(1-benzyl-3-cyclopropyl-1H-indazol-4-yl)-7-(2-methoxyethoxy)imidazo[1,2-a]pyridine-3-carboxamide: To a magnetically stirred, ice cooled, suspension of 7-(2-methoxyethoxy)imidazo[1,2-a]pyridine-3-carboxylic acid (29.5 mg, 0.125 mmol) (prepared as in Example 1, steps A-D) in dichloromethane (1 mL) was added N,N-dimethylformamide (5 μL) followed by oxalyl chloride (79.7 μL, 0.159 mmol; 2M solution in dichloromethane). The mixture was stirred in a sealed vial and allowed to warm to ambient temperature. The vial was occasionally vented to allow gases to evolve. After 30 minutes a solution of 1-benzyl-3-cyclopropyl-1H-indazol-4-amine (35.0 mg, 0.133 mmol) in dichloromethane was added followed by triethylamine (27.8 μL; 0.199 mmol). The mixture was stirred for 24 hours and then concentrated under reduced pressure. The material was purified by preparative thin layer chromatography, eluting with 10% methanol in dichloromethane. Further purification was carried out eluting with hexane/ethyl acetate (3:1). The desired band was isolated and concentrated to give N-(1-benzyl-3-cyclopropyl-1H-indazol-4-yl)-7-(2-methoxyethoxy)imidazo[1,2-a]pyridine-3-carboxamide (17.5 mg). MS (APCI), positive scan, m/z=482.3 (M+H).

Example 4

N-(1-Benzyl-5-chloro-3-ethyl-1H-indazol-4-yl)-7-(2-methoxyethoxy)imidazo[1,2-a]pyridine-3-carboxamide

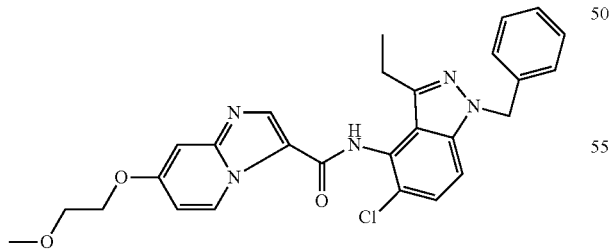

Step A: Preparation of 1-benzyl-5-chloro-3-ethyl-1H-indazol-4-amine: To a reaction vial was added 1-benzyl-3-ethyl-1H-indazol-4-amine (20.0 mg, 0.0796 mmol) (prepared as in Example 2, steps A-B), N-chlorosuccinimide (12.8 mg, 0.0955 mmol) and acetonitrile (0.4 mL). The reaction vial was sealed and heated, with magnetic stirring, at 60° C. for 4 hours. The mixture was stirred at ambient temperature for 16 hours. The solvent was removed under a stream of nitrogen. The resulting material was purified using preparative thin layer chromatography on silica, eluting with 5% methanol in chloroform containing 0.5% ammonium chloride solution. The desired mono-chlorination product, 1-benzyl-5-chloro-3-ethyl-1H-indazol-4-amine (MS, APCI, m/z=286.1, M+H) was isolated as lower eluting component (8.7 mg).

Step B: Preparation of N-(1-benzyl-5-chloro-3-ethyl-1H-indazol-4-yl)-7-(2-methoxyethoxy)imidazo[1,2-a]pyridine-3-carboxamide: To a magnetically stirred, ice cooled, suspension of 7-(2-methoxyethoxy)imidazo[1,2-a]pyridine-3-carboxylic acid (6.76 mg, 0.0286 mmol) (prepared as in Example 1, steps A-D) in dichloromethane (1 mL) was added N,N-dimethylformamide (1 μL) followed by oxalyl chloride (18.3 μL, 0.0365 mmol; 2M solution in dichloromethane). The mixture was allowed to warm to ambient temperature with occasional venting to allow gases to evolve. After stirring for 30 minutes, 1-benzyl-5-chloro-3-ethyl-1H-indazol-4-amine (8.70 mg, 0.0304 mmol) was added as a solution in dichloromethane (0.5 mL). The mixture was stirred for 60 minutes and then concentrated under reduced pressure. The material was purified using preparative thin layer chromatography on silica, eluting with 5% methanol in dichloromethane to give N-(1-benzyl-5-chloro-3-ethyl-1H-indazol-4-yl)-7-(2-methoxyethoxy)imidazo[1,2-a]pyridine-3-carboxamide (5.4 mg). MS (APCI), positive scan, m/z=504.3 (M+H).

Example 5

N-(3-Ethyl-1-((6-methylpyridin-2-yl)methyl)-1H-indazol-4-yl)imidazo[1,2-a]pyridine-3-carboxamide

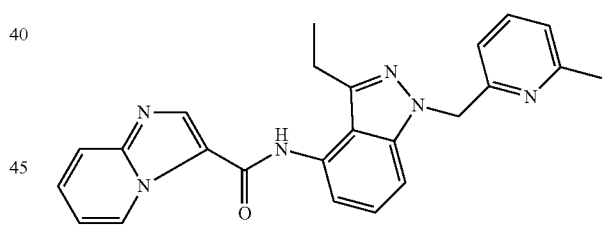

Step A: Preparation of 2-(bromomethyl)-6-methylpyridine: To an ice cooled a solution of (6-methylpyridin-2-yl)methanol (400 mg, 3.25 mmol) in dichloromethane (16 mL) under an atmosphere of dry nitrogen was added triphenylphosphine (1278 mg, 4.87 mmol) and carbon tetrabromide (1616 mg, 4.87 mmol). The mixture was stirred for 1 hour. The solvent was removed under reduced pressure and the residue was purified by chromatography on silica, eluting with 2-4% methanol in dichloromethane to give 2-(bromomethyl)-6-methylpyridine as an oil (402 mg).

Step B: Preparation of 3-iodo-1-((6-methylpyridin-2-yl)methyl)-4-nitro-1H-indazole: To a solution of 3-iodo-4-nitro-1H-indazole (172 mg, 0.596 mmol) (prepared as in Example 1, step E) in dry N,N-dimethylformamide (3 mL) under an atmosphere of dry nitrogen was added 2-(bromomethyl)-6-methylpyridine (122 mg, 0.656 mmol) and potassium carbonate (165 mg, 1.19 mmol) with magnetic stirring. The mixture was stirred at ambient temperature for 3 days. The reaction mixture was diluted with water (20 mL) and extracted into ethyl acetate. The organic phases were combined, washed with saturated sodium chloride solution, dried over sodium sulfate, filtered and concentrated under reduced pressure. The resulting material was purified using preparative chromatography on silica, eluting with hexane/ethyl acetate (3:1) to give 3-iodo-1-((6-methylpyridin-2-yl)methyl)-4-nitro-1H-indazole (213 mg).

Step C: Preparation of 1-((6-methylpyridin-2-yl)methyl)-4-nitro-3-vinyl-1H-indazole: To a reaction vial was added 3-iodo-1-((6-methylpyridin-2-yl)methyl)-4-nitro-1H-indazole (216 mg, 0.548 mmol) and potassium trifluoro(vinyl)borate (156 mg, 1.64 mmol). Isopropanol (2 mL) and tetrahydrofuran (0.5 mL) were added. Argon was bubbled through the mixture for 20 minutes. Triethylamine (229 µL, 1.64 mmol) and 1,1'-bis(diphenylphosphino)ferrocene-palladium(II)dichloride dichloromethane complex (44.8 mg, 0.0548 mmol) were added. The vial was sealed and the mixture was heated at 90-100° C. for 3 hours. The mixture was allowed to cool and filtered through glass fiber filter paper, washing with ethyl acetate. The solution was concentrated under reduced pressure. The residue was dissolved in chloroform (30 mL) and washed with water (10 mL). The solution was dried over magnesium sulfate, filtered and concentrated under reduced pressure to give 1-((6-methylpyridin-2-yl)methyl)-4-nitro-3-vinyl-1H-indazole as an oil (141 mg).

Step D: Preparation of 3-ethyl-1-((6-methylpyridin-2-yl)methyl)-1H-indazol-4-amine: A mixture of 1-((6-methylpyridin-2-yl)methyl)-4-nitro-3-vinyl-1H-indazole (161 mg, 0.547 mmol) and 20% palladium hydroxide on carbon (38.4 mg, 0.0547 mmol) was stirred in methanol (3 mL) under an atmosphere of hydrogen for 3 hours. The mixture was diluted with methanol and filtered through glass fiber filter paper. The filtrate was concentrated under reduced pressure to give 3-ethyl-1-((6-methylpyridin-2-yl)methyl)-1H-indazol-4-amine (142 mg).

Step E: Preparation of N-(3-Ethyl-1-((6-methylpyridin-2-yl)methyl)-1H-indazol-4-yl)imidazo[1,2-a]pyridine-3-carboxamide: To a stirred suspension of imidazo[1,2-a]pyridine-3-carboxylic acid (36.5 mg, 0.225 mmol) in dichloromethane (0.6 mL) was added N,N-dimethylformamide. Oxalyl chloride (84.5 µL, 0.169 mmol) was added and the mixture was stirred in a sealed vessel with ice cooling. The cooling was removed and the mixture was stirred for 3 hours with occasional venting to allow gases to escape. Diisopropylethylamine (21.6 µL, 0.124 mmol) and 3-ethyl-((6-methylpyridin-2-yl)methyl)-1H-indazol-4-amine (30 mg, 0.113 mmol) were added. The mixture was stirred for 30 minutes and then concentrated under reduced pressure. The material was purified using preparative thin layer chromatography, eluting with 10% methanol in dichloromethane containing 0.5% ammonium hydroxide solution. A second purification eluting with 5% methanol in ethyl acetate containing 0.5% ammonium hydroxide solution was carried out to provide N-(3-Ethyl-1-((6-methylpyridin-2-yl)methyl)-1H-indazol-4-yl) imidazo[1,2-a]pyridine-3-carboxamide (12.5 mg). MS (APCI), positive scan, m/z=411.3 (M+H).

Example 6

N-(3-ethyl-1-((2-methoxy-6-methylpyridin-3-yl)methyl)-1H-indazol-4-yl)imidazo[1,2-a]pyridine-3-carboxamide dihydrochloride

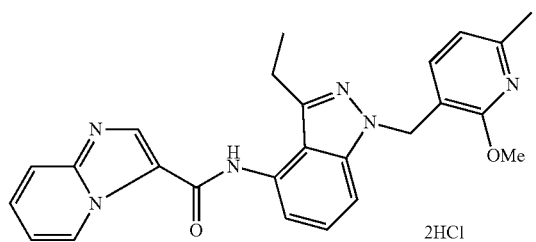 [SMILES: CCc1nn(Cc2ccc(C)nc2OC)c2cccc(NC(=O)c3cnc4ccccn34)c12]

Step A: Preparation of methyl 2-methoxy-6-methylnicotinate: To a stirred mixture of 2-hydroxy-6-methylnicotinic acid (5.00 g, 32.7 mmol) in chloroform (160 mL) under an atmosphere of nitrogen was added silver carbonate (9.00 g, 32.7 mmol) and methyl iodide (6.11 mL, 98.0 mmol). The reaction mixture was heated at 65° C. for 16 hours. The mixture was allowed to cool and filtered through Celite® and the filtrate was concentrated under reduced pressure to give methyl 2-methoxy-6-methylnicotinate (5.60 g) which was used without purification.

Step B: Preparation of (2-methoxy-6-methylpyridin-3-yl)methanol: A solution of methyl 2-methoxy-6-methylnicotinate (5.60 g, 30.9 mmol) in dry tetrahydrofuran (155 mL, 30.9 mmol) under an atmosphere of nitrogen was cooled in an ice bath. Lithium aluminum hydride (1.23 g, 30.9 mmol) was added as a slurry in tetrahydrofuran and the mixture was stirred with cooling in an ice bath for 75 minutes. The reaction mixture was diluted with tetrahydrofuran (30 mL). Some Celite® was added followed by sodium sulfate decahydrate to quench. The mixture was filtered and concentrated under vacuum to give (2-methoxy-6-methylpyridin-3-yl)methanol (4.7 g) which was used without purification.

Step C: Preparation of 3-(bromomethyl)-2-methoxy-6-methylpyridine: To a solution of (2-methoxy-6-methylpyridin-3-yl)methanol (4.7 g, 30.7 mmol) in dichloromethane (150 mL) was added triphenylphosphine (12.1 g, 46.0 mmol). The mixture was cooled in an ice bath with stirring under an atmosphere of nitrogen. Carbon tetrabromide (15.3 g; 46.0 mmol) was added and the mixture was stirred for 90 minutes. The mixture was concentrated under reduced pressure and purified using column chromatography on silica, eluting with dichloromethane/hexanes (1:1) to give 3-(bromomethyl)-2-methoxy-6-methylpyridine (2.0 g).

Step D: Preparation of 3-iodo-1-((2-methoxy-6-methylpyridin-3-yl)methyl)-4-nitro-1H-indazole: A mixture of 3-(bromomethyl)-2-methoxy-6-methylpyridine (500 mg, 2.314 mmol) and 3-iodo-4-nitro-1H-indazole (668.8 mg, 2.314 mmol) (prepared as in Example 1, step E) was dissolved in dry N,N-dimethylformamide (11.6 mL) with stirring under an atmosphere of nitrogen. Potassium carbonate (479.7 mg, 3.471 mmol) was added and the mixture was stirred at ambient temperature for 16 hours. The mixture was diluted with water (50 mL) and extracted into ethyl acetate. The combined organic extracts were washed with brine and dried over sodium sulfate. The solution was filtered and concentrated under reduced pressure to give 3-iodo-1-((2-methoxy-6-methylpyridin-3-yl)methyl)-4-nitro-1H-indazole (1.0 g) which was used without purification.

Step E: Preparation of 1-((2-methoxy-6-methylpyridin-3-yl)methyl)-4-nitro-3-vinyl-1H-indazole: A solution of 3-iodo-1-((2-methoxy-6-methylpyridin-3-yl)methyl)-4-nitro-1H-indazole (982 mg, 2.31 mmol) in a 4:1 mixture of isopropyl alcohol/tetrahydrofuran (10 mL) was stirred under an argon atmosphere. Argon was bubbled through the solution for 20 minutes. Triethylamine (968 μL, 6.94 mmol), 1,1'-bis(diphenylphosphino)ferrocene-palladium(II)dichloride dichloromethane complex (189 mg, 0.231 mmol) and potassium trifluoro(vinyl)borate (659 mg, 6.94 mmol) were added to the solution. The reaction mixture was heated at 90° C. for 24 hour. The mixture was allowed to cool and then filtered through Celite®, rinsing with ethyl acetate. The filtrate was concentrated under reduced pressure. The material was dissolved in ethyl acetate (50 mL), transferred to a reparatory funnel and washed with water and brine. The solution was dried over sodium sulfate, filtered and concentrated under reduced pressure. The material was purified using column chromatography on silica, eluting with 15-20% ethyl acetate in hexanes to give 1-((2-methoxy-6-methylpyridin-3-yl)methyl)-4-nitro-3-vinyl-1H-indazole (395 mg).

Step F: Preparation of 3-ethyl-1-((2-methoxy-6-methylpyridin-3-yl)methyl)-1H-indazol-4-amine: 1-((2-M ethoxy-6-methylpyridin-3-yl)methyl)-4-nitro-3-vinyl-1H-indazole (395 mg, 1.22 mmol) and palladium hydroxide on carbon (171 mg, 0.244 mmol; 20%) were added to a hydrogenation flask. Methanol (6 mL) was added along with a small amount of dichloromethane. The reaction flask was evacuated and purged with nitrogen prior to being shaken on a Parr apparatus under an atmosphere of hydrogen at 40 psi for 7 hours. The mixture was filtered through Celite, rinsing with methanol and the filtrated was concentrated under reduced pressure. The material was purified using preparative thin layer chromatography on silica, eluting with 10% methanol in dichloromethane containing 0.5% ammonium hydroxide solution. Further purification was carried out using column chromatography on silica, eluting with 1% methanol in dichloromethane containing 0.5% ammonium hydroxide solution to provide 3-ethyl-1-((2-methoxy-6-methylpyridin-3-yl)methyl)-1H-indazol-4-amine (108 mg). Some material was isolated where the nitro group had not been completely reduced (186 mg). This material was dissolved in ethanol (3 mL). Iron powder (318 mg; 5.70 mmol) and ammonium chloride (15.2 mg; 0.285 mmol) were added and the mixture was heated at reflux for 1 hour. The mixture was allowed to cool and filtered through glass fiber filter paper rinsing with ethanol. The solution was concentrated under reduced pressure and purified using preparative thin layer chromatography, eluting with 2% methanol in dichloromethane containing 0.25% ammonium hydroxide solution to provide an additional 108 mg of 3-ethyl-1-((2-methoxy-6-methylpyridin-3-yl)methyl)-1H-indazol-4-amine.

Step G: Preparation of N-(3-ethyl-1-((2-methoxy-6-methylpyridin-3-yl)methyl)-1H-indazol-4-yl)imidazo[1,2-a]pyridine-3-carboxamide dihydrochloride: Imidazo[1,2-a]pyridine-3-carboxylic acid (118 mg, 0.729 mmol) was added to a mixture of dichloromethane (4 mL) and thionyl chloride (1 mL; 13.7 mmol). The mixture was stirred at ambient temperature under an inert atmosphere for 3 hours. The mixture was concentrated under reduced pressure. To this material was added 3-ethyl-1-((2-methoxy-6-methylpyridin-3-yl)methyl)-1H-indazol-4-amine suspended in tetrahydrofuran (4 mL) and 1,2-dichloroethane (4 mL). The mixture was heated with stirring at 75° C. for 30 minutes under an inert atmosphere. After allowing to cool the mixture was diluted with dichloromethane (30 mL) in a reparatory funnel. The solution was washed with aqueous sodium bicarbonate solution, dried over sodium sulfate, filtered and concentrated under reduced pressure. The material was purified using column chromatography on silica, eluting with 5% methanol in dichloromethane containing 0.5% ammonium hydroxide solution to give N-(3-ethyl-1-((2-methoxy-6-methylpyridin-3-yl)methyl)-1H-indazol-4-yl)imidazo[1,2-a]pyridine-3-carboxamide (57.6 mg). MS (APCI), positive scan, m/z=441.2 (M+H). A portion of this material (8.5 mg) was converted to the dihydrochloride salt: N-(3-ethyl-1-((2-methoxy-6-methylpyridin-3-yl)methyl)-1H-indazol-4-yl)imidazo[1,2-a]pyridine-3-carboxamide dihydrochloride by dissolving in a mixture of methanol and dichloromethane followed by addition of 1 drop of concentrated hydrochloric acid. Removal of the solvent under reduced pressure gave the desired salt (9.9 mg).

Example 7

N-(3-ethyl-1-((1-(2-(piperazin-1-yl)ethyl)-1H-pyrazol-3-yl)methyl)-1H-indazol-4-yl)imidazo[1,2-a]pyridine-3-carboxamide trihydrochloride

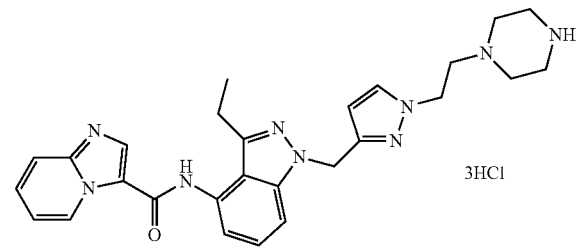 [SMILES: CCc1nn(Cc2ccn(CCN3CCNCC3)n2)c2cccc(NC(=O)c3cnc4ccccn34)c12]

Step A: Preparation of N-(1-((1H-pyrazol-3-yl)methyl)-3-ethyl-1H-indazol-4-yl)imidazo[1,2-a]pyridine-3-carboxamide: Prepared according to the method of Example 39, Step H.

Step B: Preparation of tert-butyl 4-(2-(3-((3-ethyl-4-(imidazo[1,2-a]pyridine-3-carboxamido)-1H-indazol-1-yl)methyl)-1H-pyrazol-1-yl)ethyl)piperazine-1-carboxylate: To a solution of N-(1-((1H-pyrazol-3-yl)methyl)-3-ethyl-1H-indazol-4-yl)imidazo[1,2-a]pyridine-3-carboxamide (40.0 mg; 0.104 mmol) in dry DMF (0.5 mL) was added tert-butyl 4-(2-bromoethyl)piperazine-1-carboxylate (30.4 mg; 0.104 mmol) and cesium hydroxide hydrate (17.4 mg; 0.104 mmol). The mixture was stirred under a nitrogen atmosphere for 30 minutes. The mixture was filtered, washing with methanol and ethyl acetate, and the solvent was removed under reduced pressure. The residue (a mixture of two regioisomers) was purified by preparative thin layer chromatography on silica, eluting with 10% methanol in dichloromethane. The desired isomer tert-butyl 4-(2-(3-((3-ethyl-4-(imidazo[1,2-a]pyridine-3-carboxamido)-1H-indazol-1-yl)methyl)-1H-pyrazol-1-yl)ethyl)piperazine-1-carboxylate was isolated (21.5 mg) along with some of the alternate isomer.

Step C: Preparation of N-(3-ethyl-1-((1-(2-(piperazin-1-yl)ethyl)-1H-pyrazol-3-yl)methyl)-1H-indazol-4-yl)imidazo[1,2-a]pyridine-3-carboxamide trihydrochloride: To a solution of tert-butyl 4-(2-(3-((3-ethyl-4-(imidazo[1,2-a]pyridine-3-carboxamido)-1H-indazol-1-yl)methyl)-1H-pyrazol-1-yl)ethyl)piperazine-1-carboxylate (21.5 mg; 0.0360 mmol) in dichloromethane (1 mL) was added trifluoroacetic acid (1 mL). The mixture was stirred for 1 hour. The solvent was removed under reduced pressure and the residue was dissolved in a mixture of methanol and dichloromethane. Ammonium hydroxide solution was added to neutralize. The material was purified by preparative thin layer chromatography on silica, eluting with 15% methanol in dichloromethane containing 0.5% ammonium hydroxide solution. The isolated product was dissolved in a mixture of methanol and ethyl acetate and treated with hydrogen chloride (1 mL; 2M in ether). Removal of solvent under reduced pressure followed by high vacuum gave N-(3-ethyl-1-((1-(2-(piperazin-1-yl)ethyl)-1H-pyrazol-3-yl)methyl)-1H-indazol-4-yl)imidazo[1,2-a]pyridine-3-carboxamide trihydrochloride (9.5 mg). MS (APCI), positive scan, m/z=498.3 (M+H).

Example 8

N-(1-((1-(2,3-dihydroxypropyl)-1H-pyrazol-5-yl)methyl)-3-ethyl-1H-indazol-4-yl)imidazo[1,2-a]pyridine-3-carboxamide hydrochloride

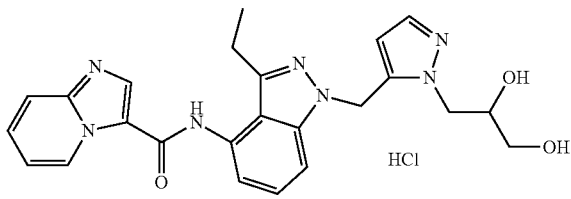 [SMILES: CCc1nn(Cc2ccnn2CC(O)CO)c2cccc(NC(=O)c3cnc4ccccn34)c12 ; Cl]

Step A: Preparation of N-(1-((1-((2,2-dimethyl-1,3-dioxolan-4-yl)methyl)-1H-pyrazol-5-yl)methyl)-3-ethyl-1H-indazol-4-yl)imidazo[1,2-a]pyridine-3-carboxamide: To a solution of N-(1-((1H-pyrazol-3-yl)methyl)-3-ethyl-1H-indazol-4-yl)imidazo[1,2-a]pyridine-3-carboxamide (40 mg, 0.104 mmol) in N,N-dimethylformamide (0.5 mL) was added 4-(bromomethyl)-2,2-dimethyl-1,3-dioxolane (20.2 mg, 0.104 mmol) and cesium hydroxide hydrate (17.4 mg, 0.104 mmol). The mixture was stirred for 16 hours at ambient temperature, filtered, washing with methanol and ethyl acetate, and concentrated under a stream of nitrogen. The resulting material was purified using preparative thin layer chromatography on silica, eluting with 10% methanol in dichloromethane. The isolated product (22.5 mg) was a 7:3 mixture of two regioisomers, N-(1-((1-((2,2-dimethyl-1,3-dioxolan-4-yl)methyl)-1H-pyrazol-5-yl)methyl)-3-ethyl-1H-indazol-4-yl)imidazo[1,2-a]pyridine-3-carboxamide and N-(1-((1-(2,3-dihydroxypropyl)-1H-pyrazol-3-yl)methyl)-3-ethyl-1H-indazol-4-yl)imidazo[1,2-a]pyridine-3-carboxamide. This material was continued to the next step as a mixture.

Step B: Preparation of N-(1-((1-(2,3-dihydroxypropyl)-1H-pyrazol-5-yl)methyl)-3-ethyl-1H-indazol-4-yl)imidazo[1,2-a]pyridine-3-carboxamide hydrochloride: To a solution of the mixture obtained from Step A (22.5 mg; 0.0450 mmol) in tetrahydrofuran (1 mL) was added hydrogen chloride (4M in 1,4-dioxane; 0.5 mL; 2 mmol). The mixture was stirred for 3 hours and then evaporated under a stream of nitrogen. The residue was dissolved in a mixture of methanol and dichloromethane and neutralized by the addition of ammonium hydroxide solution. Purification was carried out using preparative thin layer chromatography on silica, eluting with 15% methanol in dichloromethane containing 0.5% ammonium hydroxide solution. The desired isomer was isolated, dissolved in a mixture of dichloromethane and methanol and treated with hydrogen chloride (2M in ether) to convert to the salt: N-(1-((1-(2,3-dihydroxypropyl)-1H-pyrazol-5-yl)methyl)-3-ethyl-1H-indazol-4-yl)imidazo[1,2-a]pyridine-3-carboxamide hydrochloride (13.3 mg). MS (APCI), positive scan, m/z=460.2 (M+H).

Example 9

N-(1-((6-(2-aminoethoxy)pyridin-2-yl)methyl)-3-ethyl-1H-indazol-4-yl)imidazo[1,2-a]pyridine-3-carboxamide dihydrochloride

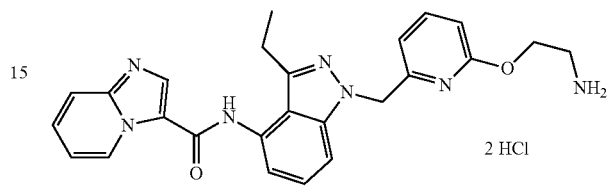

Step A: Preparation of tert-butyl 2-(6-((3-ethyl-4-(imidazo[1,2-a]pyridine-3-carboxamido)-1H-indazol-1-yl)methyl)pyridin-2-yloxy)ethylcarbamate: To a solution of N-(3-ethyl-1-((6-hydroxypyridin-2-yl)methyl)-1H-indazol-4-yl)imidazo[1,2-a]pyridine-3-carboxamide (Example 17, Step A; 50 mg, 0.121 mmol) and 2-(tert-butoxycarbonylamino)ethyl methanesulfonate (71 mg, 0.297 mmol) in N,N-dimethylacetamide (2 mL) was added cesium carbonate (79.0 mg, 0.242 mmol). The mixture was heated to 80-85° C. for 90 minutes. After allowing to cool the mixture was diluted with ethyl acetate and methanol, filtered and concentrated under a stream of nitrogen. The material was purified using preparative thin layer chromatography on silica, eluting with 5% methanol and 1% triethylamine in ethyl acetate to give the product 21.9 mg (33%).

Step B: Preparation of N-(1-((6-(2-aminoethoxy)pyridin-2-yl)methyl)-3-ethyl-1H-indazol-4-yl)imidazo[1,2-a]pyridine-3-carboxamide dihydrochloride: To a solution of tert-butyl 2-(6-((3-ethyl-4-(imidazo[1,2-a]pyridine-3-carboxamido)-1H-indazol-1-yl)methyl)pyridin-2-yloxy)ethylcarbamate (21.9 mg, 0.0394 mmol) in ethyl acetate was added hydrogen chloride (1 mL; 4M in dioxane). The mixture was stirred for 30 minutes and the solvent was removed under reduced pressure to give N-(1-((6-(2-aminoethoxy)pyridin-2-yl)methyl)-3-ethyl-1H-indazol-4-yl)imidazo[1,2-a]pyridine-3-carboxamide dihydrochloride (14.3 mg; 69%). MS (APCI), positive scan, m/z=456.1 (M+H).

Example 10

N-(1-((6-(3-aminopropoxy)pyridin-2-yl)methyl)-3-ethyl-1H-indazol-4-yl)imidazo[1,2-a]pyridine-3-carboxamide dihydrochloride

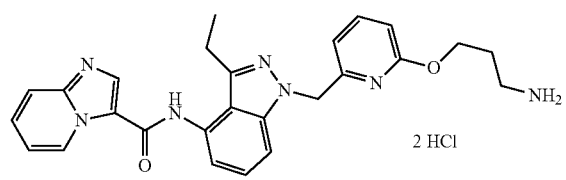 [SMILES: CCc1nn(Cc2cccc(OCCCN)n2)c2cccc(NC(=O)c3cnc4ccccn34)c12]

Step A: Preparation of tert-butyl 3-(6-((3-ethyl-4-(imidazo[1,2-a]pyridine-3-carboxamido)-1H-indazol-1-yl)methyl)pyridin-2-yloxy)propylcarbamate: To a solution of N-(3- ethyl-1-((6-hydroxypyridin-2-yl)methyl)-1H-indazol-4-yl)imidazo[1,2-a]pyridine-3-carboxamide (50 mg, 0.121 mmol) (Prepared as in Example 17, Step A) and 3-(tert-butoxycarbonylamino)propyl methanesulfonate (107 mg, 0.422 mmol) in N,N-dimethylacetamide (2.0 mL) was added cesium carbonate (79.0 mg, 0.242 mmol). The mixture was heated at 80-85° C. for 90 minutes. The mixture was allowed to cool and diluted with ethyl acetate and methanol. The suspension was filtered and concentrated under a stream of nitrogen. The material was purified using preparative thin layer chromatography on silica, eluting with 5% methanol and 1% triethylamine in ethyl acetate to give the product (17.2 mg).

Step B: Preparation of N-(1-((6-(3-aminopropoxy)pyridin-2-yl)methyl)-3-ethyl-1H-indazol-4-yl)imidazo[1,2-a]pyridine-3-carboxamide dihydrochloride: To a solution of tert-butyl 3-(6-((3-ethyl-4-(imidazo[1,2-a]pyridine-3-carboxamido)-1H-indazol-1-yl)methyl)pyridin-2-yloxy)propylcarbamate (17.2 mg, 0.0302 mmol) in ethyl acetate was added hydrogen chloride (1 mL; 4M in dioxane). The mixture was stirred for 30 minutes. The solvent was removed under reduced pressure to give N-(1-((6-(3-aminopropoxy)pyridin-2-yl)methyl)-3-ethyl-1H-indazol-4-yl)imidazo[1,2-a]pyridine-3-carboxamide dihydrochloride (11.6 mg). MS (APCI), positive scan, m/z=470.1 (M+H).

Example 11

N-(1-((6-(3-(dimethylamino)propoxy)pyridin-2-yl)methyl)-3-ethyl-1H-indazol-4-yl)imidazo[1,2-a]pyridine-3-carboxamide dihydrochloride

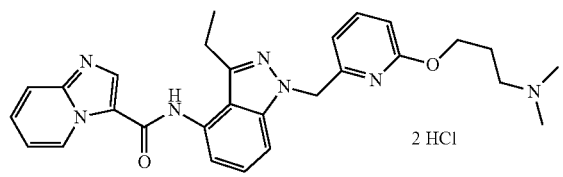 [SMILES: CCc1nn(Cc2cccc(OCCCN(C)C)n2)c2cccc(NC(=O)c3cnc4ccccn34)c12]

To a stirred mixture of N-(1-((6-(3-aminopropoxy)pyridin-2-yl)methyl)-3-ethyl-1H-indazol-4-yl)imidazo[1,2-a]pyridine-3-carboxamide dihydrochloride (10 mg, 0.018 mmol) in dichloromethane (1 mL) was added formaldehyde (0.55 mg, 0.01 mmol; 30% in water) and sodium triacetoxyborohydride (20 mg, 0.092 mmol). The mixture was stirred for 45 minutes at ambient temperature and then filtered, rinsing with dichloromethane and methanol. The solution was concentrated under a stream of nitrogen. The residue was purified using preparative thin layer chromatography on silica, eluting with 15% methanol and 0.5% ammonium hydroxide in dichloromethane to provide the desired product (free base form), which was dissolved in methanol/dichloromethane and treated with 1M hydrogen chloride in ether (0.5 mL). The mixture was concentrated under reduced pressure and dried under high vacuum to give N-(1-((6-(3-(dimethylamino)propoxy)pyridin-2-yl)methyl)-3-ethyl-1H-indazol-4-yl)imidazo[1,2-a]pyridine-3-carboxamide dihydrochloride (1.7 mg). MS (APCI), positive scan, m/z=498.1 (M+H).

Example 12

N-(3-ethyl-1-((6-methylpyridin-2-yl)methyl)-1H-indazol-4-yl)-7-(piperazine-1-carbonyl)imidazo[1,2-a]pyridine-3-carboxamide dihydrochloride

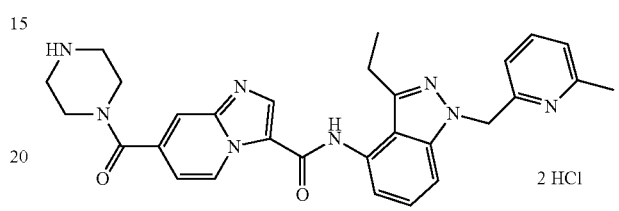

Step A: Preparation of 3-(3-ethyl-1-((6-methylpyridin-2-yl)methyl)-1H-indazol-4-ylcarbamoyl)imidazo[1,2-a]pyridine-7-carboxylic acid: To a solution of ethyl 3-(3-ethyl-1-((6-methylpyridin-2-yl)methyl)-1H-indazol-4-ylcarbamoyl)imidazo[1,2-a]pyridine-7-carboxylate (430 mg, 0.891 mmol) (Example 23) in THF/water (6 mL/1 mL) was added lithium hydroxide (21.3 mg, 0.89 mmol). The mixture was heated at 70° C. with stirring in a sealed tube for 2 hours. The mixture was allowed to cool and hydrogen chloride (0.45 mL, 4M in dioxane) was added. The solvent was removed under reduced pressure to give a mixture of the product and lithium chloride (410 mg) which was carried on directly to the next step.

Step B: Preparation of tert-butyl 4-(3-(3-ethyl-1-((6-methylpyridin-2-yl)methyl)-1H-indazol-4-ylcarbamoyl)imidazo[1,2-a]pyridine-7-carbonyl)piperazine-1-carboxylate: To a solution of 3-(3-ethyl-1-((6-methylpyridin-2-yl)methyl)-1H-indazol-4-ylcarbamoyl)imidazo[1,2-a]pyridine-7-carboxylic acid (50 mg, 0.110 mmol) in dry DMF (0.55 mL) was added tert-butyl piperazine-1-carboxylate (24.6 mg, 0.132 mmol), 1-(3-dimethylaminopropyl)-3-ethylcarbodiimide hydrochloride (31.6 mg, 0.16 mmol), 1-hydroxybenzotriazole (22.3 mg, 0.165 mmol) and triethylamine (23.0 μL, 0.165 mmol). The mixture was stirred at ambient temperature for 12 hours, diluted with dichloromethane and methanol and filtered. The filtrate was concentrated under a stream of nitrogen. The residue was purified using preparative thin layer chromatography, eluting with 8% methanol and 0.5% ammonium hydroxide in dichloromethane to give the product (10.2 mg).

Step C: Preparation of N-(3-ethyl-1-((6-methylpyridin-2-yl)methyl)-1H-indazol-4-yl)-7-(piperazine-1-carbonyl)imidazo[1,2-a]pyridine-3-carboxamide dihydrochloride: To a solution of tert-butyl 4-(3-(3-ethyl-1-((6-methylpyridin-2-yl)methyl)-1H-indazol-4-ylcarbamoyl)imidazo[1,2-a]pyridine-7-carbonyl)piperazine-1-carboxylate (10.2 mg, 0.0164 mmol) in ethyl acetate (1 mL) was added hydrogen chloride (1 mL; 4M in dioxane) and the mixture was stirred for 45 minutes. The solvent was removed under reduced pressure and dried under high vacuum to give N-(3-ethyl-1-((6-methylpyridin-2-yl)methyl)-1H-indazol-4-yl)-7-(piperazine-1- carbonyl)imidazo[1,2-a]pyridine-3-carboxamide dihydrochloride (9.5 mg). MS (APCI), positive scan, m/z=523.3 (M+H).

Example 13

N-(3-ethyl-1-((6-methylpyridin-2-yl)methyl)-1H-indazol-4-yl)-7-(4-methylpiperazine-1-carbonyl)imidazo[1,2-a]pyridine-3-carboxamide dihydrochloride

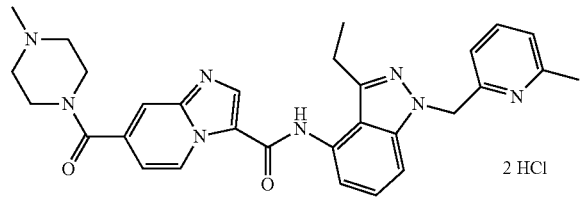 [SMILES: CCc1nn(Cc2cccc(C)n2)c2cccc(NC(=O)c3cnc4cc(C(=O)N5CCN(C)CC5)ccn34)c12]

To a solution of N-(3-ethyl-1-((6-methylpyridin-2-yl)methyl)-1H-indazol-4-yl)-7-(piperazine-1-carbonyl)imidazo[1,2-a]pyridine-3-carboxamide dihydrochloride (Example 12; 5 mg, 0.0084 mmol) in dichloromethane/methanol (1:1; 1 mL) was added an excess of sodium triacetoxyborohydride and formaldehyde solution. The mixture was stirred at ambient temperature for 2 hours. Further excess sodium triacetoxyborohydride and formaldehyde solution were added and the mixture was stirred an additional 0.5 hours. The mixture was concentrated under a stream of nitrogen and the residue was purified using preparative thin layer chromatography on silica, eluting with 15% methanol and 0.5% ammonium hydroxide in dichloromethane to provide the desired product (free base form). This material was dissolved in methanol and filtered. To the filtrate was added hydrogen chloride (1 mL; 2M in ether) and the solvent was evaporated to a residual film under a stream of nitrogen. The material was dried under high vacuum to give N-(3-ethyl-1-((6-methylpyridin-2-yl)methyl)-1H-indazol-4-yl)-7-(4-methylpiperazine-1-carbonyl)imidazo[1,2-a]pyridine-3-carboxamide dihydrochloride (3.3 mg). MS (APCI), positive scan, m/z=537.3 (M+H).

Example 14

N-(3-ethyl-1-((6-(piperazin-1-ylmethyl)pyridin-2-yl)methyl)-1H-indazol-4-yl)imidazo[1,2-a]pyridine-3-carboxamide dihydrochloride

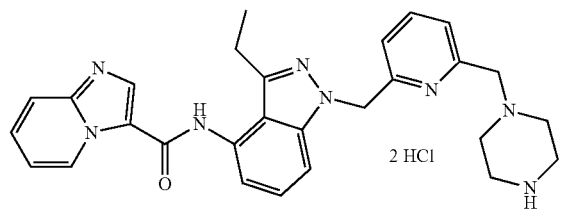 [SMILES: CCc1nn(Cc2cccc(CN3CCNCC3)n2)c2cccc(NC(=O)c3cnc4ccccn34)c12]

Step A: Preparation of N-(1-((6-(1,2-dihydroxyethyl)pyridin-2-yl)methyl)-3-ethyl-1H-indazol-4-yl)imidazo[1,2-a]pyridine-3-carboxamide: To a solution of N-(3-ethyl-1-((6-vinylpyridin-2-yl)methyl)-1H-indazol-4-yl)imidazo[1,2-a]pyridine-3-carboxamide (Example 24, Step B; 40 mg, 0.095 mmol) in acetone/water (2 mL/0.5 mL) was added N-methylmorpholine N-oxide (44 mg, 0.19 mmol), followed by osmium tetroxide (2.5% in tert-butanol, 15 µL). The mixture was stirred for 1 hour and then quenched by the addition of a saturated solution of sodium thiosulfate (1 mL). The mixture was concentrated under reduced pressure to remove acetone and diluted with dichloromethane and saturated sodium chloride solution (5 mL). The phases were separated and the aqueous was extracted with dichloromethane/isopropanol (10:1; 2×10 mL). The combined organic phases were dried over sodium sulfate, filtered and concentrated under reduced pressure to give the product (40 mg).

Step B: Preparation of N-(3-ethyl-1-((6-formylpyridin-2-yl)methyl)-1H-indazol-4-yl)imidazo[1,2-a]pyridine-3-carboxamide: To a slurry of silica gel (200 mg) in dichloromethane (1 mL) was added, drop wise, sodium periodate solution (202 µL, 0.13 mmol; 0.65M in water). The slurry was stirred for 10 minutes and broken up into a fine slurry with a spatula. To this was slowly added N-(1-((6-(1,2-dihydroxyethyl)pyridin-2-yl)methyl)-3-ethyl-1H-indazol-4-yl)imidazo[1,2-a]pyridine-3-carboxamide (40 mg, 0.088 mmol) in dichloromethane (1 mL). The slurry was stirred for 30 minutes, then filtered and washed with dichloromethane (5 mL). The solution was concentrated under reduced pressure to provide the desired product (28 mg).

Step C: Preparation of tert-butyl 4-((6-((3-ethyl-4-(imidazo[1,2-a]pyridine-3-carboxamido)-1H-indazol-1-yl)methyl)pyridin-2-yl)methyl)piperazine-1-carboxylate: To a mixture of N-(3-ethyl-1-((6-formylpyridin-2-yl)methyl)-1H-indazol-4-yl)imidazo[1,2-a]pyridine-3-carboxamide (20 mg, 0.0471 mmol) and sodium triacetoxyborohydride (49.9 mg, 0.236 mmol) in a 1:1 mixture of dichloromethane/methanol (1 mL) was added tert-butyl piperazine-1-carboxylate (10.5 mg, 0.0565 mmol). The mixture was stirred for 30 minutes at ambient temperature. The solvent was removed under reduced pressure and the residue was purified using preparative thin layer chromatography on silica, eluting with 12% methanol and 0.5% ammonium hydroxide in dichloromethane to give the desired product (12.6 mg).

Step D: Preparation of N-(3-ethyl-1-((6-(piperazin-1-ylmethyl)pyridin-2-yl)methyl)-1H-indazol-4-yl)imidazo[1,2-a]pyridine-3-carboxamide dihydrochloride: To a solution of tert-butyl 4-((6-((3-ethyl-4-(imidazo[1,2-a]pyridine-3-carboxamido)-1H-indazol-1-yl)methyl)pyridin-2-yl)methyl)piperazine-1-carboxylate in ethyl acetate was added hydrogen chloride (1 mL; 4M in dioxane) and the mixture was stirred for 45 minutes. The solvent was removed under reduced pressure and the material was dried under high vacuum to give N-(3-ethyl-1-((6-(piperazin-1-ylmethyl)pyridin-2-yl)methyl)-1H-indazol-4-yl)imidazo[1,2-a]pyridine-3-carboxamide dihydrochloride (12 mg). MS (APCI), positive scan, m/z=495.3 (M+H).

Example 15

N-(3-ethyl-1-((6-methoxypyridin-2-yl)methyl)-1H-indazol-4-yl)imidazo[1,2-a]pyridine-3-carboxamide

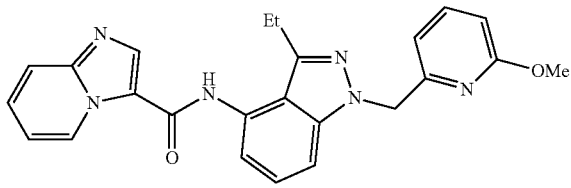 [SMILES: CCc1nn(Cc2cccc(OC)n2)c2cccc(NC(=O)c3cnc4ccccn34)c12]

Step A: Preparation of methyl 6-methoxypicolinate: To 6-hydroxypicolinic acid (4.08 g, 29.3 mmol) in CHCl$_3$ (100 mL) was added iodomethane (9.16 g, 64.5 mmol) and Ag$_2$CO$_3$ (8.90 g, 32.3 mmol). The reaction mixture was covered from light, heated to 60° C. and stirred for 2 days. The reaction mixture was cooled to ambient temperature, filtered through Celite and concentrated to provide the desired product (4.65 g).

Step B: Preparation of (6-methoxypyridin-2-yl)methanol: To methyl 6-methoxypicolinate (4.65 g, 27.8 mmol) in Et$_2$O (100 mL) was added LAH (1.06 g). The reaction mixture was stirred for 4 hours. Celite (10 g) was added, followed by sodium sulfate-decahydrate (5 g). The reaction mixture was filtered and concentrated to provide the desired product (3.36 g).

Step C: Preparation of 2-(bromomethyl)-6-methoxypyridine: To (6-methoxypyridin-2-yl)methanol (3.36 g, 24.1 mmol) in DCM (30 mL) was added perbromomethane (12.0 g, 36.2 mmol) and triphenylphosphine (9.50 g, 36.2 mmol). The reaction mixture was stirred for 1 hour, concentrated and silica gel chromatography (EtOAc/Hexane 1:5) to provide the desired product (4.23 g).

Step D: Preparation of 3-iodo-1-((6-methoxypyridin-2-yl)methyl)-4-nitro-1H-indazole: To 3-iodo-4-nitro-1H-indazole (5.01 g, 17.3 mmol) in DMF (40 mL) was added K$_2$CO$_3$ (4.79 g, 34.7 mmol) and 2-(bromomethyl)-6-methoxypyridine (4.20 g, 20.8 mmol). The reaction mixture was stirred for 4 hours. The reaction mixture was concentrated to remove DMF, diluted with EtOAc and washed with H$_2$O and brine. The organic phase was dried (Na$_2$SO$_4$) and concentrated. Silica gel chromatography (EtOAc/Hexane 1:5) gave the desired product (5.68 g).

Step E: Preparation of 1-((6-methoxypyridin-2-yl)methyl)-4-nitro-3-vinyl-1H-indazole: To 3-iodo-1-((6-methoxypyridin-2-yl)methyl)-4-nitro-1H-indazole (2.65 g, 6.46 mmol) in IPA/THF (40 mL/10 mL) was added potassium vinyltrifluoroborate (1.30 g, 9.69 mmol), triethylamine (1.31 g, 12.9 mmol) and 1,1'-Bis(diphenylphosphino)ferrocene-palladium(II)dichloride dichloromethane complex (0.264 g, 0.323 mmol). The reaction mixture was heated to reflux and stirred for 16 hours. The reaction mixture was cooled to ambient temperature and concentrated to remove solvent. The residue was dissolved with EtOAc (100 mL) and washed with saturated NH$_4$Cl, H$_2$O and brine. The solution was dried (Na$_2$SO$_4$) and concentrated to provide the desired product (1.89 g).

Step F: Preparation of 3-ethyl-1-((6-methoxypyridin-2-yl)methyl)-1H-indazol-4-amine: To 1-((6-methoxypyridin-2-yl)methyl)-4-nitro-3-vinyl-1H-indazole (1.89 g, 6.09 mmol) in MeOH (60 mL) was added Pd(OH)$_2$/C (20 wt %, 400 mg). The reaction mixture was purged with N$_2$ and charge with H$_2$ (45 psi). The reaction mixture was recharged H$_2$ to 45 psi after 45 minute. The reaction was stopped after 5 hours. The reaction mixture was filtered through Celite®, washed with MeOH (200 mL) and concentrated to provide the desired product (1.36 g).

Step G: Preparation of N-(3-ethyl-1-((6-methoxypyridin-2-yl)methyl)-1H-indazol-4-yl)imidazo[1,2-a]pyridine-3-carboxamide: To imidazo[1,2-a]pyridine-3-carboxylic acid (194 mg, 1.20 mmol) in DCM (5 mL) was added thionyl chloride (2 mL). The reaction mixture was stirred for 2 hours and concentrated to give crude acylchloride HCl salt, to which DCE/THF (2 mL/2 mL) and 3-ethyl-1-((6-methoxypyridin-2-yl)methyl)-1H-indazol-4-amine (211 mg, 0.747 mmol) was added. The reaction mixture was heated to 70° C. and stirred for 1 hour. The reaction mixture was diluted with DCM (20 mL) and washed with saturated NaHCO$_3$ aqueous solution. The organic solution was dried over Na$_2$SO$_4$, filtered and concentrated. Silica gel chromatography (DCM/MeOH 10:1) provided the desired product (226 mg). MS (ES+APCI) m/z=427 (M+H).

Example 16

N-(3-ethyl-1-((6-methylpyridin-2-yl)methyl)-1H-indazol-4-yl)-7-(2-morpholinoethoxy)imidazo[1,2-a]pyridine-3-carboxamide hydrochloride

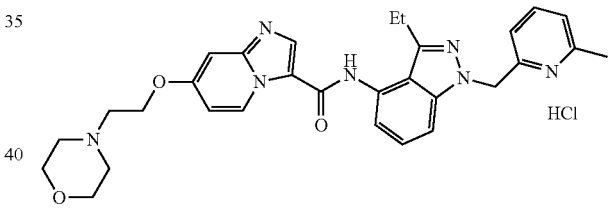

Step A: Preparation of 3-ethyl-1-((6-methylpyridin-2-yl)methyl)-1H-indazol-4-amine: To 1-((6-methylpyridin-2-yl)methyl)-4-nitro-3-vinyl-1H-indazole (28.2 g, 95.8 mmol, Example 5, step C) in EtOH/DCM (300 mL/10 mL) was added palladium hydroxide (15 g, 20% wt). The reaction was purged with N$_2$ and charged with hydrogen to 45 psi. The reaction was recharged during the reaction to 45 psi 4-5 times for the first 30 minutes. After 2 hours, the reaction was stopped, filtered through Celite, and the filter pad was washed with MeOH/DCM/Et$_3$N (1 L, 10:1:1). The filtrate was concentrated and silica gel chromatography (EtOAc/hexanes 1:3) to provide the desired product (22.4 g).

Step B: Preparation of lithium 7-(2-morpholinoethoxy)imidazo[1,2-a]pyridine-3-carboxylate:

Step B1: Preparation of 4-(2-morpholinoethoxy)pyridin-2-amine: 2-Morpholinoethanol (2.2 g, 16.8 mmol) was treated with sodium (116 mg, 5.0 mmol) in a sealed tube and stirred at ambient temperature until homogeneous. 4-Chloropyridin-2-amine (1.1 g, 8.9 mmol) was added and the reaction mixture was heated to 145° C. and stirred in sealed tube for 10 hours. The mixture was cooled to ambient temperature before diluting with ethyl acetate and water. After separation of layers, the aqueous phase was extracted twice more with ethyl acetate. Concentration under vacuum afforded a viscous oil which required purification using a Biotage 40+Silica column eluting with 10% methanol/dichloromethane to give 4-(2-morpholinoethoxy)pyridin-2-amine as a viscous oil which solidified upon further drying under high vacuum (1.4 g).

Step B2: Preparation of ethyl 7-(2-morpholinoethoxy)imidazo[1,2-a]pyridine-3-carboxylate: 4-(2-Morpholinoethoxy)pyridin-2-amine (1.37 g, 6.14 mmol) was dissolved in ethanol (20 mL) in 250 mL round bottom flask. Ethyl 2-chloro-3-oxopropanoate (5% in benzene; 30 mL; Commercial solution from Toronto Research Chemicals Inc.) was added and the mixture was heated to reflux with stirring for 16 hours. The mixture was concentrated under vacuum to give a beige solid (1.31 g). This material was purified using a Biotage silica column (25+) eluting with a gradient from 50-100% ethyl acetate/hexanes over 800 mL followed by a switch to 10% methanol/dichloromethane eluting with 400 mL. Product eluted cleanly after switching to methanol/dichloromethane to give ethyl 7-(2-morpholinoethoxy)imidazo[1,2-a]pyridine-3-carboxylate as a white solid (1 g).

Step B3: Preparation of lithium 7-(2-morpholinoethoxy)imidazo[1,2-a]pyridine-3-carboxylate: Ethyl 7-(2-morpholinoethoxy)imidazo[1,2-a]pyridine-3-carboxylate (1 g, 3.13 mmol) was dissolved in tetrahydrofuran/water (4:1, 0.5 M). Lithium hydroxide monohydrate (131 mg, 3.13 mmol) was added and the mixture was stirred at ambient temperature for 16 hours. The mixture was diluted with additional tetrahydrofuran and concentrated. Drying under high vacuum for 6 hours gave lithium 7-(2-morpholinoethoxy)imidazo[1,2-a]pyridine-3-carboxylate as a pale yellow solid (979 mg).

Step C: Preparation of N-(3-ethyl-1-((6-methylpyridin-2-yl)methyl)-1H-indazol-4-yl)-7-(2-morpholinoethoxy)imidazo[1,2-a]pyridine-3-carboxamide: To 3-ethyl-1-(158 mg, 0.593 mmol) in DMA (4 mL) was added lithium 7-(2-morpholinoethoxy)imidazo[1,2-a]pyridine-3-carboxylate (168 mg, 0.565 mmol), HATU (430 mg, 1.13 mmol) and hydrogen chloride (0.14 mL, 4M in dioxane). The reaction was heated at 90° C. for 16 hours. The reaction was cooled to ambient temperature, filtered through Celite and concentrated. Silica gel chromatography (DCM/MeOH/NH$_4$OH 10:1:0.1) provided the desired product as the free base. The free base was dissolved in MeOH (2 mL) and HCl (0.1 mL, 4M in dioxane) was added. The mixture was concentrated to give final product as hydrogen chloride salt (50 mg). MS (ES+APCI) m/z=540 (M+H).

Example 17

(S)—N-(3-ethyl-1-((6-(pyrrolidin-3-yloxy)pyridin-2-yl)methyl)-1H-indazol-4-yl)imidazo[1,2-a]pyridine-3-carboxamide

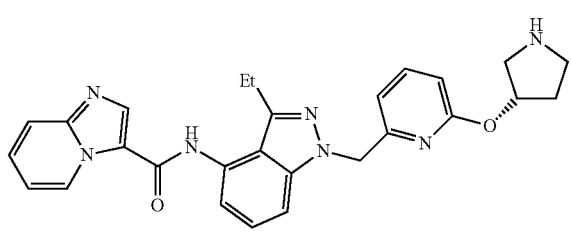

Step A: Preparation of N-(3-ethyl-1-((6-hydroxypyridin-2-yl)methyl)-1H-indazol-4-yl)imidazo[1,2-a]pyridine-3-carboxamide: To N-(3-ethyl-1-((6-methoxypyridin-2-yl)methyl)-1H-indazol-4-yl)imidazo[1,2-a]pyridine-3-carboxamide (210 mg, 0.492 mmol) in THF (6 mL) was added hydrochloric acid (4M in dioxane, 2 mL). The reaction vial was sealed, heated to 80° C. and stirred for 24 hours. The reaction was cooled to ambient temperature and saturated NaHCO$_3$ aqueous solution was added until pH=7. THF and H$_2$O were removed under reduced pressure. The resulting solid was washed with H$_2$O (20 mL) and dried under vacuum to provide the desired product (198 mg).

Step B: Preparation of (R)-tert-butyl 3-(methylsulfonyloxy)pyrrolidine-1-carboxylate: To (R)-tert-butyl 3-hydroxypyrrolidine-1-carboxylate (87 mg, 0.465 mmol) in DCM (2 mL) at 0° C. was added methanesulfonyl chloride (58.5 mg, 0.511 mmol) and triethylamine (56.4 mg, 0.558 mmol). The cold bath was removed and the reaction was stirred for 30 minutes. The reaction was diluted with 5 mL DCM, washed with water and brine, dried (Na$_2$SO$_4$) and concentrated to give final product (131 mg).

Step C: Preparation of (S)-tert-butyl 3-(6-((3-ethyl-4-(imidazo[1,2-a]pyridine-3-carboxamido)-1H-indazol-1-yl)methyl)pyridin-2-yloxy)pyrrolidine-1-carboxylate: To N-(3-ethyl-1-((6-hydroxypyridin-2-yl)methyl)-1H-indazol-4-yl)imidazo[1,2-a]pyridine-3-carboxamide (21 mg, 0.051 mmol) in DMA (2 mL) was added (R)-tert-butyl 3-(methylsulfonyloxy)pyrrolidine-1-carboxylate (20 mg, 0.076 mmol) and Cs$_2$CO$_3$ (33 mg, 0.10 mmol). The reaction vial was sealed, and the reaction was heated to 90° C. and stirred for 6 hours. DMA was removed under reduce pressure. The residue was diluted with EtOAc (20 mL), washed with saturated NaHCO$_3$ aqueous solution (5 mL) and brine (5 mL), and concentrated. Silica gel chromatography of the crude material (DCM/MeOH 10:0.5) provided the desired product (15 mg).

Step D: Preparation of ((S)—N-(3-ethyl-1-((6-(pyrrolidin-3-yloxy)pyridin-2-yl)methyl)-1H-indazol-4-yl)imidazo[1,2-a]pyridine-3-carboxamide: To (S)-tert-butyl 3-(6-((3-ethyl-4-(imidazo[1,2-a]pyridine-3-carboxamido)-1H-indazol-1-yl)methyl)pyridin-2-yloxy)pyrrolidine-1-carboxylate (15 mg, 0.026 mmol) in DCM (1 mL) was added TFA (0.5 mL). The reaction mixture was stirred for one hour and then concentrated. Silica gel chromatography of the crude material (DCM/MeOH/NH$_4$OH 10:1:0.1) provided the desired product (10 mg). MS (ES+APCI) m/z=482 (M+H).

Example 18

N-(3-ethyl-1-((6-(((3R,4R)-3-fluoropiperidin-4-yloxy)pyridin-2-yl)methyl)-1H-indazol-4-yl)imidazo[1,2-a]pyridine-3-carboxamide

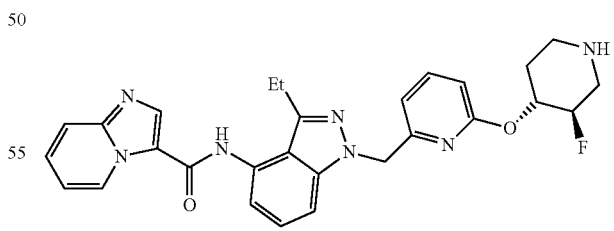

Step A: Preparation of (3R,4R)-tert-butyl 4-(6-((3-ethyl-4-(imidazo[1,2-a]pyridine-3-carboxamido)-1H-indazol-1-yl)methyl)pyridin-2-yloxy)-3-fluoropiperidine-1-carboxylate: To N-(3-ethyl-1-((6-hydroxypyridin-2-yl)methyl)-1H-indazol-4-yl)imidazo[1,2-a]pyridine-3-carboxamide (25 mg, 0.061 mmol; prepared according to Example 17, Step A) in DMA (2 mL) was added a mixture (approximately 9:1) of (3R,4S)-tert-butyl 3-fluoro-4-(methylsulfonyloxy)piperidine-1-carboxylate (prepared as described in WO 2008/124323) and tert-butyl 4-(methylsulfonyloxy)piperidine-1-carboxylate (27 mg). Cs₂CO₃ (39 mg, 0.12 mmol) was added, the reaction vial was sealed, and the mixture was heated to 90° C. and stirred for 6 hours. DMA was removed under reduce pressure. The residue was diluted with EtOAc (20 mL), washed with saturated NaHCO₃ aqueous solution and brine, and concentrated. Silica gel chromatography (DCM/MeOH 10:0.5) gave the desired product (12 mg). (The non-fluorinated product, which was also isolated, was utilized in Example 19, Step A).

Step B: Preparation of (N-(3-ethyl-1-((6-((3R,4R)-3-fluoropiperidin-4-yloxy)pyridin-2-yl)methyl)-1H-indazol-4-yl)imidazo[1,2-a]pyridine-3-carboxamide: To (3R,4R)-tert-butyl 4-(6-((3-ethyl-4-(imidazo[1,2-a]pyridine-3-carboxamido)-1H-indazol-1-yl)methyl)pyridin-2-yloxy)-3-fluoropiperidine-1-carboxylate (12 mg, 0.02 mmol) in DCM (1 mL) was added TFA (1 mL). The reaction was stirred for one hour and concentrated. Silica gel chromatography (DCM/MeOH/NH₄OH 10:1:0.1) provided the desired product (7 mg). MS (ES+APCI) m/z=514 (M+H).

Example 19

N-(3-ethyl-1-((6-(piperidin-4-yloxy)pyridin-2-yl)methyl)-1H-indazol-4-yl)imidazo[1,2-a]pyridine-3-carboxamide

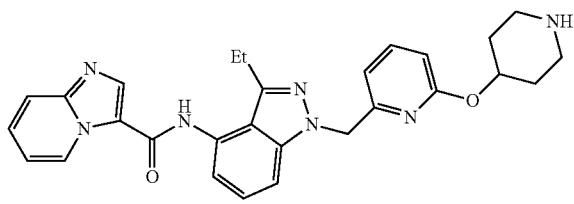 [SMILES: CCc1nn(Cc2cccc(OC3CCNCC3)n2)c2cccc(NC(=O)c3cnc4ccccn34)c12]

Step A: Preparation of tert-butyl 4-(6-((3-ethyl-4-(imidazo[1,2-a]pyridine-3-carboxamido)-1H-indazol-1-yl)methyl)pyridin-2-yloxy)piperidine-1-carboxylate: Isolated in Example 18, Step A.

Step B: Preparation of N-(3-ethyl-1-((6-(piperidin-4-yloxy)pyridin-2-yl)methyl)-1H-indazol-4-yl)imidazo[1,2-a]pyridine-3-carboxamide: To tert-butyl 4-(6-((3-ethyl-4-(imidazo[1,2-a]pyridine-3-carboxamido)-1H-indazol-1-yl)methyl)pyridin-2-yloxy)piperidine-1-carboxylate (3 mg, 0.02 mmol) in DCM (1 mL) was added TFA (1 mL). The reaction mixture was stirred for one hour and concentrated. Silica gel chromatography of the crude material (DCM/MeOH/NH₄OH 10:1:0.1) provided the desired product (2 mg). MS (ES+APCI) m/z=496 (M+H).

Example 20

N-(3-ethyl-1-((1-(4-methoxybenzyl-1H-pyrazol-4-yl)imidazo[1,2-a]pyridine-3-carboxamide

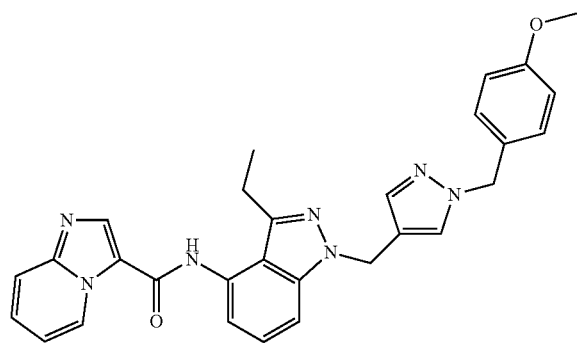 [SMILES: CCc1nn(Cc2cnn(Cc3ccc(OC)cc3)c2)c2cccc(NC(=O)c3cnc4ccccn34)c12]

Step A: Preparation of ethyl 1-(4-methoxybenzyl)-1H-pyrazole-4-carboxylate: To ethyl 1H-pyrazole-4-carboxylate (5.01 g, 35.7 mmol) in DMF (60 mL) was added 1-(chloromethyl)-4-methoxybenzene (6.16 g, 39.3 mmol) and K₂CO₃ (7.41 g, 53.6 mmol). The reaction mixture was stirred for 16 hours and concentrated under reduced pressure to remove DMF. The residue was diluted with EtOAc (100 mL), washed with H₂O (30 mL) and brine (20 mL), dried (Na₂SO₄) and concentrated. Silica gel chromatography (EtOAc/hexanes 1:5) provided the desired product (8.31 g).

Step B: Preparation of (1-(4-methoxybenzyl)-1H-pyrazol-4-yl)methanol: To ethyl 1-(4-methoxybenzyl)-1H-pyrazole-4-carboxylate (8.31 g, 31.9 mmol) in THF (100 mL) at 0° C. was added lithium aluminum hydride (1.45 g, 38.3 mmol). The cold bath was removed and the reaction was stirred for 3 hours. The reaction mixture was diluted with Et₂O (200 mL) and Celite (10 g) was added to the reaction mixture. The mixture was cooled to 0° C. and sodium sulfate decahydrate was cautiously added to quench the reaction, which was then filtered, and the filter pad was washed with EtOAc (100 mL) and concentrated to provide the desired product (5.26 g).

Step C: Preparation of 4-(chloromethyl)-1-(4-methoxybenzyl)-1H-pyrazole: To (1-(4-methoxybenzyl)-1H-pyrazol-4-yl)methanol (5.01 g, 23.0 mmol) in DCM (20 mL) was added thionyl chloride (8 mL). The reaction mixture was stirred for 3 hours and concentrated to provide the desired product (6.37 g).

Step D: Preparation of 3-iodo-1-((1-(4-methoxybenzyl)-1H-pyrazol-4-yl)methyl)-4-nitro-1H-indazole: To 3-iodo-4-nitro-1H-indazole (2.13 g, 7.37 mmol) in DMF (20 mL) was added 4-(chloromethyl)-1-(4-methoxybenzyl)-1H-pyrazole hydrochloride (2.21 g, 8.11 mmol) and K₂CO₃ (3.06 g, 22.1 mmol). The reaction mixture was stirred for 16 hours. The reaction mixture was diluted with EtOAc, washed with H₂O, and brine, and the filtrate was concentrated under reduced pressure. Silica gel chromatography (hexanes/EtOAc 5:1) provided the desired product (2.88 g).

Step E: Preparation of 3-iodo-1-((1-(4-methoxybenzyl)-1H-pyrazol-4-yl)methyl)-1H-indazol-4-amine: To 3-iodo-1-((1-(4-methoxybenzyl)-1H-pyrazol-4-yl)methyl)-1H-indazole (1.13 g, 2.31 mmol) in EtOH/H₂O (20 mL/5 mL) was added iron (1.29 g, 23.1 mmol) and NH₄Cl (0.124 g, 2.31 mmol). The reaction mixture was heated to 80° C. and stirred for 3 hours. The reaction mixture was concentrated, diluted with EtOAc (30 mL) and Et₃N (5 mL). The reaction mixture was heated to reflux for 30 minutes and filtered through Celite®, and the filter pad was washed with DCM/MeOH (50 mL, 10:1). The filtrate was concentrated to provide the desired product (0.89 g).

Step F: Preparation of N-(3-iodo-1-((1-(4-methoxybenzyl)-1H-pyrazol-4-yl)methyl)-1H-indazol-4-yl)imidazo[1,2-a]pyridine-3-carboxamide: To imidazo[1,2-a]pyridine-3-carboxylic acid (0.44 g, 2.7 mmol) in DCM (5 mL) was added thionyl chloride (3 mL). The reaction mixture was stirred for 3 hours, and concentrated under vacuum to give the acyl chloride intermediate, to which was added 3-iodo-1-((1-(4-methoxybenzyl)-1H-pyrazol-4-yl)methyl)-1H-indazol-4-amine (0.83 g, 1.8 mmol) and DCE/THF (2 mL/2 mL). The reaction mixture was heated to 80° C. for 2 hours. The reaction mixture was cooled to ambient temperature, diluted with DCM (20 mL), and washed with saturated NaHCO₃ aqueous solution (10 mL) and brine (10 mL). The organic phase was dried (Na₂SO₄) and concentrated. Silica gel chromatography (DCM/MeOH 10:1) provided the desired product (0.56 g).

Step G: Preparation of N-(3-ethyl-1-((1-(4-methoxybenzyl)-1H-pyrazol-4-yl)methyl)-1H-indazol-4-yl)imidazo[1,2-a]pyridine-3-carboxamide: To N-(3-iodo-1-((1-(4-methoxybenzyl)-1H-pyrazol-4-yl)methyl)-1H-indazol-4-yl)imidazo[1,2-a]pyridine-3-carboxamide (0.59 g, 0.98 mmol) in THF/IPA (1 mL/3 mL) was added trifluorovinylpotassium borate (0.20 g, 1.5 mmol), triethylamine (0.20 g, 2.0 mmol) and 1,1'-Bis(diphenylphosphino)ferrocene-palladium(II) dichloride dichloromethane complex (0.080 g, 0.098 mmol). The reaction mixture was heated at 86° C. and stirred for 5 hours. The reaction mixture was cooled to ambient temperature, concentrated under reduced pressure, and triturated with Et₂O (30 mL) to give crude vinyl product, to which palladium hydroxide on carbon (20% wt, 0.27 mmol) and MeOH (20 mL) was added. The system was purged with N₂ three times and a H₂ balloon was applied to the system for 2 hours. The reaction mixture was filtered through Celite, washed with MeOH (20 mL), and concentrated to give the product (0.32 g). MS (ES+APCI) m/z=506 (M+H).

Example 21

N-(3-ethyl-1-((1-(2-hydroxyethyl)-1H-pyrazol-4-yl)-imidazo[1,2-a]pyridine-3-carboxamide

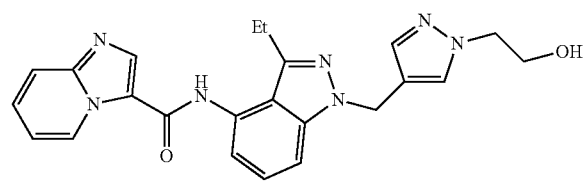 [SMILES: CCc1nn(Cc2cnn(CCO)c2)c2cccc(NC(=O)c3cnc4ccccn34)c12]

Step A: Preparation of ethyl N-(1-((1H-pyrazol-4-yl)methyl)-3-ethyl-1H-indazol-4-yl)imidazo[1,2-a]pyridine-3-carboxamide: To N-(3-ethyl-1-((1-(4-methoxybenzyl)-1H-pyrazol-4-yl)methyl)-1H-indazol-4-yl)imidazo[1,2-a]pyridine-3-carboxamide (320 mg, 0.633 mmol; prepared as in Example 20) in TFA (2 mL) was added Et₃SiH (2 mL). The reaction mixture was sealed and heated to 90° C. for 3 hours. The reaction mixture was concentrated and silica gel chromatography (MeOH/DCM/NH₄OH 10:1:0.1) provided the desired product (176 mg).

Step B: Preparation of N-(1-((1-(2-(tert-butyldimethylsilyloxy)ethyl)-1H-pyrazol-4-yl)methyl)-3-ethyl-1H-indazol-4-yl)imidazo[1,2-a]pyridine-3-carboxamide: To N-(1-((1H-pyrazol-4-yl)methyl)-3-ethyl-1H-indazol-4-yl)imidazo[1,2-a]pyridine-3-carboxamide (20 mg, 0.052 mmol) in DMF (5 mL) was added (2-bromoethoxy)(tert-butyl)dimethylsilane (37 mg, 0.16 mmol), cesium hydroxide hydrate (17 mg, 0.10 mmol) and 4 angstrom molecular sieves (2 g). The reaction mixture was stirred for 3 hours and then concentrated. Purification by silica gel chromatography (DCM/MeOH 10:1) gave the desired product (16 mg).

Step C: Preparation of N-(3-ethyl-1-((1-(2-hydroxyethyl)-1H-pyrazol-4-yl)methyl)-1H-indazol-4-yl)imidazo[1,2-a]pyridine-3-carboxamide: To N-(1-((1-(2-(tert-butyldimethylsilyloxy)ethyl)-1H-pyrazol-4-yl)methyl)-3-ethyl-1H-indazol-4-yl)imidazo[1,2-a]pyridine-3-carboxamide (15 mg, 0.028 mmol) in MeOH (2 mL) was added concentrated hydrochloric acid (5 drops). The reaction was stirred for 3 hours and concentrated. Silica gel chromatography (DCM/MeOH 10:1) gave the desired product (8 mg). MS (ES+APCI) m/z=430 (M+H).

Example 22

N-(3-ethyl-1-((1-((3R,4R)-3-fluoropiperidin-4-yl)-1H-pyrazol-4-yl)methyl)-1H-indazol-4-yl)imidazo[1,2-a]pyridine-3-carboxamide

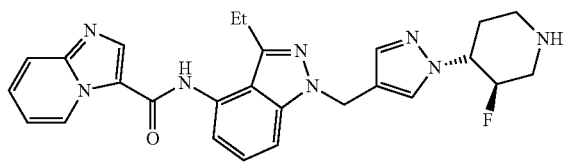

Step A: Preparation of (3R,4R)-tert-butyl 4-(4-((3-ethyl-4-(imidazo[1,2-a]pyridine-3-carboxamido)-1H-indazol-1-yl)methyl)-1H-pyrazol-1-yl)-3-fluoropiperidine-1-carboxylate: To N-(1-((1H-pyrazol-4-yl)methyl)-3-ethyl-1H-indazol-4-yl)imidazo[1,2-a]pyridine-3-carboxamide (40 mg, 0.10 mmol; prepared according to Example 21, Step A) in DMA (5 mL) was added sodium hydride (7.5 mg, 0.31 mmol) and a mixture (approximately 9:1) of (3R,4S)-tert-butyl 3-fluoro-4-(methylsulfonyloxy)piperidine-1-carboxylate (prepared as in WO 2008/124323) and tert-butyl 4-(methylsulfonyloxy)piperidine-1-carboxylate (62 mg). The reaction mixture was heated to 80° C. and stirred for 3 hours. The mixture was concentrated under reduced pressure and silica gel chromatography (DCM/MeOH 10:1) gave the product (21 mg).

Step B: Preparation of N-(3-ethyl-1-((1-((3R,4R)-3-fluoropiperidin-4-yl)-1H-pyrazol-4-yl)methyl)-1H-indazol-4-yl)imidazo[1,2-a]pyridine-3-carboxamide]: To (3R,4R)-tert-butyl 4-(4-((3-ethyl-4-(imidazo[1,2-a]pyridine-3-carboxamido)-1H-indazol-1-yl)methyl)-1H-pyrazol-1-yl)-3-fluoropiperidine-1-carboxylate (7 mg, 0.01 mmol) in DCM (2 mL) was added TFA (1 mL). The reaction mixture was stirred for 30 minutes, concentrated and silica gel chromatography (DCM/MeOH/NH$_4$OH 10:1:0.1) gave the final product (3 mg). MS (ES+APCI) m/z=487 (M+H).

Example 23

Ethyl 3(3-ethyl-1-((6-methylpyridin-2-yl)methyl)-1H-indazol-4-ylcarbamoyl)imidazo[1,2-a]pyridine-7-carboxylate

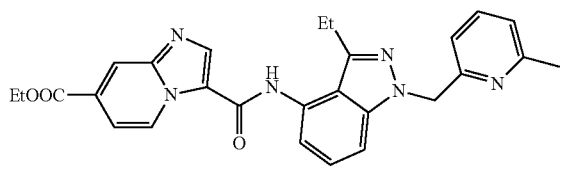 [SMILES: CCOC(=O)c1ccn2c(C(=O)Nc3cccc4c3c(CC)nn4Cc3cccc(C)n3)cnc2c1]

Step A: Preparation of benzyl 2-chloro-3-oxopropanoate: To potassium tert-butoxide (141 mL, 141 mmol) at 0° C. was added dropwise a solution of benzyl 2-chloroacetate (26.8 g, 141 mmol) and ethyl formate (11.6 mL, 141 mmol) in Et$_2$O (45 mL). The reaction was warmed to ambient temperature and stirred for 16 hours. The reaction mixture was filtered and washed with cold ether (100 mL). The potassium salt was dissolved in H$_2$O (50 mL) and the solution was acidified with concentrated HCl to pH=4 in a cold bath. The solution was extracted with ether and the organic phase was dried (MgSO$_4$) and concentrated to give the crude product. A lower boiling point impurity was removed by vacuum distillation (90° C., 5 mm Hg) and the residue was taken directly to the next step.

Step B: Preparation of 3-benzyl 7-ethyl imidazo[1,2-a]pyridine-3,7-dicarboxylate: To ethyl 2-aminoisonicotinate (2.35 g, 14.1 mmol) in t-BuOH (30 mL) was added benzyl 2-chloro-3-oxopropanoate (6.01 g, 28.3 mmol). The reaction was heated to 75° C. and stirred for 4 hours. The reaction mixture was concentrated and silica gel chromatography (EtOAc/hexanes 5:1) provided the product (3.12 g).

Step C: Preparation of 7-(ethoxycarbonyl)imidazo[1,2-a]pyridine-3-carboxylic acid hydrochloride: To 3-benzyl 7-ethyl imidazo[1,2-a]pyridine-3,7-dicarboxylate (2.12 g, 6.54 mmol) in EtOH/DCM (30 mL/5 mL) was added palladium on carbon (10% wt, 0.752 mmol). The system was purged with N$_2$ and then with H$_2$. A H$_2$ balloon was applied to the reaction mixture for 5 hours. The reaction mixture was filtered through Celite, washed with DCM/MeOH/AcOH (10:1:0.1) and concentrated under reduced pressure. Hydrochloric acid (2 mL, 4M in 1,4-dioxane) was added to the residue, which was concentrated again under reduced pressure to remove AcOH to give the product as its hydrochloride salt (1.36 g).

Step D: Preparation of ethyl 3-(3-ethyl-1-((6-methylpyridin-2-yl)methyl)-1H-indazol-4-ylcarbamoyl)imidazo[1,2-a]pyridine-7-carboxylate: To 7-(ethoxycarbonyl) imidazo[1,2-a]pyridine-3-carboxylic acid hydrochloride (501 mg, 1.85 mmol) in NMP (10 mL) was added triethylamine (468 mg, 4.63 mmol). The suspension turned into a clear solution. 2,4,6-trichlorobenzoyl chloride (474 mg, 1.94 mmol) was added dropwise to the reaction mixture. A milky suspension resulted after 10 minutes. The mixture was stirred for another 30 minutes. 3-Ethyl-1-((6-methylpyridin-2-yl)methyl)-1H-indazol-4-amine (444 mg, 1.67 mmol) was added in one portion to the reaction mixture. The mixture was sealed and heated to 75° C. for 3 hours. The mixture was cooled to ambient temperature and concentrated under reduced pressure to remove NMP. The residue was diluted with EtOAc/H$_2$O (20 mL/10 mL). The organic phase was washed with H$_2$O (5 mL) and brine (5 mL), dried (Na$_2$SO$_4$), and concentrated. Silica gel chromatography (EtOAc/Hexane 5:1 to 10:1) provided the final product (665 mg). MS (ES+APCI) m/z=483 (M+H).

Example 24

N-(3-ethyl-1-((6-ethylpyridin-2-yl)methyl)-1H-indazol-4-yl)imidazo[1,2-a]pyridine-3-carboxamide

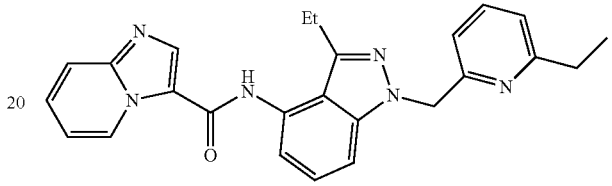

Step A: Preparation of 6-((3-ethyl-4-(imidazo[1,2-a]pyridine-3-carboxamido)-1H-indazol-1-yl)methyl)pyridin-2-yl trifluoromethanesulfonate: To N-(3-ethyl-1-((6-hydroxypyridin-2-yl)methyl)-1H-indazol-4-yl)imidazo[1,2-a]pyridine-3-carboxamide (110 mg, 0.267 mmol; prepared as in Example 17, Step A) in DMF (6 mL) was added 1,1,1-trifluoro-N-phenyl-N-(trifluoromethylsulfonyl)methanesulfonamide (114 mg, 0.320 mmol) and triethylamine (35.1 mg, 0.347 mmol). The reaction mixture was sealed and heated to 50° C. for 16 hours. DMF was removed under reduced pressure. The residue was diluted with EtOAc (20 mL) and washed with saturated NaHCO$_3$ aqueous solution (5 mL) and brine (5 mL). The organic layer was concentrated, and the crude material was purified by silica gel chromatography (EtOAc) to provide the desired product (128 mg).

Step B: Preparation of N-(3-ethyl-1-((6-vinylpyridin-2-yl)methyl)-1H-indazol-4-yl)imidazo[1,2-a]pyridine-3-carboxamide: To 6-((3-ethyl-4-(imidazo[1,2-a]pyridine-3-carboxamido)-1H-indazol-1-yl)methyl)pyridin-2-yl trifluoromethanesulfonate (100 mg, 0.184 mmol) in IPA/THF (3 mL/1 mL) was added potassium trifluoro(vinyl)borate (36.9 mg, 0.275 mmol), 1,1'-bis(diphenylphosphino)ferrocene-palladium(II)dichloride dichloromethane complex (15.0 mg, 0.0184 mmol) and triethylamine (37.2 mg, 0.367 mmol). The reaction mixture was sealed and heated to 80° C. for 16 hours. The mixture was cooled to ambient temperature and concentrated under reduce pressure. The residue was filtered through a plug of silica gel washing with EtOAc. The solution was concentrated to give the product (72 mg).

Step C: Preparation of N-(3-ethyl-1-((6-ethylpyridin-2-yl)methyl)-1H-indazol-4-yl)imidazo[1,2-a]pyridine-3-carboxamide: To N-(3-ethyl-1-((6-vinylpyridin-2-yl)methyl)-1H-indazol-4-yl)imidazo[1,2-a]pyridine-3-carboxamide (11 mg, 0.026 mmol) in MeOH (3 mL) was added palladium on carbon (10% wt, 8 mg). The reaction mixture was purged with N$_2$ three times followed by a purge with H$_2$. A H$_2$ balloon was applied to the reaction mixture. The mixture was stirred for one hour and filtered through a plug of silica gel. The plug was washed with MeOH (20 mL). The filtrate was concentrated under reduced pressure and the residue was purified by silica gel chromatography (DCM/MeOH 10:1) to give the final product (6 mg). MS (ES+APCI) m/z=425 (M+H).

Example 25

N-(3-ethyl-1-((1-methyl-6-oxo-1,6-dihydropyridin-2-yl)methyl)-1H-indazol-4-yl)imidazo[1,2-a]pyridine-3-carboxamide

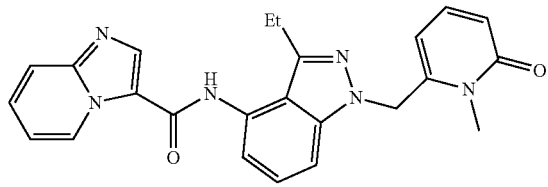 [SMILES: CCc1nn(Cc2cccc(=O)n2C)c2cccc(NC(=O)c3cnc4ccccn34)c12]

To N-(3-ethyl-1-((6-hydroxypyridin-2-yl)methyl)-1H-indazol-4-yl)imidazo[1,2-a]pyridine-carboxamide (11 mg, 0.027 mmol; prepared as in Example 17, Step A) in DMF (2 mL) was added K₂CO₃ (7.4 mg, 0.053 mmol) and iodomethane (19 mg, 0.13 mmol). The reaction mixture was stirred for one hour and concentrated under reduced pressure to remove DMF. Silica gel chromatography (DCM/MeOH 10:1) provided the desired product (3 mg). MS (ES+APCI) m/z=427 (M+H).

Example 26

N-(3-ethyl-1-((1-ethyl-6-oxo-1,6-dihydropyridin-2-yl)methyl)-1H-indazol-4-yl)imidazo[1,2-a]pyridine-3-carboxamide

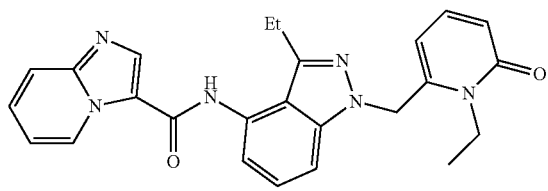 [SMILES: CCc1nn(Cc2cccc(=O)n2CC)c2cccc(NC(=O)c3cnc4ccccn34)c12]

To N-(3-ethyl-1-((6-hydroxypyridin-2-yl)methyl)-1H-indazol-4-yl)imidazo[1,2-a]pyridine-3-carboxamide (11 mg, 0.027 mmol; prepared as in Example 17, Step A) in DMF (2 mL) was added K₂CO₃ (7.4 mg, 0.053 mmol) and iodoethane (21 mg, 0.13 mmol). The reaction mixture was stirred for 16 hours and then concentrated under reduced pressure to remove DMF. Silica gel chromatography (DCM/MeOH 10:1) gave the final product (2 mg). MS (ES+APCI) m/z=441 (M+H). The O-alkylated product was also isolated (See Example 27).

Example 27

N-(1-((6-ethoxypyridin-2-yl)methyl)-3-ethyl-1H-indazol-4-yl)imidazo[1,2-a]pyridine-3-carboxamide

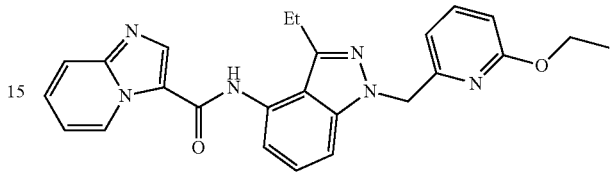

This product (2 mg) was isolated in Example 26, Step A. MS (ES+APCI) m/z=441 (M+H).

Example 28

N-(3-ethyl-1-((6-methylpyridin-2-yl)methyl)-1H-indazol-4-yl)-7-(1,3,4-oxadiazol-2-yl)imidazo[1,2-a]pyridine-3-carboxamide

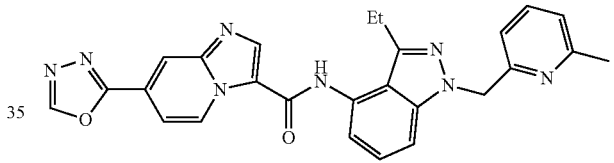

Step A: Preparation of 3-(3-ethyl-1-((6-methylpyridin-2-yl)methyl)-1H-indazol-4-ylcarbamoyl)imidazo[1,2-a]pyridine-7-carboxylic acid: To ethyl 3-(3-ethyl-1-((6-methylpyridin-2-yl)methyl)-1H-indazol-4-ylcarbamoyl)imidazo[1,2-a]pyridine-7-carboxylate (430 mg, 0.891 mmol; prepared as in Example 23) in THF/H₂O (6 mL/1 mL) was added lithium hydroxide (21.3 mg, 0.891 mmol). The reaction mixture was sealed and heated to 70° C. for 2 hours. The mixture was cooled to ambient temperature and HCl (0.45 mL, 4M in dioxane) was added. The mixture was concentrated under reduced pressure to give crude product (410 mg, mixed with LiCl).

Step B: Preparation of N-(3-ethyl-1-((6-methylpyridin-2-yl)methyl)-1H-indazol-4-yl)-7-(hydrazinecarbonyl)imidazo[1,2-a]pyridine-3-carboxamide: To 3-(3-ethyl-1-((6-methylpyridin-2-yl)methyl)-1H-indazol-4-ylcarbamoyl)imidazo[1,2-a]pyridine-7-carboxylicacid (250 mg, 0.550 mmol) in DMF (5 mL) was added tert-butyl hydrazinecarboxylate (80.0 mg, 0.605 mmol), N1-((ethylimino)methylene)-N3,N3-dimethylpropane-1,3-diamine hydrochloride (116 mg, 0.605 mmol), 1H-benzo[c/][1,2,3]triazol-1-ol hydrate (92.7 mg, 0.605 mmol) and triethylamine (66.8 mg, 0.660 mmol). The reaction mixture was stirred overnight and concentrated under reduced pressure to remove DMF. Silica gel chromatography (DCM/MeOH 10:1) provided tert-butyl 2-(3-(3-ethyl-1-((6-methylpyridin-2-yl)methyl)-1H-indazol-4-ylcarbamoyl)imidazo[1,2-a]pyridine-7-carbonyl)hydrazinecarboxylate (188 mg), to which was added TFA/

DCM (2 mL/3 mL). The mixture was stirred for 30 minutes and concentrated to give the product as the TFA salt (156 mg).

Step C: Preparation of N-(3-ethyl-1-((6-methylpyridin-2-yl)methyl)-1H-indazol-4-yl)-7-(1,3,4-oxadiazol-2-yl)imidazo[1,2-a]pyridine-3-carboxamide: To N-(3-ethyl-1-((6-methylpyridin-2-yl)methyl)-1H-indazol-4-yl)-7-(hydrazinecarbonyl)imidazo[1,2-a]pyridine-3-carboxamide (15 mg, 0.0320 mmol) was added trimethoxymethane (340 mg, 3.20 mmol). The reaction mixture was sealed and heated to 110° C. for 30 minutes. The mixture was cooled to ambient temperature and concentrated under reduced pressure. Silica gel chromatography (DCM/MeOH 10:1) gave the final product (5 mg). MS (ES+APCI) m/z=479 (M+H).

Example 29

N3-ethyl-1-((6-methylpyridin-2-yl)methyl)-1H-indazol-4-yl)-7-(5-methyl-1,3,4-oxadiazol-2-yl)imidazo[1,2-a]pyridine-3-carboxamide

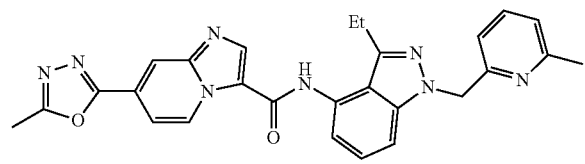

To N-(3-ethyl-1-((6-methylpyridin-2-yl)methyl)-1H-indazol-4-yl)-7-(hydrazinecarbonyl)imidazo[1,2-a]pyridine-3-carboxamide (15 mg, 0.0320 mmol; prepared as in Example 28, step B) was added 1,1,1-triethoxyethane (519 mg, 3.20 mmol). The reaction mixture was sealed and heated to 110° C. for 30 minutes. The mixture was cooled to ambient temperature and concentrated under reduced pressure. Silica gel chromatography (DCM/MeOH 10:1) gave the final product (3 mg). MS (ES+APCI) m/z=493 (M+H).

Example 30

N-(3-ethyl-1-((6-methylpyridin-2-yl)methyl)-1H-indazol-4-yl)-7-(piperazin-1-ylmethyl)imidazo[1,2-a]pyridine-3-carboxamide

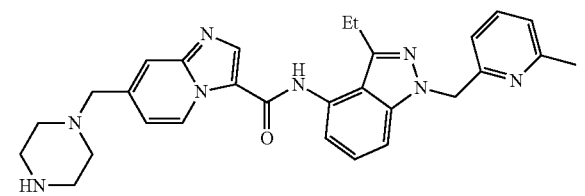 [SMILES: CCc1nn(Cc2cccc(C)n2)c2cccc(NC(=O)c3cnc4cc(CN5CCNCC5)ccn34)c12]

Step A: Preparation of N-(3-ethyl-1-((6-methylpyridin-2-yl)methyl)-1H-indazol-4-yl)-7-(hydroxymethyl)imidazo[1,2-a]pyridine-3-carboxamide: To ethyl 3-(3-ethyl-1-((6-methylpyridin-2-yl)methyl)-1H-indazol-4-ylcarbamoyl)imidazo[1,2-a]pyridine-7-carboxylate (201 mg, 0.417 mmol; prepared as in Example 23) in THF (20 mL) was added lithium aluminum hydride (47.4 mg, 1.25 mmol). The reaction mixture was stirred overnight, quenched with sodium sulfate decahydrate, filtered through Celite and the filter pad was washed with EtOAc. The filtrate was concentrated under reduced pressure to give the product (156 mg).

Step B: Preparation of tert-butyl 4-((3-(3-ethyl-1-((6-methylpyridin-2-yl)methyl)-1H-indazol-4-ylcarbamoyl)imidazo[1,2-a]pyridin-7-yl)methyl)piperazine-1-carboxylate: To N-(3-ethyl-1-((6-methylpyridin-2-yl)methyl)-1H-indazol-4-yl)-7-(hydroxymethyl)imidazo[1,2-a]pyridine-3-carboxamide (40 mg, 0.091 mmol) in DCM (3 mL) was added methanesulfonyl chloride (21 mg, 0.18 mmol). The reaction mixture was stirred for 30 minutes, diluted with DCM (10 mL), washed with saturated NaHCO₃ aqueous solution (3 mL) and brine (3 mL). The organic phase was concentrated under reduced pressure to a residue, to which was added DMF (2 mL), K₂CO₃ (38 mg, 0.27 mmol) and tert-butyl piperazine-1-carboxylate (51 mg, 0.27 mmol). The reaction mixture was heated to 50° C. for 2 hours. The mixture was concentrated under reduced pressure to remove DMF. Silica gel chromatography (DCM/MeOH) gave the product (22 mg).

Step C: Preparation of N-(3-ethyl-1-((6-methylpyridin-2-yl)methyl)-1H-indazol-4-yl)-7-(piperazin-1-ylmethyl)imidazo[1,2-a]pyridine-3-carboxamide: To tert-butyl 4-((3-(3-ethyl-1-((6-methylpyridin-2-yl)methyl)-1H-indazol-4-ylcarbamoyl)imidazo[1,2-a]pyridin-7-yl)methyl)piperazine-1-carboxylate (11 mg, 0.018 mmol) in DCM (1 mL) was added TFA (1 mL). The reaction mixture was stirred for 30 minutes, and then concentrated under reduced pressure. Silica gel chromatography (DCM/MeOH/NH₄OH 10:1:0.1) provided the final product (6 mg). MS (ES+APCI) m/z=509 (M+H).

Example 31

N-(3-ethyl-1-((6-methylpyridin-2-yl)methyl)-1H-indazol-4-yl)-7-((4-methylpiperazin-1-yl)methyl)imidazo[1,2-a]pyridine-3-carboxamide

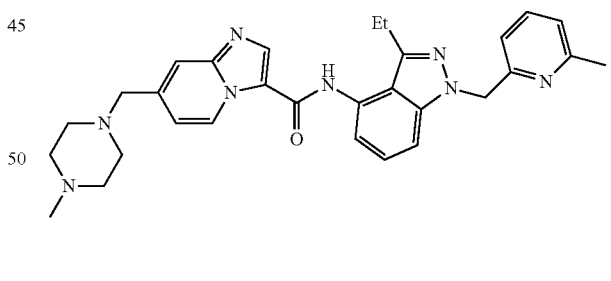

To N-(3-ethyl-1-((6-methylpyridin-2-yl)methyl)-1H-indazol-4-yl)-7-(piperazin-1-ylmethyl)imidazo[1,2-a]pyridine-3-carboxamide (4 mg, 0.0079 mmol; prepared as in Example 30) in MeOH/DCM (1 mL/0.5 mL) was added NaBH(OAc)₃ (5.0 mg, 0.024 mmol) and HCHO (as a 35% aqueous solution) (2.4 mg, 0.079 mmol). The reaction mixture was stirred for 30 minutes, and then concentrated under reduced pressure. Silica gel chromatography (DCM/MeOH/NH₄OH 10:1:0.1) provided the final product (3 mg). MS (ES+APCI) m/z=523 (M+H).

Example 32

N-(3-ethyl-1-((6-methylpyridin-2-yl)methyl)-1H-indazol-4-yl)-7-((3S,4S)-4-hydroxypyrrolidin-3-yloxy)imidazo[1,2-a]pyridine-3-carboxamide

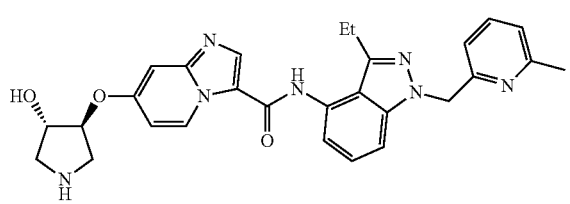 [SMILES: CCc1nn(Cc2cccc(C)n2)c2cccc(NC(=O)c3cnc4cc(O[C@H]5CNC[C@@H]5O)ccn34)c12]

Step A: Preparation of (3S,4S)-tert-butyl 3,4-dihydroxypyrrolidine-1-carboxylate: To (3S,4S)-pyrrolidine-3,4-diol (800 mg, 7.76 mmol) in DCM (20 mL) was added di-tert-butyl dicarbonate (1.69 g) and triethylamine (0.79 g). The reaction mixture was stirred for 3 hours and then concentrated under reduced pressure. Silica gel chromatography (EtOAc/hexanes 1:1) gave the product (356 mg).

Step B: Preparation of (3S,4S)-tert-butyl 3-(3-(3-ethyl-1-((6-methylpyridin-2-yl)methyl)-1H-indazol-4-ylcarbamoyl)imidazo[1,2-a]pyridin-7-yloxy)-4-hydroxypyrrolidine-1-carboxylate: To N-(3-ethyl-1-((6-methylpyridin-2-yl)methyl)-1H-indazol-4-yl)-7-fluoroimidazo[1,2-a]pyridine-3-carboxamide (32 mg, 0.075 mmol; prepared as in Example 74, Step A) in THF/t-BuOH (1 mL/1 mL) was added (3S,4S)-tert-butyl 3,4-dihydroxypyrrolidine-1-carboxylate (61 mg, 0.30 mmol) and potassium tert-butoxide (67 mg, 0.60 mmol). The reaction was heated with microwave at 100° C. for 50 minutes, and then concentrated under reduced pressure. Silica gel chromatography (DCM/MeOH 10:1) gave the crude product (42 mg).

Step C: Preparation of N-(3-ethyl-1-((6-methylpyridin-2-yl)methyl)-1H-indazol-4-yl)-7-((3S,4S)-4-hydroxypyrrolidin-3-yloxy)imidazo[1,2-a]pyridine-3-carboxamide: To (3S,4S)-tert-butyl 3-(3-(3-ethyl-1-((6-methylpyridin-2-yl)methyl)-1H-indazol-4-ylcarbamoyl)imidazo[1,2-a]pyridin-7-yloxy)-4-hydroxypyrrolidine-1-carboxylate (22 mg, 0.036 mmol) in DCM (1 mL) was added TFA (1 mL). The reaction mixture was stirred for one hour, and then concentrated under reduced pressure. Silica gel chromatography (DCM/MeOH/NH₄OH 10:1:0.1) provided the desired product (10 mg). MS (ES+APCI) m/z=512 (M+H).

Example 33

N-(3-ethyl-1-((6-methylpyridin-2-yl)methyl)-1H-indazol-4-yl)-7-((3R,4R)-4-hydroxypyrrolidin-3-yloxy)imidazo[1,2-a]pyridine-3-carboxamide

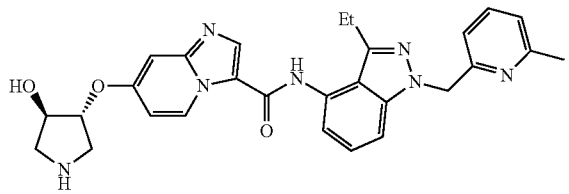 [SMILES: CCc1nn(Cc2cccc(C)n2)c2cccc(NC(=O)c3cnc4cc(O[C@@H]5CNC[C@H]5O)ccn34)c12]

Prepared according to the method of Example 32 using (3R,4R)-pyrrolidine-3,4-diol in Step A. MS (ES+APCI) m/z=512 (M+H).

Example 34

N-(3-ethyl-1-((6-methylpyridin-2-yl)-methyl)-1H-indazol-4-yl)-7-((3S,4S)-4-hydroxy-1-methylpyrrolidin-3-yloxy)imidazo[1,2-a]pyridine-3-carboxamide

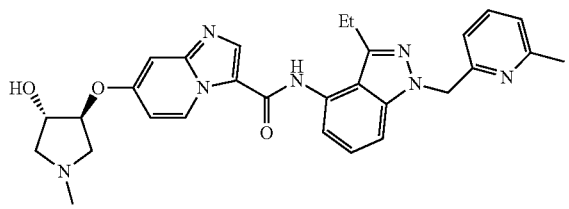 [SMILES: CCc1nn(Cc2cccc(C)n2)c2cccc(NC(=O)c3cnc4cc(O[C@H]5CN(C)C[C@@H]5O)ccn34)c12]

To N-(3-ethyl-1-((6-methylpyridin-2-yl)methyl)-1H-indazol-4-yl)-7-((3S,4S)-4-hydroxypyrrolidin-3-yloxy)imidazo[1,2-a]pyridine-3-carboxamide (11 mg, 0.022 mmol; prepared as in Example 32) in MeOH/DCM (1 mL/0.5 mL) was added NaBH(OAc)₃ (23 mg, 0.11 mmol) and HCHO (as a 35% aqueous solution) (6.5 mg, 0.22 mmol). The reaction mixture was stirred for 30 minutes and then concentrated under reduced pressure. Silica gel chromatography (DCM/

MeOH/NH$_4$OH 10:1:0.1) provided the final product (3 mg). MS (ES+APCI) m/z=526 (M+H).

Example 35

N-(3-ethyl-1-((6-methylpyridin-2-yl)methyl)-1H-indazol-4-yl)-7-((3R,4R)-4-hydroxy-1-methylpyrrolidin-3-yloxy)imidazo[1,2-a]pyridine-3-carboxamide

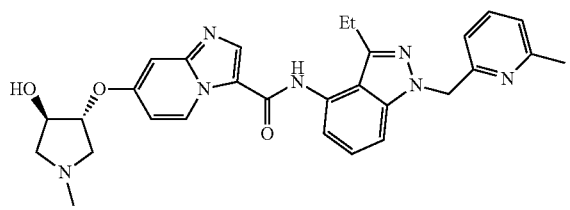 [SMILES: CCc1nn(Cc2cccc(C)n2)c2cccc(NC(=O)c3cnc4cc(O[C@@H]5CN(C)C[C@H]5O)ccn34)c12]

To N-(3-ethyl-1-((6-methylpyridin-2-yl)methyl)-1H-indazol-4-yl)-7-((3R,4R)-4-hydroxypyrrolidin-3-yloxy)imidazo[1,2-a]pyridine-3-carboxamide (11 mg, 0.022 mmol; prepared as in Example 33) in MeOH/DCM (1 mL/0.5 mL) was added NaBH(OAc)$_3$ (23 mg, 0.11 mmol) and HCHO (as a 35% aqueous solution) (6.5 mg, 0.22 mmol). The reaction mixture was stirred for 30 minutes and then concentrated under reduced pressure. Silica gel chromatography (DCM/MeOH/NH$_4$OH 10:1:0.1) provided the desired product (3 mg). MS (ES+APCI) m/z=526 (M+H).

Example 36

N-(3-ethyl-1-((6-(((2R,3S)-3-hydroxypyrrolidin-2-yl)methoxy)pyridin-2-yl)methyl)-1H-indazol-4-yl)imidazo[1,2-a]pyridine-3-carboxamide

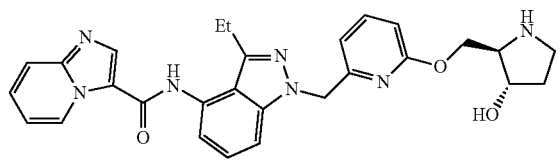 [SMILES: CCc1nn(Cc2cccc(OC[C@H]3NCC[C@@H]3O)n2)c2cccc(NC(=O)c3cnc4ccccn34)c12]

Step A: Preparation of (2R,3S)-1-(tert-butoxycarbonyl)-3-hydroxypyrrolidine-2-carboxylic acid: To (2R,3S)-3-hydroxypyrrolidine-2-carboxylic acid (3.12 g, 23.8 mmol) in dioxane/H$_2$O (40 mL/20 mL) was added sodium hydroxide (1.90 g, 47.6 mmol), followed by the dropwise addition of di-tert-butyl dicarbonate (6.23 g, 28.6 mmol) in dioxane (10 mL). The reaction mixture was stirred at ambient temperature for 2 hours. The mixture was diluted with EtOAc (50 mL) and the phases were separated. The organic layer was washed with 10% NaOH aqueous solution (30 mL). The combined aqueous was acidified with concentrated HCl until pH=2. The aqueous layer was extracted with DCM. The organic phases were dried (Na$_2$SO$_4$) and concentrated to give the crude product (4.8 g).

Step B: Preparation of (2R,3S)-1-(tert-butoxycarbonyl)-3-(tert-butyldimethylsilyloxy)pyrrolidine-2-carboxylic acid: To (2R,3S)-1-(tert-butoxycarbonyl)-3-hydroxypyrrolidine-2-carboxylic acid (4.812 g, 20.81 mmol) in DMF (30 mL) at 0° C. was added tert-butylchlorodimethylsilane (9.409 g, 62.43 mmol) and triethylamine (10.53 g, 104.0 mmol). The cold bath was removed and the reaction mixture was stirred for 16 hours. The mixture was diluted with EtOAc (50 mL) and 10% NaOH (30 mL), and the phases were separated. The organic phase was washed with 10% NaOH. The combined aqueous phases were acidified with concentrated HCl until pH=2. The aqueous phase was extracted with DCM. The combined organic phases were dried (Na$_2$SO$_4$) and concentrated under reduced pressure to give the crude product 6.86 g).

Step C: Preparation of (2S,3S)-tert-butyl 3-(tert-butyldimethylsilyloxy)-2-hydroxymethyl)pyrrolidine-1-carboxylate: To (2R,3S)-1-(tert-butoxycarbonyl)-3-(tert-butyldimethylsilyloxy)pyrrolidine-2-carboxylic acid (6.86 g, 19.9 mmol) in Et$_2$O (100 mL) at 0° C. was added cautiously lithium aluminum hydride (0.754 g, 19.9 mmol). The reaction mixture was stirred for 30 minutes and the cold bath was removed. Stirring continued at ambient temperature for 3 hours. The reaction mixture was diluted with Et$_2$O (200 mL) and cooled back to 0° C. Sodium sulfate decahydrate was added until no further effervescence occurred. The mixture was filtered, washed with EtOAc (100 mL), and concentrated under reduced pressure to give the product (4.65 g).

Step D: Preparation of (2S,3S)-tert-butyl 3-(tert-butyldimethylsilyloxy)-2-((6-((3-ethyl-4-(imidazo[1,2-a]pyridine-3-carboxamido)-1H-indazol-1-yl)methyl)pyridin-2-yloxy)methyl)pyrrolidine-1-carboxylate: To a suspension of N-(3-ethyl-1-((6-hydroxypyridin-2-yl)methyl)-1H-indazol-4-yl)imidazo[1,2-a]pyridine-3-carboxamide (26 mg, 0.0630 mmol; prepared as in Example 17, Step A) in THF (5 mL) was added (2S,3S)-tert-butyl 3-(tert-butyldimethylsilyloxy)-2-(hydroxymethyl)pyrrolidine-1-carboxylate (62.7 mg, 0.189 mmol), triphenylphosphine (54.6 mg, 0.208 mmol) and diethyl azodicarboxylate (81.9 µL, 0.208 mmol). The suspension became a clear solution, which was stirred for 16 hours. The reaction mixture was concentrated under reduced pressure and silica gel chromatography (DCM/MeOH 10:1) provided the product mixed with triphenyl phosphine oxide (65.6 mg).

Step E: Preparation of N-(3-ethyl-1-((6-(((2R,3S)-3-hydroxypyrrolidin-2-yl)methoxy)pyridin-2-yl)methyl)-1H-indazol-4-yl)imidazo[1,2-a]pyridine-3-carboxamide: To (2S,3S)-tert-butyl 3-(tert-butyldimethylsilyloxy)-2-((6-((3-ethyl-4-(imidazo[1,2-a]pyridine-3-carboxamido)-1H-indazol-1-yl)methyl)pyridin-2-yloxy)methyl)pyrrolidine-1-carboxylate (66 mg, 0.091 mmol) in MeOH (2 mL) was added HCl (4M in dioxane, 1 mL). The reaction mixture was stirred for one hour. The mixture was concentrated and silica gel chromatography (DCM/MeOH/NH₄OH 10:1:0.1) provided the final product (22 mg). MS (ES+APCI) m/z=512 (M+H).

Example 37

4-(2-(3(3-ethyl-1-((6-methylpyridin-2-yl)methyl)-1H-indazol-4-ylcarbamoyl)imidazo[1,2-a]pyridin-7-yloxy)ethyl)-1-methylpiperazine 1-oxide

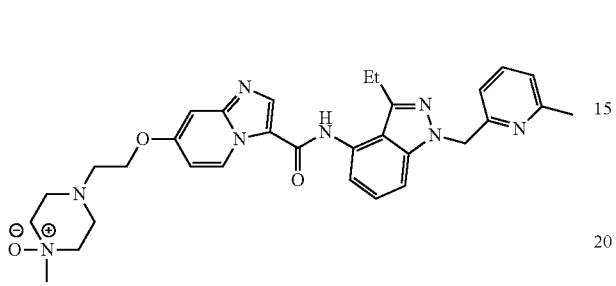

To N-(3-ethyl-1-(((6-methylpyridin-2-yl)methyl)-1H-indazol-4-yl)-7-(2-(4-methylpiperazin-1-yl)ethoxy)imidazo[1,2-a]pyridine-3-carboxamide (25 mg, 0.045 mmol; prepared according to Example 45) in DCM (3 mL) at 0° C. was added metachloroperbenzoic acid (7.8 mg, 0.032 mmol). The reaction mixture was stirred at 0° C. for one hour. The reaction mixture was concentrated under reduced pressure and silica gel chromatography (DCM/MeOH/NH₄OH 10:1:0.1) provided the final product (10 mg). MS (ES+APCI) m/z=569 (M+H).

Example 38

N-(3-ethyl-1-((6-methylpyridin-2-yl)methyl)-1H-indazol-4-yl)-7-(((2R,3S)-3-hydroxypyrrolidin-2-ylmethoxy)imidazo[1,2-a]pyridine-3-carboxamide

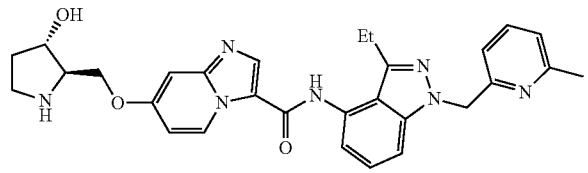 [SMILES: CCc1nn(Cc2cccc(C)n2)c2cccc(NC(=O)c3cnc4cc(OC[C@H]5NCC[C@@H]5O)ccn34)c12]

To N-(3-ethyl-1-(((6-methylpyridin-2-yl)methyl)-1H-indazol-4-yl)-7-fluoroimidazo[1,2-a]pyridine-3-carboxamide (prepared as in Example 74, Step A; 25 mg, 0.058 mmol) in THF/t-BuOH (2 mL/2 mL) was added (2R,3S)-tert-butyl 3-(tert-butyldimethylsilyloxy)-2-(hydroxymethyl)pyrrolidine-1-carboxylate (97 mg, 0.29 mmol) and potassium t-butoxide (65 mg, 0.58 mmol). The reaction mixture was sealed and heated in a microwave reactor to 100° C. for 2 hours. The reaction mixture was concentrated under reduced pressure and silica gel chromatography (DCM/MeOH 10:1) provided intermediate product, to which was added DCM/TFA (2 mL/1 mL). The mixture was stirred for 30 minutes, and then concentrated under reduced pressure. Silica gel chromatography (DCM/MeOH/NH₄OH 10:1:0.1) provided the final product (10 mg). MS (ES+APCI) m/z=526 (M+H).

Example 39

N-(3-ethyl-1-((1-ethyl-1H-pyrazol-5-yl)methyl)-1H-indazol-4-yl)imidazo[1,2-a]pyridine-3-carboxamide

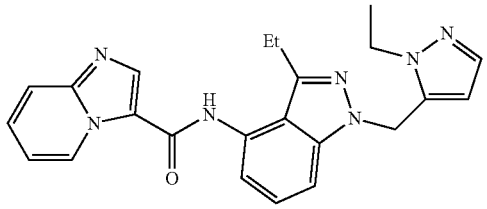 [SMILES: CCc1nn(Cc2ccnn2CC)c2cccc(NC(=O)c3cnc4ccccn34)c12]

Step A: Preparation of ethyl 1H-pyrazole-5-carboxylate: To 1H-pyrazole-5-carboxylic acid (8.21 g, 73.2 mmol) in EtOH (100 mL) was added concentrated sulfuric acid (21.6 g, 220 mmol). The reaction mixture was heated to 80° C. for 16 hours. The mixture was cooled to ambient temperature and concentrated under reduced pressure. The residue was diluted with EtOAc (200 mL) and 2N NaOH aqueous solution was added until pH=8. The phases were separated and the organic phase was washed with saturated NaHCO₃ aqueous solution (50 mL) and brine (20 mL), dried (Na₂SO₄), and concentrated to give the product (6.36 g).

Step B: Preparation of ethyl 1-(4-methoxybenzyl)-1H-pyrazole-5-carboxylate: To ethyl 1H-pyrazole-5-carboxylate (2.31 g, 16.5 mmol) in DMF (20 mL) was added 1-(chloromethyl)-4-methoxybenzene (2.58 g, 16.5 mmol) and K₂CO₃ (2.28 g, 16.5 mmol). The reaction mixture was stirred for 5 hours, diluted with EtOAc and washed with water. The organic phase was concentrated, and silica gel chromatography (EtOAc/hexanes 1:2) provided the product (1.8 g).

Step C: Preparation of (1-(4-methoxybenzyl)-1H-pyrazol-5-yl)methanol: To ethyl 1-(4-methoxybenzyl)-1H-pyrazole-5-carboxylate (1.81 g, 6.95 mmol) in THF (20 mL) at 0° C. was added lithium aluminum hydride (0.317 g, 8.34 mmol). The cold bath was removed. The reaction mixture was stirred for 5 hours, diluted with Et₂O (50 mL) and Celite (5 g) was added to the reaction mixture. The mixture was cooled to 0° C. and sodium sulfate decahydrate was cautiously added to quench the reaction. The mixture was filtered and washed with EtOAc (100 mL). The solution was concentrated under reduced pressure to give the product (1.36 g).

Step D: Preparation of 5-(bromomethyl)-1-(4-methoxybenzyl)-1H-pyrazole: To (1-(4-methoxybenzyl)-1H-pyrazol-5-yl)methanol (1.36 g, 6.23 mmol) in DCM (10 mL) at 0° C. was added perbromomethane (3.10 g, 9.35 mmol) and triphenylphosphine (2.45 g, 9.35 mmol). The cold bath was removed. The reaction mixture was stirred for 2 hours and then concentrated under reduced pressure. Silica gel chromatography (EtOAc/Hexanes 1:3) gave the product (1.56 g).

Step E: Preparation of 3-iodo-1-((1-(4-methoxybenzyl)-1H-pyrazol-5-yl)methyl)-4-nitro-1H-indazole: To 3-iodo-4-nitro-1H-indazole (1.55 g, 5.37 mmol) in DMF (20 mL) was added 5-(bromomethyl)-1-(4-methoxybenzyl)-1H-pyrazole (1.51 g, 5.37 mmol) and K₂CO₃ (1.11 g, 8.06 mmol). The reaction mixture was stirred overnight, diluted with EtOAc (100 mL), washed with H₂O and brine (10 mL), and then concentrated under reduced pressure. Silica gel chromatography (Hexanes/EtOAc 5:1) provided the desired product (2.35 g).

Step F: Preparation of 1-((1-(4-methoxybenzyl)-1H-pyrazol-5-yl)methyl)-4-nitro-3-vinyl-1H-indazole: To 3-iodo-1-((1-(4-methoxybenzyl)-1H-pyrazol-5-yl)methyl)-4-nitro-1H-indazole (2.35 g, 4.80 mmol) in THF/IPA (10 mL/30 mL) was added trifluorovinylpotassium borate (0.965 g, 7.20 mmol), 1,1'-bis(diphenylphosphino)ferrocene-palladium(II) dichloride dichloromethane complex (0.392 g, 0.480 mmol) and triethylamine (0.972 g, 9.61 mmol). The reaction mixture was heated to 80° C. for 16 hours, diluted with EtOAc (100 mL), washed with H$_2$O and brine, then concentrated under reduced pressure. Silica gel chromatography (hexanes/EtOAc 5:1) provided the product (1.61 g).

Step G: Preparation of N-(3-ethyl-1-((1-(4-methoxybenzyl)-1H-pyrazol-5-yl)methyl)-1H-indazol-4-yl)imidazo[1,2-a]pyridine-3-carboxamide: To 1-((1-(4-methoxybenzyl)-1H-pyrazol-5-yl)methyl)-4-nitro-3-vinyl-1H-indazole (0.86 g, 2.2 mmol) in EtOH/DCM (20 mL/2 mL) was added palladium hydroxide on carbon (400 mg, 20% wt). The reaction mixture was purged with nitrogen and hydrogen three times each. The mixture was then stirred under hydrogen for 3 hours. The reaction mixture was filtered, washed with MeOH/DCM (10:1, 50 mL) and concentrated under reduced pressure to give the crude product 3-ethyl-1-((1-(4-methoxybenzyl)-1H-pyrazol-5-yl)methyl)-1H-indazol-4-amine. To imidazo[1,2-a]pyridine-3-carboxylic acid (0.43 g, 2.7 mmol) in DCE (5 mL) was added thionyl chloride (1.3 g, 11 mmol). The slurry was stirred for one hour. The reaction mixture was then concentrated under reduced pressure and dried under vacuum for 30 minutes. The resulting acid chloride was then resuspended in THF/DCE (5 mL/5 mL), to which the previously prepared 3-ethyl-1-((1-(4-methoxybenzyl)-1H-pyrazol-5-yl)methyl)-1H-indazol-4-amine was added. The reaction mixture was heated to 80° C. for three hours. The mixture was cooled to ambient temperature, diluted with DCM (20 mL), washed with saturated NaHCO$_3$ aqueous solution (20 mL) and brine (10 mL), and then concentrated under reduced pressure. Silica gel chromatography (DCM/MeOH 10:1) provided the product (0.36 g).

Step H: Preparation of N-(1-((1H-pyrazol-3-yl)methyl)-3-ethyl-1H-indazol-4-yl)imidazo[1,2-a]pyridine-3-carboxamide: To N-(3-ethyl-1-((1-(4-methoxybenzyl)-1H-pyrazol-5-yl)methyl)-1H-indazol-4-yl)imidazo[1,2-a]pyridine-3-carboxamide (400 mg, 0.791 mmol) was added in TFA (4 mL) and Et$_3$SiH (2 mL). The mixture was heated at 80° C. for 3 hours, and then at 100° C. for an additional 2 hours. The reaction mixture was concentrated under reduced pressure to a residue. Purification by silica gel chromatography (EtOAc/hexanes 1:2) provided the product (197 mg).

Step I: Preparation of N-(3-ethyl-1-((1-ethyl-1H-pyrazol-5-yl)methyl)-1H-indazol-4-yl)imidazo[1,2-a]pyridine-3-carboxamide: To N-(1-((1H-pyrazol-3-yl)methyl)-3-ethyl-1H-indazol-4-yl)imidazo[1,2-a]pyridine-3-carboxamide (40 mg, 0.10 mmol) in dry DMF (519 µl, 0.10 mmol) was added bromoethane (11 mg, 0.10 mmol), cesium hydroxide hydrate (17 mg, 0.10 mmol) and 4 angstrom molecular sieves. The reaction mixture was stirred for one hour, filtered through an Acrodisk, rinsed with DCM and MeOH, and concentrated under a nitrogen stream to a residue. Preparative thin layer chromatography eluting with 10% MeOH, 0.5% NH$_4$OH in CHCl$_3$ provided the desired product (2 mg). MS (ES+APCI) m/z=414 (M+H). (The other regioisomer, N-(1-((1H-pyrazol-3-yl)methyl)-3-ethyl-1H-indazol-4-yl)imidazo[1,2-a]pyridine-3-carboxamide, was also isolated and was utilized in Example 40).

Example 40

N-(3-ethyl-1-((1-ethyl-1H-pyrazol-3-yl)methyl)-1H-indazol-4-yl)imidazo[1,2-a]pyridine-3-carboxamide

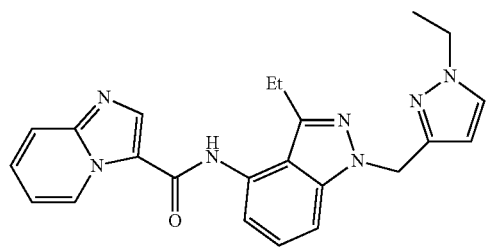 [SMILES: CCc1nn(Cc2ccn(CC)n2)c2cccc(NC(=O)c3cnc4ccccn34)c12]

To N-(1-((1H-pyrazol-3-yl)methyl)-3-ethyl-1H-indazol-4-yl)imidazo[1,2-a]pyridine-3-carboxamide (40 mg, 0.10 mmol; prepared as in Example 39, Step H) in dry DMF (519 µL, 0.10 mmol) was added bromoethane (11 mg, 0.10 mmol), cesium hydroxide hydrate (17 mg, 0.10 mmol) and 4 angstrom molecular sieves. The reaction mixture was stirred for one hour, filtered through an Acrodisk, rinsed with DCM and MeOH, and concentrated under a nitrogen stream to a residue. Preparative thin layer chromatography eluting with 10% MeOH, 0.5% NH$_4$OH in CHCl$_3$ provided the final product (10 mg). MS (ES+APCI) m/z=414 (M+H).

Example 41

N-(3-ethyl-1-((6-(((2R,3S)-3-hydroxy-1-methylpyrrolidin-2-yl)methoxy)pyridin-2-yl)methyl)-1H-indazol-4-yl)imidazo[1,2-a]pyridine-3-carboxamide

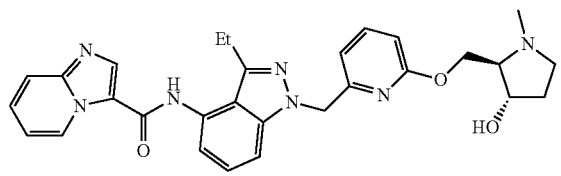 [SMILES: CCc1nn(Cc2cccc(OC[C@@H]3[C@@H](O)CCN3C)n2)c2cccc(NC(=O)c3cnc4ccccn34)c12]

To N-(3-ethyl-1-((6-(((2R,3S)-3-hydroxypyrrolidin-2-yl)methoxy)pyridin-2-yl)methyl)-1H-indazol-4-yl)imidazo[1,2-a]pyridine-3-carboxamide (5 mg, 0.0098 mmol; prepared as in Example 36) in MeOH (1 mL) was added HCHO as a 35% aqueous solution (16 mg, 0.20 mmol) and NaBH(OAc)$_3$ (10 mg, 0.049 mmol). The reaction mixture was stirred for 30 minutes, concentrated under reduced pressure and purified by silica gel chromatography (DCM/MeOH/NH4OH 10:1:0.1) to provide the final product (4 mg). MS (ES+APCI) m/z=526 (M+H).

Example 42

N-(3-ethyl-1-((6-methylpyridin-2yl)methyl)-1H-indazol-4-yl)-7-(((2R,3S)-3-hydroxy-1-methylpyrrolidin-2-yl)methoxy)imidazo[1,2-a]pyridine-3-carboxamide

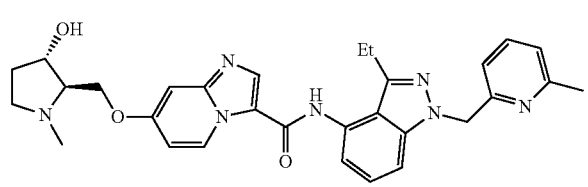 [SMILES: CCc1nn(Cc2cccc(C)n2)c2cccc(NC(=O)c3cnc4cc(OC[C@@H]5[C@@H](O)CCN5C)ccn34)c12]

To N-(3-ethyl-1-((6-methylpyridin-2-yl)methyl)-1H-indazol-4-yl)-7-(((2R,3S)-3-hydroxypyrrolidin-2-yl)methoxy)imidazo[1,2-a]pyridine-3-carboxamide (5 mg, 0.0095 mmol; Example 38 in MeOH (1 mL) was added HCHO (as a 35% aqueous solution) (7.7 mg, 0.095 mmol) and NaBH(OAc)3 (10 mg, 0.048 mmol). The reaction mixture was stirred for 30 minutes and concentrated under reduced pressure. Purification by silica gel chromatography (DCM/MeOH/NH4OH 10:1:0.1) provided the final product (3 mg). MS (ES+APCI) m/z=540 (M+H).

Example 43

N-(3-ethyl-1-((6-(2-(piperazin-1-yl)ethoxy)pyridin-2-yl)methyl)-1H-indazol-4-yl)imidazo[1,2-a]pyridine-3-carboxamide

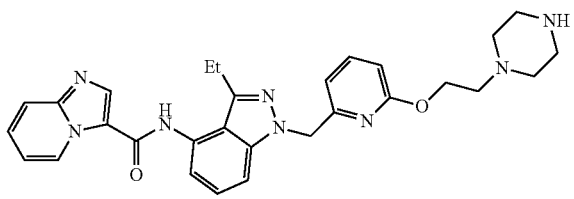 [SMILES: CCc1nn(Cc2cccc(OCCN3CCNCC3)n2)c2cccc(NC(=O)c3cnc4ccccn34)c12]

To a suspension of N-(3-ethyl-1-((6-hydroxypyridin-2-yl)methyl)-1H-indazol-4-yl)imidazo[1,2-a]pyridine-3-carboxamide (26 mg, 0.0630 mmol; prepared as in Example 17, Step A) in THF (5 mL) was added tert-butyl 4-(2-hydroxyethyl)piperazine-1-carboxylate (43.6 mg, 0.189 mmol), triphenylphosphine (41.3 mg, 0.158 mmol) and diethyl azodicarboxylate (62.0 μL, 0.158 mmol). The suspension became a clear solution and was stirred for 16 hours. The reaction mixture was concentrated under reduced pressure and the residue was purified by silica gel chromatography (DCM/MeOH 10:1) to provide the intermediate tert-butyl 4-(2-(6-((3-ethyl-4-(imidazo[1,2-a]pyridine-3-carboxamido)-1H-indazol-1-yl)methyl)pyridin-2-yloxy)ethyl)piperazine-1-carboxylate mixed with triphenyl phosphine oxide, to which was added DCM/TFA (2 mL/1 mL). The reaction mixture was stirred for 30 minutes and then concentrated under reduced pressure. Silica gel chromatography (DCM/MeOH/NH4OH 10:1:0.1) provided the desired product (10 mg). MS (ES+APCI) m/z=525 (M+H).

Example 44

N-(3-ethyl-1-((6-methylpyridin-2-yl)methyl)-1H-indazol-4-yl)-7-(1,3,4-thiadiazol-2-yl)imidazo[1,2-a]pyridine-3-carboxamide

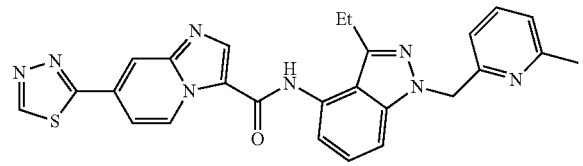 [SMILES: CCc1nn(Cc2cccc(C)n2)c2cccc(NC(=O)c3cnc4cc(-c5nncs5)ccn34)c12]

Step A: Preparation of N-(3-ethyl-1-((6-methylpyridin-2-yl)methyl)-1H-indazol-4-yl)-7-(2-formylhydrazinecarbonyl)imidazo[1,2-a]pyridine-3-carboxamide: To 3-(3-ethyl-1-((6-methylpyridin-2-yl)methyl)-1H-indazol-4-ylcarbamoyl)imidazo[1,2-a]pyridine-7-carboxylic acid (26 mg, 0.057 mmol; prepared as in Example 28, Step A) in DMF was added formohydrazide (6.9 mg, 0.11 mmol), N1-((ethylimino)methylene)-N3,N3-dimethylpropane-1,3-diamine hydrochloride (22 mg, 0.11 mmol), 1H-benzo[c/][1,2,3]triazol-1-ol hydrate (15 mg, 0.11 mmol) and triethylamine (17 mg, 0.17 mmol). The reaction mixture was stirred for 16 hours at ambient temperature, diluted with DCM (30 mL), washed with H2O, dried (Na2SO4) and concentrated under reduced pressure. The residue was triturated with Et2O (30 mL) to give the product (20 mg).

Step B: Preparation of N-(3-ethyl-1-((6-methylpyridin-2-yl)methyl)-1H-indazol-4-yl)-7-(1,3,4-thiadiazol-2-yl)imidazo[1,2-a]pyridine-3-carboxamide: To N-(3-ethyl-1-((6-methylpyridin-2-yl)methyl)-1H-indazol-4-yl)-7-(2-formylhydrazinecarbonyl)imidazo[1,2-a]pyridine-3-carboxamide (36 mg, 0.073 mmol) in toluene/dioxane (1 mL/1 mL) was added hexamethyldisiloxane (71 mg, 0.44 mmol) and P2S5 (81 mg, 0.36 mmol). The reaction mixture was sealed and heated in a microwave reactor to 110° C. for 3 hours. The mixture was then concentrated under reduced pressure and the residue was purified by silica gel chromatography (DCM/MeOH 10:1) to provide the final product (1.5 mg). MS (ES+APCI) m/z=495 (M+H).

Example 45

N-(3-ethyl-1-((6-methylpyridin-2-yl)methyl)-1H-indazol-4-yl)-7-(2-(4-methylpiperazin-1-yl)ethoxy)imidazo[1,2-a]pyridine-3-carboxamide Step A: Preparation of 2-(bromomethyl)-6-methylpyridine: To an ice cooled a solution of (6-methylpyridin-2-yl)methanol (400 mg, 3.25 mmol) in dichloromethane (16 mL) under an atmosphere of dry nitrogen was added triphenylphosphine (1278 mg, 4.87 mmol) and carbon tetrabromide (1616 mg, 4.87 mmol). The mixture was stirred for 1 hour. The solvent was removed under reduced pressure and the residue was purified by chromatography on silica, eluting with 2-4% methanol in dichloromethane to give 2-(bromomethyl)-6-methylpyridine as an oil (402 mg).

Step B: Preparation of 3-iodo-4-nitro-1H-indazole: A solution of 4-nitro-1H-indazole (50.0 g; 306 mmol) in N,N-dimethylformamide (600 mL) was cooled to 5° C. under a nitrogen atmosphere with stirring. Powdered potassium hydroxide (68.8 g; 1226 mmol) was added. A solution of iodine (156 g; 613 mmol) in DMF (200 mL) was added slowly to the reaction mixture over 2 hours maintaining the temperature between 5 and 10° C. The mixture was stirred at 25° C. for 24 hours. Additional iodine (39.0 g; 153.2 mmol) and potassium hydroxide (17.2 g; 306.5 mmol) was added. The mixture was stirred at 25° C. for a further 12 hours. The reaction mixture was added to an aqueous solution of sodium bisulfite (10% solution; 3300 mL) with stirring. The resulting precipitate was collected by filtration and washed with water. The material was dried in a vacuum oven at 40° C. The material was dissolved in methylene chloride/methanol (10:1; 1.5 L) and filtered through Celite® to remove inorganic impurities. Concentration of the solution under vacuum gave 3-iodo-4-nitro-1H-indazole as a yellow solid (75 g).

Step C: Preparation of 3-iodo-1-((6-methylpyridin-2-yl)methyl)-4-nitro-1H-indazole: To a solution of 3-iodo-4-nitro-1H-indazole (172 mg, 0.596 mmol) in dry N,N-dimethylformamide (3 mL) under an atmosphere of dry nitrogen was added 2-(bromomethyl)-6-methylpyridine (122 mg, 0.656 mmol) and potassium carbonate (165 mg, 1.19 mmol) with magnetic stirring. The mixture was stirred at ambient temperature for 3 days. The reaction mixture was diluted with water (20 mL) and extracted into ethyl acetate. The organic phases were combined, washed with saturated sodium chloride solution, dried over sodium sulfate, filtered and concentrated under reduced pressure. The resulting material was purified using preparative chromatography on silica, eluting with hexane/ethyl acetate (3:1) to give 3-iodo-1-((6-methylpyridin-2-yl)methyl)-4-nitro-1H-indazole (213 mg).

Step D: Preparation of 1-((6-methylpyridin-2-yl)methyl)-4-nitro-3-vinyl-1H-indazole: To a reaction vial was added 3-iodo-1-((6-methylpyridin-2-yl)methyl)-4-nitro-1H-indazole (216 mg, 0.548 mmol) and potassium trifluoro(vinyl)borate (156 mg, 1.64 mmol). Isopropanol (2 mL) and tetrahydrofuran (0.5 mL) were added. Argon was bubbled through the mixture for 20 minutes. Triethylamine (229 μL, 1.64 mmol) and 1,1'-bis(diphenylphosphino)ferrocene-palladium(II)dichloride dichloromethane complex (44.8 mg, 0.0548 mmol) were added. The vial was sealed and the mixture was heated at 90-100° C. for 3 hours. The mixture was allowed to cool and filtered through glass fiber filter paper, washing with ethyl acetate. The solution was concentrated under reduced pressure. The residue was dissolved in chloroform (30 mL) and washed with water (10 mL). The solution was dried over magnesium sulfate, filtered and concentrated under reduced pressure to give 1-((6-methylpyridin-2-yl)methyl)-4-nitro-3-vinyl-1H-indazole as an oil (141 mg).

Step E: Preparation of 3-ethyl-1-((6-methylpyridin-2-yl)methyl)-1H-indazol-4-amine: A mixture of 1-((6-methylpyridin-2-yl)methyl)-4-nitro-3-vinyl-1H-indazole (161 mg, 0.547 mmol) and 20% palladium hydroxide on carbon (38.4 mg, 0.0547 mmol) was stirred in methanol (3 mL) under an atmosphere of hydrogen for 3 hours. The mixture was diluted with methanol and filtered through glass fiber filter paper. The filtrate was concentrated under reduced pressure to give 3-ethyl-1-((6-methylpyridin-2-yl)methyl)-1H-indazol-4-amine (142 mg).

Step F: Preparation of N-(3-ethyl-1-((6-methylpyridin-2-yl)methyl)-1H-indazol-4-yl)-7-(2-(4-methylpiperazin-1-yl)ethoxy)imidazo[1,2-a]pyridine-3-carboxamide: To a cooled (ice/water bath) solution of 3-ethyl-1-((6-methylpyridin-2-yl)methyl)-1H-indazol-4-amine (0.080 g; 0.30 mmol) in anhydrous THF (2 mL) under nitrogen was added drop wise LHMDS (1.0 M solution in THF; 0.32 mmol). The mixture was stirred with cooling for 10 minutes and then added to a solution of ethyl 7-(2-(4-methylpiperazin-1-yl)ethoxy)imidazo[1,2-a]pyridine-3-carboxylate (Preparation D) in anhydrous THF (2 mL) with ice/water cooling. An excess of saturated aqueous ammonium chloride solution was added to quench the reaction. The mixture was extracted with DCM. The aqueous phase was then rendered basic by the addition of saturated aqueous sodium carbonate solution and extracted multiple times with DCM and EtOAc. The combined organic extracts were dried over sodium sulfate and concentrated under reduced pressure. The residue was purified by preparative thin layer chromatography on silica, eluting with DCM/MeOH/NH$_4$OH (100:8:1). Purification by thin layer chromatography of the isolated material was repeated under the same conditions to provide N-(3-ethyl-1-((6-methylpyridin-2-yl)methyl)-1H-indazol-4-yl)-7-(2-(4-methylpiperazin-1-yl)ethoxy)imidazo[1,2-a]pyridine-3-carboxamide (53 mg). MS (ES+APCI) m/z=553.1 (M+H).

Example 46

N3-(3-ethyl-1-((6-methylpyridin-2-yl)methyl)-1H-indazol-4-yl)-N7-(pyrrolidin-3-yl)imidazo[1,2-a]pyridine-3,7-dicarboxamide

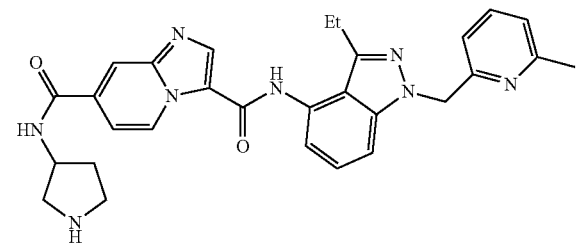 [SMILES: CCc1nn(Cc2cccc(C)n2)c2cccc(NC(=O)c3cnc4cc(C(=O)NC5CCNC5)ccn34)c12]

To 3-(3-ethyl-1-((6-methylpyridin-2-yl)methyl)-1H-indazol-4-ylcarbamoyl) imidazo[1,2-a]pyridine-7-carboxylic acid (26 mg, 0.057 mmol; prepared as in Example 28, step A) in DMF (2 mL) was added di(1H-imidazol-1-yl)methanone (14 mg, 0.086 mmol). The reaction mixture was stirred at ambient temperature for 1 hour. tert-Butyl 3-aminopyrrolidine-1-carboxylate (32 mg, 0.17 mmol) was added to the reaction mixture. The mixture was sealed and heated at 70° C. for 2 hours and cooled to ambient temperature. DMF was removed under reduced pressure. The residue was triturated with Et$_2$O. The resulting tan solid was dissolved in DCM (1 mL). TFA (1 mL) was added to the DCM solution. The reaction mixture was stirred for 30 minutes and then concentrated under reduced pressure. The residue was purified by silica gel chromatography (DCM/MeOH/NH₄OH 10:1:0.1) to provide the final product (10 mg). MS (ES+APCI) m/z=523 (M+H).

Example 47

N7-(2-aminoethyl)-N-3-(3-ethyl-1-((6-methylpyridin-2-yl)methyl)-1H-indazol-4-yl)imidazo[1,2-a]pyridine-3,7-dicarboxamide

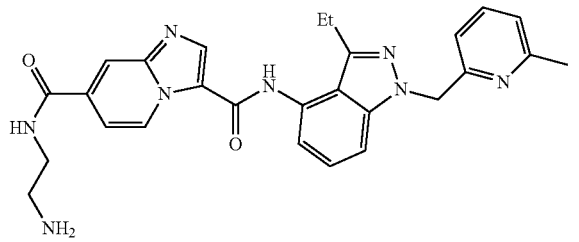 [SMILES: CCc1nn(Cc2cccc(C)n2)c2cccc(NC(=O)c3cnc4cc(C(=O)NCCN)ccn34)c12]

To 3-(3-ethyl-1-((6-methylpyridin-2-yl)methyl)-1H-indazol-4-ylcarbamoyl) imidazo[1,2-a]pyridine-7-carboxylic acid (26 mg, 0.057 mmol; prepared as in Example 28, step A) in DMF (2 mL) was added di(1H-imidazol-1-yl)methanone (14 mg, 0.086 mmol). The reaction mixture was stirred at ambient temperature for 1 hour. tert-Butyl 2-aminoethylcarbamate (27 mg, 0.17 mmol) was added to the mixture. The reaction vial was sealed and the mixture was heated to 70° C. for 2 hours. The mixture was cooled to ambient temperature. The DMF was removed under reduced pressure. The residue was triturated with Et₂O. The resulting tan solid was dissolved in DCM (1 mL). TFA (1 mL) was added to the solution. The reaction mixture was stirred for 30 minutes and then concentrated under reduced pressure. The residue was purified by silica gel chromatography (DCM/MeOH/NH₄OH 10:1:0.1) to give the final product (10 mg). MS (ES+APCI) m/z=497 (M+H).

Example 48

N3-(3-ethyl-1-((6-methylpyridin-2-yl)methyl)-1H-indazol-4-yl)-N7-methylimidazo[1,2-a]pyridine-3,7-dicarboxamide

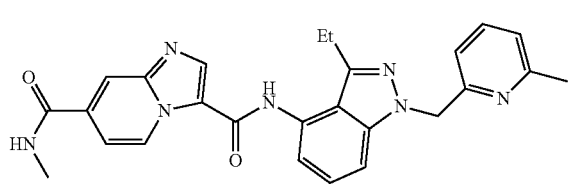 [SMILES: CCc1nn(Cc2cccc(C)n2)c2cccc(NC(=O)c3cnc4cc(C(=O)NC)ccn34)c12]

To 3-(3-ethyl-1-((6-methylpyridin-2-yl)methyl)-1H-indazol-4-ylcarbamoyl) imidazo[1,2-a]pyridine-7-carboxylic acid (26 mg, 0.057 mmol; prepared as in Example 28, step A) in DMF (2 mL) was added di(1H-imidazol-1-yl)methanone (14 mg, 0.086 mmol). The reaction mixture was stirred at ambient temperature for 1 hour. Methanamine (286 µL, 0.57 mmol) was added to the reaction mixture. The reaction vial was sealed and the mixture was heated at 70° C. for 2 hours. The mixture was cooled to ambient temperature. The DMF was removed under reduced pressure. The residue was purified by silica gel chromatography (DCM/MeOH 10:1) to provide the final product (13 mg). MS (ES+APCI) m/z=468 (M+H).

Example 49

N3-(3-ethyl-1-((6-methylpyridin-2-yl)methyl)-1H-indazol-4-yl)-N7,N7-dimethylimidazo[1,2-a]pyridine-3,7-dicarboxamide

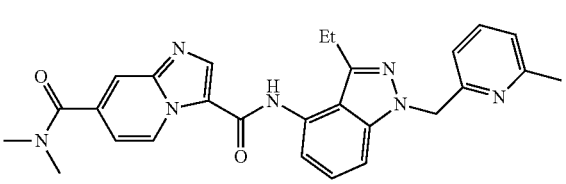

To 3-(3-ethyl-1-((6-methylpyridin-2-yl)methyl)-1H-indazol-4-ylcarbamoyl) imidazo[1,2-a]pyridine-7-carboxylic acid (26 mg, 0.057 mmol; prepared as in Example 28, step A) in DMF (2 mL) was added di(1H-imidazol-1-yl)methanone (14 mg, 0.086 mmol). The reaction mixture was stirred at ambient temperature for 1 hour. Dimethylamine (286 µL, 0.57 mmol) was added to the reaction mixture. The reaction vial was sealed and the mixture was heated at 70° C. for 2 hours. The mixture was cooled to ambient temperature. The DMF was removed under reduced pressure. The residue was purified by silica gel chromatography (DCM/MeOH 10:1) to provide the final product (10 mg). MS (ES+APCI) m/z=482 (M+H).

Example 50

N3-(3-ethyl-1-((6-methylpyridin-2-yl)methyl)-1H-indazol-4-yl)-N7-(1-methylpyrrolidin-3-yl)imidazo[1,2-a]pyridine-3,7-dicarboxamide

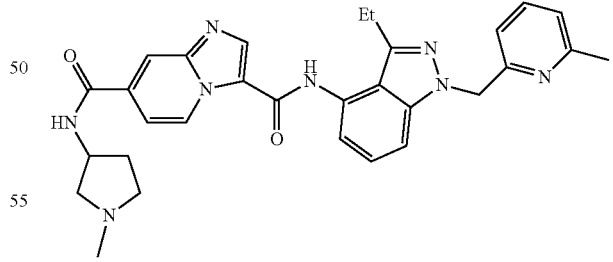

To N3-(3-ethyl-1-((6-methylpyridin-2-yl)methyl)-1H-indazol-4-yl)-N7-(pyrrolidin-3-yl)imidazo[1,2-a]pyridine-3,7-dicarboxamide (5 mg, 0.0096 mmol; prepared as in Example 46) in DCM/MeOH (1 mL/1 mL) was added HCHO as a 35% aqueous solution (16 mg, 0.19 mmol) and NaBH(OAc)₃ (10 mg, 0.048 mmol). The reaction mixture was stirred for one hour, concentrated under reduced pressure and the residue was purified by silica gel chromatography (DCM/

MeOH/NH₄OH 10:1:0.1) to provide the final product (4 mg). MS (ES+APCI) m/z=537 (M+H).

Example 51

N7-(2-(dimethylamino)ethyl)-N-3-(3-ethyl-1-((6-methylpyridin-2-yl)methyl)-1H-indazol-4-yl)imidazo[1,2-a]pyridine-3,7-dicarboxamide

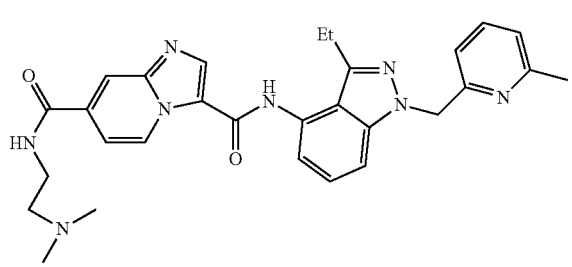 [SMILES: CCc1nn(Cc2cccc(C)n2)c2cccc(NC(=O)c3cnc4cc(C(=O)NCCN(C)C)ccn34)c12]

To N7-(2-aminoethyl)-N-3-(3-ethyl-1-((6-methylpyridin-2-yl)methyl)-1H-indazol-4-yl)imidazo[1,2-a]pyridine-3,7-dicarboxamide (5 mg, 0.010 mmol; prepared as in Example 47) in DCM/MeOH (1 mL/1 mL) was added HCHO as a 35% aqueous solution (16 mg, 0.19 mmol) and NaBH(OAc)₃ (11 mg, 0.05 mmol). The reaction mixture was stirred for one hour, concentrated under reduced pressure and the residue was purified by silica gel chromatography (DCM/MeOH/NH₄OH 10:1:0.1) to provide the final product (4 mg). MS (ES+APCI) m/z=525 (M+H).

Example 52

7-(1,2-dimethyl-1H-imidazol-5-yl)-N-(3-ethyl-1-((6-methylpyridin-2-yl)methyl)-1H-indazol-4-yl)imidazo[1,2-a]pyridine-3-carboxamide

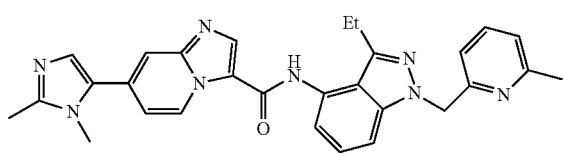

To 7-bromo-N-(3-ethyl-1-((6-methylpyridin-2-yl)methyl)-1H-indazol-4-yl) imidazo[1,2-a]pyridine-3-carboxamide (prepared as in Example 127, Step A; 129 mg, 0.264 mmol) in DMF (4 mL) was added trifuran-2-ylphosphine (12.2 mg, 0.0527 mmol), 1,2-dimethyl-1H-imidazole (50.7 mg, 0.527 mmol), palladium diacetate (5.92 mg, 0.0264 mmol) and K₂CO₃ (72.9 mg, 0.527 mmol). The reaction mixture was purged with argon, sealed and heated to 140° C. for 3 hours. The mixture was cooled to ambient temperature, diluted with DCM (20 mL) and washed with H₂O. The organic phase was dried (Na₂SO₄) and concentrated under reduced pressure. The residue was purified by silica gel chromatography (DCM/MeOH/NH₄OH, 10:1:0.1) to provide the final product (20 mg). MS (ES+APCI) m/z=505 (M+H).

Example 53

N-(1-((1,6-dimethyl-2-oxo-1,2-dihydropyridin-3-yl)methyl)-3-ethyl-1H-indazol-4-yl)imidazo[1,2-a]pyridine-3-carboxamide

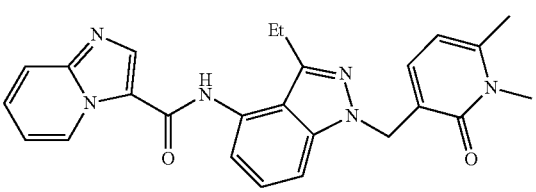 [SMILES: CCc1nn(Cc2ccc(C)n(C)c2=O)c2cccc(NC(=O)c3cnc4ccccn34)c12]

Step A: Preparation of methyl 2-methoxy-6-methylnicotinate: To 2-hydroxy-6-methylnicotinic acid (5.00 g, 32.7 mmol) in CHCl₃ (163 mL) was added Ag₂CO₃ (9.00 g, 32.7 mmol) and MeI (6.11 mL, 98.0 mmol). The reaction mixture was heated at 65° C. for 16 hours. The mixture was cooled to ambient temperature, filtered through Celite and the filtrate was concentrated under reduced pressure to give the crude product (5.6 g).

Step B: Preparation of ethyl 1 (2-methoxy-6-methylpyridin-3-yl)methanol: To methyl 2-methoxy-6-methylnicotinate (5.60 g, 30.9 mmol) in THF (155 mL, 30.9 mmol) to 0° C. was added lithium aluminum hydride (1.23 g, 30.9 mmol) and the mixture was stirred at 0° C. for 75 minutes. The mixture was diluted with 30 mL THF and a scoop of Celite was added. The mixture was stirred for a few minutes. Sodium sulfate decahydrate was added to quench the reaction. The mixture was filtered and the filtrate was concentrated to give the product (4.7 g).

Step C: Preparation of (3-(bromomethyl)-2-methoxy-6-methylpyridine: (2-Methoxy-6-methylpyridin-3-yl)methanol (4.7 g, 30.7 mmol) was combined with triphenylphosphine (12.1 g, 46.0 mmol) and CBr₄ (15.3 g, 46.0 mmol). DCM (153 mL, 30.7 mmol) was added and the mixture was stirred at 0° C. for 90 minutes. The mixture was concentrated under reduced pressure and the residue was purified by silica gel chromatography eluting with 1:1 DCM/Hexanes to provide the final product (2.0 g).

Step D: Preparation of 3-iodo-1-((2-methoxy-6-methylpyridin-3-yl)methyl)-4-nitro-1H-indazole: To 3-(bromomethyl)-2-methoxy-6-methylpyridine (500 mg, 2.314 mmol) and 3-iodo-4-nitro-1H-indazole (668.8 mg, 2.314 mmol) in DMF (10 mL) was added K₂CO₃ (479.7 mg, 3.471 mmol). The reaction mixture was stirred at ambient temperature for 16 hours. The reaction mixture was diluted with EtOAc, washed with water, brine and concentrated under reduced pressure to give the product (1.0 g).

Step E: Preparation of 1-((2-methoxy-6-methylpyridin-3-yl)methyl)-4-nitro-3-vinyl-1H-indazole: A mixture of 3-iodo-1-((2-methoxy-6-methylpyridin-3-yl)methyl)-4-nitro-1H-indazole (982 mg, 2.31 mmol) in 10 mL of 4:1 IPA/THF was degassed for 20 minutes with an argon balloon, to which TEA (968 µL, 6.94 mmol), 1,1'-bis(diphenylphosphino)ferrocene-palladium(II)dichloride dichloromethane complex (189 mg, 0.231 mmol) and potassium trifluoro(vinyl)borate (659 mg, 6.94 mmol) were added. The reaction mixture was heated at 90° C. for 3 hours. The mixture was filtered through Celite, and the filter pad was rinsed with ethyl acetate. The filtrate was washed with water and brine 3 times. The organic phase was concentrated to a residue under vacuum. The residue was purified by silica gel chromatography eluting with 15-20% EtOAc/hexanes to give the product (395 mg).

Step F: Preparation of 3-ethyl-1-((2-methoxy-6-methylpyridin-3-yl)methyl)-1H-indazol-4-amine: To 1-((2-methoxy-6-methylpyridin-3-yl)methyl)-4-nitro-3-vinyl-1H-indazole (395 mg, 1.22 mmol) in a Parr flask was added palladium hydroxide on carbon (171 mg, 20% wt) and MeOH (6 mL) for solubility. The Parr flask was attached to the shaker and applied with 40 psi H$_2$ for seven hours. The reaction mixture was evacuated, purged with nitrogen, filtered through Celite, and the filter pad was rinsed with MeOH. The filtrate was concentrated to a yellow oily residue under reduced pressure. Silica gel chromatography eluting with 1% MeOH, 0.5% NH$_4$OH in DCM gave the product (108 mg).

Step G: Preparation of 3-ethyl-1-((2-methoxy-6-methylpyridin-3-yl)methyl)-1H-indazol-4-amine: A mixture of 3-ethyl-1-((2-methoxy-6-methylpyridin-3-yl)methyl)-4-nitro-1H-indazole (186 mg, 0.57 mmol), iron powder (318 mg, 5.7 mmol) and NH$_4$Cl (15.2 mg, 0.285 mmol) in EtOH/water (3 mL/0.75 mL) was heated to reflux for 60 minutes. The reaction mixture was filtered through GF/F paper and concentrated to a residue under reduced pressure. Preparative thin layer chromatography eluting with 2% MeOH 0.25% NH$_4$OH in DCM provided the product (108 mg).

Step H: Preparation of N-(3-ethyl-1-((2-methoxy-6-methylpyridin-3-yl)methyl)-1H-indazol-4-yl)imidazo[1,2-a]pyridine-3-carboxamide: To imidazo[1,2-a]pyridine-3-carboxylic acid (118 mg, 0.729 mmol) was added a mixture of 3:1 DCM/thionyl chloride (4 mL). The mixture was stirred at ambient temperature for 3 hours and then concentrated to a residue under N$_2$ stream. The residue was dried under high vacuum for 30 minutes. 3-Ethyl-1-((2-methoxy-6-methylpyridin-3-yl)methyl)-1H-indazol-4-amine (108 mg, 0.364 mmol) in THF/DCE (1:1; 8 mL) was added to the dry acid-chloride residue. The reaction mixture was heated at 75° C. for 30 minutes. The mixture was concentrated under reduced pressure and diluted with DCM. The solution was washed with saturated NaHCO$_3$ aqueous solution, dried (Na$_2$SO$_4$) and concentrated under reduced pressure. The residue was purified by silica gel chromatography eluting with 5% MeOH 0.5% NH$_4$OH in DCM to give the product (57.6 mg).

Step I: Preparation of N-(3-ethyl-1-((2-hydroxy-6-methylpyridin-3-yl)methyl)-1H-indazol-4-yl)imidazo[1,2-a]pyridine-3-carboxamide: A mixture of N-(3-ethyl-1-((2-methoxy-6-methylpyridin-3-yl)methyl)-1H-indazol-4-yl)imidazo[1,2-a]pyridine-3-carboxamide (50 mg, 0.11 mmol) and HCl (2 mL, 4M in dioxane) was heated at 80° C. in a sealed vial for 4 hours. The reaction mixture was diluted with ethyl acetate (20 mL) and water (5 mL). Saturated NaHCO$_3$ aqueous solution was added to adjust pH=7. The solution was concentrated under reduced pressure to a solid residue. The residue was dissolved in DCM/MeOH and filtered to remove inorganic impurities. The solution was concentrated under reduced pressure to give the product (48 mg).

Step J: Preparation of N-(1-((1,6-dimethyl-2-oxo-1,2-dihydropyridin-3-yl)methyl)-3-ethyl-1H-indazol-4-yl)imidazo[1,2-a]pyridine-3-carboxamide: A mixture of N-(3-ethyl-1-((2-hydroxy-6-methylpyridin-3-yl)methyl)-1H-indazol-4-yl)imidazo[1,2-a]pyridine-3-carboxamide (18.3 mg, 0.0429 mmol) and methyl iodide (2.68 µL, 0.0429 mmol) with K$_2$CO$_3$ (17.8 mg, 0.129 mmol) in DMF (3 mL) was stirred at ambient temperature for 16 hours. The reaction mixture was diluted with ethyl acetate and water. The aqueous phase was extracted 3 times with EtOAc. The organic phases were combined and washed with brine. The solvent was removed under reduced pressure and the residue was purified by silica gel chromatography (10:1 DCM/MeOH) to provide the final product (6 mg). MS (ES+APCI) m/z=441 (M+H).

Example 54

N-(3-ethyl-1-((6-(2-(4-methylpiperazin-1-yl)ethoxy)pyridin-2-yl)methyl)-1H-indazol-4-yl)imidazo[1,2-a]pyridine-3-carboxamide

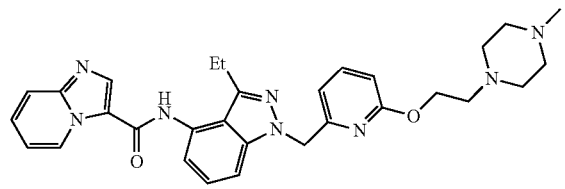 [SMILES: CCc1nn(Cc2cccc(OCCN3CCN(C)CC3)n2)c2cccc(NC(=O)c3cnc4ccccn34)c12]

To N-(3-ethyl-1-((6-(2-(piperazin-1-yl)ethoxy)pyridin-2-yl)methyl)-1H-indazol-4-yl)imidazo[1,2-a]pyridine-3-carboxamide (5 mg, 0.0095 mmol; prepared as in Example 43) in MeOH (2 mL) was added NaBH(OAc)$_3$ (6.1 mg, 0.029 mmol) and HCHO (as a 35% aqueous solution) (19 mg, 0.19 mmol). The reaction mixture was stirred for 30 minutes, concentrated under reduced pressure and the residue was purified by silica gel chromatography (DCM/MeOH/NH$_4$OH 10:1:0.1) to provide the final product (4 mg). MS (ES+APCI) m/z=539 (M+H).

Example 55

N-(1-((1,5-dimethyl-1H-pyrazol-3-yl)methyl)-3-ethyl-1H-indazol-4-yl)imidazo[1,2-a]pyridine-3-carboxamide

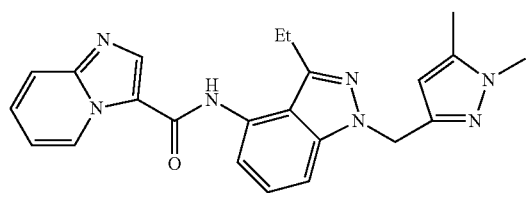 [SMILES: CCc1nn(Cc2cc(C)n(C)n2)c2cccc(NC(=O)c3cnc4ccccn34)c12]

Step A: Preparation of 3-(chloromethyl)-1,5-dimethyl-1H-pyrazole hydrochloride: To (1,5-dimethyl-1H-pyrazol-3-yl)methanol (5.01 g, 39.71 mmol) in DCM (80 mL) at 0° C. was cautiously added thionyl chloride (25 mL, 343.6 mmol). The cold bath was removed and the reaction mixture was stirred at ambient temperature for 3 hours. The reaction mixture was concentrated under reduced pressure to give crude product (7.32 g).

Step B: Preparation of 1-((1,5-dimethyl-1H-pyrazol-3-yl)methyl)-3-iodo-4-nitro-1H-indazole: To 3-(chloromethyl)-1,5-dimethyl-1H-pyrazole hydrochloride (5.01 g, 27.7 mmol) in DMF (50 mL) was added 3-iodo-4-nitro-1H-indazole (8.00 g, 27.7 mmol) and K$_2$CO$_3$ (15.3 g, 111 mmol). The reaction mixture was stirred for 20 hours. The mixture was concentrated under reduced pressure to remove most of the DMF. The residue was diluted with DCM (100 mL) and washed with H$_2$O. The organic phase was dried (Na$_2$SO$_4$) and concentrated under reduced pressure. The residue was purified by silica gel chromatography (EtOAc/Hexane 1:3) to provide the product (8.35 g).

Step C: Preparation of 1-((1,5-dimethyl-1H-pyrazol-3-yl)methyl)-4-nitro-3-vinyl-1H-indazole: To 1-((1,5-dimethyl-1H-pyrazol-3-yl)methyl)-3-iodo-4-nitro-1H-indazole (8.35 g, 21.0 mmol) in THF/IPA (10 mL/30 mL) was added trifluorovinylpotassium borate (5.63 g, 42.0 mmol), 1,1'-bis(diphenylphosphino)ferrocene-palladium(II)dichloride dichloromethane complex (0.858 g, 1.05 mmol) and triethylamine (8.79 mL, 63.1 mmol). The reaction mixture was heated to 80° C. for 16 hours. The mixture was diluted with EtOAc (100 mL), washed with H₂O and brine, and concentrated under reduced pressure. The residue was purified by silica gel chromatography (Hexane/EtOAc 5:1) to provide the product (5.12 g).

Step D: Preparation of 1-((1,5-dimethyl-1H-pyrazol-3-yl)methyl)-3-ethyl-1H-indazol-4-amine: To 1-((1,5-dimethyl-1H-pyrazol-3-yl)methyl)-4-nitro-3-vinyl-1H-indazole (5.15 g, 17.3 mmol) in EtOH/DCM (100 mL/10 mL) was cautiously added palladium hydroxide on carbon (2.2 g, 20% wt). The reaction mixture was purged with nitrogen and hydrogen three times each. The reaction was agitated under H₂ (45 psi) for 3 hours. The system was evacuated and purged with nitrogen. The mixture was filtered through Celite and the filter pad was washed with MeOH/DCM (10:1, 300 mL). The solution was concentrated under reduced pressure and the residue was purified by silica gel chromatography (EtOAc/Hexane 2:1) to provide the product (4.35 g).

Step E: Preparation of N-(1-((1,5-dimethyl-1H-pyrazol-3-yl)methyl)-3-ethyl-1H-indazol-4-yl)imidazo[1,2-a]pyridine-3-carboxamide: To a suspension of imidazo[1,2-a]pyridine-3-carboxylic acid (45.1 mg, 0.278 mmol) in NMP (5 mL) was added 2,4,6-trichlorobenzoyl chloride (43.5 µL, 0.278 mmol) and triethylamine (38.8 µL, 0.278 mmol). The reaction mixture was stirred for 30 minutes. 1-((1,5-Dimethyl-1H-pyrazol-3-yl)methyl)-3-ethyl-1H-indazol-4-amine (50 mg, 0.186 mmol) was added to the reaction mixture, which was heated to 87° C. for 3 hours. The mixture was cooled to ambient temperature, and diluted with 10% NaOH aqueous solution (5 mL) and EtOAc (20 mL). The organic phase was washed with water and brine, then concentrated under reduced pressure. The residue was triturated with Et₂O to give final product (35 mg). MS (ES+APCI) m/z=414 (M+H).

Example 56

N-(1-((1,5-dimethyl-1H-pyrazol-3-yl)methyl)-3-ethyl-1H-indazol-4-yl)-7-(2-(4-methylpiperazin-1-yl)ethoxy)imidazo[1,2-a]pyridine-3-carboxamide

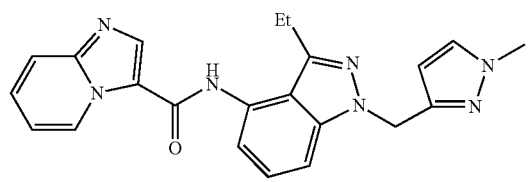

Step A: Preparation of lithium 7-(2-(4-methylpiperazin-1-yl)ethoxy)imidazo[1,2-a]pyridine-3-carboxylate: To ethyl 7-(2-(4-methylpiperazin-1-yl)ethoxy)imidazo[1,2-a]pyridine-3-carboxylate (Preparation D; 43.93 g, 132.2 mmol) in H₂O (150 mL) was added lithium hydroxide hydrate (6.31 g, 150.4 mmol). The reaction mixture was heated to 95° C. for 4 hours. The mixture was cooled to ambient temperature and hydrogen chloride (4.626 mL, 4M in dioxane) was added followed by stirring for 10 minutes. Water was removed under reduced pressure, and the residue was dried under vacuum for 16 hours to give the product (42.78 g).

Step B: Preparation of N-(1-((1,5-dimethyl-1H-pyrazol-3-yl)methyl)-3-ethyl-1H-indazol-4-yl)-7-(2-(4-methylpiperazin-1-yl)ethoxy)imidazo[1,2-a]pyridine-3-carboxamide:
To a solution of lithium 7-(2-(4-methylpiperazin-1-yl)ethoxy)imidazo[1,2-a]pyridine-3-carboxylate (89.1 mg, 0.278 mmol) in NMP (6 mL) at 0° C. was added 2,4,6-trichlorobenzoyl chloride (43.5 µL, 0.278 mmol). The reaction mixture was stirred for 30 minutes. 1-((1,5-Dimethyl-1H-pyrazol-3-yl)methyl)-3-ethyl-1H-indazol-4-amine (50 mg, 0.186 mmol) was added and the mixture was heated at 87° C. for 3 hours. The reaction mixture was cooled to ambient temperature, and diluted with 10% NaOH aqueous solution (5 mL) and EtOAc (20 mL). The organic phase was washed with water and brine and then concentrated under reduced pressure. The residue was triturated with Et₂O to give final product (71 mg). MS (ES+APCI) m/z=556 (M+H).

Example 57

N-(3-ethyl-1-((1-methyl-1H-pyrazol-3-yl)methyl)-1H-indazol-4-yl)imidazo[1,2-a]pyridine-3-carboxamide

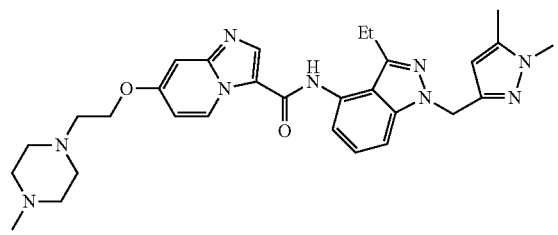 [SMILES: CCc1nn(Cc2cc(C)n(C)n2)c2cccc(NC(=O)c3cnc4cc(OCCN5CCN(C)CC5)ccn34)c12]

Step A: Preparation of 3-iodo-1-((1-methyl-1H-pyrazol-3-yl)methyl)-4-nitro-1H-indazole: To (1-methyl-1H-pyrazol-3-yl)methanol (2.01 g, 17.93 mmol) in DCM (80 mL) at 0° C. was cautiously added thionyl chloride (10.43 mL, 143.4 mmol). The cold bath was removed and the reaction mixture was stirred at ambient temperature for 3 hours. The reaction mixture was concentrated under reduced pressure. The residual yellow solid was diluted with DMF (30 mL). 3-Iodo-4-nitro-1H-indazole (5.181 g, 17.93 mmol) and K₂CO₃ (7.432 g, 53.78 mmol) were added to the DMF solution. The reaction mixture was stirred for 20 hours, and concentrated under reduced pressure to remove most of the DMF. The residue was diluted with DCM (100 mL) and washed with H₂O. The organic phase was dried (Na₂SO₄) and concentrated under reduced pressure. The residue was purified by silica gel chromatography (EtOAc/Hexane 1:3) to provide the product (5.11 g).

Step B: Preparation of 1-((1-methyl-1H-pyrazol-3-yl)methyl)-4-nitro-3-vinyl-1H-indazole: To 3-iodo-1-((1-methyl-1H-pyrazol-3-yl)methyl)-4-nitro-1H-indazole (5.11 g, 13.3 mmol) in THF/IPA (10 mL/30 mL) was added trifluorovinylpotassium borate (3.57 g, 26.7 mmol), 1,1'-bis(diphenylphosphino)ferrocene-palladium(II)dichloride dichloromethane complex (0.545 g, 0.667 mmol) and triethylamine (5.58 mL, 40.0 mmol). The reaction mixture was heated to 80° C. for 16 hours. The reaction mixture was diluted with EtOAc (100 mL), washed with H₂O and brine. The organic phase was concentrated under reduced pressure and the residue was purified by silica gel chromatography (hexanes/EtOAc 5:1) to provide the product (2.36 g).

Step C: Preparation of 3-ethyl-1-((1-methyl-1H-pyrazol-3-yl)methyl)-1H-indazol-4-amine: To 1-((1-methyl-1H-pyrazol-3-yl)methyl)-4-nitro-3-vinyl-1H-indazole (2.36 g, 8.33 mmol) in EtOH (80 mL) was cautiously added palladium hydroxide on carbon (1.5 g, 20% wt). The reaction mixture was purged with nitrogen and hydrogen three times each. The mixture was agitated under H₂ (45 psi) for 3 hours. The system was evacuated and purged with nitrogen. The mixture was filtered through Celite® and the filter pad was washed with MeOH/DCM (10:1, 300 mL). The filtrate was concentrated under reduced pressure and the residue was purified by silica gel chromatography (EtOAc/hexanes 2:1) to provide the product (1.52 g).

Step D: Preparation of N-(3-ethyl-1-((1-methyl-1H-pyrazol-3-yl)methyl)-1H-indazol-4-yl)imidazo[1,2-a]pyridine-3-carboxamide: To a suspension of imidazo[1,2-a]pyridine-3-carboxylic acid (47.6 mg, 0.294 mmol) in NMP (4 mL) was added 2,4,6-trichlorobenzoyl chloride (45.9 µL, 0.294 mmol) and triethylamine (40.9 µL, 0.294 mmol). The reaction mixture was stirred for 30 minutes. 3-Ethyl-1-((1-methyl-1H-pyrazol-3-yl)methyl)-1H-indazol-4-amine (50 mg, 0.196 mmol) was added and the mixture was heated at 87° C. for three hours. The mixture was cooled to ambient temperature and diluted with 10% NaOH aqueous solution (5 mL) and EtOAc (20 mL). The organic phase was washed with water and brine and concentrated under reduced pressure. The residue was triturated with Et₂O to give the final product (52 mg). MS (ES+APCI) m/z=400 (M+H).

Example 58

N-(3-ethyl-1-((1-methyl-1H-pyrazol-3-yl)methyl)-1H-indazol-4-yl)-7-(2-(4-methylpiperazin-1-yl)ethoxy)imidazo[1,2-a]pyridine-3-carboxamide

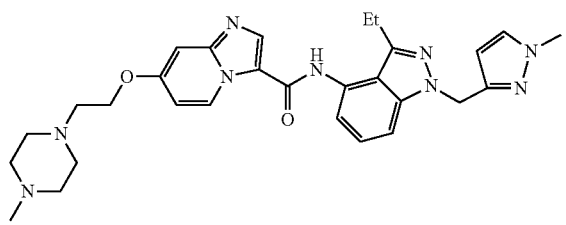 [SMILES: CCc1nn(Cc2ccn(C)n2)c2cccc(NC(=O)c3cnc4cc(OCCN5CCN(C)CC5)ccn34)c12]

To a suspension of lithium 7-(2-(4-methylpiperazin-1-yl)ethoxy)imidazo[1,2-a]pyridine-3-carboxylate (94.0 mg, 0.294 mmol) (Example 56, step A) in NMP (4 mL) was added 2,4,6-trichlorobenzoyl chloride (45.9 µL, 0.294 mmol). The reaction mixture was stirred for 30 minutes. 3-Ethyl-1-((1-methyl-1H-pyrazol-3-yl)methyl)-1H-indazol-4-amine (50 mg, 0.196 mmol) was added and the mixture was heated at 87° C. for 3 hours. The mixture was cooled to ambient temperature and diluted with 10% NaOH aqueous solution (5 mL) and EtOAc. The organic phase was washed with water and brine, concentrated under reduced pressure and the residue was triturated with Et₂O to give the final product (71 mg). MS (ES+APCI) m/z=542 (M+H).

Example 59

N-(3-ethyl-1-((6-methylpyridin-2-yl)methyl)-1H-indazol-4-yl)-7-(5,6,7,8-tetrahydroimidazo[1,2-a]pyrazin-3-yl)imidazo[1,2-a]pyridine-3-carboxamide

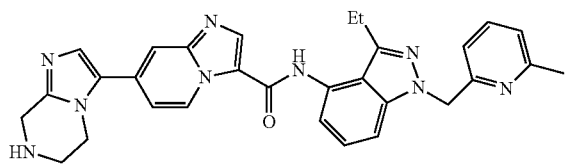 [SMILES: CCc1nn(Cc2cccc(C)n2)c2cccc(NC(=O)c3cnc4cc(-c5cnc6n5CCNC6)ccn34)c12]

7-Bromo-N-(3-ethyl-1-((6-methylpyridin-2-yl)methyl)-1H-indazol-4-yl)imidazo[1,2-a]pyridine-3-carboxamide (prepared as in Example 127, Step A; 50 mg, 0.10 mmol) in DMF (4 mL) was added tert-butyl 5,6-dihydroimidazo[1,2-a]pyrazine-7(8H)-carboxylate (68 mg, 0.31 mmol), Pd(PPh₃)₄ (12 mg, 0.01 mmol), palladium diacetate (2.3 mg, 0.010 mmol) and K₂CO₃ (42 mg, 0.31 mmol). The reaction mixture was purged with argon and the reaction vial was sealed and the mixture was heated to 140° C. for 3 hours. The mixture was cooled to ambient temperature and diluted with DCM (20 mL). The solution was washed with H₂O, dried (Na₂SO₄) and concentrated under reduced pressure. The residue was purified by silica gel chromatography (DCM/MeOH/NH₄OH 10:1:0.1) to provide the final product (14 mg). MS (ES+APCI) m/z=532 (M+H).

Example 60

N-(3-ethyl-1-((6-methylpyridin-2-yl)methyl)-1H-indazol-4-yl)-7-(7-methyl-5,6,7,8-tetrahydroimidazo[1,2-a]pyrazin-3-yl)imidazo[1,2-a]pyridine-3-carboxamide

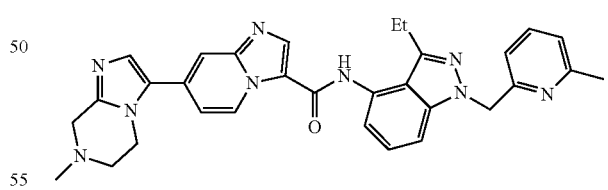

To N-(3-ethyl-1-((6-methylpyridin-2-yl)methyl)-1H-indazol-4-yl)-7-(5,6,7,8-tetrahydroimidazo[1,2-a]pyrazin-3-yl)imidazo[1,2-a]pyridine-3-carboxamide (5 mg, 0.0094 mmol; prepared as in Example 59) in MeOH (4 mL) was added NaBH(OAc)₃ (8.0 mg, 0.038 mmol), and HCHO (as a 35% aqueous solution) (15 mg, 0.19 mmol). The reaction mixture was stirred for 30 minutes then concentrated under reduced pressure. The residue was purified by silica gel chromatography (DCM/MeOH/NH₄OH 10:1:0.1) to provide the final product (3.2 mg). MS (ES+APCI) m/z=546 (M+H).

Example 61

N-(3-cyclopropyl-1-((1-ethyl-1H-pyrazol-3-yl)methyl)-1H-indazol-4-yl)-7-(2-(4-methylpiperazin-1-yl)ethoxy)imidazo[1,2-a]pyridine-3-carboxamide

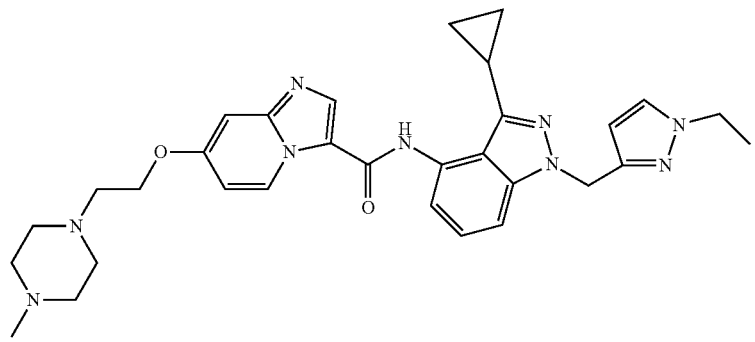 [SMILES: CCn1ccc(Cn2nc(C3CC3)c3c(NC(=O)c4cnc5cc(OCCN6CCN(C)CC6)ccn45)cccc32)n1]

Step A: Preparation of (1-ethyl-1H-pyrazol-3-yl)methanol: To 1-ethyl-1H-pyrazole-3-carboxylic acid (5.01 g, 35.7 mmol) in benzene/MeOH (45 mL/10 mL) at 0° C. was added dropwise (diazomethyl)trimethylsilane (19.7 mL, 39.3 mmol) in hexanes (2M). The cold bath was removed and the reaction mixture was stirred at ambient temperature for one hour. The reaction was quenched with the addition of acetic acid (0.25 mL). The mixture was concentrated under reduced pressure to give crude product, to which was added THF (50 mL) and the solution was cooled to 0° C. Lithium aluminum hydride (1.36 g, 35.7 mmol) was added cautiously to the solution. The cold bath was removed once the addition was complete. The mixture was stirred at ambient temperature for 2 hours and the reaction was quenched by careful addition of sodium sulfate decahydrate. The mixture was filtered through Celite, and the filter pad was washed with EtOAc (200 mL). The filtrate was concentrated under reduced pressure to give the product (4.41 g).

Step B: Preparation of 3-(chloromethyl)-1-ethyl-1H-pyrazole hydrochloride: To (1-ethyl-1H-pyrazol-3-yl)methanol (4.41 g, 34.96 mmol) in DCM (30 mL) at 0° C. was cautiously added thionyl chloride (15.26 mL, 209.7 mmol). The cold bath was removed and the reaction mixture was stirred at ambient temperature for 3 hours. The mixture was concentrated under reduced pressure to give the crude product (5.78 g) which was used directly in the next step.

Step C: Preparation of 3-bromo-1-((1-ethyl-1H-pyrazol-3-yl)methyl)-4-nitro-1H-indazole: To a suspension of 3-bromo-4-nitro-1H-indazole (Preparation B; 8.51 g, 35.2 mmol) in DMF (60 mL) was added 3-(chloromethyl)-1-ethyl-1H-pyrazole hydrochloride (6.37 g, 35.2 mmol) and $K_2CO_3$ (14.6 g, 106 mmol). The reaction mixture was stirred for 16 hours. Most of DMF was removed under reduced pressure. The remaining residue was diluted with EtOAc (300 mL) and washed with $H_2O$. The organic phase was dried ($Na_2SO_4$) and concentrated under reduced pressure. The residue was purified by silica gel chromatography (EtOAc/hexanes 1:5) to provide the product (9.26 g).

Step D: Preparation of 3-cyclopropyl-1-((1-ethyl-1H-pyrazol-3-yl)methyl)-4-nitro-1H-indazole: A 100 mL flask was charged with 1,4-dioxane/$H_2O$ (50 mL/10 mL). The flask was cooled to 0° C. under vacuum for 20 minutes. A 250 mL round bottom flask was charged with cyclopropylboronic acid (5.22 g, 60.8 mmol), 3-bromo-1-((1-ethyl-1H-pyrazol-3-yl)methyl)-4-nitro-1H-indazole (8.51 g, 24.3 mmol), palladium diacetate (0.218 g, 0.972 mmol) and sodium 2'-(dicyclohexylphosphino)-2,6-dimethoxybiphenyl-3-sulfonate (0.997 g, 1.94 mmol). The flask was evacuated and back filled with $N_2$ (repeated 3 times). The cold degassed dioxane/$H_2O$ mixture was added to the 250 mL flask, which was evacuated and back filled with argon (repeated 5 times). The reaction mixture was heated to 100° C. for 6 hours. The mixture was cooled to ambient temperature, filtered through a pad of Celite, and the filter pad was washed with $H_2O$ and EtOAc. The aqueous layer was extracted with EtOAc. The combined organic phases were dried ($Na_2SO_4$) and concentrated under reduced pressure to give a dark colored residue, which was dissolved in DCM (20 mL) and silica gel (20 g) was added. DCM was removed under reduced pressure. The crude product absorbed by silica gel was loaded onto a short pad of silica gel and eluted with EtOAc/hexanes (1:1). The desired fractions were concentrated under reduced pressure to give the product (7.55 g).

Step E: Preparation of 3-cyclopropyl-1-((1-ethyl-1H-pyrazol-3-yl)methyl)-1H-indazol-4-amine: To a suspension of 3-cyclopropyl-1-((1-ethyl-1H-pyrazol-3-yl)methyl)-4-nitro-1H-indazole (7.55 g, 24.3 mmol) in EtOH/$H_2O$ (70 mL/15 mL) was added iron powder (27.1 g, 485 mmol) and $NH_4Cl$ (1.30 g, 24.3 mmol). The reaction mixture was heated to reflux for 3 hours. The mixture was cooled to 60° C. and filtered through a pad of Celite washing with a 20:1 EtOH/$Et_3N$ (300 mL) and 1:1 MeOH/DCM (300 mL). The filtrate was concentrated under reduced pressure. The residue was dissolved in EtOAc (300 mL), washed with saturated $NaHCO_3$ solution, dried ($Na_2SO_4$) and concentrated under reduced pressure to give the product (7.1 g).

Step F: Preparation of N-(3-cyclopropyl-1-((1-ethyl-1H-pyrazol-3-yl)methyl)-1H-indazol-4-yl)-7-(2-(4-methylpiperazin-1-yl)ethoxy)imidazo[1,2-a]pyridine-3-carboxamide: To lithium 7-(2-(4-methylpiperazin-1-yl)ethoxy)imidazo[1,2-a]pyridine-3-carboxylate (100 mg, 0.316 mmol; prepared as in Example 56, step A) was added NMP (60 mL). The reaction mixture was cooled to 0° C. and 2,4,6-trichlorobenzoyl chloride (50.4 µL, 0.316 mmol) was added dropwise. The cold bath was removed once the addition was complete. The reaction mixture was stirred for 1 hour. The reaction mixture became cloudy. 3-Cyclopropyl-1-((1-ethyl-1H-pyrazol-3-yl)methyl)-1H-indazol-4-amine (59.4 mg, 0.211 mmol) was added and the mixture was heated to 88° C. for 11 hours. The mixture was cooled to ambient temperature. Vacuum distillation was set up and NMP was removed until the reaction mixture became a thick oily residue, to which 10% NaOH aqueous solution (100 mL) was added and the resulting clear solution was stirred at 80° C. for 30 minutes.

The mixture was cooled to ambient temperature and extracted with DCM. The organic phases were combined, dried (Na₂SO₄) and concentrated under vacuum (bath temperature at 80° C. to remove left over NMP) to a thick residue, which was triturated with Et₂O (500 mL) to give the final product (80 mg). MS (ES+APCI) m/z=568 (M+H).

Example 62

N-(3-cyclopropyl-1-((1-ethyl-1H-pyrazol-3-yl)methyl)-1H-indazol-4-yl)-7-(2-(4-isopropylpiperazin-1-yl)ethoxy)imidazo[1,2-a]pyridine-3-carboxamide

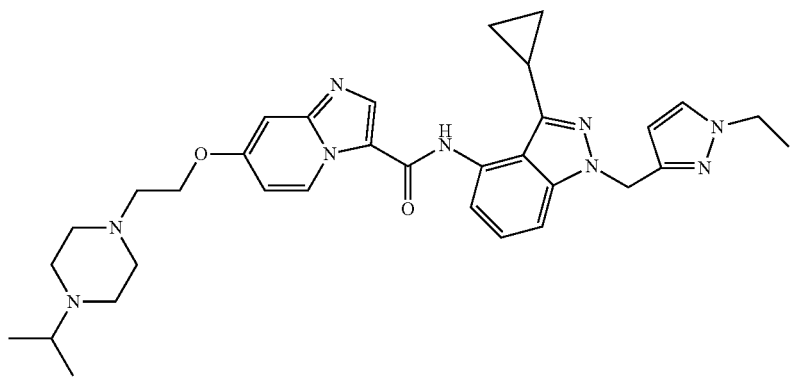 [SMILES: CCn1ccc(Cn2nc(C3CC3)c3c(NC(=O)c4cnc5cc(OCCN6CCN(C(C)C)CC6)ccn45)cccc32)n1]

Step A: Preparation of ethyl 7-(2-(4-isopropylpiperazin-1-yl)ethoxy)imidazo[1,2-a]pyridine-3-carboxylate: Potassium (E)-2-chloro-3-ethoxy-3-oxoprop-1-en-1-olate (Preparation E; 41.32 g, 219.0 mmol) was suspended (through vigorous magnetic stirring) in anhydrous ether (365 mL) and 6N sulfuric acid (18.25 mL, 109.5 mmol) was added. Water (100 mL) was added to aid in phase separation. When the pH of the bottom (aqueous) phase, dropped below 3, the ether layer was separated. The aqueous phase was further extracted with ether (400 mL). The combined ether phases were dried over sodium sulfate and magnesium sulfate for 10 minutes. The solution was filtered and concentrated under reduced pressure, with the temperature of the water bath not exceeding 20° C. A residual oil was obtained, which crystallized upon drying under high vacuum overnight. This residue was dissolved in absolute EtOH (360 mL). 4-(2-(4-Isopropylpiperazin-1-yl)ethoxy)pyridin-2-amine (Preparation G; 28.95 g, 109.5 mmol) was added, and the mixture was heated under nitrogen at 65° C. for 18 hours. After allowing the mixture to cool, the resulting suspension was evaporated to dryness. The resulting solids were shaken with THF and collected by filtration, then dried under vacuum. This material (HCl salt) was mixed with water (400 mL) and ethanol (200 mL). Sodium bicarbonate (20 g) was added and the mixture was stirred for 16 hours (some effervescence occurred). The suspension was evaporated to dryness under vacuum. The solids were shaken in EtOAc/THF and filtered. These solids were washed with a large volume of ethyl acetate and THF. The organic solution was further dried with sodium sulfate and magnesium sulfate, filtered and evaporated under vacuum to give an amber gum. This material was triturated with 2:1 ether-hexanes, and the resulting solids were collected by filtration to afford ethyl 7-(2-(4-isopropylpiperazin-1-yl)ethoxy)imidazo[1,2-a]pyridine-3-carboxylate (23.46 g, 59% yield) as beige solids.

Step B: Preparation of lithium 7-(2-(4-isopropylpiperazin-1-yl)ethoxy)imidazo[1,2-a]pyridine-3-carboxylate: To ethyl 7-(2-(4-isopropylpiperazin-1-yl)ethoxy)imidazo[1,2-a]pyridine-3-carboxylate (5.68 g, 15.8 mmol) in H₂O (30 mL) was added lithium hydroxide hydrate (0.67 g, 16.0 mmol). The reaction mixture was heated to 95° C. for 4 hours. The mixture was cooled to ambient temperature and hydrogen chloride (0.0394 mL, 4M in dioxane) was added. The mixture was stirred for 10 minutes. The H₂O was removed under reduced pressure and the residue placed under high vacuum for 16 hours to give the product (5.43 g).

Step C: Preparation of N-(3-cyclopropyl-1-((1-ethyl-1H-pyrazol-3-yl)methyl)-1H-indazol-4-yl)-7-(2-(4-isopropylpiperazin-1-yl)ethoxy)imidazo[1,2-a]pyridine-3-carboxamide: To a solution of lithium 7-(2-(4-isopropylpiperazin-1-yl)ethoxy)imidazo[1,2-a]pyridine-3-carboxylate (531 mg, 1.57 mmol) in NMP (6 mL) at 0° C. was added 2,4,6-trichlorobenzoyl chloride (250 μL, 1.56 mmol). The cold bath was removed once the addition was complete. The mixture was stirred for a further 1 hour. 3-Cyclopropyl-1-((1-ethyl-1H-pyrazol-3-yl)methyl)-1H-indazol-4-amine (310 mg, 1.10 mmol; prepared as in Example 61, step E) was added and the reaction mixture was heated to 88° C. for 11 hours. The mixture was cooled to ambient temperature. Vacuum distillation was set up and NMP was removed until the reaction mixture became a thick oily residue, to which 10% NaOH aqueous solution (10 mL) was added and the resulting clear solution was stirred at 80° C. for 30 minutes. The solution was cooled to ambient temperature and extracted with DCM. The organic extracts were combined, dried (Na₂SO₄) and concentrated under vacuum to give a residual oil, which was triturates with Et₂O (50 mL). The resulting solids were washed with Et₂O (40 mL) to give the final product (492 mg). MS (ES+APCI) m/z=596 (M+H).

Example 63

N-(3-cyclopropyl-1-((1-isopropyl-1H-pyrazol-3-yl)methyl)-1H-indazol-4-yl)-7-(2-(4-methylpiperazin-1-yl)ethoxy)imidazo[1,2-a]pyridine-3-carboxamide

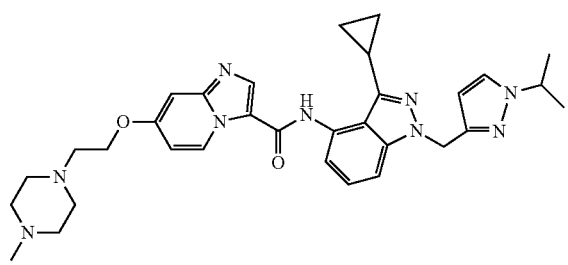 [SMILES: CC(C)n1ccc(Cn2nc(C3CC3)c3c(NC(=O)c4cnc5cc(OCCN6CCN(C)CC6)ccn45)cccc32)n1]

Step A: Preparation of (1-isopropyl-1H-pyrazol-3-yl)methanol: To methyl 1-isopropyl-1H-pyrazole-3-carboxylate (5.0 g, 29.7 mmol) in anhydrous ether (0.5M, 60 mL) at 0° C. was added lithium aluminum hydride (32.7 mL, 32.7 mmol). The cold bath was removed and the mixture stirred for 3 hours. The mixture was poured slowly into an Erlenmeyer flask containing cold (0° C.) Rochelle's salt solution (1 L). After stirring for 1 hour, the mixture was diluted with Et₂O (200 mL). The organic phase was separated, and the aqueous phase was further extracted with Et₂O. The combined extracts were concentrated and dried under high vacuum to afford (1-isopropyl-1H-pyrazol-3-yl)methanol (3.45 g, 83% yield) as a clear oil.

Step B: Preparation of 3-(chloromethyl)-1-isopropyl-1H-pyrazole hydrochloride: To a solution of (1-isopropyl-1H-pyrazol-3-yl)methanol (3.45 g, 24.61 mmol) in DCM (50 mL) was added thionyl chloride (5.386 mL, 73.83 mmol) at ambient temperature. The mixture was allowed to stir at ambient temperature for 18 hours. The mixture was concentrated under vacuum to afford 3-(chloromethyl)-1-isopropyl-1H-pyrazole hydrochloride (4.1 g, 85% yield) as a yellow gum.

Step C: Preparation of 3-bromo-1-((1-isopropyl-1H-pyrazol-3-yl)methyl)-4-nitro-1H-indazole: To a solution of 3-bromo-4-nitro-1H-indazole (Preparation B; 2.2 g, 9.1 mmol) in DMF (18 mL) was added potassium carbonate (2.5 g, 18 mmol) at ambient temperature. After 15 minutes, at ambient temperature, 3-(chloromethyl)-1-isopropyl-1H-pyrazole hydrochloride (1.8 g, 9.1 mmol) was added. The mixture was allowed to stir for 18 hours. The mixture was concentrated, diluted with ice-water and stirred for one hour. The resulting fine solids were collected by filtration and dried under vacuum to give 3-bromo-1-((1-isopropyl-1H-pyrazol-3-yl)methyl)-4-nitro-1H-indazole (3 g, 91% yield).

Step D: Preparation of 3-cyclopropyl-1-((1-isopropyl-1H-pyrazol-3-yl)methyl)-4-nitro-1H-indazole: A flask was charged with 3-bromo-1-((1-isopropyl-1H-pyrazol-3-yl)methyl)-4-nitro-1H-indazole (1.8 g, 4.94 mmol), cyclopropylboronic acid (0.849 g, 9.88 mmol), potassium phosphate (3.15 g, 14.8 mmol) and 20:1 toluene/water (10.5 mL). The mixture was degassed for 30 minutes with an argon filled balloon. Palladium acetate was added (55.5 mg, 0.247 mmol) followed by tricyclohexyl phosphine (0.139 g, 0.494 mmol). The mixture was further degassed with argon and heated at 100-110° C. for 16 hours. The mixture was filtered through GF/F paper, rinsing with EtOAc, concentrated under vacuum and the residue was purified by silica gel chromatography (1-20% EtOAc in hexanes) to provide 3-cyclopropyl-1-((1-isopropyl-1H-pyrazol-3-yl)methyl)-4-nitro-1H-indazole (1.08 g, 67% yield) as a yellow solid.

Step E: Preparation of 3-cyclopropyl-1-((1-isopropyl-1H-pyrazol-3-yl)methyl)-1H-indazol-4-amine: To a mixture of 3-cyclopropyl-1-((1-isopropyl-1H-pyrazol-3-yl)methyl)-4-nitro-1H-indazole (1.08 g, 3.32 mmol), ammonium chloride (88.8 mg, 1.66 mmol) in 4:1 EtOH/water (15 mL) was added iron powder (1.85 g, 33.2 mmol) and the mixture was heated at reflux for 3 hours. The solvent was removed under reduced pressure and the residue was mixed with in EtOAc/water and filtered through GF/F paper. The organic phase was separated and concentrated under reduced pressure to provide 3-cyclopropyl-1-((1-isopropyl-1H-pyrazol-3-yl)methyl)-1H-indazol-4-amine (0.815 g, 83% yield) as a yellow solid.

Step F: Preparation of N-(3-cyclopropyl-1-((1-isopropyl-1H-pyrazol-3-yl)methyl)-1H-indazol-4-yl)-7-(2-(4-methylpiperazin-1-yl)ethoxy)imidazo[1,2-a]pyridine-3-carboxamide: To lithium 7-(2-(4-methylpiperazin-1-yl)ethoxy)imidazo[1,2-a]pyridine-3-carboxylate (130 mg, 0.411 mmol) was added NMP (10 mL). The solution was cooled to 0° C. and 2,4,6-trichlorobenzoyl chloride (65.6 μl, 0.411 mmol) was added dropwise. The cold bath was removed once the addition was complete. The reaction mixture was stirred for 1 hour during which time a cloudy suspension formed. 3-Cyclopropyl-1-((1-isopropyl-1H-pyrazol-3-yl)methyl)-1H-indazol-4-amine (90 mg, 0.305 mmol) was added and the reaction mixture was heated at 88° C. for 11 hours. The mixture was cooled to ambient temperature and NMP was removed by vacuum distillation to give an oily residue. To this was added 10% NaOH aqueous solution (10 mL) and the resulting clear solution was stirred at 80° C. for 30 minutes. The solution was cooled to ambient temperature and extracted with DCM. The combined organic extracts were dried (Na₂SO₄) and concentrated under reduced pressure and the residue was triturated with Et₂O (50 mL). The resulting solids were collected by filtration, washed with Et₂O (40 mL) and dried under vacuum to give the final product (125 mg). MS (ES+APCI) m/z=582 (M+H).

Example 64

N-(3-cyclopropyl-1-((1-isopropyl-1H-pyrazol-3-yl)methyl)-1H-indazol-4-yl)-7-(2-(4-isopropylpiperazin-1-yl)ethoxy)imidazo[1,2-a]pyridine-3-carboxamide

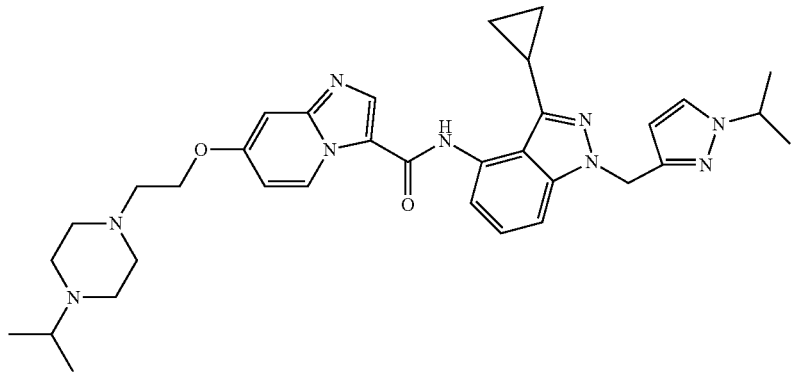 [SMILES: CC(C)N1CCN(CCOc2ccn3c(C(=O)Nc4cccc5c4c(C4CC4)nn5Cc4ccn(C(C)C)n4)cnc3c2)CC1]

To a solution of lithium 7-(2-(4-isopropylpiperazin-1-yl)ethoxy)imidazo[1,2-a]pyridine-3-carboxylate (123 mg, 0.364 mmol; prepared according to Example 62, Step B) in NMP (10 mL) at 0° C. was added 2,4,6-trichlorobenzoyl chloride (57.9 µL, 0.363 mmol). The cold bath was removed once the addition was complete. The mixture was stirred for one hour. 3-Cyclopropyl-1-((1-isopropyl-1H-pyrazol-3-yl)methyl)-1H-indazol-4-amine (80 mg, 0.271 mmol; prepared according to Example 63, step E) was added and the reaction mixture was heated at 88° C. for 11 hours. The reaction mixture was cooled to ambient temperature, and NMP was removed under reduced pressure to give an oily residue. To this was added 10% NaOH aqueous solution (10 mL) and the resulting clear solution was stirred at 80° C. for 30 minutes. The solution was cooled to ambient temperature and extracted with DCM. The combined organic extracts were dried ($Na_2SO_4$) and concentrated under reduced pressure to give a residue, which was triturated with $Et_2O$ (50 mL). The resulting solids were isolated by filtration, washed with ether and dried under vacuum to give the product (101 mg). MS (ES+APCI) m/z=610 (M+H).

Example 65

N-(3-cyclopropyl-1-((6-methylpyridin-2-yl)methyl)-1H-indazol-4-yl)-7-(2-(4-methylpiperazin-1-yl)ethoxy)imidazo[1,2-a]pyridine-3-carboxamide

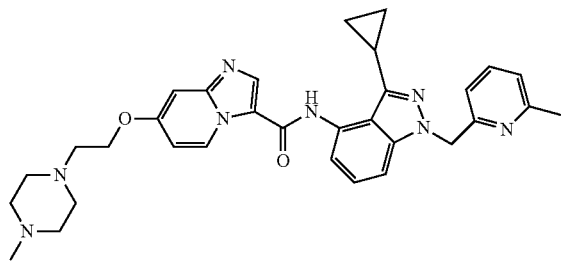 [SMILES: Cc1cccc(Cn2nc(C3CC3)c3c(NC(=O)c4cnc5cc(OCCN6CCN(C)CC6)ccn45)cccc32)n1]

Steps A1-A3: Preparation of 3-cyclopropyl-1-((6-methylpyridin-2-yl)methyl)-1H-indazol-4-amine:

Step A1: Preparation of 3-Bromo-1-((6-methylpyridin-2-yl)methyl)-4-nitro-1H-indazole: 4-Nitro-1H-indazole (1.0 g, 6.1 mmol) and N-bromosuccinimide (1.1 g, 6.4 mmol) were mixed with anhydrous DMF (10 mL) in a 20 mL vial. The reaction was stirred at ambient temperature for 5 minutes. KOH (1.1 g, 18.3 mmol) and 2-(chloromethyl)-6-methylpyridine hydrochloride (1.4 g, 7.6 mmol) were added to the vial and the reaction mixture was stirred for 18 hours. The product was precipitated from solution by addition of $H_2O$ (10 mL) to the reaction mixture. The solids were collected vacuum filtration, washed with $H_2O$ and dried under vacuum to afford 3-bromo-1-((6-methylpyridin-2-yl)methyl)-4-nitro-1H-indazole (1.7 g).

Step A2: Preparation of 3-cyclopropyl-1-((6-methylpyridin-2-yl)methyl)-4-nitro-1H-indazole: 3-Bromo-1-((6-methylpyridin-2-yl)methyl)-4-nitro-1H-indazole (10.0 g, 28.8 mmol), cyclopropylboronic acid (6.2 g, 72.0 mmol), palladium acetate (0.2 g, 0.9 mmol), triphenylphosphine (0.5 g, 1.7 mmol) and potassium carbonate (15.9 g, 115.2 mmol) were added to a mixture of $H_2O$ (50 mL) and toluene (50 mL) in a 250 mL round bottomed flask equipped with mechanical stirring, a thermal couple, a reflux condenser and a static pressure $N_2$ line. The solution was degassed by sparging with $N_2$ for 15 minutes and then heated with stirring under $N_2$ at 90° C. for 18 hours. The solution was cooled to ambient temperature, treated with activated carbon, filtered through Celite®, and the filter cake was rinsed with toluene (100 mL). The filtrate was partitioned using a reparatory funnel and after extraction of the organic phase with $H_2O$ (2×50 mL) the organic layer was concentrated to dryness. The crude product was triturated with isopropyl alcohol (50 mL). The solids were collected by vacuum filtration, washed with heptane and dried under vacuum to afford 3-cyclopropyl-1-((6-methylpyridin-2-yl)methyl)-4-nitro-1H-indazole (6.9 g).

Step A3: Preparation of 3-cyclopropyl-1-((6-methylpyridin-2-yl)methyl)-1H-indazol-4-amine: 3-Cyclopropyl-1-((6-methylpyridin-2-yl)methyl)-4-nitro-1H-indazole (17.0 g, 55.1 mmol) and 10% Pd/C (1.2 g, 0.6 mmol) were added to toluene (170 mL) in an autoclave. The solution was stirred under 40 psi of $H_2$ at 75° C. for 18 hours. The catalyst was removed by filtration through Celite® and the filter cake was rinsed with toluene (34 mL). The filtrate was concentrated to about 35 mL and heptane (85 mL) was added to the filtrate to precipitate the product which was collected by vacuum filtration and dried under vacuum for 18 hours to afford 3-cyclopropyl-1-((6-methylpyridin-2-yl)methyl)-1H-indazol-4-amine (12.2 g).

Steps B1-B2: Preparation of ethyl 7-chloroimidazo[1,2-a]pyridine-3-carboxylate

Step B1: Preparation of potassium (E)-2-chloro-3-ethoxy-3-oxoprop-1-en-1-olate: A mixture of ethyl 2-chloroacetate (110.0 g; 897.6 mmol) and ethyl formate (73.14 g; 987.4 mmol) was added slowly to a suspension of potassium t-butoxide (110.8 g; 987.4 mmol) in THF (1000 mL) at −5° C. (maintaining the temperature<10° C.) with mechanical stirring. The mixture was stirred at ambient temperature for 24 hours. The solids were collected by filtration and washed with THF (200 mL) and acetonitrile (200 mL). The material was dried under vacuum to give the product (152.7 g) which was used without further purification.

Step B2: Preparation of ethyl 7-chloroimidazo[1,2-a]pyridine-3-carboxylate: Potassium (E)-2-chloro-3-ethoxy-3-oxoprop-1-en-1-olate (300.8 g, 1594 mmol) was suspended in acetonitrile (800 mL) and 12.1 M aqueous HCl (32.1 mL, 388.9 mmol) was added slowly. The mixture was stirred at ambient temperature for 15 minutes. 4-Chloropyridin-2-amine (100 g, 777.8 mmol) was added to the mixture and heated to 35° C. for 20 hours. The mixture was cooled to ambient temperature and water (2500 mL) was added. The pH of the mixture was adjusted to 8.0-8.5 with 2.5 N aqueous NaOH (100 mL, 250 mmol) to precipitate the product. The solids were collected by filtration and washed with water (4000 mL). The material was dried under vacuum at 40° C. to the crude product (174.1 g, 100% yield). The crude material was further purified by dissolving the material in IPA (220 mL) at 65° C. At 65° C., water (130 mL) was added to the solution (maintaining a temperature>60° C.). The solution was slowly cooled over four hours to 20° C., during which time solid product crystallized out of the solution. The mixture was cooled to 10° C. and stirred for 16 hours. The solids were collected by filtration and washed with 10% IPA/water (v:v) (1000 mL). The material was dried under vacuum at 40° C. to give the purified product (134 g, 76.6% yield).

Step C: Preparation of 7-chloro-N-(3-cyclopropyl-1-((6-methylpyridin-2-yl)methyl)-1H-indazol-4-yl)imidazo[1,2-a]pyridine-3-carboxamide: A mixture of ethyl 7-chloroimidazo[1,2-a]pyridine-3-carboxylate (10.0 g, 44.5 mmol) and 3-cyclopropyl-1-((6-methylpyridin-2-yl)methyl)-1H-indazol-4-amine (12.4 g, 44.5 mmol) in THF (100 mL) was cooled to 0° C. using an ice/water bath. A solution of 1.0M lithium bis(trimethylsilyl)amide (102 mL, 102 mmol) was added slowly over 40 minutes keeping the internal temperature below 5° C. The mixture was stirred at 0° C. for 30 minutes, diluted with IPA (100 mL), and then concentrated under reduced pressure. The residue was diluted with IPA (100 mL) and concentrated under reduced pressure. The residue was dissolved in IPA (100 mL) and treated with a 10% aqueous ammonium chloride solution (200 mL) to give a slurry which was filtered and dried to give 7-chloro-N-(3-cyclopropyl-1-((6-methylpyridin-2-yl)methyl)-1H-indazol-4-yl)imidazo[1,2-a]pyridine-3-carboxamide as a light brown solid (18.4 g).

Step D: Preparation of N-(3-cyclopropyl-1-((6-methylpyridin-2-yl)methyl)-1H-indazol-4-yl)-7-(2-(4-methylpiperazin-1-yl)ethoxy)imidazo[1,2-a]pyridine-3-carboxamide: 7-Chloro-N-(3-cyclopropyl-1-((6-methylpyridin-2-yl)methyl)-1H-indazol-4-yl)imidazo[1,2-a]pyridine-3-carboxamide (5.0 g, 10.9 mmol), potassium hydroxide (3.38 g, 60.2 mmol), DMSO (50 mL), and 2-(4-methylpiperazin-1-yl)ethanol (3.16 g, 21.9 mmol) were combined under nitrogen and heated to 95° C. for 16 hours. The mixture was cooled to ambient temperature and THF (300 mL) was added. The slurry was stirred at ambient temperature for 3 hours. The solids were filtered off and the THF removed from the filtrates under vacuum to give a DMSO solution of the product. The DMSO solution was heated to 60° C. and water (100 mL) was added to precipitate out the product. The slurry was cooled to ambient temperature and stirred for 18 hours. The solids were collected by filtration and washed with water (100 mL) and MTBE (50 mL). The material was dried under vacuum at 40° C. to give N-(3-cyclopropyl-1-((6-methylpyridin-2-yl)methyl)-1H-indazol-4-yl)-7-(2-(4-methylpiperazin-1-yl)ethoxy)imidazo[1,2-a]pyridine-3-carboxamide (4.54 g). MS (ES+APCI) m/z=565.1 (M+H).

Example 66

N-(1-((6-(2,3-dihydroxypropoxy)pyridin-2-yl)methyl)-3-ethyl-1H-indazol-4-yl)imidazo[1,2-a]pyridine-3-carboxamide dihydrochloride

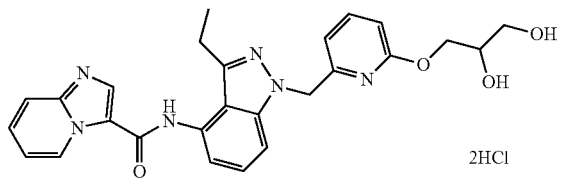 [SMILES: CCc1nn(Cc2cccc(OCC(O)CO)n2)c2cccc(NC(=O)c3cnc4ccccn34)c12]

Step A: Preparation of (2,2-dimethyl-1,3-dioxolan-4-yl)methyl methanesulfonate: To (2,2-dimethyl-1,3-dioxolan-4-yl)methanol (400 mg, 3.03 mmol) in DCM (6 mL) at 0° C. was added methanesulfonyl chloride (381 mg, 3.33 mmol) and triethylamine (368 mg, 3.63 mmol. The cold bath was removed and the reaction mixture was stirred for 30 minutes. The mixture was diluted with DCM (5 mL). The organic phase was washed with water (4 mL) and brine (2 mL), and dried (Na$_2$SO$_4$). The solution was concentrated under reduced pressure to give the product (642 mg).

Step B: Preparation of N-(1-((6-((2,2-dimethyl-1,3-dioxolan-4-yl)methoxy)pyridin-2-yl)methyl)-3-ethyl-1H-indazol-4-yl)imidazo[1,2-a]pyridine-3-carboxamide: To N-(3-ethyl-1-((6-hydroxypyridin-2-yl)methyl)-1H-indazol-4-yl)imidazo[1,2-a]pyridine-3-carboxamide (17, Step A) (16 mg, 0.039 mmol) in DMA (2 mL) was added (2,2-dimethyl-1,3-dioxolan-4-yl)methyl methanesulfonate (8.2 mg, 0.039 mmol) and Cs$_2$CO$_3$ (25 mg, 0.078 mmol). The reaction vial was sealed and the mixture was heated at 90° C. for 6 hours. The DMA was removed under reduced pressure. The residue was diluted with EtOAc (20 mL). The organic solution was washed with saturated NaHCO$_3$ aqueous solution and brine, and then concentrated under reduced pressure. Silica gel chromatography (DCM/MeOH 10:0.5) gave the product (12 mg).

Step C: Preparation of N-(1-((6-(2,3-dihydroxypropoxy)pyridin-2-yl)methyl)-3-ethyl-1H-indazol-4-yl)imidazo[1,2-a]pyridine-3-carboxamide dihydrochloride: To a solution of N-(1-((6-((2,2-dimethyl-1,3-dioxolan-4-yl)methoxy)pyridin-2-yl)methyl)-3-ethyl-1H-indazol-4-yl)imidazo[1,2-a]pyridine-3-carboxamide (12 mg, 0.023 mmol) in THF (1 mL) was added hydrogen chloride (0.5 mL, 2.0 mmol; 4M solution in 1,4-dioxane). The mixture was stirred at ambient temperature for 3 hours. The mixture was concentrated under a stream of nitrogen and the residue was dissolved in a mixture of methanol and dichloromethane. A solution of ammonium hydroxide was added to neutralize. The material was purified using preparative thin layer chromatography, eluting with 10% methanol in dichloromethane containing 0.5% ammonium hydroxide. The isolated product was dissolved in a mixture of methanol and dichloromethane and treated with concentrated hydrochloric acid (0.05 mL). The solvent was removed under reduced pressure to give N-(1-((6-(2,3-dihydroxypropoxy)pyridin-2-yl)methyl)-3-ethyl-1H-indazol-4-yl)imidazo[1,2-a]pyridine-3-carboxamide dihydrochloride (8 mg). MS (APCI), positive scan, m/z=487.2 (M+H).

Example 67

N-(3-ethyl-1-((6-(piperazin-1-yl)pyridin-2-yl)methyl)-1H-indazol-4-yl)imidazo[1,2-a]pyridine-3-carboxamide trihydrochloride

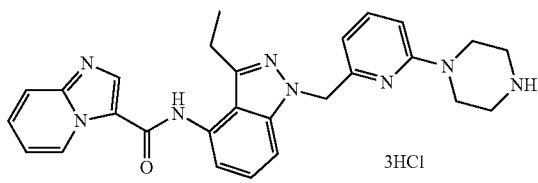 [SMILES: CCc1nn(Cc2cccc(N3CCNCC3)n2)c2cccc(NC(=O)c3cnc4ccccn34)c12]

3HCl

Step A: Preparation of tert-butyl 4-(6-((3-ethyl-4-(imidazo[1,2-a]pyridine-3-carboxamido)-1H-indazol-1-yl)methyl)pyridin-2-yl)piperazine-1-carboxylate: To a reaction vial was added 6-((3-ethyl-4-(imidazo[1,2-a]pyridine-3-carboxamido)-1H-indazol-1-yl)methyl)pyridin-2-yl trifluoromethanesulfonate (30 mg, 0.0551 mmol; prepared according to Example 24, Step A), tert-butyl piperazine-1-carboxylate (20.5 mg, 0.110 mmol) and cesium carbonate (53.9 mg, 0.165 mmol). Toluene (2 mL) was added and argon was bubbled through the mixture for 10 minutes. To this solution was added rac-2,2'-bis(diphenylphosphino)-1,1'-binaphthyl (6.86 mg, 0.0110 mmol) and tris(dibenzylideneacetonyl)bis-palladium (5.05 mg; 0.00551 mmol). The reaction vial was sealed and the mixture was heated at 90° C. for 3 hours. The mixture was allowed to cool, filtered through Celite®, rinsing with toluene and concentrated under a stream of nitrogen. The material was purified using preparative thin layer chromatography on silica, eluting with 10% methanol in dichloromethane containing 0.5% ammonium hydroxide solution to provide tert-butyl 4-(6-((3-ethyl-4-(imidazo[1,2-a]pyridine-3-carboxamido)-1H-indazol-1-yl)methyl)pyridin-2-yl)piperazine-1-carboxylate (12 mg).

Step B: Preparation of N-(3-ethyl-1-((6-(piperazin-1-yl)pyridin-2-yl)methyl)-1H-indazol-4-yl)imidazo[1,2-a]pyridine-3-carboxamide trihydrochloride: To a solution of tert-butyl 4-(6-((3-ethyl-4-(imidazo[1,2-a]pyridine-3-carboxamido)-1H-indazol-1-yl)methyl)pyridin-2-yl)piperazine-1-carboxylate (12 mg, 0.021 mmol) in dichloromethane (2 mL) was added trifluoroacetic acid (1 mL). The mixture was stirred for 1 hour at ambient temperature. The solution was concentrated under reduced pressure. The residue was re-dissolved in a mixture of dichloromethane and methanol and neutralized by the addition of ammonium hydroxide solution. The solvent was removed under reduced pressure. The residue was purified by preparative thin layer chromatography on silica, eluting with 15% methanol in dichloromethane containing 1% ammonium hydroxide solution. The isolated product was dissolved in a mixture of ethyl acetate, methanol and dichloromethane. Concentrated hydrochloric acid (2 drops) was added. Concentration under reduced pressure followed by high vacuum gave N-(3-ethyl-1-((6-(piperazin-1-yl)pyridin-2-yl)methyl)-1H-indazol-4-yl)imidazo[1,2-a]pyridine-3-carboxamide trihydrochloride (5.0 mg). MS (APCI), positive scan, m/z=481.3 (M+H).

Example 68

N-(1-((6-(4-aminopiperidin-1-yl)pyridin-2-yl)methyl)-3-ethyl-1H-indazol-4-yl)imidazo[1,2-a]pyridine-3-carboxamide trihydrochloride

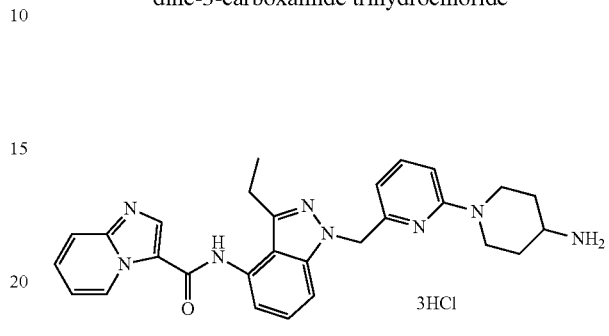

3HCl

Step A: Preparation of tert-butyl 1-(6-((3-ethyl-4-(imidazo[1,2-a]pyridine-3-carboxamido)-1H-indazol-1-yl)methyl)pyridin-2-yl)piperidin-4-ylcarbamate: To a reaction vial was added 6-((3-ethyl-4-(imidazo[1,2-a]pyridine-3-carboxamido)-1H-indazol-1-yl)methyl)pyridin-2-yl trifluoromethanesulfonate (30 mg, 0.0551 mmol; prepared according to Example 24, Step A), tert-butyl piperidin-4-ylcarbamate (22.1 mg, 0.110 mmol) and cesium carbonate (53.9 mg, 0.165 mmol). Toluene (2 mL) was added and argon was bubbled through the mixture for 10 minutes. To this mixture was added rac-2,2'-bis(diphenylphosphino)-1,1'-binaphthyl (6.86 mg, 0.0110 mmol) and tris(dibenzylideneacetonyl)bis-palladium (5.05 mg, 0.00551 mmol). The reaction mixture was heated at 90° C. for 4 hours. The mixture was filtered through Celite®, washing with dichloromethane and methanol. The solution was concentrated under a stream of nitrogen and the residue was purified by preparative thin layer chromatography on silica, eluting with 10% methanol in dichloromethane containing 0.5% ammonium hydroxide solution to give tert-butyl 1-(6-((3-ethyl-4-(imidazo[1,2-a]pyridine-3-carboxamido)-1H-indazol-1-yl)methyl)pyridin-2-yl)piperidin-4-ylcarbamate (14.6 mg).

Step B: Preparation of N-(1-((6-(4-aminopiperidin-1-yl)pyridin-2-yl)methyl)-3-ethyl-1H-indazol-4-yl)imidazo[1,2-a]pyridine-3-carboxamide trihydrochloride: To a solution of tert-butyl 1-((6-((3-ethyl-4-(imidazo[1,2-a]pyridine-3-carboxamido)-1H-indazol-1-yl)methyl)pyridin-2-yl)piperidin-4-ylcarbamate (14.6 mg, 0.0245 mmol) in dichloromethane (2 mL) at ambient temperature and added trifluoroacetic acid (1 mL). The mixture was stirred for 1 hour at ambient temperature. The solvent was removed under vacuum and the residue was dissolved in a mixture of dichloromethane and methanol. Ammonium hydroxide solution was added to neutralize. The material was purified using preparative thin layer chromatography, eluting with 15% methanol in dichloromethane containing 1% ammonium hydroxide. The product was dissolved in a mixture of ethyl acetate, methanol and dichloromethane. Concentrated hydrochloric acid (2 drops) was added and the material was concentrated under reduced pressure and under high vacuum to provide N-(1-((6-(4-aminopiperidin-1-yl)pyridin-2-yl)methyl)-3-ethyl-1H-indazol- 4-yl)imidazo[1,2-a]pyridine-3-carboxamide trihydrochloride (2.8 mg). MS (APCI), positive scan, m/z=495.2 (M+H).

Example 69

N-(3-ethyl-1-((1-ethyl-1H-pyrazol-4-yl)methyl)-1H-indazol-4-yl)imidazo[1,2-a]pyridine-3-carboxamide dihydrochloride

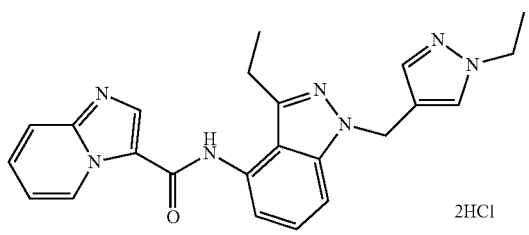 [SMILES: CCc1nn(Cc2cnn(CC)c2)c2cccc(NC(=O)c3cnc4ccccn34)c12]

To a solution of N-(1-((1H-pyrazol-4-yl)methyl)-3-ethyl-1H-indazol-4-yl)imidazo[1,2-a]pyridine-3-carboxamide (20 mg, 0.052 mmol; prepared according to Example 21, Step A) in dry N,N-dimethyl formamide (0.5 mL) was added cesium hydroxide hydrate (8.7 mg, 0.052 mmol) and bromoethane (5.7 mg, 0.052 mmol). The mixture was stirred under a nitrogen atmosphere for 60 minutes at ambient temperature. The mixture was filtered, washed with methanol and ethyl acetate, and concentrated under a stream of nitrogen. The material was purified using preparative thin layer chromatography on silica, eluting with 10% methanol in dichloromethane. The isolated product was dissolved in a mixture of dichloromethane and methanol. Hydrogen chloride (0.5 mmol; 2M solution in diethyl ether) was added. Removal of the solvent under reduced pressure followed by high vacuum gave N-(3-ethyl-1-((1-ethyl-1H-pyrazol-4-yl)methyl)-1H-indazol-4-yl)imidazo[1,2-a]pyridine-3-carboxamide dihydrochloride (5.0 mg). MS (APCI), positive scan, m/z=414.2 (M+H).

Example 70

N-(1-((1-(cyclopropylmethyl)-1H-pyrazol-4-yl)methyl)-3-ethyl-1H-indazol-4-yl)imidazo[1,2-a]pyridine-3-carboxamide dihydrochloride

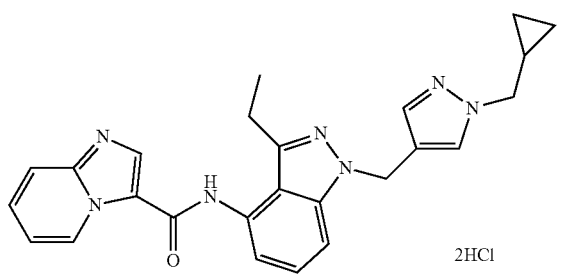 [SMILES: CCc1nn(Cc2cnn(CC3CC3)c2)c2cccc(NC(=O)c3cnc4ccccn34)c12]

To a solution of N-(1-((1H-pyrazol-4-yl)methyl)-3-ethyl-1H-indazol-4-yl)imidazo[1,2-a]pyridine-3-carboxamide (20 mg, 0.052 mmol; prepared according to Example 21, Step A) in dry DMF (0.5 mL) was added (bromomethyl)cyclopropane (7.0 mg, 0.052 mmol) and cesium hydroxide hydrate (8.7 mg, 0.052 mmol). The mixture was stirred at ambient temperature for 60 minutes. The mixture was filtered, washed with methanol and ethyl acetate, and concentrated under reduced pressure. The residue was purified using preparative thin layer chromatography on silica, eluting with 10% methanol in dichloromethane. The product was dissolved in a mixture of dichloromethane and methanol. Hydrogen chloride (0.52 mmol; 2M solution in diethyl ether) was added and the solvent was removed under reduced pressure, followed by high vacuum to give N-(1-((1-(cyclopropylmethyl)-1H-pyrazol-4-yl)methyl)-3-ethyl-1H-indazol-4-yl)imidazo[1,2-a]pyridine-3-carboxamide dihydrochloride (5.6 mg). MS (APCI), positive scan, m/z=440.2 (M+H).

Example 71

4-(2-(3-(3-cyclopropyl-1-((6-methylpyridin-2-yl)methyl)-1H-indazol-4-ylcarbamoyl)imidazo[1,2-a]pyridin-7-yloxy)ethyl)-1-methylpiperazine 1-oxide

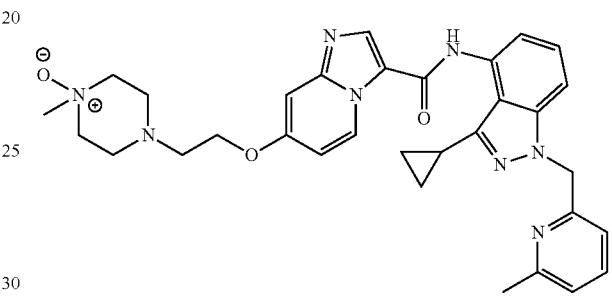

Prepared according to Example 37 from N-(3-cyclopropyl-1-((6-methylpyridin-2-yl)methyl)-1H-indazol-4-yl)-7-(2-(4-methylpiperazin-1-yl)ethoxy)imidazo[1,2-a]pyridine-3-carboxamide (see Example 65). MS (ES+APCI) m/z=581.2 (M+H).

Example 72

N-(3-cyclopropyl-1-((6-methylpyridin-2-yl)methyl)-1H-indazol-4-yl)-7-(2-(piperazin-1-yl)ethoxy)imidazo[1,2-a]pyridine-3-carboxamide

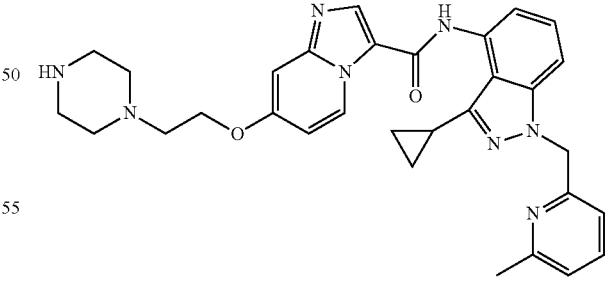

Prepared according to Example 77, Step B, utilizing 7-fluoro-N-(3-ethyl-1-((6-methylpyridin-2-yl)methyl)-1H-indazol-4-yl)imidazo[1,2-a]pyridine-3-carboxamide and tert-butyl 4-(2-hydroxyethyl)piperazine-1-carboxylate, followed by removal of the Boc protecting group. Removal of the Boc-protecting group was achieved by dissolving the Boc-protected intermediate in methanol and treating with concentrated HCl, followed by stirring at ambient temperature for 2 hours before concentrating under high vacuum and drying under high vacuum overnight. MS (ES+APCI) m/z=551.2 (M+H).

Example 73

6-cyano-N-(3-ethyl-1-((6-methylpyridin-2-yl)methyl)-1H-indazol-4-yl)imidazo[1,2-a]pyridine-3-carboxamide

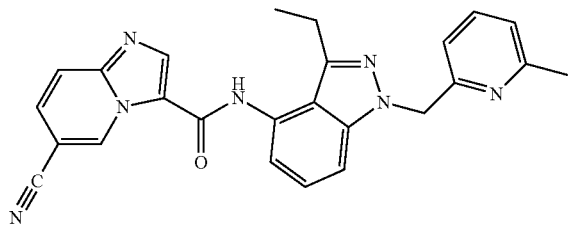 [SMILES: CCc1nn(Cc2cccc(C)n2)c2cccc(NC(=O)c3cnc4ccc(C#N)cn34)c12]

Step A: Preparation of ethyl 6-cyanoimidazo[1,2-a]pyridine-3-carboxylate: 2-Amino-5-cyanopyridine (15.5 g, 152 mmol) was dissolved in ethanol (500 mL) in 2 L round bottom flask. Ethyl 2-chloro-3-oxopropanoate (5% in benzene; 730 mL; Commercial solution from Toronto Research Chemicals Inc.) was added and the mixture was heated at reflux for 10 hours. The mixture was concentrated under reduced pressure and the residue was purified by silica-gel chromatography to give ethyl 6-cyanoimidazo[1,2-a]pyridine-3-carboxylate as a pale yellow solid (13.9 g).

Step B: Preparation of lithium 6-cyanoimidazo[1,2-a]pyridine-3-carboxylate: Ethyl 6-cyanoimidazo[1,2-a]pyridine-3-carboxylate (13.9 g, 65 mmol) and lithium hydroxide monohydrate (2.7 g, 65 mmol) were dissolved in tetrahydrofuran/ethanol/water (1:2:1, 150 mL:300 mL:150 mL). After stirring for 16 hours at ambient temperature, the solvent was removed under vacuum to give lithium 6-cyanoimidazo[1,2-a]pyridine-3-carboxylate (12.6 g).

Step C: Preparation of 6-cyano-N-(3-ethyl-1-((6-methylpyridin-2-yl)methyl)-1H-indazol-4-yl)imidazo[1,2-a]pyridine-3-carboxamide: Lithium 6-cyanoimidazo[1,2-a]pyridine-3-carboxylate (107 mg, 0.6 mmol) was dissolved in anhydrous NMP (2.8 mL) and 2,4,6-trichlorobenzoyl chloride (94 mL, 0.6 mmol) was added dropwise. The mixture was stirred at ambient temperature for 30 minutes. 3-Ethyl-1-((6-methylpyridin-2-yl)methyl)-1H-indazol-4-amine (137 mg, 0.5 mmol) was added in one portion and the reaction mixture was heated to 80° C. for 6 hours. Saturated sodium bicarbonate solution was added until a precipitate formed and the mixture was allowed to stir at ambient temperature for 1 hour. The precipitate was collected by filtration and dried under high vacuum for 2 hours to give cyano-N-(3-ethyl-1-((6-methylpyridin-2-yl)methyl)-1H-indazol-4-yl)imidazo[1,2-a]pyridine-3-carboxamide as a beige solid (147 mg). MS m/z 436.3 (M+1, APCI+).

Example 74

N-(3-ethyl-1-((6-methylpyridin-2-yl)methyl)-1H-indazol-4-yl)-7-(2-(4-isopropylpiperazin-1-yl)ethoxy)imidazo[1,2-a]pyridine-3-carboxamide

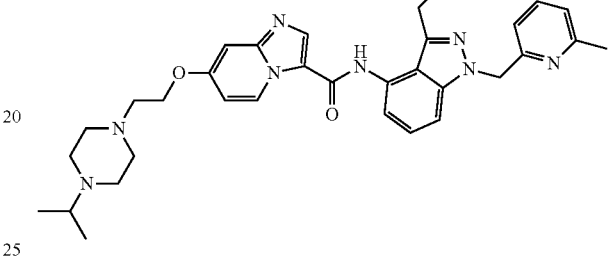

Step A: Preparation of 7-fluoro-N-(3-ethyl-1-((6-methylpyridin-2-yl)methyl)-1H-indazol-4-yl)imidazo[1,2-a]pyridine-3-carboxamide: A solution of 7-fluoroimidazo[1,2-a]pyridine-3-carboxylic acid (Preparation I; 1.3 g, 7.11 mmol) in anhydrous 1-methyl-2-pyrrolidinone (35 mL) was treated with anhydrous triethylamine (2.5 mL, 17.8 mmol) allowing to stir until the mixture became homogeneous. 2,4,6-Trichlorobenzoyl chloride (1.82 g, 7.47 mmol) was added dropwise and the mixture was allowed to stir for 30 minutes at ambient temperature. Within 5 minutes, the anhydride precipitate formed and vigorous stirring was required. 3-Ethyl-1-((6-methylpyridin-2-yl)methyl)-1H-indazol-4-amine (1.7 g, 6.38 mmol) was added as a 0.5 M solution in anhydrous 1-methyl-2-pyrrolidinone. The reaction mixture was heated at 80° C. and stirred for 16 hours. The mixture was cooled to ambient temperature and solids were removed by filtration washing the filter cake with ethyl acetate. The filtrate was concentrated under vacuum to remove ethyl acetate. The 1-methyl-2-pyrrolidinone solution was diluted with saturated sodium bicarbonate solution and a beige precipitate formed which was collected by filtration to give 7-fluoro-N-(3-ethyl-1-((6-methylpyridin-2-yl)methyl)-1H-indazol-4-yl)imidazo[1,2-a]pyridine-3-carboxamide as a beige solid (2.1 g).

Step B: Preparation of N-(3-ethyl-1-((6-methylpyridin-2-yl)methyl)-1H-indazol-4-yl)-7-(2-(4-isopropylpiperazin-1-yl)ethoxy)imidazo[1,2-a]pyridine-3-carboxamide: A 50 mL round bottom flask was charged with solid potassium tert-butoxide (1.7 g, 14.8 mmol), 2-(4-isopropylpiperazin-1-yl)ethanol (2.88 g, 16.7 mmol), and tert-butanol (10 mL, 103 mmol). The mixture was stirred at ambient temperature for 1 hour before heating at 90° C. for 15 minutes to give a homogeneous mixture. 7-Fluoro-N-(3-ethyl-1-((6-methylpyridin-2-yl)methyl)-1H-indazol-4-yl)imidazo[1,2-a]pyridine-3-carboxamide (1.0 g, 2.3 mmol) was added in one portion. The mixture was heated at 90° C. with stirring for 16 hours. The mixture was cooled to ambient temperature before pouring into a 250 mL round bottom flask containing 150 mL of water. Vigorous stirring at ambient temperature for 2 hours resulted in a beige precipitate. The precipitate was collected by filtration and dried under high vacuum to give the product. MS (APCI), positive scan, m/z=581.1 (M+).

Example 75

N-(3-cyclopropyl-1-((6-methylpyridin-2-yl)methyl)-1H-indazol-4-yl)-7-(2-(4-isopropylpiperazin-1-yl)ethoxy)imidazo[1,2-a]pyridine-3-carboxamide

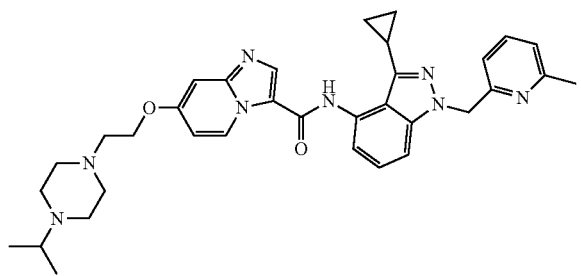 [SMILES: Cc1cccc(Cn2nc(C3CC3)c3c(NC(=O)c4cnc5cc(OCCN6CCN(C(C)C)CC6)ccn45)cccc32)n1]

Step A: Preparation of tert-butyl 4-fluoropyridin-2-ylcarbamate: A 2 L flask was charged 2-chloro-4-fluoropyridine (20 g, 152 mmol), tert-butyl carbamate (89 g, 760 mmol), tris(dibenzylideneacetone) dipalladium (1.39 g, 1.52 mmol), X-PHOS (2-(dicyclohexylphosphino)-2',4',6'-triisopropyl-1,1'-biphenyl) (1.48 g, 3.10 mmol), cesium carbonate (99 g, 588 mmol), and tetrahydrofuran (500 mL) under an atmosphere of dry nitrogen. This mixture was heated at reflux under nitrogen for 7 hours. An additional 1 equivalent of cesium carbonate was added to drive the reaction to completion (heated a further 7 hours). The mixture was cooled to ambient temperature, filtered through Celite and washed with ethyl acetate. The filtrate was partitioned between saturated sodium bicarbonate and ethyl acetate. The aqueous phase was extracted with ethyl acetate twice. The combined organic phases were washed with brine and dried with sodium sulfate, concentrated under vacuum, and purified by column chromatography to give tert-butyl 4-fluoropyridin-2-ylcarbamate as a pale yellow solid (22.6 g).

Step B: Preparation of 4-fluoropyridin-2-amine: To a 1 L, single-neck, round-bottomed flask was added tert-butyl 4-fluoropyridin-2-ylcarbamate (3.5 g, 16.5 mmol) and dichloromethane (100 mL). The mixture was cooled to 0-5° C. using an ice/water bath. Trifluoroacetic acid (75 mL) was added slowly with continued stirring. The mixture was stirred at ambient temperature for 16 hours. The mixture was concentrated under vacuum before partitioning between saturated sodium bicarbonate and ethyl acetate. The aqueous layer was washed with ethyl acetate twice. The combined organic phases were washed with brine and dried with sodium sulfate before concentrating under vacuum to give 4-fluoropyridin-2-amine as a pale yellow solid (1.76 g).

Step C: Preparation of ethyl 7-fluoroimidazo[1,2-a]pyridine-3-carboxylate: 4-Fluoropyridin-2-amine (10.0 g, 48.0 mmol) was mixed with ethanol (40 mL) in a reaction flask, under an atmosphere of dry nitrogen. A solution of ethyl 2-chloro-3-oxopropanoate (5% in benzene, 178 mL, Commercial solution from Toronto Research Chemicals Inc.) was added. The mixture was heated to 60° C. under nitrogen for 4 hours. After allowing the mixture to cool the solvent was removed under vacuum to give a brown solid. The solid was mixed with ethyl acetate (300 mL) and sodium bicarbonate solution (75 mL) and stirred to dissolve. The phases were separated and the bicarbonate solution was extracted further with ethyl acetate (75 mL). The combined ethyl acetate extracts were dried over sodium sulfate, filtered and concentrated under vacuum to give a solid. The crude material was dissolved in ethyl acetate and passed through a short column of silica, eluting with ethyl acetate. Fractions containing the product were concentrated to give ethyl 7-fluoroimidazo[1,2-a]pyridine-3-carboxylate as a white solid (13 g).

Step D: Preparation of 7-fluoroimidazo[1,2-a]pyridine-3-carboxylic acid: Ethyl 7-fluoroimidazo[1,2-a]pyridine-3-carboxylate (8.0 g; 44.4 mmol) was mixed with tetrahydrofuran (225 mL), ethanol (110 mL) and water (55 mL). Lithium hydroxide monohydrate (0.962 g; 22.9 mmol) was added. The mixture was stirred at ambient temperature for 16 hours. The mixture was concentrated under reduced pressure to remove tetrahydrofuran and ethanol. 2 N hydrochloric acid was added to the mixture to adjust to pH 3. A white precipitate formed which was collected by filtration and dried under high vacuum to give 7-fluoroimidazo[1,2-a]pyridine-3-carboxylic acid as a white solid (6.3 g).

Step E: Preparation of 3-cyclopropyl-1-((6-methylpyridin-2-yl)methyl)-4-nitro-1H-indazole: A 250 mL round bottom flask was charged with 1,4-dioxane/H$_2$O (150 mL/30 mL). The flask was cooled to 0° C. and vacuum was applied for 20 minutes. A 500 mL round bottom flask was charged with cyclopropylboronic acid (Preparation C, 15.90 g, 185.1 mmol), 3-bromo-1-((6-methylpyridin-2-yl)methyl)-4-nitro-1H-indazole (Preparation C, 25.71 g, 74.06 mmol), K$_2$CO$_3$ (40.94 g, 296.2 mmol), palladium acetate (0.4988 g, 2.222 mmol) and sodium 2'-(dicyclohexylphosphino)-2,6-dimethoxybiphenyl-3-sulfonate (2.278 g, 4.443 mmol). The flask was evacuated and back filled with nitrogen three times. The cold degassed dioxane/H$_2$O mixture was added to the 500 mL flask, which was evacuated and back filled with argon 5 times. The reaction mixture was heated at reflux for 5 hours under argon. The reaction mixture was cooled to ambient temperature, filtered through a pad of Celite, and the filter pad was washed with H$_2$O (100 mL) and EtOAc (300 mL). The aqueous layer with extracted with EtOAc. The combined organic phases were dried (Na$_2$SO$_4$) and concentrated under reduced pressure. The resulting solid was dissolved in DCM and washed with saturated NaHCO$_3$ aqueous solution. The organic phase was dried (Na$_2$SO$_4$) and concentrated under reduced pressure to give a dark colored residue, which was dissolved in DCM (30 mL) and silica gel (50 g) was added. The DCM was removed under reduced pressure. The crude product absorbed by silica gel was loaded onto a column of silica gel and the column was eluted with EtOAc/hexanes (1:1). The fractions containing product were concentrated under reduced pressure to provide the product (22.1 g).

Step F: Preparation of 3-cyclopropyl-1-((6-methylpyridin-2-yl)methyl)-1H-indazol-4-amine: To a suspension of 3-cyclopropyl-1-((6-methylpyridin-2-yl)methyl)-4-nitro-1H-indazole (22.01 g, 71.38 mmol) in EtOH/H$_2$O (200 mL/50 mL) was added iron powder (79.73 g, 1428 mmol) and NH$_4$Cl (3.818 g, 71.38 mmol). The reaction mixture was heated to reflux for three hours, cooled to 60° C. and filtered through a pad of Celite. The pad of Celite was washed with 20:1 EtOH/Et$_3$N (800 mL) and 1:1 MeOH/DCM (600 mL). The combined filtrate was concentrated under reduced pressure. The residue was dissolved in EtOAc (800 mL), washed with saturated NaHCO$_3$ aqueous solution, dried (Na$_2$SO$_4$) and concentrated under reduced pressure to give the product (16.87 g).

Step G: Preparation of 7-fluoro-N-(3-cyclopropyl-1-((6-methylpyridin-2-yl)methyl)-1H-indazol-4-yl)imidazo[1,2-a]pyridine-3-carboxamide: A solution of 7-fluoroimidazo[1,2-a]pyridine-3-carboxylic acid (0.12 g, 0.65 mmol) in anhydrous 1-methyl-2-pyrrolidinone (1 mL) was treated with anhydrous triethylamine (0.2 mL, 1.6 mmol) allowing to stir until the reaction mixture became homogeneous. 2,4,6-Trichlorobenzoyl chloride (0.1 mL, 0.68 mmol) was added dropwise and the mixture was allowed to stir for 30 minutes at ambient temperature. Within 5 minutes, the anhydride precipitate formed and vigorous stirring was required. 3-Cyclopropyl-1-((6-methylpyridin-2-yl)methyl)-1H-indazol-4-amine (0.16 g, 0.59 mmol) was added as a 0.5 M solution in anhydrous 1-methyl-2-pyrrolidinone. The reaction mixture was heated at 90° C. and stirred for 16 hours. The mixture was cooled to ambient temperature and solids were removed by filtration, washing the filter cake with ethyl acetate. The filtrate was concentrated to remove ethyl acetate. The remaining solution was diluted with saturated sodium bicarbonate and a beige precipitate formed which was collected by filtration to give 7-fluoro-N-(3-ethyl-1-((6-methylpyridin-2-yl)methyl)-1H-indazol-4-yl)imidazo[1,2-a]pyridine-3-carboxamide as a beige solid (119 mg).

Step H: Preparation of N-(3-cyclopropyl-1-((6-methylpyridin-2-yl)methyl)-1H-indazol-4-yl)-7-(2-(4-isopropylpiperazin-1-yl)ethoxy)imidazo[1,2-a]pyridine-3-carboxamide: A one dram vial was charged with solid potassium tert-butoxide (55 mg, 0.49 mmol), 2-(4-isopropylpiperazin-1-yl)ethanol (0.099 g, 0.57 mmol), and tert-butanol (0.3 mL, 3.4 mmol). The mixture was stirred at ambient temperature for 30 minutes. 7-Fluoro-N-(3-cyclopropyl-1-((6-methylpyridin-2-yl)methyl)-1H-indazol-4-yl)imidazo[1,2-a]pyridine-3-carboxamide (0.034 g, 0.077 mmol) was added in one portion. The mixture was heated at 90° C. with stirring for 16 hours. The mixture was cooled to ambient temperature and diluted with water until a precipitate formed. The precipitate was collected by filtration and dried under high vacuum to give the product (0.019 g). MS (APCI), positive scan, m/z=593.1 (M+H).

Example 76

N-(3-cyclopropyl-1-((1-methyl-2-oxo-1,2-dihydropyridin-3-yl)methyl)-1H-indazol-4-yl)-7-(2-(4-methylpiperazin-1-yl)ethoxy)imidazo[1,2-a]pyridine-3-carboxamide

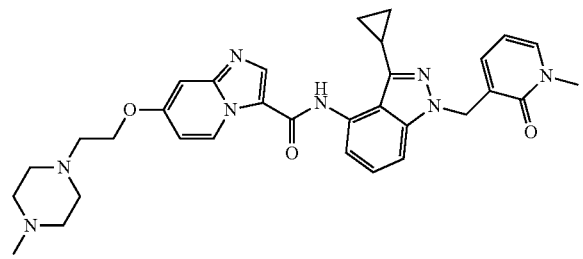 [SMILES: CN1CCN(CCOc2ccn3c(C(=O)Nc4cccc5c4c(C4CC4)nn5Cc4cccn(C)c4=O)cnc3c2)CC1]

Step A: Preparation of 1,3-dimethylpyridin-2(1H)-one: Iodomethane (10.62 mL, 111.6 mmol) was added to a mixture of 3-methyl-2-pyridone (4.06 g, 37.20 mmol) and potassium carbonate (15.43 g, 111.6 mmol) in acetone (150 mL) in a sealable flask. The mixture was vigorously stirred in an oil bath at 55° C. for 16 hours. The reaction mixture was cooled to ambient temperature then filtered through glass fiber filter paper and the filtrate was concentrated under vacuum until a solid formed (5.4 g). The solid was partitioned between water (50 mL) and dichloromethane (100 mL). The aqueous phase was extracted once more with dichloromethane (50 mL). The combined organic phases were dried over magnesium sulfate and concentrated under vacuum to give 1,3-dimethylpyridin-2(1H)-one as an oil (3.6 g).

Step B: Preparation of 3-(bromomethyl)-1-methylpyridin-2(1H)-one: N-Bromosuccinimide (2.17 g, 12.2 mmol) and benzoic peroxyanhydride (0.295 g, 1.22 mmol) were added to a flask containing a solution of 1,3-dimethylpyridin-2(1H)-one (1.50 g, 12.2 mmol) in carbon tetrachloride (250 mL, degassed with flowing $N_2$ for 5 minutes). The mixture was heated at reflux for 3 hours. The reaction mixture was cooled to ambient temperature, filtered through filter paper, and the filtrate was concentrated under vacuum. The residue was suspended in diethyl ether (20 mL), stirred for 15 minutes, and the liquid was decanted. The solids were rinsed with diethyl ether (3×5 mL), then dried under vacuum to give 3-(bromomethyl)-1-methylpyridin-2(1H)-one as a yellow solid (1.1 g).

Step C: Preparation of 3-((3-bromo-4-nitro-1H-indazol-1-yl)methyl)-1-methylpyridin-2(1H)-one: 3-Bromo-4-nitro-1H-indazole (Preparation B; 0.49 g, 2.04 mmol) was dissolved in dimethyl formamide (5 mL). Potassium carbonate (1.13 g, 8.15 mmol) was added followed by 3-(bromomethyl)-1-methylpyridin-2(1H)-one (0.41 g, 2.04 mmol). The mixture was stirred at ambient temperature for two days. The mixture was diluted with ethyl acetate (8 mL) and concentrated under vacuum to give a dark solid which was dried overnight under high vacuum. This material was dissolved in ethyl acetate (80 mL) and washed with water (40 mL). The aqueous layer was extracted twice with ethyl acetate. The combined organic extracts were dried over sodium sulfate and concentrated under vacuum to give a green solid. This material was triturated with diethyl ether and the solids were collected by filtration and dried under high vacuum to give 3-((3-bromo-4-nitro-1H-indazol-1-yl)methyl)-1-methylpyridin-2(1H)-one as a beige solid (552 mg).

Step D: Preparation of 3-((-cyclopropyl-4-nitro-1H-indazol-1-yl)methyl)-1-methylpyridine-2(1H)-one: To a 50 mL pear shaped flask was added 4-dioxane/water (3.2 mL/0.6 mL). The flask was cooled in an ice/water bath before applying vacuum for 20 minutes. 3-((3-Bromo-4-nitro-1H-indazol-1-yl)methyl)-1-methylpyridin-2(1H)-one (0.55 g, 1.52 mmol), cyclopropylboronic acid (0.33 g, 3.79 mmol), sodium 2'-(dicyclohexylphosphino)-2,6-dimethoxybiphenyl-3-sulfonate (0.047 g, 0.091 mmol), palladium acetate (0.01 g, 0.4 mmol), and potassium carbonate (0.84 g, 6.07 mmol) were combined in a 25 mL round bottom flask and placed under vacuum. The degassed solvent mixture was added to the solid reagents and the flask was affixed with a condenser. The apparatus was evacuated and back filled with argon 5 times before heating at reflux under argon for 5 hours. The mixture was cooled to ambient temperature and filtered through a pad of Celite®. The filter cake was washed with ethyl acetate and water. The filtrate phases were separated and the aqueous phase was extracted with ethyl acetate 3 times. The combined organic extracts were washed with saturated sodium bicarbonate 3 times. The organic phase was concentrated under vacuum and dried under high vacuum to give 3-((-cyclopropyl-4-nitro-1H-indazol-1-yl)methyl)-1-methylpyridine-2(1H)-one as a beige solid (413 mg).

Step E: Preparation of 3-((4-amino-3-cyclopropyl-1H-indazol-1-yl)methyl)-1-methylpyridin-2(1H)-one: 3-((3-Cyclopropyl-4-nitro-1H-indazol-1-yl)methyl)-1-methylpyridin-2(1H)-one (413 mg, 1.27 mmol) was dissolved in a mixture of ethanol (6.8 mL) and water (1.7 mL). Ammonium chloride (34 mg; 0.63 mmol) and iron powder (709 mg; 12.7 mmol) were added and the mixture was stirred with heating to 75° C. under a nitrogen atmosphere for 16 hours. The mixture was allowed to cool, diluted with ethyl acetate (50 mL) and filtered through a pad of Celite®. The filtrate was concentrated under reduced pressure to give the crude product as a colored oil. Purification using a silica gel preparative thin layer chromatography plate (20×20 cm, 2 mm) developed in a chamber with 40% ethyl acetate/dichloromethane, drying, and eluting with 80% ethyl acetate/dichloromethane gave 3-((4-amino-3-cyclopropyl-1H-indazol-1-yl)methyl)-1-methylpyridin-2(1H)-one as a viscous oil which began to crystallize upon drying under high vacuum (175 mg).

Step F: Preparation of N-(3-cyclopropyl-1-((1-methyl-2-oxo-1,2-dihydropyridin-3-yl)methyl)-1H-indazol-4-yl)-7-fluoroimidazo[1,2-a]pyridine-3-carboxamide: A solution of 7-fluoroimidazo[1,2-a]pyridine-3-carboxylic acid (Preparation I; 0.09 g, 0.50 mmol) in anhydrous 1-methyl-2-pyrrolidinone (1 mL) was treated with anhydrous triethylamine (0.17 mL, 1.25 mmol) allowing to stir until the mixture became homogeneous. 2, 4, 6-Trichlorobenzoyl chloride (0.08 mL, 0.50 mmol) was added drop wise and the mixture was allowed to stir for 30 minutes at ambient temperature. Within 5 minutes, the anhydride precipitate formed and vigorous stirring was required. 3-((4-Amino-3-cyclopropyl-1H-indazol-1-yl)methyl)-1-methylpyridin-2(1H)-one (0.13 g, 0.45 mmol) was added as a 0.5 M solution in anhydrous 1-methyl-2-pyrrolidinone. The reaction mixture was heated at 90° C. and stirred for 16 hours. The mixture was cooled to ambient temperature and solids were removed by filtration washing the filter cake with ethyl acetate. The filtrate was concentrated under vacuum to remove ethyl acetate. The remaining solution was diluted with saturated sodium bicarbonate solution and a beige precipitate formed which was isolated by filtration, washed with water and dried under vacuum to give N-(3-cyclopropyl-1-((1-methyl-2-oxo-1,2-dihydropyridin-3-yl)methyl)-1H-indazol-4-yl)-7-fluoroimidazo[1,2-a]pyridine-3-carboxamide as a beige solid (180 mg).

Step G: Preparation of N-(3-cyclopropyl-1-((1-methyl-2-oxo-1,2-dihydropyridin-3-yl)methyl)-1H-indazol-4-yl)-7-(2-(4-methylpiperazin-1-yl)ethoxy)imidazo[1,2-a]pyridine-3-carboxamide: A one dram vial was charged with solid potassium tert-butoxide (54 mg, 0.48 mmol), 2-(4-methylpiperazin-1-yl)ethanol (0.075 g, 0.52 mmol), and tert-butanol (0.3 mL, 3.4 mmol). The mixture was stirred at ambient temperature for 30 minutes. N-(3-cyclopropyl-1-((1-methyl-2-oxo-1,2-dihydropyridin-3-yl)methyl)-1H-indazol-4-yl)-7-fluoroimidazo[1,2-a]pyridine-3-carboxamide (0.032 g, 0.070 mmol) was added in one portion. The mixture was heated at 88° C. with stirring for 16 hours. The mixture was cooled to ambient temperature and diluted with water until a precipitate formed. The precipitate was isolated by filtration and dried under high vacuum. Purification using silica preparative thin layer chromatography plate (20×20 cm, 0.5 mm) developed in a chamber with 10% methanol/dichloromethane with 0.6% concentrated ammonium hydroxide gave the product. MS (APCI), positive scan, m/z=581.2 (M+).

Example 77

7-(2-(azetidin-1-yl)ethoxy)-N-(3-cyclopropyl-1-((6-methylpyridin-2-yl)methyl)-1H-indazol-4-yl)imidazo[1,2-a]pyridine-3-carboxamide

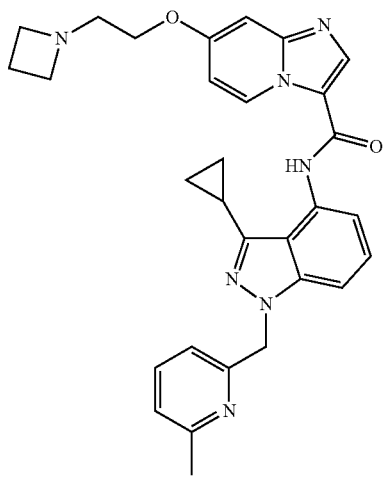 [SMILES: Cc1cccc(Cn2nc(C3CC3)c3c(NC(=O)c4cnc5cc(OCCN6CCC6)ccn45)cccc32)n1]

Step A: Preparation of 2-(azetidin-1-yl)ethanol: Azetidine (546 mg, 9.56 mmol) was dissolved in dichloromethane (20 mL) in a 50 mL round bottom flask and treated with triethylamine (1.47 mL, 10.5 mmol) stirring at ambient temperature for 30 minutes. 2-chloro-2-oxoethyl acetate (1.03 mL, 9.56 mmol) was added to the mixture dropwise. The mixture was stirred at ambient temperature for 16 hours. The precipitated salt was removed by filtration and the filtrate was washed with water. The solution was concentrated under vacuum to give 2-(azetidin-1-yl)-2-oxoethyl acetate as a brown oil. Lithium aluminum hydride (10.0 mL, 10.0 mmol, 1 M in THF) in a 100 mL round bottom flask was cooled in an ice-water bath. 2-(Azetidin-1-yl)-2-oxoethyl acetate as a 0.6 M solution in THF was added dropwise to the lithium aluminum hydride solution. The ice bath was removed and the mixture was stirred at ambient temperature for 2 hours. A mixture of 1:1 Celite®/sodium sulfate decahydrate was added and the mixture was stirred at ambient temperature for 16 hours. The mixture was filtered and the filter cake was washed with THF. The filtrated was concentrated under vacuum to give 2-(azetidin-1-yl)ethanol as a viscous, colorless oil (504 mg).

Step B: Preparation of 7-fluoro-N-(3-cyclopropyl-1-((6-methylpyridin-2-yl)methyl)-1H-indazol-4-yl)imidazo[1,2-a]pyridine-3-carboxamide: Prepared according to Example 75, Steps A-G; 31 mg, 0.07 mmol).

Step C: Preparation of 7-(2-(azetidin-1-yl)ethoxy)-N-(3-cyclopropyl-1-((6-methylpyridin-2-yl)methyl)-1H-indazol-4-yl)imidazo[1,2-a]pyridine-3-carboxamide: 2-(Azetidin-1-yl)ethanol (52 mg, 0.51 mmol) was dissolved in tert-butanol (0.3 mL) and treated with potassium tert-butoxide (51 mg, 0.45 mmol). The mixture was stirred at 88° C. for 5 minutes before adding 7-fluoro-N-(3-cyclopropyl-1-((6-methylpyridin-2-yl)methyl)-1H-indazol-4-yl)imidazo[1,2-a]pyridine-3-carboxamide in one portion. The mixture was stirred at 88° C. for 16 hours. The mixture was cooled to ambient temperature and quenched with water (2 mL) followed by vigorous stirring for 2 hours at ambient temperature. The precipitate was isolated by filtration and dried under vacuum to give a pale yellow residue which was triturated with diethyl ether 3 times to give a solid. Purification by Preparative Thin Layer Chromatography (Silica, 20×20, 0.5 mm thickness) eluting with 10% MeOH/DCM with 0.6% ammonium hydroxide gave 7-(2-(azetidin-1-yl)ethoxy)-N-(3-cyclopropyl-1-((6-methylpyridin-2-yl)methyl)-1H-indazol-4-yl)imidazo[1,2-a]pyridine-3-carboxamide as a white solid (18 mg). MS (APCI), positive scan, m/z=522.2 (M+1).

The compounds shown in Table 1 were synthesized according to the method of Example 77, step B, using the appropriate alcohol and substituting one of the following intermediates for 7-fluoro-N-(3-cyclopropyl-1-((6-methylpyridin-2-yl)methyl)-1H-indazol-4-yl)imidazo[1,2-a]pyridine-3-carboxamide:

7-fluoro-N-(3-methyl-1-((6-methylpyridin-2-yl)methyl)-1H-indazol-4-yl)imidazo[1,2-a]pyridine-3-carboxamide (Preparation J);

7-fluoro-N-(3-ethyl-1-((6-methylpyridin-2-yl)methyl)-1H-indazol-4-yl)imidazo[1,2-a]pyridine-3-carboxamide (Example 74, Step A);

7-fluoro-N-(3-cyclopropyl-1-((6-methylpyridin-2-yl)methyl)-1H-indazol-4-yl)imidazo[1,2-a]pyridine-3-carboxamide (Example 75, Steps A-G);

N-(3-cyclopropyl-1-((1-methyl-2-oxo-1,2-dihydropyridin-3-yl)methyl)-1H-indazol-4-yl)-7-fluoroimidazo[1,2-a]pyridine-3-carboxamide (Example 76, Step F); or N-(3-ethyl-1-((1-ethyl-1H-pyrazol-3-yl)methyl)-1H-indazol-4-yl)-7-fluoroimidazo[1,2-a]pyridine-3-carboxamide (Example 117, Step A).

Certain compounds in Table 1 were prepared with an intermediate containing a t-butylcarbamate (Boc) protecting group and were deprotected as described in Example 72.

TABLE 1

| Ex. # | Structure | Name | MS m/z |
|---|---|---|---|
| 78 | 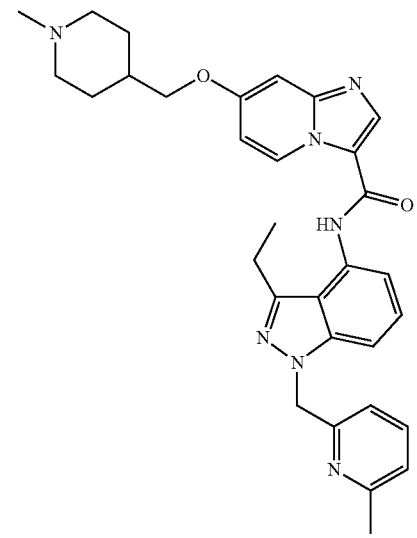 [SMILES: CCc1nn(Cc2cccc(C)n2)c2cccc(NC(=O)c3cnc4cc(OCC5CCN(C)CC5)ccn34)c12] | N-(3-ethyl-1-((6-methylpyridin-2-yl)methyl)-1H-indazol-4-yl)-7-((1-methylpiperidin-4-yl)methoxy)imidazo[1,2-a]pyridine-3-carboxamide | 538.0 (M+, APCI+) |
| 79 | 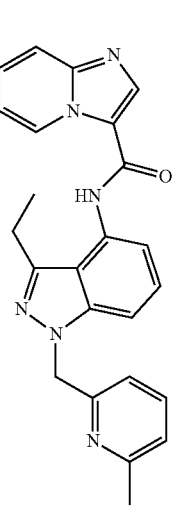 | N-(3-ethyl-1-((6-methylpyridin-2-yl)methyl)-1H-indazol-4-yl)-7-(2-(4-ethylpiperazin-1-yl)ethoxy)imidazo[1,2-a]pyridine-3-carboxamide | 567.1 (M+, APCI+) |

TABLE 1-continued

| Ex. # | Structure | Name | MS m/z |
|---|---|---|---|
| 80 | 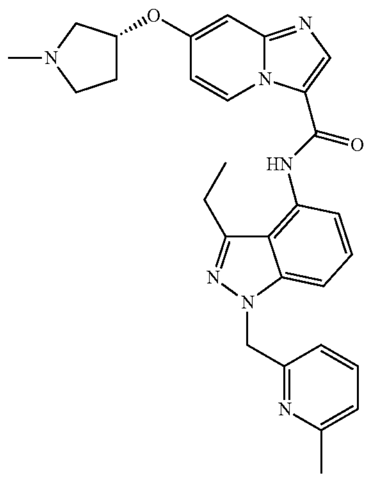 [SMILES: CCc1nn(Cc2cccc(C)n2)c2cccc(NC(=O)c3cnc4cc(O[C@@H]5CCN(C)C5)ccn34)c12] | (R)-N-(3-ethyl-1-((6-methylpyridin-2-yl)methyl)-1H-indazol-4-yl)-7-(1-methylpyrrolidin-3-yloxy)imidazo[1,2-a]pyridine-3-carboxamide | 510.2 (M + 1, APCI+) |
| 81 | 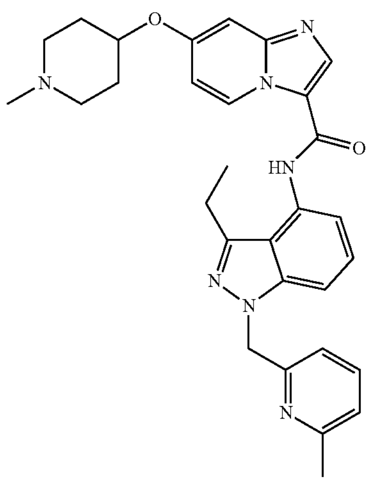 [SMILES: CCc1nn(Cc2cccc(C)n2)c2cccc(NC(=O)c3cnc4cc(OC5CCN(C)CC5)ccn34)c12] | N-(3-ethyl-1-((6-methylpyridin-2-yl)methyl)-1H-indazol-4-yl)-7-(1-methylpiperidin-4-yloxy)imidazo[1,2-a]pyridine-3-carboxamide | 524.1 (M+, APCI+) |
| 82 | 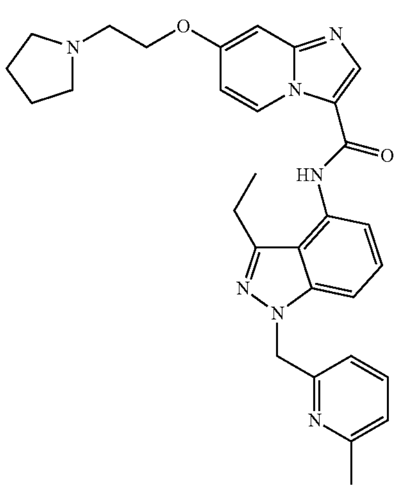 [SMILES: CCc1nn(Cc2cccc(C)n2)c2cccc(NC(=O)c3cnc4cc(OCCN5CCCC5)ccn34)c12] | N-(3-ethyl-1-((6-methylpyridin-2-yl)methyl)-1H-indazol-4-yl)-7-(2-(pyrrolidin-1-yl)ethoxy)imidazo[1,2-a]pyridine-3-carboxamide | 524.1 (M+, APCI+) |

| Ex. # | Structure | Name | MS m/z |
|---|---|---|---|
| 83 | 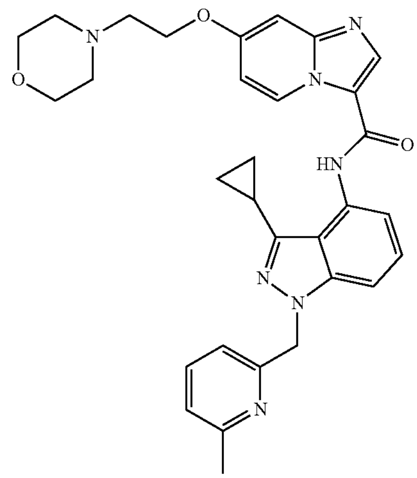 [SMILES: Cc1cccc(Cn2nc(C3CC3)c3c(NC(=O)c4cnc5cc(OCCN6CCOCC6)ccn45)cccc32)n1] | N-(3-cyclopropyl-1-((6-methylpyridin-2-yl)methyl)-1H-indazol-4-yl)-7-(2-morpholinoethoxy)imidazo[1,2-a]pyridine-3-carboxamide | 552.1 (M+, APCI+) |
| 84 | 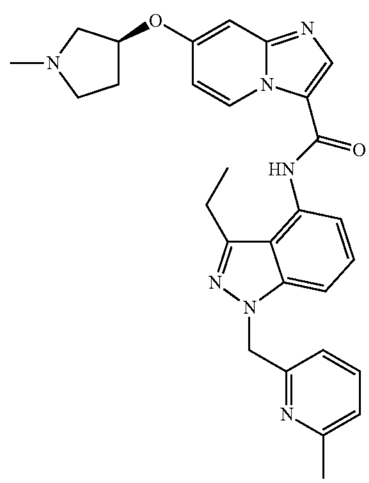 [SMILES: CCc1nn(Cc2cccc(C)n2)c2cccc(NC(=O)c3cnc4cc(O[C@H]5CCN(C)C5)ccn34)c12] | (S)-N-(3-ethyl-1-((6-methylpyridin-2-yl)methyl)-1H-indazol-4-yl)-7-(1-methylpyrrolidin-3-yloxy)imidazo[1,2-a]pyridine-3-carboxamide | 510.2 (M + 1, APCI+) |
| 85 | 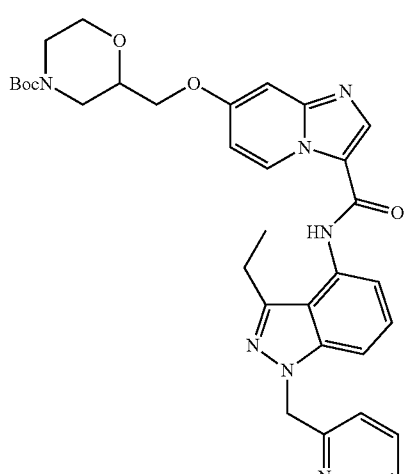 | tert-butyl 2-((3-(3-ethyl-1-((6-methylpyridin-2-yl)methyl)-1H-indazol-4-ylcarbamoyl)imidazo[1,2-a]pyridin-7-yloxy)methyl)morpholine-4-carboxylate | 626.1 (M+, APCI+) |

TABLE 1-continued

| Ex. # | Structure | Name | MS m/z |
|---|---|---|---|
| 86 | 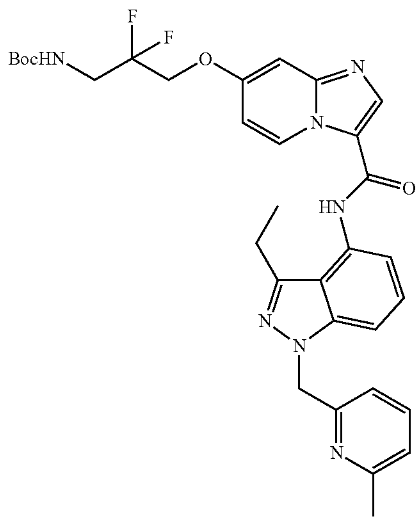 [SMILES: CCc1nn(Cc2cccc(C)n2)c2cccc(NC(=O)c3cnc4cc(OCC(F)(F)CNC(=O)OC(C)(C)C)ccn34)c12] | tert-butyl 3-(3-(3-ethyl-1-((6-methylpyridin-2-yl)methyl)-1H-indazol-4-ylcarbamoyl)imidazo[1,2-a]pyridin-7-yloxy)-2,2-difluoropropylcarbamate | 620.1 (M + 1, APCI+) |
| 87 | 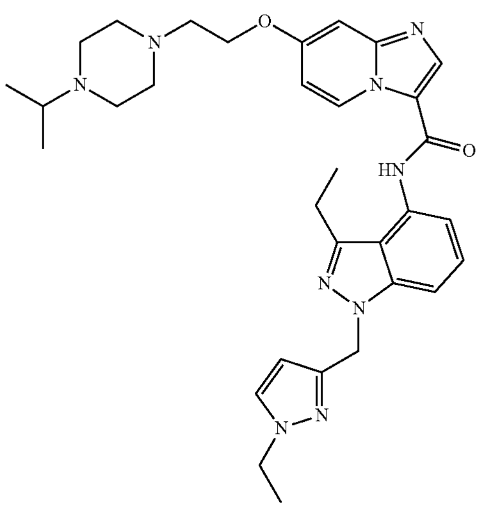 [SMILES: CCc1nn(Cc2ccn(CC)n2)c2cccc(NC(=O)c3cnc4cc(OCCN5CCN(C(C)C)CC5)ccn34)c12] | N-(3-ethyl-1-((1-ethyl-1H-pyrazol-3-yl)methyl)-1H-indazol-4-yl)-7-(2-(4-isopropylpiperazin-1-yl)ethoxy)imidazo[1,2-a]pyridine-3-carboxamide | 584.1 (M+, APCI+) |
| 88 | 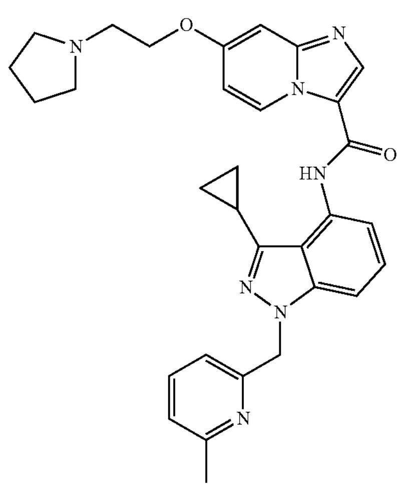 [SMILES: Cc1cccc(Cn2nc(C3CC3)c3c(NC(=O)c4cnc5cc(OCCN6CCCC6)ccn45)cccc32)n1] | N-(3-cyclopropyl-1-((6-methylpyridin-2-yl)methyl)-1H-indazol-4-yl)-7-(2-(pyrrolidin-1-yl)ethoxy)imidazo[1,2-a]pyridine-3-carboxamide | 536.1 (M+, APCI+) |

TABLE 1-continued

| Ex. # | Structure | Name | MS m/z |
|---|---|---|---|
| 89 | 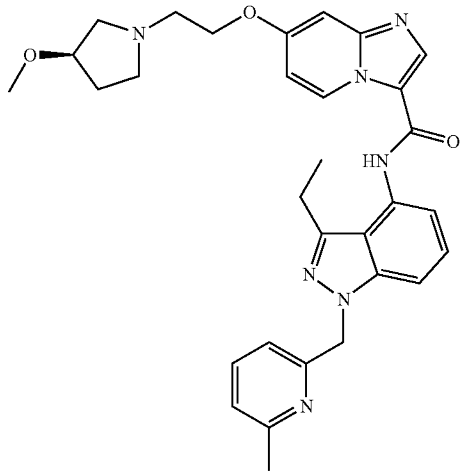 [SMILES: CCc1nn(Cc2cccc(C)n2)c2cccc(NC(=O)c3cnc4cc(OCCN5CC[C@@H](OC)C5)ccn34)c12] | (R)-N-(3-ethyl-1-((6-methylpyridin-2-yl)methyl)-1H-indazol-4-yl)-7-(2-(3-methoxypyrrolidin-1-yl)ethoxy)imidazo[1,2-a]pyridine-3-carboxamide | 554.1 (M+, APCI+) |
| 90 | 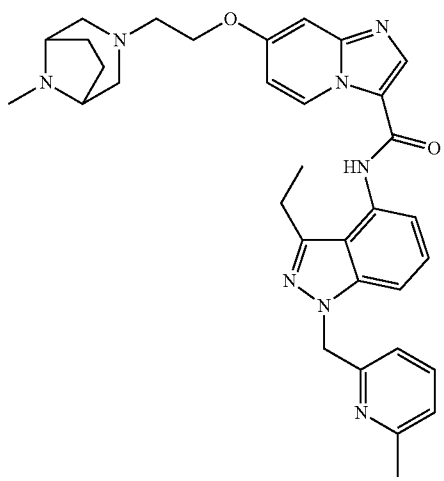 [SMILES: CCc1nn(Cc2cccc(C)n2)c2cccc(NC(=O)c3cnc4cc(OCCN5CC6CCC(C5)N6C)ccn34)c12] | N-(3-ethyl-1-((6-methylpyridin-2-yl)methyl)-1H-indazol-4-yl)-7-(2-(8-methyl-3,8-diazabicyclo[3.2.1]octan-3-yl)ethoxy)imidazo[1,2-a]pyridine-3-carboxamide | 579.1 (M+, APCI+) |
| 91 | 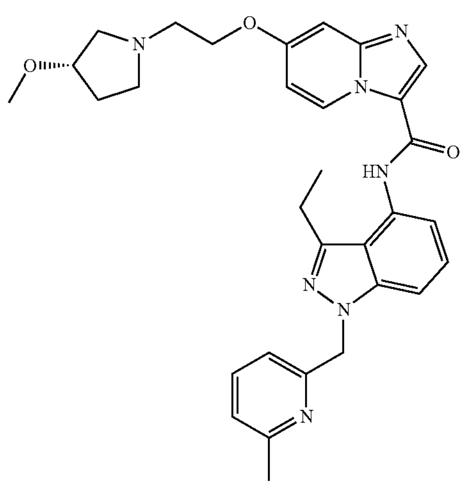 [SMILES: CCc1nn(Cc2cccc(C)n2)c2cccc(NC(=O)c3cnc4cc(OCCN5CC[C@H](OC)C5)ccn34)c12] | (S)-N-(3-ethyl-1-((6-methylpyridin-2-yl)methyl)-1H-indazol-4-yl)-7-(2-(3-methoxypyrrolidin-1-yl)ethoxy)imidazo[1,2-a]pyridine-3-carboxamide | 554.1 (M+, APCI+) |

TABLE 1-continued

| Ex. # | Structure | Name | MS m/z |
|---|---|---|---|
| 92 | 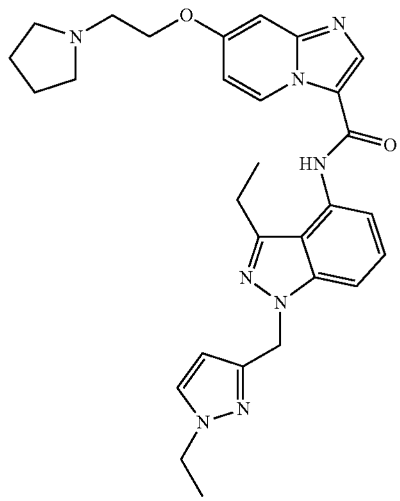 [SMILES: CCc1nn(Cc2ccn(CC)n2)c2cccc(NC(=O)c3cnc4cc(OCCN5CCCC5)ccn34)c12] | N-(3-ethyl-1-((1-ethyl-1H-pyrazol-3-yl)methyl)-1H-indazol-4-yl)-7-(2-(pyrrolidin-1-yl)ethoxy)imidazo[1,2-a]pyridine-3-carboxamide | 527.1 (M+, APCI+) |
| 93 | 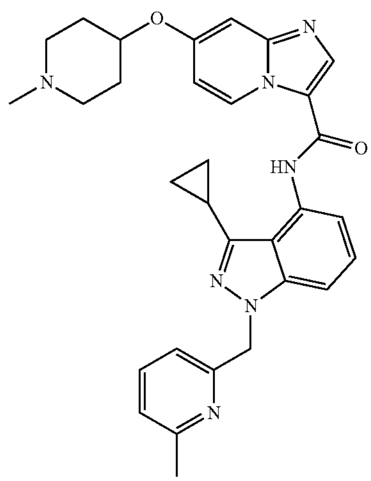 [SMILES: Cc1cccc(Cn2nc(C3CC3)c3c(NC(=O)c4cnc5cc(OC6CCN(C)CC6)ccn45)cccc32)n1] | N-(3-cyclopropyl-1-((6-methylpyridin-2-yl)methyl)-1H-indazol-4-yl)-7-(1-methylpiperidin-4-yloxy)imidazo[1,2-a]pyridine-3-carboxamide | 536.1 (M+, APCI+) |
| 94 | 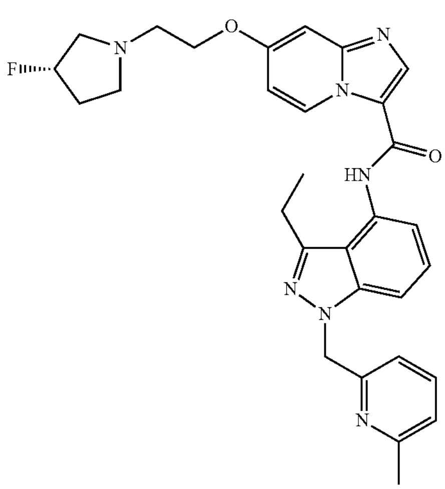 [SMILES: CCc1nn(Cc2cccc(C)n2)c2cccc(NC(=O)c3cnc4cc(OCCN5CC[C@H](F)C5)ccn34)c12] | (S)-N-(3-ethyl-1-((6-methylpyridin-2-yl)methyl)-1H-indazol-4-yl)-7-(2-(3-fluoropyrrolidin-1-yl)ethoxy)imidazo[1,2-a]pyridine-3-carboxamide | 542.2 (M + 1, APCI+) |

TABLE 1-continued

| Ex. # | Structure | Name | MS m/z |
|---|---|---|---|
| 95 | 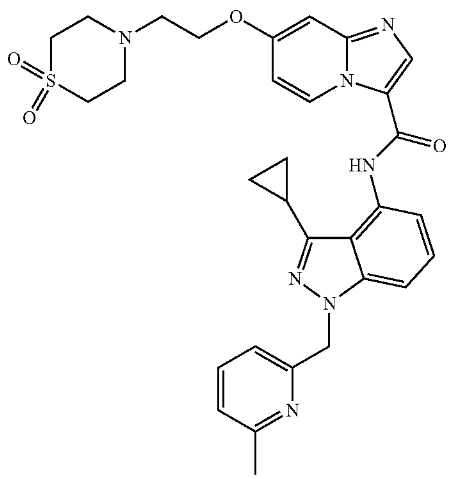 [SMILES: Cc1cccc(Cn2nc(C3CC3)c3c(NC(=O)c4cnc5cc(OCCN6CCS(=O)(=O)CC6)ccn45)cccc32)n1] | N-(3-cyclopropyl-1-((6-methylpyridin-2-yl)methyl)-1H-indazol-4-yl)-7-(2-thiomorpholine 1,1-dioxide ethoxy)imidazo[1,2-a]pyridine-3-carboxamide | 600.2 (M+, APCI+) |
| 96 | 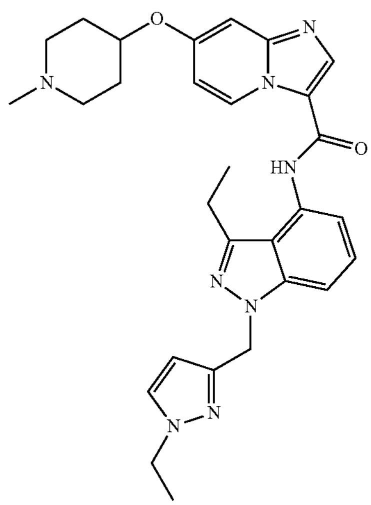 [SMILES: CCc1nn(Cc2ccn(CC)n2)c2cccc(NC(=O)c3cnc4cc(OC5CCN(C)CC5)ccn34)c12] | N-(3-ethyl-1-((1-ethyl-1H-pyrazol-3-yl)methyl)-1H-indazol-4-yl)-7-(1-methylpiperidin-4-yloxy)imidazo[1,2-a]pyridine-3-carboxamide | 527.1 (M+, APCI+) |
| 97 | 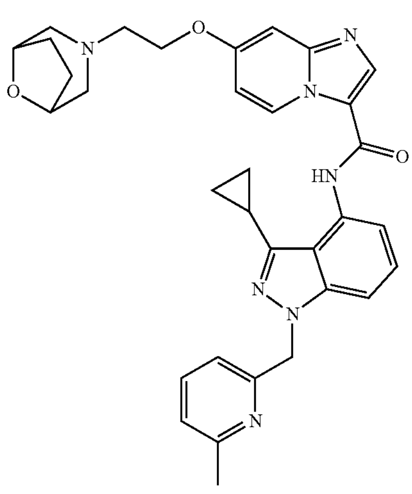 [SMILES: Cc1cccc(Cn2nc(C3CC3)c3c(NC(=O)c4cnc5cc(OCCN6CC7CCC(C6)O7)ccn45)cccc32)n1] | N-(3-ethyl-1-((6-methylpyridin-2-yl)methyl)-1H-indazol-4-yl)-7-(2-(8-Oxa-3-azabicyclo[3.2.1]octane)ethoxy)imidazo[1,2-a]pyridine-3-carboxamide | 578.1 (M+, APCI+) |

TABLE 1-continued

| Ex. # | Structure | Name | MS m/z |
|---|---|---|---|
| 98 | 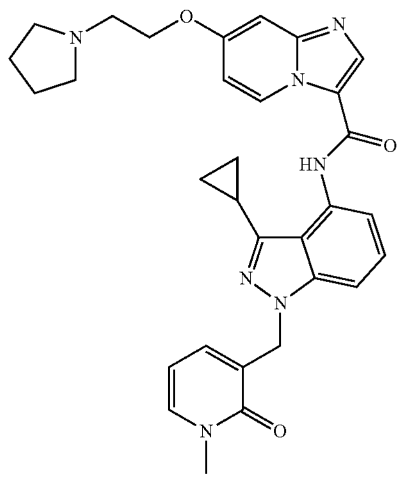 [SMILES: Cn1cccc(Cn2nc(C3CC3)c3c(NC(=O)c4cnc5cc(OCCN6CCCC6)ccn45)cccc32)c1=O] | N-(3-cyclopropyl-1-((1-methyl-2-oxo-1,2-dihydropyridin-3-yl)methyl)-1H-indazol-4-yl)-7-(2-(pyrrolidin-1-yl)ethoxy)imidazo[1,2-a]pyridine-3-carboxamide | 552.1 (M+, APCI+) |
| 99 | 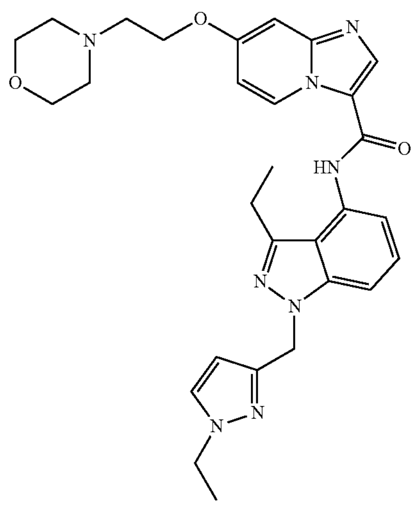 [SMILES: CCc1nn(Cc2ccn(CC)n2)c2cccc(NC(=O)c3cnc4cc(OCCN5CCOCC5)ccn34)c12] | N-(3-ethyl-1-((1-ethyl-1H-pyrazol-3-yl)methyl)-1H-indazol-4-yl)-7-(2-morpholinoethoxy)imidazo[1,2-a]pyridine-3-carboxamide | 543.1 (M+, APCI+) |
| 100 | 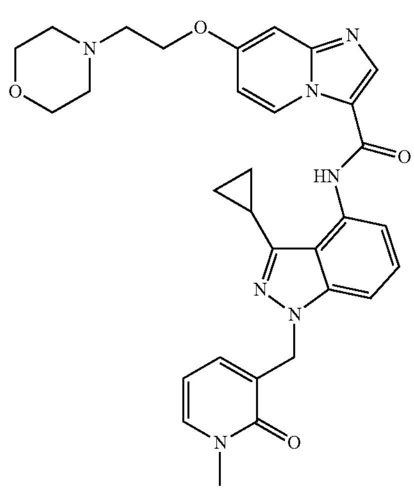 [SMILES: Cn1cccc(Cn2nc(C3CC3)c3c(NC(=O)c4cnc5cc(OCCN6CCOCC6)ccn45)cccc32)c1=O] | N-(3-cyclopropyl-1-((1-methyl-2-oxo-1,2-dihydropyridin-3-yl)methyl)-1H-indazol-4-yl)-7-(2-morpholinoethoxy)imidazo[1,2-a]pyridine-3-carboxamide | 568.2 (M + 1, APCI+) |

TABLE 1-continued

| Ex. # | Structure | Name | MS m/z |
|---|---|---|---|
| 101 | 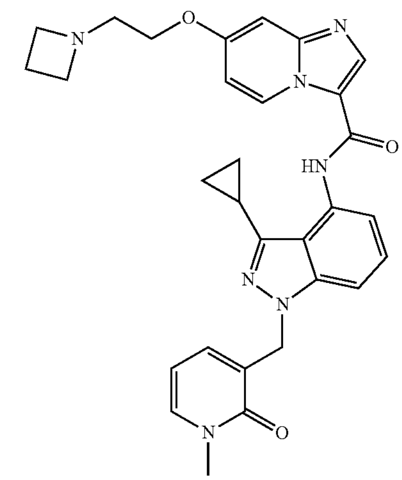 [SMILES: Cn1cccc(Cn2nc(C3CC3)c3c(NC(=O)c4cnc5cc(OCCN6CCC6)ccn45)cccc32)c1=O] | 7-(2-(azetidin-1-yl)ethoxy)-N-(3-cyclopropyl-1-((1-methyl-2-oxo-1,2-dihydropyridin-3-yl)methyl)-1H-indazol-4-yl)imidazo[1,2-a]pyridine-3-carboxamide | 538.2 (M + 1, APCI+) |
| 102 | 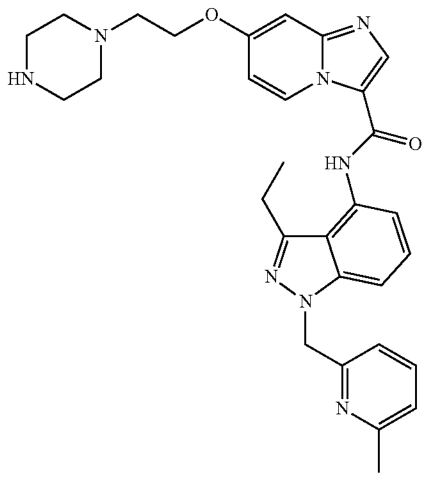 [SMILES: CCc1nn(Cc2cccc(C)n2)c2cccc(NC(=O)c3cnc4cc(OCCN5CCNCC5)ccn34)c12] | N-(3-ethyl-1-((6-methylpyridin-2-yl)methyl)-1H-indazol-4-yl)-7-(2-(piperazin-1-yl)ethoxy)imidazo[1,2-a]pyridine-3-carboxamide | 539.1 (M+, APCI+) |
| 103 | 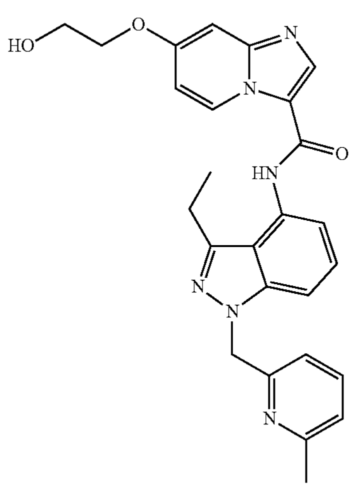 [SMILES: CCc1nn(Cc2cccc(C)n2)c2cccc(NC(=O)c3cnc4cc(OCCO)ccn34)c12] | N-(3-ethyl-1-((6-methylpyridin-2-yl)methyl)-1H-indazol-4-yl)-7-(2-hydroxyethoxy)imidazo[1,2-a]pyridine-3-carboxamide | 471.2 (M + 1, APCI+) |

TABLE 1-continued
| Ex. # | Structure | Name | MS m/z |
|---|---|---|---|
| 104 | 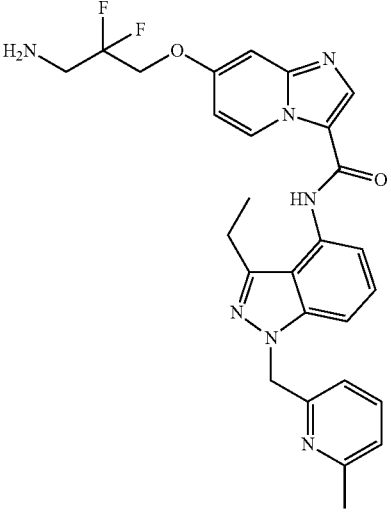 [SMILES: CCc1nn(Cc2cccc(C)n2)c2cccc(NC(=O)c3cnc4cc(OCC(F)(F)CN)ccn34)c12] | 7-(3-amino-2,2-difluoropropoxy)-N-(3-ethyl-1-((6-methylpyridin-2-yl)methyl)-1H-indazol-4-yl)imidazo[1,2-a]pyridine-3-carboxamide | 520.2 (M + 1, APCI+) |
| 105 | 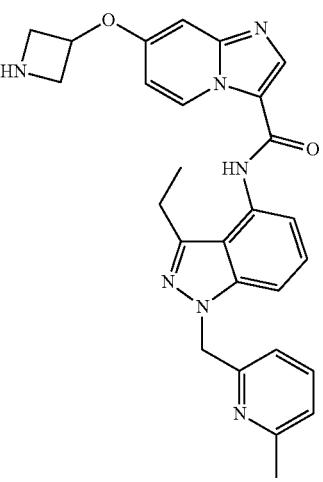 [SMILES: CCc1nn(Cc2cccc(C)n2)c2cccc(NC(=O)c3cnc4cc(OC5CNC5)ccn34)c12] | 7-(azetidin-3-yloxy)-N-(3-ethyl-1-((6-methylpyridin-2-yl)methyl)-1H-indazol-4-yl)imidazo[1,2-a]pyridine-3-carboxamide | 482.1 (M + 1, APCI+) |

TABLE 1-continued
| Ex. # | Structure | Name | MS m/z |
|---|---|---|---|
| 106 | 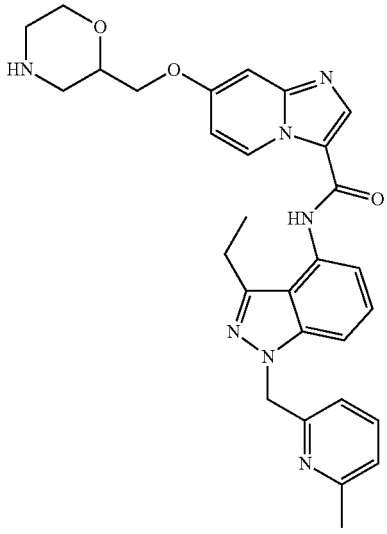 [SMILES: CCc1nn(Cc2cccc(C)n2)c2cccc(NC(=O)c3cnc4cc(OCC5CNCCO5)ccn34)c12] | N-(3-ethyl-1-((6-methylpyridin-2-yl)methyl)-1H-indazol-4-yl)-7-(morpholin-2-ylmethoxy)imidazo[1,2-a]pyridine-3-carboxamide | 526.2 (M + 1, APCI+) |
| 107 | 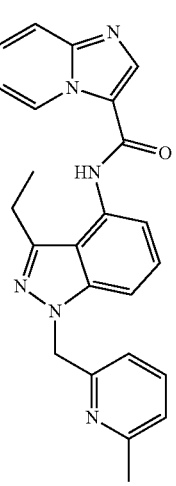 | (R)-N-(3-ethyl-1-((6-methylpyridin-2-yl)methyl)-1H-indazol-4-yl)-7-(2-(3-fluoropyrrolidin-1-yl)ethoxy)imidazo[1,2-a]pyridine-3-carboxamide | 542.1 (M+, APCI+) |

Example 108

N-(3-ethyl-1-((6-methylpyridin-2-yl)methyl)-1H-indazol-4-yl)-7-(piperazin-1-yl)imidazo[1,2-a]pyridine-3-carboxamide

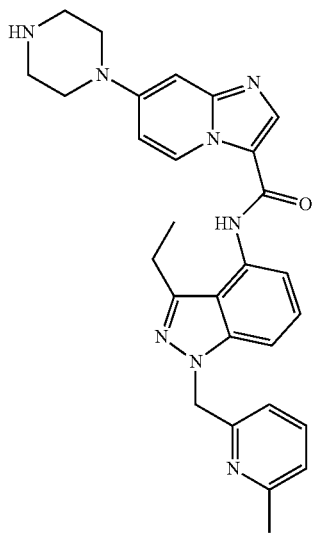 [SMILES: CCc1nn(Cc2cccc(C)n2)c2cccc(NC(=O)c3cnc4cc(N5CCNCC5)ccn34)c12]

N-(3-Ethyl-1-((6-methylpyridin-2-yl)methyl)-1H-indazol-4-yl)-7-fluoroimidazo[1,2-a]pyridine-3-carboxamide (12 mg, 0.03 mmol; Example 74, Step A) was dissolved in toluene (0.2 mL) and 1,3-dimethyl-3,4,5,6-tetrahydro-2(1H)-pyrimidinone (DMPU) (0.1 mL) and piperazine (24 mg, 0.28 mmol) was added in one portion. The mixture was heated to 105° C. and stirred for 16 hours. The crude mixture was loaded onto a Biotage 12+ C-18 samplet and purified using a gradient of 10-65% acetonitrile/water to give N-(3-ethyl-1-((6-methylpyridin-2-yl)methyl)-1H-indazol-4-yl)-7-(piperazin-1-yl)imidazo[1,2-a]pyridine-3-carboxamide as a white solid (12 mg). MS m/z 495.3 (M+1, APCI+)

The compounds shown in Table 2 were synthesized according to Example 108, using the appropriate amine and N-(3-Ethyl-1-((6-methylpyridin-2-yl)methyl)-1H-indazol-4-yl)-7-fluoroimidazo[1,2-a]pyridine-3-carboxamide (Example 74, Step A).

TABLE 2

| Ex. # | Structure | Name | MS m/z |
|---|---|---|---|
| 109 | 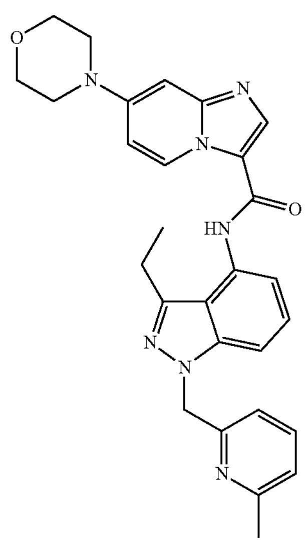 [SMILES: CCc1nn(Cc2cccc(C)n2)c2cccc(NC(=O)c3cnc4cc(N5CCOCC5)ccn34)c12] | N-(3-ethyl-1-((6-methylpyridin-2-yl)methyl)-1H-indazol-4-yl)-7-morpholinoimidazo[1,2-a]pyridine-3-carboxamide | 496.3 (M + 1, APCI+) |

TABLE 2-continued

| Ex. # | Structure | Name | MS m/z |
|---|---|---|---|
| 110 | 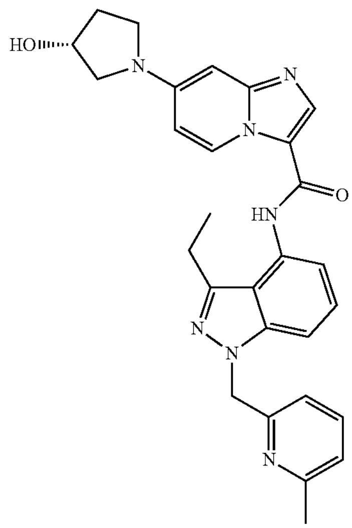 [SMILES: CCc1nn(Cc2cccc(C)n2)c2cccc(NC(=O)c3cnc4cc(N5CC[C@@H](O)C5)ccn34)c12] | (R)-N-(3-ethyl-1-((6-methylpyridin-2-yl)methyl)-1H-indazol-4-yl)-7-(3-hydroxypyrrolidin-1-yl)imidazo[1,2-a]pyridine-3-carboxamide | 496.3 (M + 1, APCI+) |
| 111 | 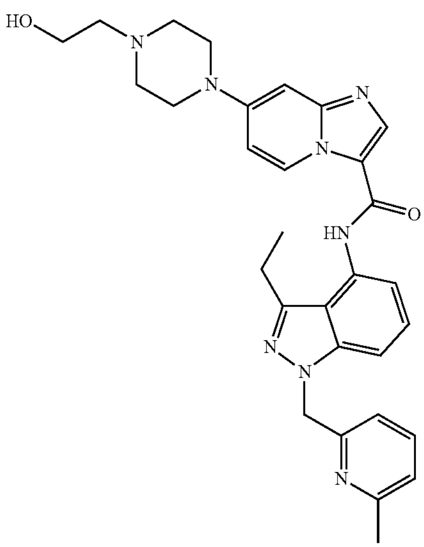 [SMILES: CCc1nn(Cc2cccc(C)n2)c2cccc(NC(=O)c3cnc4cc(N5CCN(CCO)CC5)ccn34)c12] | N-(3-ethyl-1-((6-methylpyridin-2-yl)methyl)-1H-indazol-4-yl)-7-(4-(2-hydroxyethyl)piperazin-1-yl)imidazo[1,2-a]pyridine-3-carboxamide | 539.3 (M+, APCI+) |
| 112 | 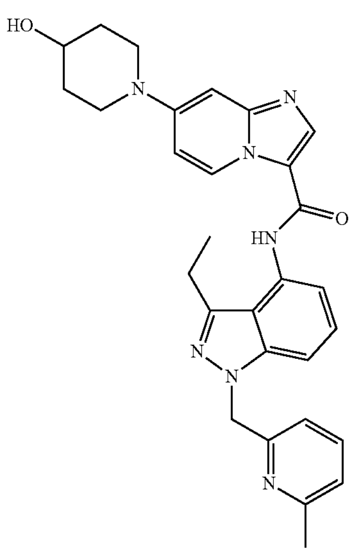 [SMILES: CCc1nn(Cc2cccc(C)n2)c2cccc(NC(=O)c3cnc4cc(N5CCC(O)CC5)ccn34)c12] | N-(3-ethyl-1-((6-methylpyridin-2-yl)methyl)-1H-indazol-4-yl)-7-(4-hydroxypiperidin-1-yl)imidazo[1,2-a]pyridine-3-carboxamide | 510.3 (M + 1, APCI+) |

TABLE 2-continued
| Ex. # | Structure | Name | MS m/z |
|---|---|---|---|
| 113 | 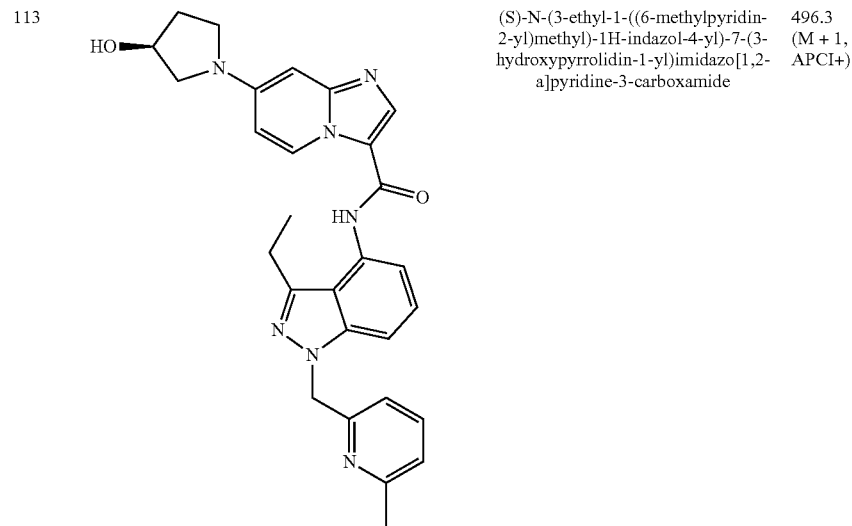 | (S)-N-(3-ethyl-1-((6-methylpyridin-2-yl)methyl)-1H-indazol-4-yl)-7-(3-hydroxypyrrolidin-1-yl)imidazo[1,2-a]pyridine-3-carboxamide | 496.3 (M + 1, APCI+) |
| 114 | 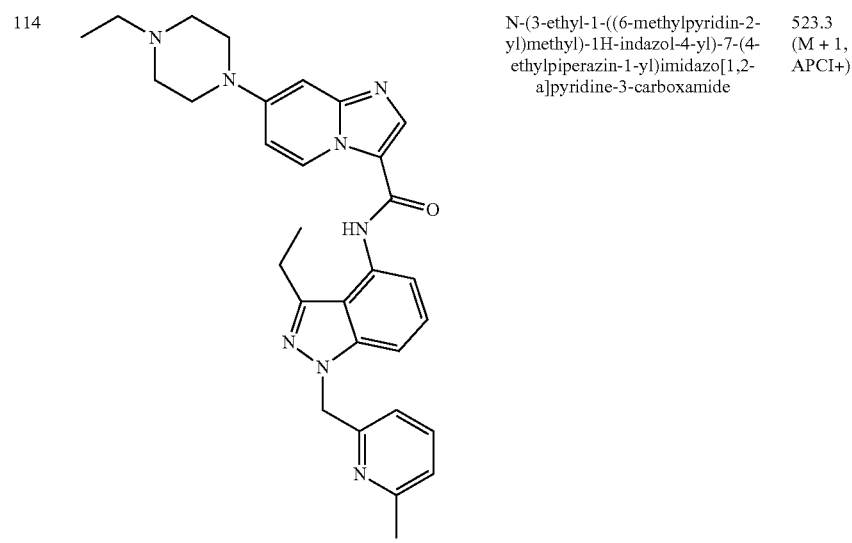 | N-(3-ethyl-1-((6-methylpyridin-2-yl)methyl)-1H-indazol-4-yl)-7-(4-ethylpiperazin-1-yl)imidazo[1,2-a]pyridine-3-carboxamide | 523.3 (M + 1, APCI+) |

TABLE 2-continued
| Ex. # | Structure | Name | MS m/z |
|---|---|---|---|
| 115 | 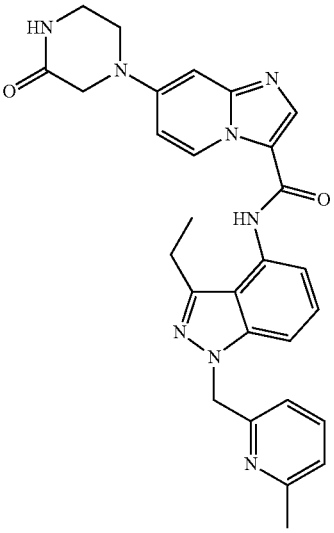 [SMILES: CCc1nn(Cc2cccc(C)n2)c2cccc(NC(=O)c3cnc4cc(N5CCNC(=O)C5)ccn34)c12] | N-(3-ethyl-1-((6-methylpyridin-2-yl)methyl)-1H-indazol-4-yl)-7-(3-oxopiperazin-1-yl)imidazo[1,2-a]pyridine-3-carboxamide | 509.3 (M + 1, APCI+) |
| 116 | 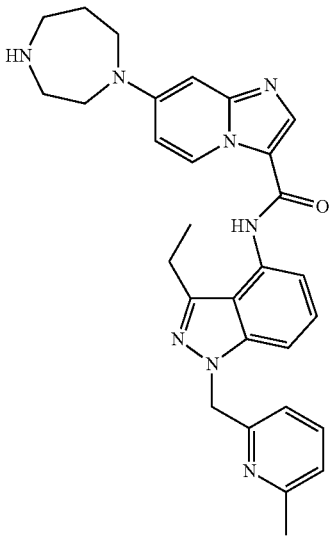 [SMILES: CCc1nn(Cc2cccc(C)n2)c2cccc(NC(=O)c3cnc4cc(N5CCCNCC5)ccn34)c12] | 7-(1,4-diazepan-1-yl)-N-(3-ethyl-1-((6-methylpyridin-2-yl)methyl)-1H-indazol-4-yl)imidazo[1,2-a]pyridine-3-carboxamide | 509.3 (M + 1, APCI+) |

Example 117

N-(3-ethyl-1-((1-ethyl-1H-pyrazol-3-yl)methyl)-1H-indazol-4-yl)-7-(1H-1,2,4-triazol-1-yl)imidazo[1,2-a]pyridine-3-carboxamide

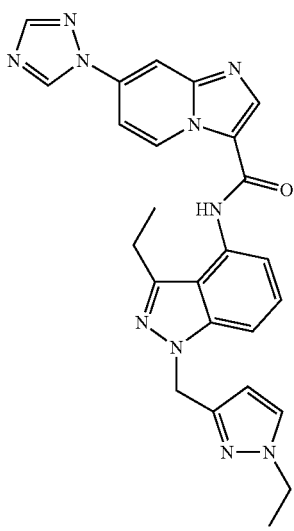 [SMILES: CCc1nn(Cc2ccn(CC)n2)c2cccc(NC(=O)c3cnc4cc(-n5cncn5)ccn34)c12]

Step A: Preparation of N-(3-ethyl-1-((1-ethyl-1H-pyrazol-3-yl)methyl)-1H-indazol-4-yl)-7-fluoroimidazo[1,2-a]pyridine-3-carboxamide: 7-Fluoroimidazo[1,2-a]pyridine-3-carboxylic acid (Preparation I; 224 mg, 1.25 mmol) was dissolved in anhydrous N-methylpyrrolidinone (0.2 M) and treated with triethylamine (0.35 mL, 2.5 mmol). When the mixture was homogeneous 2,4,6-trichlorobenzoyl chloride (0.20 mL, 1.31 mmol) was added dropwise. The mixture was stirred for 30 minutes at ambient temperature. 3-Ethyl-1-((1-ethyl-1H-pyrazol-3-yl)methyl)-1H-indazol-4-amine (0.30 mg, 1.11 mmol) was added in one portion and the sides of the flask were washed with anhydrous N-methylpyrrolidinone (2 mL). The mixture was heated to 90° C. and stirred for 16 hours. The mixture was allowed to cool and filtered through GF/F paper washing with ethyl acetate. The filtrate was concentration under reduced pressure and diluted with water to give a beige precipitate which was collected by filtration, washed with water and dried under high vacuum to give N-(3-ethyl-1-((1-ethyl-1H-pyrazol-3-yl)methyl)-1H-indazol-4-yl)-7-fluoroimidazo[1,2-a]pyridine-3-carboxamide (259 mg). MS m/z 432.1 (M+1, APCI+).

Step B: Preparation of N-(3-ethyl-1-((1-ethyl-1H-pyrazol-3-yl)methyl)-1H-indazol-4-yl)-7-(1H-1,2,4-triazol-1-yl)imidazo[1,2-a]pyridine-3-carboxamide: 1H-1,2,4-triazole was dissolved in 4-dioxane and treated with sodium hydride (20 mg, 0.48 mmol, 60% dispersion in mineral oil) with stirring at ambient temperature for 30 minutes. N-(3-Ethyl-1-((1-ethyl-1H-pyrazol-3-yl)methyl)-1H-indazol-4-yl)-7-fluoroimidazo[1,2-a]pyridine-3-carboxamide (35 mg, 0.08 mmol) was added as a solution in N,N-dimethylformamide. The mixture was heated to 98° C. and stirred for 2 days. The mixture was quenched by the addition of water. A precipitate formed and the solid was isolated by filtration, washed with water and dried under vacuum to give N-(3-ethyl-1-((1-ethyl-1H-pyrazol-3-yl)methyl)-1H-indazol-4-yl)-7-(1H-1,2,4-triazol-1-yl)imidazo[1,2-a]pyridine-3-carboxamide as a white solid (39 mg). MS m/z 481.1 (M+1, APCI+).

The compounds shown in Table 3 were synthesized according to Example 117, Step B, substituting N-(3-Ethyl-1-((1-ethyl-1H-pyrazol-3-yl)methyl)-1H-indazol-4-yl)-7-fluoroimidazo[1,2-a]pyridine-3-carboxamide with 7-fluoro-N-(3-ethyl-1-((6-methylpyridin-2-yl)methyl)-1H-indazol-4-yl)imidazo[1,2-a]pyridine-3-carboxamide (Example 74, Step A).

TABLE 3

| Ex. # | Structure | Name | MS m/z |
|---|---|---|---|
| 118 | 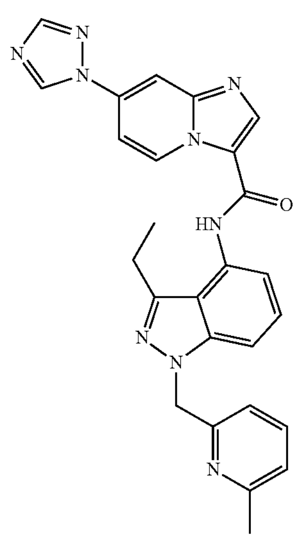 [SMILES: CCc1nn(Cc2cccc(C)n2)c2cccc(NC(=O)c3cnc4cc(-n5cncn5)ccn34)c12] | N-(3-ethyl-1-((6-methylpyridin-2-yl)methyl)-1H-indazol-4-yl)-7-(1H-1,2,4-triazol-1-yl)imidazo[1,2-a]pyridine-3-carboxamide | 478.2 (M + 1, APCI+) |

TABLE 3-continued

| Ex. # | Structure | Name | MS m/z |
|---|---|---|---|
| 119 | 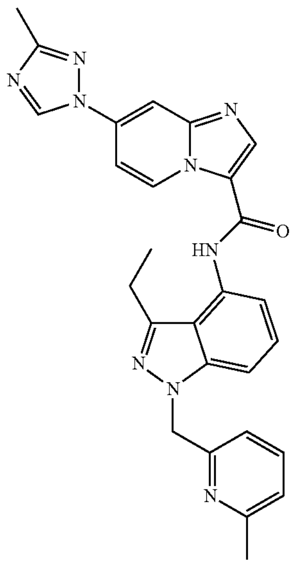 [SMILES: CCc1nn(Cc2cccc(C)n2)c2cccc(NC(=O)c3cnc4cc(-n5cnc(C)n5)ccn34)c12] | N-(3-ethyl-1-((6-methylpyridin-2-yl)methyl)-1H-indazol-4-yl)-7-(3-methyl-1H-1,2,4-triazol-1-yl)imidazo[1,2-a]pyridine-3-carboxamide | 492.2 (M + 1, APCI+) |
| 120 | 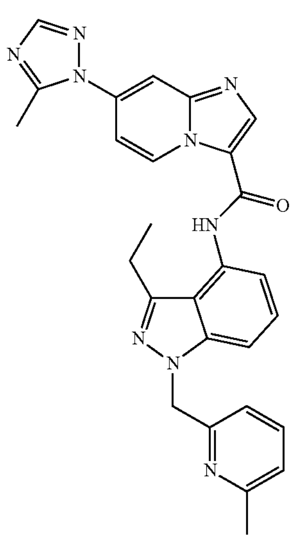 [SMILES: CCc1nn(Cc2cccc(C)n2)c2cccc(NC(=O)c3cnc4cc(-n5ncnc5C)ccn34)c12] | N-(3-ethyl-1-((6-methylpyridin-2-yl)methyl)-1H-indazol-4-yl)-7-(5-methyl-1H-1,2,4-triazol-1-yl)imidazo[1,2-a]pyridine-3-carboxamide | 492.2 (M + 1, APCI+) |

| Ex. # | Structure | Name | MS m/z |
|---|---|---|---|
| 121 | 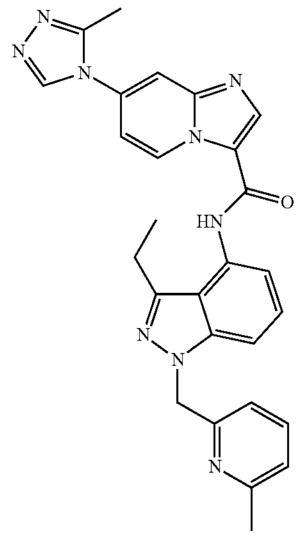 [SMILES: CCc1nn(Cc2cccc(C)n2)c2cccc(NC(=O)c3cnc4cc(-n5cnnc5C)ccn34)c12] | N-(3-ethyl-1-((6-methylpyridin-2-yl)methyl)-1H-indazol-4-yl)-7-(3-methyl-4H-1,2,4-triazol-4-yl)imidazo[1,2-a]pyridine-3-carboxamide | 492.2 (M + 1, APCI+) |

Example 122

7-(2,3-dihydroxypropoxy)-N-(3-ethyl-1-((6-methylpyridin-2-yl)methyl)-1H-indazol-4-yl)imidazo[1,2-a]pyridine-3-carboxamide dihydrochloride

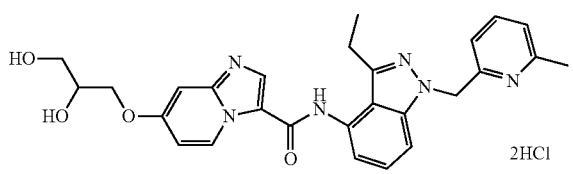 [SMILES: CCc1nn(Cc2cccc(C)n2)c2cccc(NC(=O)c3cnc4cc(OCC(O)CO)ccn34)c12]

Step A: Preparation of 4-((2,2-dimethyl-1,3-dioxolan-4-yl)methoxy)pyridin-2-amine: A sealed tube containing 4-chloro-2-pyridinamine (4 g, 31.2 mmol), (2,2-dimethyl-1,3-dioxolan-4-yl)methanol (8.4 g, 60.6 mmol), and sodium (1.46 g, 63.5 mmol) was heated at 145° C. for 8 hours. The mixture was cooled to ambient temperature; water (25 mL) and dichloromethane (50 mL) were added. The organic phase was separated, dried with sodium sulfate, and concentrated under reduced pressure. The resulting residue was purified by chromatography on silica-gel to give 4-((2,2-dimethyl-1,3-dioxolan-4-yl)methoxy)pyridin-2-amine as a pale yellow solid (5.6 g).

Step B: Preparation of ethyl 7-((2,2-dimethyl-1,3-dioxolan-4-yl)methoxy)imidazo[1,2-a]pyridine-3-carboxylate: 4-((2,2-Dimethyl-1,3-dioxolan-4-yl)methoxy)pyridin-2-amine (5.6 g, 0.025 mol) was mixed with ethanol (60 mL) in a reaction flask, under an atmosphere of dry nitrogen. A solution of ethyl 2-chloro-3-oxopropanoate (5% in benzene; 93 mL; Commercial solution from Toronto Research Chemicals Inc.) was added. The mixture was heated to 60° C. under nitrogen for 2 hours. After allowing the mixture to cool the solvent was removed under vacuum to give a brown solid. The solid was mixed with ethyl acetate (200 mL) and sodium bicarbonate solution (100 mL) and stirred to dissolve. The phases were separated and the bicarbonate solution was extracted further with ethyl acetate (50 mL). The combined ethyl acetate extracts were dried over sodium sulfate, filtered and concentrated under vacuum to give a solid. The crude material was dissolved in ethyl acetate and passed through a short column of silica, eluting with ethyl acetate. Fractions containing the product were concentrated to give ethyl 7-((2,2-dimethyl-1,3-dioxolan-4-yl)methoxy)imidazo[1,2-a]pyridine-3-carboxylate as a pale yellow solid (5.76 g).

Step C: Preparation of 7-((2,2-dimethyl-1,3-dioxolan-4-yl)methoxy)imidazo[1,2-a]pyridine-3-carboxylic acid: Ethyl 7-((2,2-dimethyl-1,3-dioxolan-4-yl)methoxy)imidazo[1,2-a]pyridine-3-carboxylate (1.8 g, 5.63 mmol) and lithium hydroxide monohydrate (0.284 g, 6.75 mmol) were combined in a 250 mL round bottom flask containing tetrahydrofuran/ethanol/water (1:2:1, 56 mL). After stirring overnight at ambient temperature, the solvent was removed under vacuum to give a yellow gum. Water (20 mL) and dichloromethane was added. The aqueous layer was separated and cooled in an ice-water bath before adjusting to pH 4 with 20% citric acid. A precipitate formed and was collected by filtration. The solids were washed with a small amount of water (5 mL) and dried under vacuum to give 7-((2,2-dimethyl-1,3-dioxolan-4-yl)methoxy)imidazo[1,2-a]pyridine-3-carboxylic acid as a white solid (1.3 g).

Step D: Preparation of 7-((2,2-dimethyl-1,3-dioxolan-4-yl)methoxy)-N-(3-ethyl-1-((6-methylpyridin-2-yl)methyl)-1H-indazol-4-yl)imidazo[1,2-a]pyridine-3-carboxamide: To a stirred mixture of 7-((2,2-dimethyl-1,3-dioxolan-4-yl)methoxy)imidazo[1,2-a]pyridine-3-carboxylic acid (128 mg, 0.44 mmol) in tetrahydrofuran (6 mL), under nitrogen, was added 2,4,6-trichlorobenzoyl chloride (115 mg, 0.47 mmol) and triethylamine (51 mg, 0.51 mmol). The mixture was stirred for 30 minutes. To the reaction mixture was added 3-ethyl-1-((6-methylpyridin-2-yl)methyl)-1H-indazol-4-amine (90 mg, 0.34 mmol), followed by lithium bis(trimethylsilyl)amide (1.7 mL, 1.7 mmol; 1M solution in tetrahydrofuran). The mixture was concentrated under reduced pressure and purified by flash chromatography on silica, eluting with dichloromethane/methanol (10:1) to give 7-((2,2-dimethyl-1, 3-dioxolan-4-yl)methoxy)-N-(3-ethyl-1-((6-methylpyridin-2-yl)methyl)-1H-indazol-4-yl)imidazo[1,2-a]pyridine-3-carboxamide (30 mg).

Step E: Preparation of 7-(2,3-dihydroxypropoxy)-N-(3-ethyl-1-((6-methylpyridin-2-yl)methyl)-1H-indazol-4-yl) imidazo[1,2-a]pyridine-3-carboxamide: A solution of 7-((2,2-dimethyl-1,3-dioxolan-4-yl)methoxy)-N-(3-ethyl-1-((6-methylpyridin-2-yl)methyl)-1H-indazol-4-yl)imidazo[1,2-a]pyridine-3-carboxamide (77 mg, 0.142 mmol) in water (4 mL), trifluoroacetic acid (4 mL) and 1,4-dioxane (1 mL) was stirred for 1 hour at ambient temperature. The mixture was concentrated under reduced pressure to give a residual oil. The oil was dissolved in a mixture of diethyl ether, dichloromethane and methanol. A solution of hydrogen chloride (0.5 mL; 4M in 1,4-dioxane) was added. The mixture was concentrated under reduced pressure and placed under high vacuum for 16 hours to provide 7-(2,3-dihydroxypropoxy)-N-(3-ethyl-1-((6-methylpyridin-2-yl)methyl)-1H-indazol-4-yl)imidazo[1,2-a]pyridine-3-carboxamide dihydrochloride (74 mg) as a beige solid. MS (APCI), positive scan, m/z=501.2 (M+H).

Example 123

N-(3-ethyl-1-((1-ethyl-1H-pyrazol-3-yl)methyl)-1H-indazol-4-yl)-7-(1-methyl-1H-pyrazol-4-yl)imidazo[1,2-a]pyridine-3-carboxamide

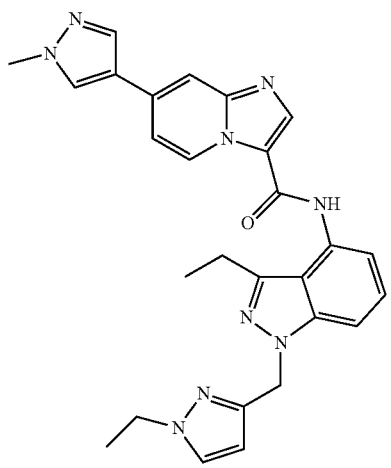 [SMILES: CCc1nn(Cc2ccn(CC)n2)c2cccc(NC(=O)c3cnc4cc(-c5cnn(C)c5)ccn34)c12]

Step A: Preparation of 7-bromo-N-(3-ethyl-1-((1-ethyl-1H-pyrazol-3-yl)methyl)-1H-indazol-4-yl)imidazo[1,2-a]pyridine-3-carboxamide: To a solution 3-ethyl-1-((1-ethyl-1H-pyrazol-3-yl)methyl)-1H-indazol-4-amine (328 mg, 1.22 mmol) in anhydrous THF (3 mL) was added under a nitrogen atmosphere at ambient temperature lithium bis(trimethylsilyl)amide (1.0 M in THF, 1.15 mL). The resulting mixture was stirred at ambient temperature for 10 minutes, then added dropwise to a chilled (ice-water bath) solution of methyl 7-bromoimidazo[1,2-a]pyridine-3-carboxylate (140 mg, 0.55 mmol) in anhydrous THF (3 mL). The cold bath was removed, and the reaction mixture was allowed to warm to ambient temperature, and quenched with water. The resulting suspension was extracted thoroughly with DCM, the combined organic extracts were dried over anhydrous sodium sulfate, and concentrated to afford the crude product. The crude product was subjected to preparative thin-layer chromatography on silica with 5% MeOH-DCM as eluent to afford 219 mg of desired product as a yellow solid.

Step B: Preparation of N-(3-ethyl-1-((1-ethyl-1H-pyrazol-3-yl)methyl)-1H-indazol-4-yl)-7-(1-methyl-1H-pyrazol-4-yl)imidazo[1,2-a]pyridine-3-carboxamide: A dry, 10 mL round bottom flask equipped with a reflux condenser and a nitrogen line was charged with 1-methyl-4-(4,4,5,5-tetramethyl-1,3,2-dioxaborolan-2-yl)-1H-pyrazole (25.4 mg, 0.122 mmol), 7-bromo-N-(3-ethyl-1-((1-ethyl-1H-pyrazol-3-yl)methyl)-1H-indazol-4-yl)imidazo[1,2-a]pyridine-3-carboxamide (50 mg, 0.102 mmol), Pd(PPh$_3$)$_4$ (5.9 mg, 0.005 mmol), and potassium carbonate (70 mg, 0.51 mmol). To the flask was added a water:DMF:CH$_3$CN (1:1:4.5; 0.3:0.3:1.4 mL) mixture, and the reaction mixture was degassed under nitrogen, and heated at 80° C. for 5 hours. The cooled reaction mixture was diluted with water, the resulting suspension was extracted thoroughly with EtOAc and DCM, the combined organic extracts were dried over anhydrous sodium sulfate, and concentrated to afford the crude product. The crude product was subjected to preparative thin-layer chromatography on silica with 5% MeOH-DCM as eluent to afford 30.8 mg of product as a yellow solid. MS (ES+APCI) m/z=494 (M+H) detected Example 124

N-(3-ethyl-1-((1-ethyl-1H-pyrazol-3-yl)methyl)-1H-indazol-4-yl)-7-(1-methyl-1H-pyrazol-4-yl)imidazo[1,2-a]pyridine-3-carboxamide

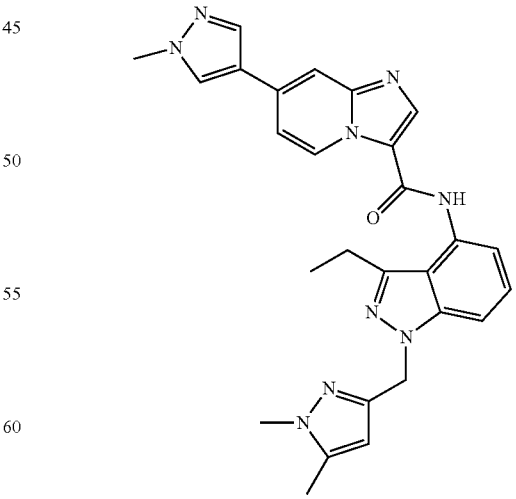

Prepared according to the procedure for Example 123 from 1-((1,5-dimethyl-1H-pyrazol-3-yl)methyl)-3-ethyl-1H-indazol-4-amine (Example 55, Steps A-D) and 1-methyl-4-(4,4, 5,5-tetramethyl-1,3,2-dioxaborolan-2-yl)-1H-pyrazole. MS (ES+APCI) m/z=494 (M+H) detected.

Example 125

N-(1-((1,5-dimethyl-1H-pyrazol-3-yl)methyl)-3-ethyl-1H-indazol-4-yl)-7-(5-((dimethylamino)methyl)furan-2-yl)imidazo[1,2-a]pyridine-3-carboxamide

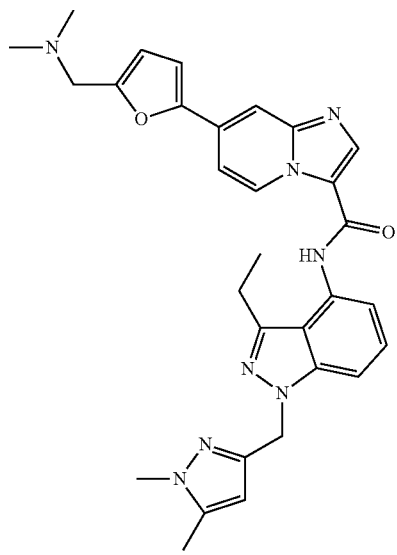 [SMILES: CCc1nn(Cc2cc(C)n(C)n2)c2cccc(NC(=O)c3cnc4cc(-c5ccc(CN(C)C)o5)ccn34)c12]

Step A: Preparation of N-(1-((1,5-dimethyl-1H-pyrazol-3-yl)methyl)-3-ethyl-1H-indazol-4-yl)-7-(5-formylfuran-2-yl)imidazo[1,2-a]pyridine-3-carboxamide: A round bottom flask was charged with 7-bromo-N-(1-((1,5-dimethyl-1H-pyrazol-3-yl)methyl)-3-ethyl-1H-indazol-4-yl)imidazo[1,2-a]pyridine-3-carboxamide (Preparation H; 100 mg, 0.20 mmol), sodium 2'-(dicyclohexylphosphino)-2,6-dimethoxybiphenyl-3-sulfonate (8.3 mg, 0.016 mmol), potassium carbonate (93 mg, 0.67 mmol), palladium acetate (1.8 mg, 0.008 mmol), and 5-formylfuran-2-ylboronic acid (57 mg, 0.4 mmol). To the flask was added a 5:1 dioxane:water mixture (3 mL), the reaction mixture was degassed under nitrogen, and stirred at 65° C. for 10 hours. The reaction mixture was cooled, diluted with water, and extracted multiple times with DCM and EtOAc. The combined organic extracts were dried over anhydrous sodium sulfate, and concentrated under vacuum. The crude product was subjected to preparative thin-layer chromatography on silica with 10% MeOH-DCM as eluent to afford the product (36 mg) as a yellow solid.

Step B: Preparation of N-(1-((1,5-dimethyl-1H-pyrazol-3-yl)methyl)-3-ethyl-1H-indazol-4-yl)-7-(5-((dimethylamino)methyl)furan-2-yl)imidazo[1,2-a]pyridine-3-carboxamide: A solution of N-(1-((1,5-dimethyl-1H-pyrazol-3-yl)methyl)-3-ethyl-1H-indazol-4-yl)-7-(5-formylfuran-2-yl)imidazo[1,2-a]pyridine-3-carboxamide (36 mg) in 1 mL of a 1:1 DCM:THF mixture was treated at ambient temperature with excess 2.0 M dimethylamine solution in MeOH. The reaction mixture was stirred at ambient temperature for 30 minutes. A large excess of sodium triacetoxyborohydride (10 equivalents) was added, and the reaction stirred at ambient temperature for 4 hours. The reaction mixture was concentrated under reduced pressure, dissolved in a small amount of MeOH, and subjected to preparative thin-layer chromatography with a 2% 7N ammonia-MeOH, 8% MeOH in DCM solution as eluent to give the desired product (12.8 mg). MS (ES+APCI) m/z=537 (M+H) detected.

Example 126

(R)—N-(3-ethyl-1-((6-methylpyridin-2-yl)methyl)-1H-indazol-4-yl)-7-(2-(3-fluoropyrrolidin-1-yl)ethyl)imidazo[1,2-a]pyridine-3-carboxamide

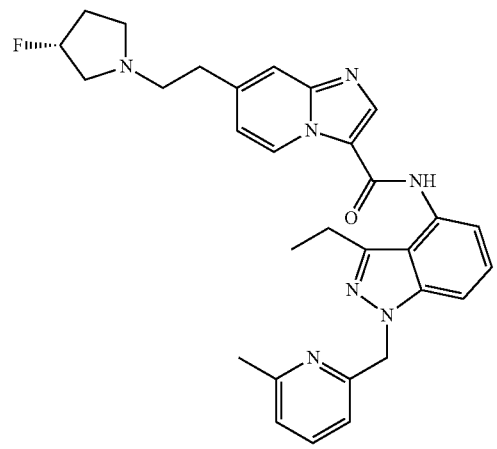 [SMILES: CCc1nn(Cc2cccc(C)n2)c2cccc(NC(=O)c3cnc4cc(CCN5CC[C@@H](F)C5)ccn34)c12]

Prepared according to procedure for Example 128 from N-(3-ethyl-1-((6-methylpyridin-2-yl)methyl)-1H-indazol-4-yl)-7-(2-oxoethyl)imidazo[1,2-a]pyridine-3-carboxamide (Example 127, Steps A-B) and (R)-3-fluoropyrrolidin hydrochloride. MS (ES+APCI) m/z=526 (M+H) detected.

Example 127

N-(3-ethyl-1-((6-methylpyridin-2-yl)methyl)-1H-indazol-4-yl)-7-(2-(4-methylpiperazin-1-yl)ethyl)imidazo[1,2-a]pyridine-3-carboxamide

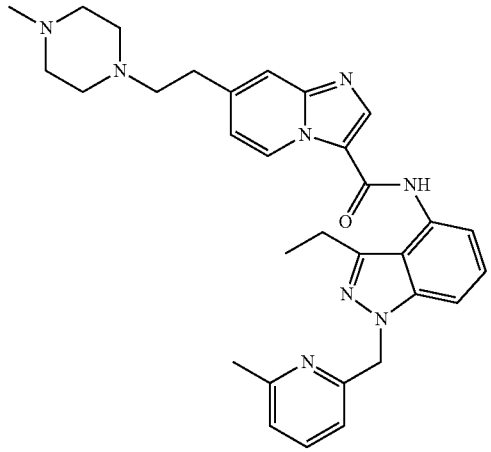 [SMILES: CCc1nn(Cc2cccc(C)n2)c2cccc(NC(=O)c3cnc4cc(CCN5CCN(C)CC5)ccn34)c12]

Step A: Preparation of 7-Bromo-N-(3-ethyl-1-((6-methylpyridin-2-yl)methyl)-1H-indazol-4-yl)imidazo[1,2-a]pyridine-3-carboxamide: Prepared according to procedure for Example 123, using 3-ethyl-1-((6-methylpyridin-2-yl)methyl)-1H-indazol-4-amine (Example 16, Step A) in place of 3-ethyl-1-((1-ethyl-1H-pyrazol-3-yl)methyl)-1H-indazol-4-amine.

Step B: Preparation of (Z)-7-(2-ethoxyvinyl)-N-(3-ethyl-1-((6-methylpyridin-2-yl)methyl)-1H-indazol-4-yl)imidazo[1,2-a]pyridine-3-carboxamide: A round bottom flask was charged with 7-Bromo-N-(3-ethyl-1-((6-methylpyridin-2-yl)methyl)-1H-indazol-4-yl)imidazo[1,2-a]pyridine-3-carboxamide (330 mg, 0.674 mmol), trio-tolylphosphine (41 mg, 0.135 mmol), tris(dibenzylideneacetone)dipalladium (62 mg, 0.067 mmol) To the flask were added 10 mL of anhydrous dimethylformamide, followed by (Z)-tributyl(2-ethoxyvinyl)stannane (0.34 ml, 1.01 mmol), and triethylamine (0.11 mL, 0.81 mmol). The reaction mixture was degassed under nitrogen, and stirred at 100° C. for 10 hours. The reaction mixture was cooled, diluted with water, and extracted thoroughly with DCM and EtOAc. The combined organic extracts were dried over anhydrous sodium sulfate, and concentrated. The crude product was subjected to preparative thin-layer chromatography on silica with 5% MeOH-DCM as eluent to afford 246 mg of product as a yellow, foamy solid.

Step C: Preparation of N-(3-Ethyl-1-((6-methylpyridin-2-yl)methyl)-1H-indazol-4-yl)-7-(2-oxoethyl)imidazo[1,2-a]pyridine-3-carboxamide: A solution of (Z)-7-(2-ethoxyvinyl)-N-(3-ethyl-1-((6-methylpyridin-2-yl)methyl)-1H-indazol-4-yl)imidazo[1,2-a]pyridine-3-carboxamide (211 mg, 0.439 mmol) in dioxane (6 mL) was treated at ambient temperature with 2.0 M HCl-ether. The resulting suspension was stirred at ambient temperature for 30 minutes. At that time 3 drops of water were added, so as not to collapse the suspension, and stirring was continued for another 30 minutes. The reaction mixture was neutralized with saturated aqueous sodium bicarbonate, extracted with DCM and EtOAc, and the combined organic extracts dried over anhydrous sodium sulfate. Concentration of the organic extracts afforded 190 mg of a solid which was used directly in next step.

Step D: Preparation of N-(3-ethyl-1-((6-methylpyridin-2-yl)methyl)-1H-indazol-4-yl)-7-(2-(4-methylpiperazin-1-yl)ethyl)imidazo[1,2-a]pyridine-3-carboxamide: The crude N-(3-Ethyl-1-((6-methylpyridin-2-yl)methyl)-1H-indazol-4-yl)-7-(2-oxoethyl)imidazo[1,2-a]pyridine-3-carboxamide (112 mg, 0.248 mmol), and N-methylpiperazine (25 mg, 0.25 mmol) were dissolved in DCM (5 mL), and treated with 10 equivalents of sodium triacetoxyborohydride, followed by 2 drops of glacial acetic acid. The reaction mixture was stirred at ambient temperature for 48 hours. The reaction mixture was concentrated, and resuspended in saturated aqueous sodium carbonate. The mixture was extracted with DCM and EtOAc, the combined organic layers were dried over anhydrous sodium sulfate, then filtered and concentrated. Purification of the crude material by preparative thin-layer chromatography on silica with 7N NH$_3$-MeOH/MeOH/DCM, 2/8/98 as eluent afforded 83.5 mg of a foamy, white solid. MS (ES+APCI) m/z=537 (M+H) detected.

Example 128

N-(3-ethyl-1-((6-methylpyridin-2-yl)methyl)-1H-indazol-4-yl)-7-(2-(3-fluoroazetidin-1-yl)ethyl)imidazo[1,2-a]pyridine-3-carboxamide

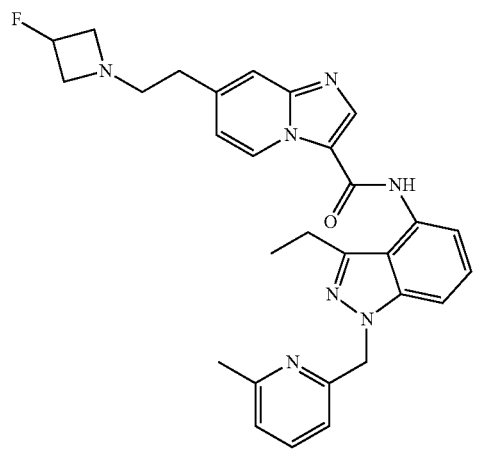 [SMILES: CCc1nn(Cc2cccc(C)n2)c2cccc(NC(=O)c3cnc4cc(CCN5CC(F)C5)ccn34)c12]

A solution of 3-fluoroazetidine hydrochloride (61 mg, 0.55 mmol) in DCM (2 mL) was treated at ambient temperature with Hunig's base (0.10 mL, 0.57 mmol). To the hazy solution was added N-(3-ethyl-1-((6-methylpyridin-2-yl)methyl)-1H-indazol-4-yl)-7-(2-oxoethyl)imidazo[1,2-a]pyridine-3-carboxamide (prepared according to (Example 127, Steps A-B; 50 mg, 0.11 mmol) (prepared according to the procedure for Example 127) and the (10 equivalents) was added, followed by 2 drops of glacial acetic acid, and the resulting mixture was stirred at ambient temperature for 16 hours. The reaction mixture was quenched with saturated aqueous sodium bicarbonate solution, and extracted multiple times with DCM and EtOAc. The combined organic extracts were dried over anhydrous sodium sulfate, concentrated under reduced pressure, and subjected to preparative thin-layer chromatography on silica, with a 10% MeOH-DCM mixture as eluent to afford the desired product (10 mg) as a white solid. MS (ES+APCI) m/z=512 (M+H) detected.

Example 129

7-(2-(Dimethylamino)ethyl)-N-(3-ethyl-1-((6-methylpyridin-2-yl)methyl)-1H-indazol-4-yl)imidazo[1,2-a]pyridine-3-carboxamide

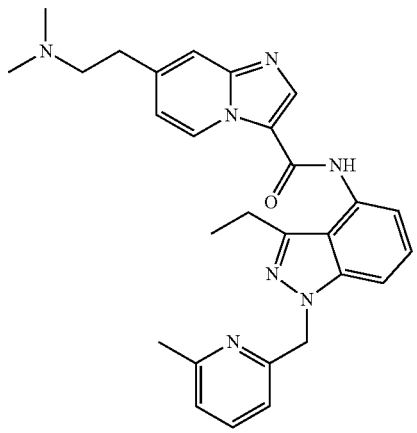 [SMILES: CCc1nn(Cc2cccc(C)n2)c2cccc(NC(=O)c3cnc4cc(CCN(C)C)ccn34)c12]

Prepared according to the procedure for Example 127, Step C, using dimethylamine in place of 1-methylpiperazine. MS (ES+APCI) m/z=481 (M+H) detected.

Example 130

N-(3-ethyl-1-((6-methylpyridin-2-yl)methyl)-1H-indazol-4-yl)-7-(2-(3-methoxyazetidin-1-yl)ethyl)imidazo[1,2-a]pyridine-3-carboxamide

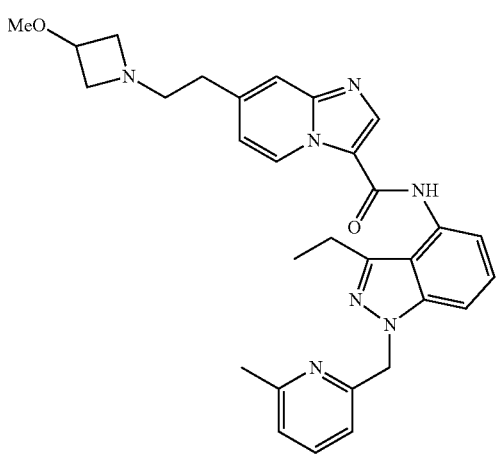 [SMILES: CCc1nn(Cc2cccc(C)n2)c2cccc(NC(=O)c3cnc4cc(CCN5CC(OC)C5)ccn34)c12]

Prepared according to the procedure for Example 128 from N-(3-ethyl-1-((6-methylpyridin-2-yl)methyl)-1H-indazol-4-yl)-7-(2-oxoethyl)imidazo[1,2-a]pyridine-3-carboxamide (Example 127, Steps A-B) and 3-methoxyazetidine hydrochloride. MS (ES+APCI) m/z=524 (M+H) detected.

Example 131

7-((Dimethylamino)methyl)-N-(3-ethyl-1-((6-methylpyridin-2-yl)methyl)-1H-indazol-4-yl)imidazo[1,2-a]pyridine-3-carboxamide

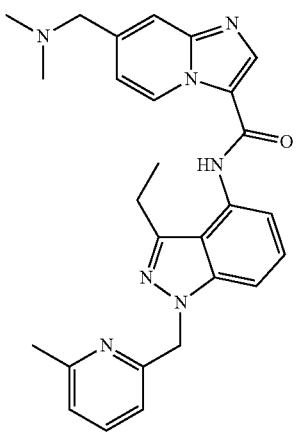 [SMILES: CCc1nn(Cc2cccc(C)n2)c2cccc(NC(=O)c3cnc4cc(CN(C)C)ccn34)c12]

A round bottom flask equipped with a reflux condenser and a nitrogen line was charged with palladium acetate (3.4 mg, 0.015 mmol), cesium carbonate (300 mg, 0.92 mmol), 2,2'-bis(diphenylphosphino)-1,1'-binaphthyl (19 mg, 0.030 mmol), 7-bromo-N-(3-ethyl-1-((6-methylpyridin-2-yl)methyl)-1H-indazol-4-yl)imidazo[1,2-a]pyridine-3-carboxamide (Example 127, Step A; 150 mg, 0.307 mmol), and potassium (dimethylaminomethyl)trifluoroborate (Frontier Scientific; 101 mg, 0.613 mmol). To the reaction flask was added a 1,4-dioxane:water mixture (10:1; 1.1 mL) and the reaction flask was immediately evacuated and refilled with nitrogen three times. The reaction mixture was heated at reflux for 16 hours under nitrogen. After cooling to ambient temperature, the reaction mixture was diluted with water, and extracted multiple times with dichloromethane. The combined dichloromethane extracts were dried over anhydrous sodium sulfate, and concentrated under reduced pressure. The crude residue was purified by preparative thin-layer chromatography (silica, 2% 7N ammonia-MeOH:8% MeOH:DCM) to afford the product (84.8 mg) as a white solid. $^1$H NMR (CDCl$_3$) δ 9.5 (d, 1H), 8.35 (s, 1H), 8.20 (s, 1H), 7.84 (d, 1H), 7.62 (m, 1H), 7.40 (t, 1H), 7.32 (t, 1H), 7.12 (m, 2H), 7.01 (d, 1H), 6.48 (d, 1H), 5.65 (s, 2H), 3.52 (s, 2H), 3.23 (q, 2H), 2.29 (s, 6H), 1.51 (t, 3H).

Example 132

7-((dimethylamino)methyl)-N-(3-ethyl-1-((1-ethyl-1H-pyrazol-3-yl)methyl)-1H-indazol-4-yl)imidazo[1,2-a]pyridine-3-carboxamide

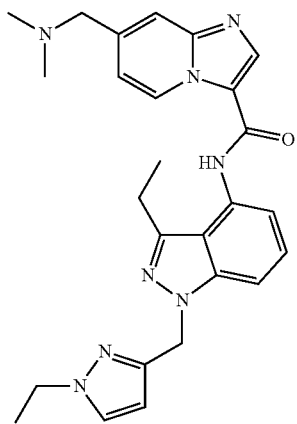 [SMILES: CCc1nn(Cc2ccn(CC)n2)c2cccc(NC(=O)c3cnc4cc(CN(C)C)ccn34)c12]

Step A: Preparation of 7-bromo-N-(3-ethyl-1-((1-ethyl-1H-pyrazol-3-yl)methyl)-1H-indazol-4-yl)imidazo[1,2-a]pyridine-3-carboxamide: Prepared according to the method of Preparation H, substituting 1-((1,5-dimethyl-1H-pyrazol-3-yl)methyl)-3-ethyl-1H-indazol-4-amine with 3-ethyl-1-((1-ethyl-1H-pyrazol-3-yl)methyl)-1H-indazol-4-amine.

Step B: Preparation of 7-((dimethylamino)methyl)-N-(3-ethyl-1-((1-ethyl-1H-pyrazol-3-yl)methyl)-1H-indazol-4-yl)imidazo[1,2-a]pyridine-3-carboxamide: Prepared according to the method for Example 131, replacing 7-bromo-N-(3-ethyl-1-((6-methylpyridin-2-yl)methyl)-1H-indazol-4-yl)imidazo[1,2-a]pyridine-3-carboxamide with 7-bromo-N-(3-ethyl-1-((1-ethyl-1H-pyrazol-3-yl)methyl)-1H-indazol-4-yl)imidazo[1,2-a]pyridine-3-carboxamide to provide the product (13.3 mg) as a white solid. $^1$H NMR (CDCl$_3$) δ 9.49 (d, 1H), 8.20 (s, 1H), 8.15 (s, 1H), 7.85 (d, 1H), 7.63 (s, 1H), 7.33 (t, 1H), 7.25 (m, 2H), 7.12 (d, 1H), 6.00 (d, 1H), 5.34 (s, 2H), 4.13 (q, 2H), 3.53 (s, 2H), 3.20 (q, 2H), 2.30 (s, 6H), 1.50 (m, 6H).

Example 133

N-(3-iodo-1-((2-methylthiazol-5-yl)methyl)-1H-indazol-4-yl)-7-(2-(4-methylpiperazin-1-yl)ethoxy)imidazo[1,2-a]pyridine-3-carboxamide

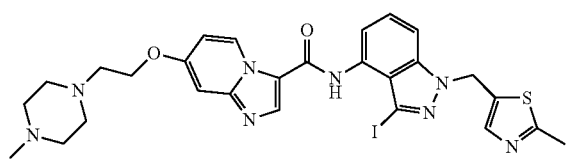

Step A: Preparation of 3-iodo-1-((2-methylthiazol-5-yl)methyl)-1H-indazol-4-amine: To a solution 4-((3-iodo-4-nitro-1H-indazol-1-yl)methyl)-2-methylthiazole (prepared according the method of Example 15, Steps A-D, using ethyl 2-methylthiazole-5-carboxylate) in EtOH/H$_2$O (8 mL/2 mL) was added iron (463 mg, 8.30 mmol) and NH$_4$Cl (44.4 mg, 0.830 mmol). The reaction mixture was heated at 85° C. for 3 hours. The reaction mixture was cooled to ambient temperature and concentrated under reduced pressure. EtOAc/Et$_3$N (40 mL/10 mL) was added to the residue. The mixture was heated at 85° C. for 20 minutes, cooled to 45° C., and filtered through Celite. The Celite pad was washed with MeOH (30 mL). The combined filtrate was concentrated under reduced pressure to remove EtOAc and MeOH. The aqueous suspension was extracted with DCM. The combined organic extracts were dried (Na$_2$SO$_4$) and concentrated under reduced pressure to give the product (156 mg).

Step B: Preparation of N-(3-iodo-1-((2-methylthiazol-5-yl)methyl)-1H-indazol-4-yl)-7-(2-(4-methylpiperazin-1-yl)ethoxy)imidazo[1,2-a]pyridine-3-carboxamide: Lithium bis(trimethylsilyl)amide (1.0 M in THF, 0.24 mL) was added dropwise at ambient temperature and under a nitrogen atmosphere to a solution of 3-iodo-1-((2-methylthiazol-5-yl)methyl)-1H-indazol-4-amine (40 mg, 0.108 mmol) in anhydrous THF (3 mL). The resulting brown mixture was added via syringe to a cooled (ice-water bath) solution of ethyl 7-(2-(4-methylpiperazin-1-yl)ethoxy)imidazo[1,2-a]pyridine-3-carboxylate (Preparation D; 35.9 mg, 0.108 mmol) in anhydrous THF (3 mL). The reaction mixture was allowed to warm to ambient temperature overnight. The reaction mixture was diluted with water, and extracted multiple times with dichloromethane. The dichloromethane extracts were dried over anhydrous sodium sulfate, and concentrated under reduced pressure. The crude residue was purified by preparative thin-layer chromatography (silica, 7 N ammonia/MeOH:MeOH:DCM in a 3:7:90 ratio as eluent) to afford the product (11.6 mg) as a tan solid. MS (ES+APCI) m/z=657 (M+H).

Example 134

N-(3-cyclopropyl-1-((5-methyl-1,3,4-thiadiazol-2-yl)methyl)-1H-indazol-4-yl)-7-(2-(4-methylpiperazin-1-yl)ethoxy)imidazo[1,2-a]pyridine-3-carboxamide

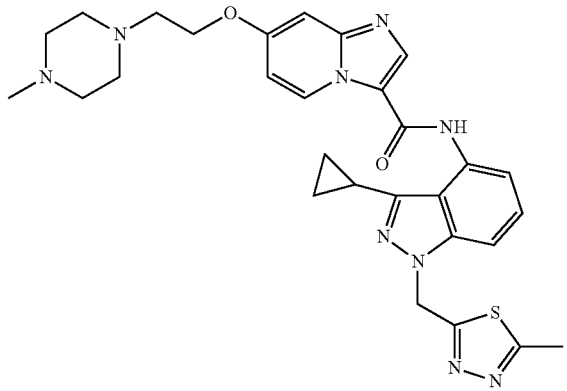

Step A: Preparation of ethyl 2-(3-bromo-4-nitro-1H-indazol-1-yl)acetate: A solution of 3-bromo-4-nitro-1H-indazole (Preparation B; 1.00 g, 4.13 mmol) in anhydrous DMF (20 mL) was treated at ambient temperature with potassium carbonate (2.28 g, 16.5 mmol). The reaction mixture was stirred at ambient temperature for 10 minutes and ethyl 2-chloroacetate (0.53 g, 4.34 mmol) was added dropwise. Stirring was continued under nitrogen for 16 hours. The reaction mixture was diluted with excess water and extracted multiple times with DCM and EtOAc. The combined extracts were dried over anhydrous sodium sulfate and concentrated under reduced pressure to afford the product (1.21 g) as a brown solid.

Step B: Preparation of 2-(3-bromo-4-nitro-1H-indazol-1-yl)acetohydrazide: A solution of ethyl 2-(3-bromo-4-nitro-1H-indazol-1-yl)acetate (1.48 g, 4.51 mmol) in absolute EtOH (20 mL) was treated at ambient temperature with hydrazine (1.45 g, 45.1 mmol) and was heated at reflux for 16 hours under a nitrogen atmosphere. The reaction mixture was cooled to ambient temperature, and the precipitate was isolated by filtration. The solids were dried under vacuum to afford the product (0.865 g) as a tan powder.

Step C: Preparation of N-acetyl-2-(3-bromo-4-nitro-1H-indazol-1-yl)acetohydrazide: A suspension of 2-(3-bromo-4-nitro-1H-indazol-1-yl)acetohydrazide (0.865 g) in anhydrous toluene (20 mL) was treated at ambient temperature with 1 equivalent of acetic anhydride. The reaction mixture was stirred at ambient temperature for 16 hours and concentrated under reduced pressure to afford the product (0.98 g) as an off-white solid.

Step D: Preparation of 2-((3-bromo-4-nitro-1H-indazol-1-yl)methyl)-5-methyl-1,3,4-thiadiazole: A suspension of N-acetyl-2-(3-bromo-4-nitro-1H-indazol-1-yl)acetohydrazide (0.4 g) in anhydrous THF (5 mL) was treated at ambient temperature with phosphorus(V) sulfide (0.77 g). The mixture was heated at reflux under a nitrogen atmosphere for 2.5 hours. The reaction mixture was diluted with a large excess of saturated aqueous sodium carbonate solution (50 mL) and DCM (50 mL). The resulting mixture was stirred at ambient temperature for 20 minutes, the phases were separated, and the organic phase was dried over anhydrous sodium sulfate, and concentrated under reduced pressure. The crude material was purified by preparative thin-layer chromatography (silica, 7% MeOH-DCM as eluent) to afford the product (235 mg) as a pale yellow solid.

Step E: Preparation of 2-((3-cyclopropyl-4-nitro-1H-indazol-1-yl)methyl)-5-methyl-1,3,4-thiadiazole: A 10 mL round bottom flask equipped with a reflux condenser and a nitrogen line was charged with 2-((3-bromo-4-nitro-1H-indazol-1-yl)methyl)-5-methyl-1,3,4-thiadiazole (195 mg, 0.551 mmol), cyclopropylboronic acid (104 mg, 1.21 mmol), palladium acetate (7 mg, 0.031 mmol), potassium carbonate (258 mg, 1.87 mmol), and sodium 2'-(dicyclohexylphosphino)-2,6-dimethoxybiphenyl-3-sulfonate (32 mg, 0.062 mmol). To the flask was added a 1,4-dioxane:water mixture (5:1; 2.4 mL) and the flask was evacuated and refilled with nitrogen three times. The reaction mixture was heated at reflux for 8 hours followed by stirring for 16 hours at ambient temperature. The cooled reaction mixture was diluted with excess water and extracted multiple times with DCM and EtOAc. The combined organic extracts were dried over anhydrous sodium sulfate and concentrated under reduced pressure. The residue was subjected to preparative thin-layer chromatography (silica, 5% MeOH-DCM as eluent) to afford the desired product (27 mg) as a solid.

Step F: Preparation of 3-cyclopropyl-1-((5-methyl-1,3,4-thiadiazol-2-yl)methyl)-1H-indazol-4-amine: To a suspension of 2-((3-cyclopropyl-4-nitro-1H-indazol-1-yl)methyl)-5-methyl-1,3,4-thiadiazole (61.7 mg, 0.196 mmol) in 4:1 EtOH/H$_2$O (2 mL) was added iron powder (0.219 g, 3.91 mmol) and ammonium chloride (10.5 mg, 0.196 mmol). The reaction mixture was heated to reflux for three hours. The reaction mixture was cooled to ambient temperature, diluted with excess dichloromethane, and the resulting suspension was dried over anhydrous sodium sulfate. The solids were removed by filtration, and the filtrate was concentrated under reduced pressure. The crude product was dissolved in dichloromethane, passed through a silica plug, eluting with 10% MeOH/DCM, and concentrated under reduced pressure to afford the product (27 mg) as a yellow solid.

Step G: Preparation of N-(3-cyclopropyl-1-((5-methyl-1,3,4-thiadiazol-2-yl)methyl)-1H-indazol-4-yl)-7-(2-(4-methylpiperazin-1-yl)ethoxy)imidazo[1,2-a]pyridine-3-carboxamide: To lithium 7-(2-(4-methylpiperazin-1-yl)ethoxy)imidazo[1,2-a]pyridine-3-carboxylate (Example 56, Step A; 70.5 mg, 0.23 mmol) was added N-Methylpyrrolidinone (1 mL). The suspension was heated in order to affect dissolution. The reaction mixture was cooled in an ice-water bath under nitrogen, and 2,4,6-trichlorobenzoyl chloride (35.5 µL, 0.23 mmol) was added dropwise. The cold bath was removed once the addition was complete and the reaction mixture was stirred for a further 1 hour. The reaction mixture became cloudy. A solution of 3-cyclopropyl-1-((5-methyl-1,3,4-thiadiazol-2-yl)methyl)-1H-indazol-4-amine (48 mg, 0.168 mmol) in anhydrous N-Methylpyrrolidinone (1 mL) was then added to the reaction mixture, and the mixture was heated to 88° C. for 13.5 hours. The reaction mixture was cooled, diluted with water, and extracted multiple times with dichloromethane. The combined dichloromethane extracts were dried over anhydrous sodium sulfate and concentrated under reduced pressure. The crude residue was purified by preparative thin-layer chromatography (silica, eluting with 7N ammonia/MeOH:MeOH:DCM in a 3:7:90 ratio) to afford the product (51.6 mg) as a dark yellow solid. MS (ES+APCI) m/z=572 (M+H).

Example 135

N-(3-cyclopropyl-1-((2-methyloxazol-4-yl)methyl)-1H-indazol-4-yl)-7-(2-(4-methylpiperazin-1-yl)ethoxy)imidazo[1,2-a]pyridine-3-carboxamide

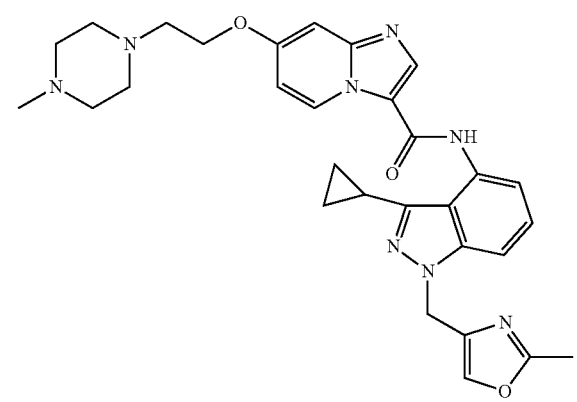

Step A: Preparation of 4-((3-bromo-4-nitro-1H-indazol-1-yl)methyl)-2-methyloxazole: A suspension of 3-bromo-4-nitro-1H-indazole (Preparation B; 500 mg, 2.07 mmol) and K₂CO₃ (1.14 g, 8.26 mmol) in anhydrous DMF (3 mL) was treated at ambient temperature, under a nitrogen atmosphere, with a solution of 4-(bromomethyl)-2-methyloxazole (727 mg, 2.07 mmol) (*Org. Biom. Chem.*, 2003, 1, 4173-4208) in anhydrous DMF (2 mL). The reaction mixture was stirred at ambient temperature for 16 hours. The reaction mixture was diluted with excess water and extracted multiple times with DCM and EtOAc. The combined extracts were dried over anhydrous sodium sulfate and concentrated under reduced pressure to afford the crude product (0.5 g). The material was purified by preparative thin-layer chromatography (silica, 5% MeOH-DCM as eluent) to afford the product (304 mg) as a solid.

Step B: Preparation of 4-((3-cyclopropyl-4-nitro-1H-indazol-1-yl)methyl)-2-methyloxazole: A 25 mL round bottom flask equipped with a reflux condenser and a nitrogen line was charged with 4-((3-bromo-4-nitro-1H-indazol-1-yl)methyl)-2-methyloxazole (304 mg, 0.902 mmol), cyclopropylboronic acid (170 mg, 1.98 mmol), palladium acetate (8 mg, 0.036 mmol), potassium carbonate (410 mg, 2.98 mmol), and sodium 2'-(dicyclohexylphosphino)-2,6-dimethoxybiphenyl-3-sulfonate (37 mg, 0.072 mmol). To the flask was added a 1,4-dioxane:water mixture (5:1; 6 mL), and the flask was evacuated and refilled with nitrogen three times. The reaction mixture was stirred and heated at reflux for 11 hours. The reaction mixture was cooled, diluted with excess water and extracted multiple times with DCM and EtOAc. The combined organic extracts were dried over anhydrous sodium sulfate, concentrated, and subjected to preparative thin-layer chromatography (silica, 1:1 EtOAc/Hexane as eluent) to afford the product (88.1 mg) as a solid.

Step C: Preparation of 3-cyclopropyl-1-((2-methyloxazol-4-yl)methyl)-1H-indazol-4-amine: To a suspension of 4-((3-cyclopropyl-4-nitro-1H-indazol-1-yl)methyl)-2-methyloxazole (88 mg, 0.295 mmol) in EtOH/H₂O (4:1; 2 mL) was added iron powder (0.33 g, 5.9 mmol) and ammonium chloride (15.8 mg, 0.295 mmol). The reaction mixture was heated at reflux for three hours. The reaction mixture was cooled to ambient temperature, diluted with excess dichloromethane, and the resulting suspension was dried over anhydrous sodium sulfate. The solids were removed by filtration and the filtrate was concentrated under reduced pressure. The crude product was dissolved in dichloromethane, passed through a silica plug, eluting with 10% MeOH/DCM, and concentrated to afford the product (60.8 mg) as a yellow oil.

Step D: Preparation of N-(3-cyclopropyl-1-((2-methyloxazol-4-yl)methyl)-1H-indazol-4-yl)-7-(2-(4-methylpiperazin-1-yl)ethoxy)imidazo[1,2-a]pyridine-3-carboxamide: To lithium 7-(2-(4-methylpiperazin-1-yl)ethoxy)imidazo[1,2-a]pyridine-3-carboxylate (Example 56, Step A; 70.5 mg, 0.23 mmol) was added N-Methylpyrrolidinone (1 mL). The material was dissolved by warming. The reaction solution was cooled in an ice-water bath, and 2,4,6-trichlorobenzoyl chloride (35.5 µL, 0.23 mmol) was added dropwise. The cold bath was removed once the addition was complete, and the mixture was stirred for an additional 1 hour. The reaction mixture became cloudy. A solution of 3-cyclopropyl-1-((2-methyloxazol-4-yl)methyl)-1H-indazol-4-amine in anhydrous N-methylpyrrolidinone (1 mL) was added and the mixture was heated to 88° C. for 13.5 hours. The reaction mixture was cooled, diluted with water, and extracted multiple times with dichloromethane. The combined dichloromethane extracts were dried over anhydrous sodium sulfate, and concentrated under reduced pressure. The crude residue was purified by preparative thin-layer chromatography (silica, eluting with 7 N NH₃/MeOH:MeOH:DCM in a 3:7:90 ratio) to afford the product (72 mg) as a white solid. MS (ES+APCI) m/z=555 (M+H).

Example 136

N-(3-ethyl-1-((6-methylpyridin-2-yl)methyl)-1H-indazol-4-yl)-7-(pyrimidin-5-yl)imidazo[1,2-a]pyridine-3-carboxamide

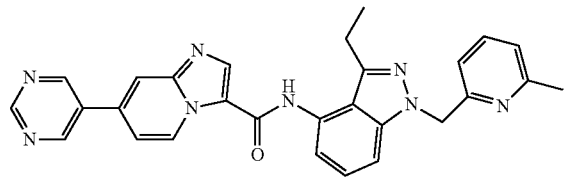 [SMILES: CCc1nn(Cc2cccc(C)n2)c2cccc(NC(=O)c3cnc4cc(-c5cncnc5)ccn34)c12]

7-Bromo-N-(3-ethyl-1-((6-methylpyridin-2-yl)methyl)-1H-indazol-4-yl)imidazo[1,2-a]pyridine-3-carboxamide (0.06 g, 0.12 mmol) (Example 127) was dissolved in a 1:1 mixture of dimethoxyethane:dimethylformamide (0.6 mL) in a 2 dram vial. Pyrimidin-5-ylboronic acid (0.02 g, 0.18 mmol), PdCl₂(dppf)*dcm (0.005 g, 0.006 mmol), and 2 M sodium carbonate solution (0.17 mL, 0.34 mmol) were added. Nitrogen was bubbled through the reaction mixture for 5 minutes before sealing the vial and heating at 90° C. for 16 hours. The reaction mixture was filtered over a 25 mm nylon filter 0.2 µM. The solids were washed with dimethylformamide (1 mL). The filtrate was concentrated under reduced pressure and dried under high vacuum to give N-(3-ethyl-1-((6-methylpyridin-2-yl)methyl)-1H-indazol-4-yl)-7-(pyrimidin-5-yl)imidazo[1,2-a]pyridine-3-carboxamide (44 mg) as a beige solid. MS (APCI), positive scan, m/z=489.2 (M+H).

Example 137

N-(3-ethyl-1-((6-methylpyridin-2-yl)methyl)-1H-indazol-4-yl)-7-(6-methylpyridin-3-yl)imidazo[1,2-a]pyridine-3-carboxamide

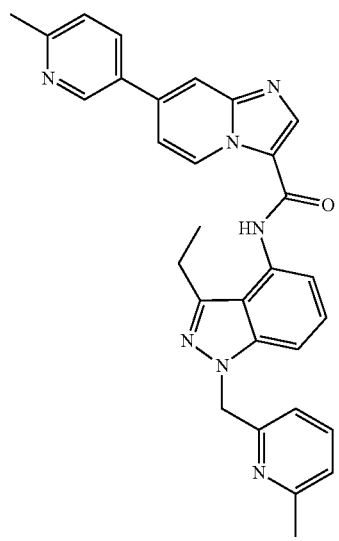 [SMILES: CCc1nn(Cc2cccc(C)n2)c2cccc(NC(=O)c3cnc4cc(-c5ccc(C)nc5)ccn34)c12]

Prepared according to the method of Example 136, using the appropriate boronic acid. 502.2 (M+1, APCI+).

Example 138

N-(3-ethyl-1-((6-methylpyridin-2-yl)methyl)-1H-indazol-4-yl)-7-(3-(4-methylpiperazin-1-yl)propyl) imidazo[1,2-a]pyridine-3-carboxamide

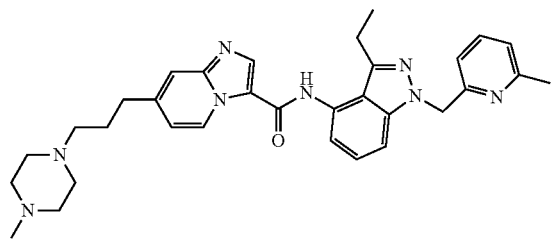 [SMILES: CCc1nn(Cc2cccc(C)n2)c2cccc(NC(=O)c3cnc4cc(CCCN5CCN(C)CC5)ccn34)c12]

Step A: Preparation of (E,Z)—N-(3-ethyl-1-((6-methylpyridin-2-yl)methyl)-1H-indazol-4-yl)-7-(3-(tetrahydro-2H-pyran-2-yloxy)prop-1-enyl)imidazo[1,2-a]pyridine-3-carboxamide: To a round bottom flask was added potassium carbonate (525 mg, 3.80 mmol), (E)-4,4,5,5-tetramethyl-2-(3-(tetrahydro-2H-pyran-2-yloxy)prop-1-enyl)-1,3,2-dioxaborolane (204 mg, 0.76 mmol), 7-bromo-N-(3-ethyl-1-((6-methylpyridin-2-yl)methyl)-1H-indazol-4-yl)imidazo[1,2-a]pyridine-3-carboxamide (prepared as in Example 127, Step A; 372 mg, 0.76 mmol), and tetrakis(triphenylphosphine) palladium (44 mg, 0.038 mmol). The flask was evacuated and purged with nitrogen. A 1:1:4.5 mixture of water:DMF:acetonitrile (13 mL) was added. The reaction mixture was degassed thoroughly under nitrogen, heated to 80° C., and stirred for 14 hours. The reaction mixture was cooled to ambient temperature, diluted with water, and extracted multiple times with DCM and EtOAc. The combined organic extracts were dried over anhydrous sodium sulfate, and concentrated under reduced pressure. The crude product was subjected to preparative thin-layer chromatography (silica, developed with 10% MeOH-DCM) to afford the partially purified desired product as a foamy, yellow solid (315.8 mg). The crude material was used in next step without further purification.

Step B: Preparation of (E,Z)—N-(3-ethyl-1-((6-methylpyridin-2-yl)methyl)-1H-indazol-4-yl)-7-(3-hydroxyprop-1-enyl)imidazo[1,2-a]pyridine-3-carboxamide: (E,Z)—N-(3-Ethyl-1-((6-methylpyridin-2-yl)methyl)-1H-indazol-4-yl)-7-(3-(tetrahydro-2H-pyran-2-yloxy)prop-1-enyl)imidazo[1,2-a]pyridine-3-carboxamide (295 mg, 0.21 mmol) was dissolved in methanol (1.5 mL) and treated with 4-methylbenzenesulfonic acid hydrate and stirred at ambient temperature for 16 hours. The mixture was loaded onto a 25+ C18 Biotage samplet and purified using reverse phase chromatography eluting with a gradient from 10-70% acetonitrile/water to give (E,Z)—N-(3-ethyl-1-((6-methylpyridin-2-yl)methyl)-1H-indazol-4-yl)-7-(3-hydroxyprop-1-enyl)imidazo[1,2-a]pyridine-3-carboxamide as a pale yellow solid (81 mg).

Step C: Preparation of N-(3-ethyl-1-((6-methylpyridin-2-yl)methyl)-1H-indazol-4-yl)-7-(3-hydroxypropyl)imidazo[1,2-a]pyridine-3-carboxamide: (E,Z)—N-(3-ethyl-1-((6-methylpyridin-2-yl)methyl)-1H-indazol-4-yl)-7-(3-hydroxyprop-1-enyl)imidazo[1,2-a]pyridine-3-carboxamide (37 mg, 0.08 mmol) was dissolved in N,N-dimethylacetamide (1 mL) and treated with 20% palladium hydroxide on carbon (6 mg, 0.01 mmol). The mixture was evacuated and purged with hydrogen gas from a balloon 3 times and stirred at ambient temperature for 1 hour. The mixture was filtered over GF/F paper and the filter cake was washed with methanol (100 mL). The filtrate was concentrated under vacuum and loaded onto a Biotage 25+ C18 samplet for reverse phase chromatography eluting with a gradient from 10-80% acetonitrile/water. This gave N-(3-ethyl-1-((6-methylpyridin-2-yl)methyl)-1H-indazol-4-yl)-7-(3-hydroxypropyl)imidazo[1,2-a]pyridine-3-carboxamide (35 mg) as a pale yellow foam.

Step D: Preparation of N-(3-ethyl-1-((6-methylpyridin-2-yl)methyl)-1H-indazol-4-yl)-7-(3-(4-methylpiperazin-1-yl) propyl)imidazo[1,2-a]pyridine-3-carboxamide: N-(3-Ethyl-1-((6-methylpyridin-2-yl)methyl)-1H-indazol-4-yl)-7-(3-hydroxypropyl)imidazo[1,2-a]pyridine-3-carboxamide (77 mg, 0.16 mmol) was dissolved in tetrahydrofuran (0.8 mL) and treated with triethylamine (66 µL, 0.48 mmol) followed by dropwise addition of methanesulfonyl chloride (38 mL, 0.49 mmol). The mixture was stirred at ambient temperature for 2.5 hours. 1-Methyl piperazine (365 µL, 3.3 mmol) was added and the mixture was heated to 60° C. for 10 hours. The mixture was quenched with the addition of saturated sodium bicarbonate solution and extracted with dichloromethane 3 times. The combined extracts were dried over sodium sulfate and concentrated under reduced pressure. The residue was purified using preparative thin layer chromatography (silica, 2 mm) eluting with 10% methanol/dichloromethane with 0.2% ammonium hydroxide to give N-(3-ethyl-1-((6-methylpyridin-2-yl)methyl)-1H-indazol-4-yl)-7-(3-(4-methylpiperazin-1-yl)propyl) imidazo[1,2-a]pyridine-3-carboxamide (10 mg). MS m/z 551.4 (M+1, APCI+).

Example 139

N-(3-methoxy-1-((6-methylpyridin-3-yl)methyl)-1H-indazol-4-yl)-7-(2-methoxyethoxy)imidazo[1,2-a] pyridine-3-carboxamide

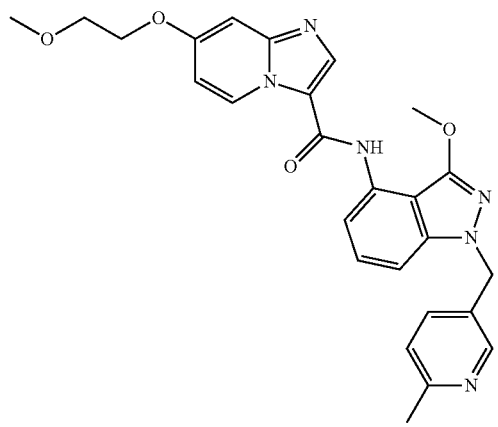 [SMILES: COCCOc1ccn2c(C(=O)Nc3cccc4c3c(OC)nn4Cc3ccc(C)nc3)cnc2c1]

Step A: Preparation of 3-iodo-1-((6-methylpyridin-3-yl) methyl)-4-nitro-1H-indazole: To a solution of 3-iodo-4-nitro-1H-indazole (3.0 g, 10.4 mmol) in DMF (25 mL) was added potassium carbonate (2.87 g, 20.8 mmol) at ambient temperature. After 15 minutes, 5-(chloromethyl)-2-methylpyridine hydrochloride (2.03 g, 11.4 mmol) was added. The mixture was allowed to stir at ambient temperature for 18 hours. The mixture was concentrated under reduced pressure and diluted with ice-water (300 mL). The precipitated solids were collected by filtration and washed with water to provide 3-iodo-1-((6-methylpyridin-3-yl)methyl)-4-nitro-1H-indazole (3.77 g, 92% yield).

Step B: Preparation of 3-methoxy-1-((6-methylpyridin-3-yl)methyl)-4-nitro-1H-indazole: A mixture of 3-iodo-1-((6-methylpyridin-3-yl)methyl)-4-nitro-1H-indazole (0.520 g, 1.32 mmol), 1,10-phenanthroline (0.238 g, 1.32 mmol), copper iodide (0.251 g, 1.32 mmol) and potassium fluoride (40% on alumina) (1.05 g, 7.26 mmol) in methanol (2.7 mL) and toluene (13 mL) was purged with argon and heated at reflux for 14 hours. After cooling, the mixture was filtered through glass fiber filter paper, concentrated under reduced pressure and purified by silica gel chromatography (5-25% EtOAc in hexanes) to give 3-methoxy-1-((6-methylpyridin-3-yl)methyl)-4-nitro-1H-indazole (0.260 g, 66% yield) as a brown gum.

Step C: Preparation of 3-methoxy-1-((6-methylpyridin-3-yl)methyl)-1H-indazol-4-amine: Prepared according to the method of Example 75, replacing 3-cyclopropyl-1-((6-methylpyridin-2-yl)methyl)-4-nitro-1H-indazole with 3-methoxy-1-((6-methylpyridin-3-yl)methyl)-4-nitro-1H-indazole.

Step D: Preparation of N-(3-methoxy-1-((6-methylpyridin-3-yl)methyl)-1H-indazol-4-yl)-7-(2-methoxyethoxy)imidazo[1,2-a]pyridine-3-carboxamide: A suspension of 7-(2-methoxyethoxy)imidazo[1,2-a]pyridine-3-carboxylic acid (Example 1, Steps A-D; 0.014 g, 0.059 mmol) and 2M oxalyl chloride in DCM solution (0.033 mL, 0.065 mmol) were suspended in DCM (1 mL) with a catalytic amount of DMF. 3-Methoxy-1-((6-methylpyridin-3-yl)methyl)-1H-indazol-4-amine (0.016 g, 0.059 mmol) in DCM (1 mL) was added, followed by diisopropylethylamine (0.012 mL, 0.071 mmol). The mixture was stirred overnight and then was in water-DCM, the organic layer was filtered through glass fiber filter paper, concentrated under reduced pressure and purified by silica gel chromatography (3% MeOH in DCM) to give N-(3-methoxy-1-((6-methylpyridin-3-yl)methyl)-1H-indazol-4-yl)-7-(2-methoxyethoxy)imidazo[1,2-a]pyridine-3-carboxamide (0.014 mg, 49% yield) as a beige solid. MS (APCI) m/z=487 (M+H).

Example 140

N-(3-bromo-1-((6-methylpyridin-3-yl)methyl-1H-indazol-4-yl)-7-(2-methoxyethoxy)imidazo[1,2-a]pyridine-3-carboxamide

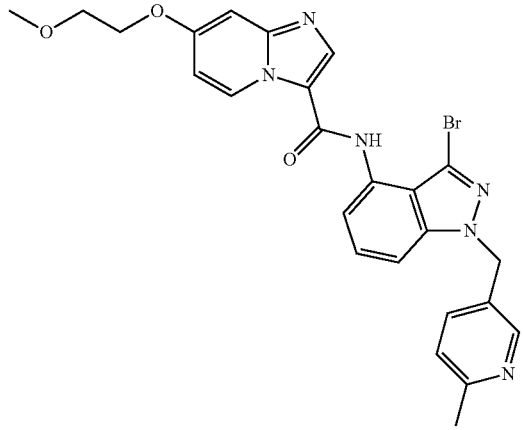 [SMILES: COCCOc1ccn2c(C(=O)Nc3cccc4c3c(Br)nn4Cc3ccc(C)nc3)cnc2c1]

Prepared according to the method of Example 139 replacing 3-methoxy-1-((6-methylpyridin-3-yl)methyl)-1H-indazol-4-amine with 3-bromo-1-((6-methylpyridin-3-yl)methyl)-1H-indazol-4-amine (prepared in a manner analogous to that described in Preparation C, followed by a reduction step as described in Example 1, Step C). MS (APCI) m/z=537 (M+H).

Example 141

N-(3-methoxy-1-((6-methylpyridin-2-yl)methyl)-1H-indazol-4-yl)-7-(2-(4-methylpiperazin-1-yl)ethoxy)imidazo[1,2-a]pyridine-3-carboxamide

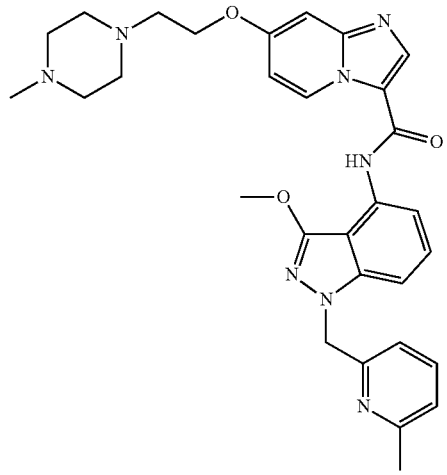 [SMILES: COc1nn(Cc2cccc(C)n2)c2cccc(NC(=O)c3cnc4cc(OCCN5CCN(C)CC5)ccn34)c12]

To a chilled (0° C.) degassed solution of 3-methoxy-1-((6-methylpyridin-2-yl)methyl)-1H-indazol-4-amine (prepared in an analogous manner described in Example 139, Steps A-C, substituting the appropriate pyridine reagent in Step A) (0.053 g, 0.20 mmol) in anhydrous THF (2 mL) was added dropwise under nitrogen, lithium bis(trimethylsilyl)amide solution (0.45 mL, 0.45 mmol) solution. After stirring for 10 minutes, a solution of ethyl 7-(2-(4-methylpiperazin-1-yl)ethoxy) imidazo[1,2-a]pyridine-3-carboxylate (0.060 g, 0.18 mmol) in THF (2 mL) was added. The mixture was then quenched with excess saturated aqueous ammonium chloride and extracted with DCM. The organic extracts were filtered through glass fiber filter paper, concentrated under reduced pressure and purified by silica gel chromatography (10% 7N NH₃/MeOH in DCM) to give the title compound (0.023 g, 23% yield) as an amber oil. MS (APCI) m/z=555 (M+H).

Example 142

N-(3-ethyl-1-(thiazol-2-ylmethyl)-1H-indazol-4-yl)imidazo[1,2-a]pyridine-3-carboxamide

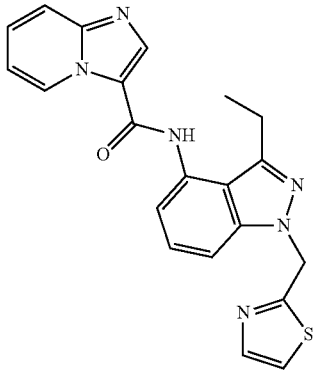 [SMILES: CCc1nn(Cc2nccs2)c2cccc(NC(=O)c3cnc4ccccn34)c12]

Prepared according to the method of Example 139, replacing 3-methoxy-1-((6-methylpyridin-3-yl)methyl)-1H-indazol-4-amine with 3-ethyl-1-(thiazol-2-ylmethyl)-1H-indazol-4-amine (prepared in a analogous manner analogous to that described in Example 146, Steps A-E, substituting the appropriate thiazole reagent in Step C). MS (APCI) m/z=403 (M+H).

Example 143

N-(3-ethyl-1-((6-methylpyridin-3-yl)methyl)-1H-indazol-4-yl)imidazo[1,2-a]pyridine-3-carboxamide

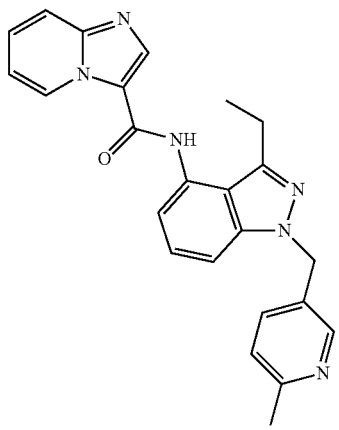 [SMILES: CCc1nn(Cc2ccc(C)nc2)c2cccc(NC(=O)c3cnc4ccccn34)c12]

Prepared according to the method of Example 139, replacing 3-methyl-1-((6-methylpyridin-3-yl)methyl)-1H-indazol-4-amine with 3-ethyl-1-((6-methylpyridin-3-yl)methyl)-1H-indazol-4-amine (prepared in a analogous manner analogous to that described in Example 5, Step D, substituting 2-methyl-5-chloromethylpyridine hydrochloride for 2-(bromomethyl)-6-methylpyridine in step B). MS (APCI) m/z=411 (M+H).

Example 144

N-(3-ethyl-1-((6-methylpyridin-3-yl)methyl)-1H-indazol-4-yl)-7-(2-(4-methylpiperazin-1-yl)ethoxy)imidazo[1,2-a]pyridine-3-carboxamide

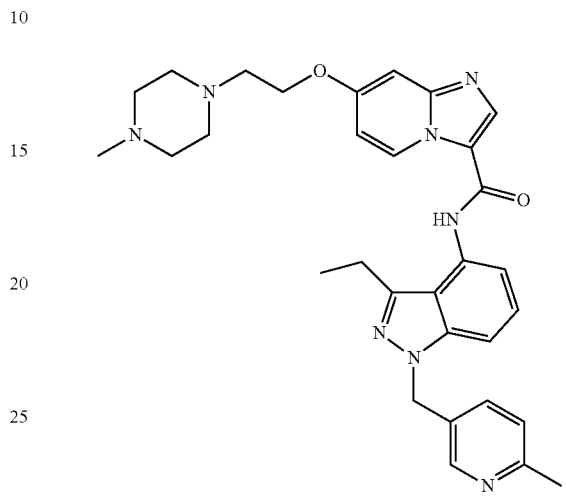

Prepared according to the method of Example 141, replacing 3-methoxy-1-((6-methylpyridin-2-yl)methyl)-1H-indazol-4-amine with 3-ethyl-1-((6-methylpyridin-3-yl)methyl)-1H-indazol-4-amine (prepared in a analogous manner analogous to that described in Example 5, Step D, substituting 2-methyl-5-chloromethylpyridine hydrochloride for 2-(bromomethyl)-6-methylpyridine in step B). MS (APCI) m/z=553 (M+H).

Example 145

N-(3-ethyl-1-(thiazol-2-ylmethyl)-1H-indazol-4-yl)-7-(2-(4-methylpiperazin-1-yl)ethoxy)imidazo[1,2-a]pyridine-3-carboxamide

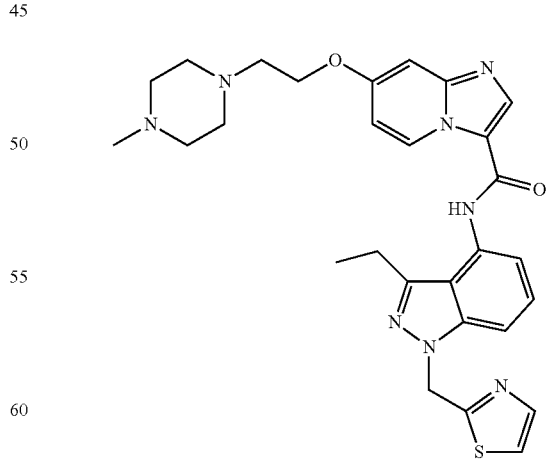

Prepared according to the method of Example 141, replacing 3-methoxy-1-((6-methylpyridin-2-yl)methyl)-1H-indazol-4-amine with 3-ethyl-1-(thiazol-2-ylmethyl)-1H-indazol-4-amine (prepared in an analogous manner described in Example 146, Steps A-E, substituting the appropriate thiazole reagent in Step C). MS (APCI) m/z=545 (M+H).

Example 146

N-(3-ethyl-1-((4-methylthiazol-2-yl)methyl)-1H-indazol-4-yl)-7-(2-(4-methylpiperazin-1-yl)ethoxy)imidazo[1,2-a]pyridine-3-carboxamide

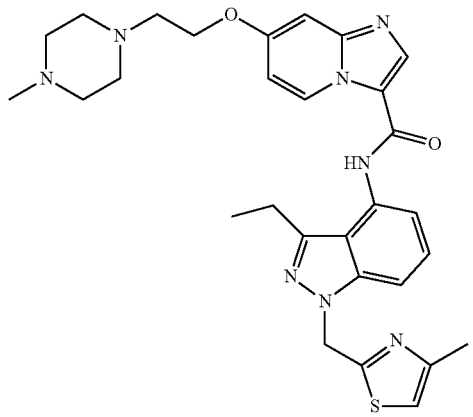

Step A: Preparation of (4-methylthiazol-2-yl)methanol: To a solution of 4-methylthiazole-2-carbaldehyde (1.882 mL, 17.54 mmol) in MeOH (50 mL) was added sodium borohydride (0.6634 g, 17.54 mmol) in portions at ambient temperature. The mixture was allowed to stir for 1 hour, and then concentrated under reduced pressure. The mixture was partitioned between DCM and water, the organic phase was washed with brine, dried (phase separator silicone treated filter paper), and concentrated under reduced pressure to a thick white paste. The material was purified by silica gel chromatography (1-5% MeOH in DCM) to afford (4-methylthiazol-2-yl)methanol (5.39 g, 76% yield) as a clear oil.

Step B: Preparation of 2-(chloromethyl)-4-methylthiazole hydrochloride: To a solution of (4-methylthiazol-2-yl)methanol (0.423 g, 3.27 mmol) in toluene (7 mL) was added thionyl chloride (0.478 mL, 6.55 mmol) dropwise. The mixture was heated to 65° C. and stirred for 1 hour. The mixture was concentrated under reduced pressure and the residue was triturated with ether. The solids were collected by filtration to afford 2-(chloromethyl)-4-methylthiazole hydrochloride (0.427 g, 71% yield) as pale yellow solids.

Step C: Preparation of 2-((3-iodo-4-nitro-1H-indazol-1-yl)methyl)-4-methylthiazole: To a solution of 3-iodo-4-nitro-1H-indazole (0.500 g, 1.73 mmol) in DMF (8 mL) was added potassium carbonate (0.478 g, 3.46 mmol) at ambient temperature. After 15 minutes, 2-(chloromethyl)-4-methylthiazole hydrochloride was added. The mixture was allowed to stir at ambient temperature for 18 hours, concentrated under reduced pressure and diluted with DCM and brine. The organic phase was dried (phase separator silicone treated filter paper), and purified by silica gel chromatography (10-50% ether in DCM) to provide 2-((3-iodo-4-nitro-1H-indazol-1-yl)methyl)-4-methylthiazole (0.414 g, 60% yield) as a yellow solid.

Step D: Preparation of 4-methyl-2-((4-nitro-3-vinyl-1H-indazol-1-yl)methyl)thiazole: A suspension of 2-((3-iodo-4-nitro-1H-indazol-1-yl)methyl)-4-methylthiazole (0.414 g, 1.03 mmol) in IPA/THF (4:1; 15 mL) was degassed with argon, treated with triethylamine (0.433 mL, 3.10 mmol), potassium trifluoro(vinyl)borate (0.416 g, 3.10 mmol) and 1,1'-bis(diphenylphosphino)ferrocene palladium (II) chloride complex with dichloromethane (0.0845 g, 0.103 mmol). The mixture was heated at 90° C. for 14 hours under argon. The mixture was filtered through glass fiber filter paper, concentrated under reduced pressure and purified by silica gel chromatography (10-75% EtOAc in hexanes) to provide 4-methyl-2-((4-nitro-3-vinyl-1H-indazol-1-yl)methyl)thiazole (0.249 g, 80% yield) as an amber gum.

Step E: Preparation of 3-ethyl-1-((4-methylthiazol-2-yl)methyl)-1H-indazol-4-amine: A solution of 4-methyl-2-((4-nitro-3-vinyl-1H-indazol-1-yl)methyl)thiazole (0.249 g, 0.829 mmol) in hot ethanol (8 mL) was purged with argon and treated with Pearlman's catalyst (124 mg). The mixture was purged with argon, purged with hydrogen gas and allowed to stir at ambient temperature under hydrogen gas for 14 hours. The mixture was filtered through glass fiber filter paper, washed with methanol and concentrated to afford 3-ethyl-1-((4-methylthiazol-2-yl)methyl)-1H-indazol-4-amine (187 mg, 83%) as a pale yellow oil.

Step F: Preparation of N-(3-ethyl-1-((4-methylthiazol-2-yl)methyl)-1H-indazol-4-yl)-7-(2-(4-methylpiperazin-1-yl)ethoxy)imidazo[1,2-a]pyridine-3-carboxamide: A solution of 7-(2-(4-methylpiperazin-1-yl)ethoxy)imidazo[1,2-a]pyridine-3-carboxylic acid (0.346 g, 0.997 mmol) in DMA (5 mL) was cooled to 0° C. and treated with phosphorous oxychloride (0.182 mL, 1.99 mmol). The mixture was warmed up to ambient temperature and after stirring for an hour, the mixture was cooled to 0° C. again and treated with a solution of 3-ethyl-1-((4-methylthiazol-2-yl)methyl)-1H-indazol-4-amine (0.181 g, 0.665 mmol) in DMA (2 mL). The mixture was allowed to warm up to ambient temperature and stirring continued overnight. The mixture was concentrated and then quenched with saturated aqueous lithium hydroxide, stirred at ambient temperature for 30 minutes and then diluted with DCM. The organic layer was filtered through glass fiber filter paper, concentrated under reduced pressure and purified by silica gel chromatography (2-10% 7N $NH_3$/MeOH in DCM) to provide N-(3-ethyl-1-((4-methylthiazol-2-yl)methyl)-1H-indazol-4-yl)-7-(2-(4-methylpiperazin-1-yl)ethoxy)imidazo

Example 147

N-(3-cyclopropyl-1-(((6-methylpyridin-3-yl)-methyl-1H-indazol-4-yl)-7-(2-(4-methylpiperazin-1-yl)ethoxy)imidazo[1,2-a]pyridine-3-carboxamide

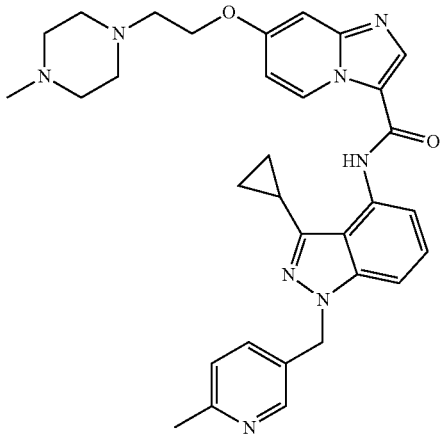 [SMILES: Cc1ccc(Cn2nc(C3CC3)c3c(NC(=O)c4cnc5cc(OCCN6CCN(C)CC6)ccn45)cccc32)cn1]

Prepared according to the method of Example 65, replacing 3-methyl-1-((6-methylpyridin-3-yl)methyl)-1H-indazol-4-amine with 3-cyclopropyl-1-((6-methylpyridin-3-yl)methyl)-1H-indazol-4-amine (which was prepared in manner analogous to that described in Preparation C and Example 75, steps E-F, by substituting the appropriate pyridine derivative in Preparation C). MS (APCI) m/z=565 (M+H).

Example 148

N-(3-ethyl-1-((2-methylthiazol-4-yl)methyl)-1H-indazol-4-yl)-7-(2-(4-methylpiperazin-1-yl)ethoxy)imidazo[1,2-a]pyridine-3-carboxamide

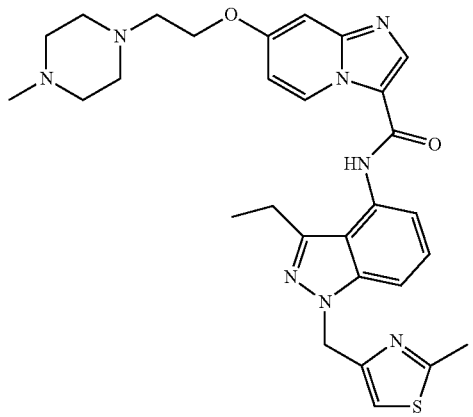

Prepared according to the method of Example 146, replacing 3-methyl-1-((6-methylpyridin-3-yl)methyl)-1H-indazol-4-amine with 3-ethyl-1-((2-methylthiazol-4-yl)methyl)-1H-indazol-4-amine (prepared in an analogous manner described in Example 146, Steps A-E, substituting the appropriate thiazole reagent in Step A). MS (APCI) m/z=559 (M+H).

Example 149

N-(3-ethyl-1-((5-fluoropyridin-2-yl)methyl)-1H-indazol-4-yl)-7-(2-(4-methylpiperazin-1-yl)ethoxy)imidazo[1,2-a]pyridine-3-carboxamide

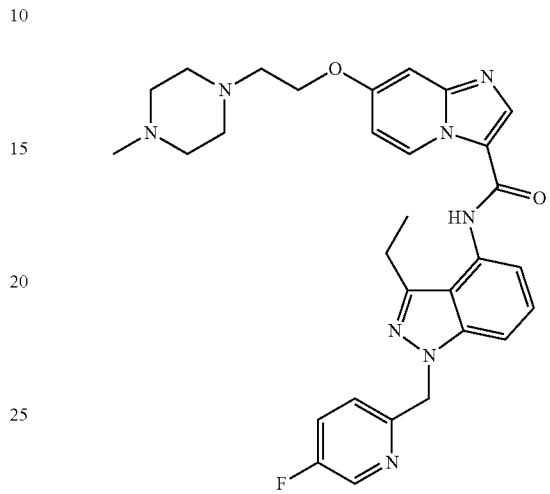

Step A: Preparation of (5-fluoropyridin-2-yl)methanol: A suspension of 5-fluoropicolinaldehyde (10.0 g, 79.94 mmol) in MeOH (160 mL) was treated with sodium borohydride (9.073 g, 239.8 mmol) in portions. The mixture was stirred at ambient temperature for 16 hours. The mixture was quenched with water, concentrated under reduced pressure, diluted with water and extracted with EtOAc. The combined organic extracts were dried (phase separator silicone treated filter paper), and concentrated under reduced pressure to give a clear oil, which was triturated with ether. The resulting solid was collected by filtration to afford (5-fluoropyridin-2-yl)methanol (10.15 g, 99% yield).

Step B: Preparation of 2-(chloromethyl)-5-fluoropyridine hydrochloride: To (5-fluoropyridin-2-yl)methanol (10.6 g, 83.39 mmol) in DCM (166 mL) was added thionyl chloride (12.17 mL, 166.8 mmol) dropwise. The mixture was allowed to stir at ambient temperature for 18 hours. The mixture was concentrated under reduced pressure to afford 2-(chloromethyl)-5-fluoropyridine hydrochloride (11.8 g, 78% yield) as white solids.

Step C: Preparation of 1-((5-fluoropyridin-2-yl)methyl)-3-iodo-4-nitro-1H-indazole: To a solution of 3-iodo-4-nitro-1H-indazole (1.0 g, 3.46 mmol) in DMF (20 mL) was added potassium carbonate (0.956 g, 6.92 mmol) and 2-(chloromethyl)-5-fluoropyridine hydrochloride (0.630 g, 3.46 mmol). The mixture was stirred at ambient temperature for 18 hours under nitrogen. The mixture was concentrated under vacuum and then diluted water (300 mL). The precipitated solids were collected by filtration and washed with water. The material was dried under high vacuum for 16 hours to give 1-((5-fluoropyridin-2-yl)methyl)-3-iodo-4-nitro-1H-indazole (0.968 g).

Step D: Preparation of 1-((5-fluoropyridin-2-yl)methyl)-4-nitro-3-vinyl-1H-indazole: A suspension of 1-((5-fluoropyridin-2-yl)methyl)-3-iodo-4-nitro-1H-indazole (0.968 g, 2.43 mmol) in 4:1 IPA/THF (10 mL) was degassed under argon. To the suspension was added TEA (0.678 mL, 4.86 mmol), potassium trifluoro(vinyl)borate (0.651 g, 4.86 mmol) and PdCl₂(dppf)*dcm (0.199 g, 0.243 mmol). The mixture was then heated with stirring at 90° C. for 16 hours under argon. The mixture was allowed to cool, filtered through GF/F paper and concentrated under reduced pressure. The residue was dissolved in DCM and purified by chromatography on silica using a Biotage system, eluting with 1-10% Et₂O in DCM. This gave 1-((5-fluoropyridin-2-yl)methyl)-4-nitro-3-vinyl-1H-indazole (229 mg).

Step E: Preparation of 3-ethyl-1-((5-fluoropyridin-2-yl)methyl)-1H-indazol-4-amine: A solution of 1-((5-fluoropyridin-2-yl)methyl)-4-nitro-3-vinyl-1H-indazole (0.229 g, 0.768 mmol) in EtOH (4 mL) was purged with argon. To this solution was added palladium hydroxide on carbon (91 mg, 40%/wt). The mixture was purged with more argon and then hydrogen. The mixture was then stirred at ambient temperature under hydrogen for 16 hours. The mixture was filtered through GF/F paper, washed with MeOH and concentrated under reduced pressure to give 3-ethyl-1-((5-fluoropyridin-2-yl)methyl)-1H-indazol-4-amine (188 mg) as an amber oil.

Step F: Preparation of lithium 7-(2-(4-methylpiperazin-1-yl)ethoxy)imidazo[1,2-a]pyridine-3-carboxylate: To ethyl 7-(2-(4-methylpiperazin-1-yl)ethoxy)imidazo[1,2-a]pyridine-3-carboxylate (Preparation D; 43.93 g, 132.2 mmol) in H₂O (150 mL) was added lithium hydroxide hydrate (6.31 g, 150.4 mmol). The reaction mixture was heated to 95° C. for 4 hours. The mixture was cooled to ambient temperature and hydrogen chloride (4.626 mL, 4M in dioxane) was added followed by stirring for 10 minutes. Water was removed under reduced pressure, and the residue was dried under vacuum for 16 hours to give the product, lithium 7-(2-(4-methylpiperazin-1-yl)ethoxy)imidazo[1,2-a]pyridine-3-carboxylate (42.78 g).

Step G: Preparation of N-(3-ethyl-1-((5-fluoropyridin-2-yl)methyl)-1H-indazol-4-yl)-7-(2-(4-methylpiperazin-1-yl)ethoxy)imidazo[1,2-a]pyridine-3-carboxamide: To lithium 7-(2-(4-methylpiperazin-1-yl)ethoxy)imidazo[1,2-a]pyridine-3-carboxylate (0.108 g, 0.331 mmol) was added NMP (2 mL). The mixture was stirred with warming under nitrogen to form a solution. The solution was cooled to 0° C. and 2,4,6-trichlorobenzoyl chloride (0.0518 ml, 0.324 mmol) was added drop wise. The mixture was stirred for one hour at ambient temperature. 3-Ethyl-1-((5-fluoropyridin-2-yl)methyl)-1H-indazol-4-amine (0.064 g, 0.237 mmol) was then added and the reaction mixture heated to 88° C. for 16 hours. The mixture was allowed to cool and then concentrated under reduced pressure to remove the majority of the NMP. To this residue was added a 10% aqueous solution of sodium hydroxide (5 mL). The resulting clear solution was stirred at 80° C. for 30 minutes and then cooled to ambient temperature. The mixture was extracted multiple times with DCM. The combined organic phases were dried (sodium sulfate) and concentrated under reduced pressure (bath temperature at 80° C. to remove remaining NMP). To the resulting residue was added ether in order to triturate. The resulting solids were collected by filtration, dissolved in DCM and subjected to purification on silica using a Biotage system, eluting with a gradient of 1-10% 7N NH₃ in MeOH/DCM. The resulting product was triturated with ether containing a small amount of DCM to give N-(3-ethyl-1-((5-fluoropyridin-2-yl)methyl)-1H-indazol-4-yl)-7-(2-(4-methylpiperazin-1-yl)ethoxy)imidazo[1,2-a]pyridine-3-carboxamide (23 mg). MS (APCI) m/z=557.1 (M+H).

Example 150

N-(3-cyclopropyl-1-((5-fluoropyridin-2-yl)methyl)-1H-indazol-4-yl)-7-(2-(4-methylpiperazin-1-yl)ethoxy)imidazo[1,2-a]pyridine-3-carboxamide

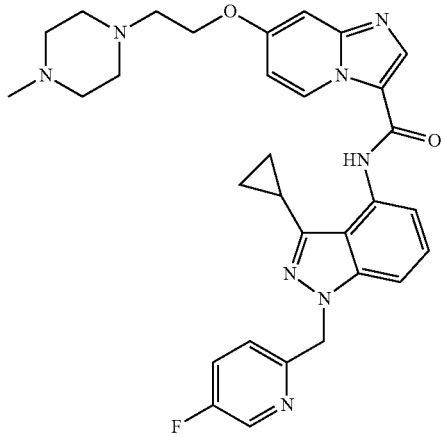 [SMILES: CN1CCN(CCOc2ccn3c(C(=O)Nc4cccc5c4c(C4CC4)nn5Cc4ccc(F)cn4)cnc3c2)CC1]

Prepared according to the method of Example 65, replacing 3-methyl-1-((6-methylpyridin-3-yl)methyl)-1H-indazol-4-amine with 3-cyclopropyl-1-((5-fluoropyridin-2-yl)methyl)-1H-indazol-4-amine. 3-Cyclopropyl-1-((5-fluoropyridin-2-yl)methyl)-1H-indazol-4-amine was prepared in manner analogous to that described in Preparation C and Example 75, steps E-F, using 2-chloromethyl-5-fluoropyridine hydrochloride in Preparation C. 2-Chloromethyl-5-fluoropyridine hydrochloride, was prepared according to PCT Int. Appl., 2007002181. MS (APCI) m/z=569 (M+H).

Example 151

N-(3-cyclopropyl-1-((2-methylthiazol-4-yl)methyl)-1H-indazol-4-yl)-7-(2-(4-methylpiperazin-1-yl)ethoxy)imidazo[1,2-a]pyridine-3-carboxamide

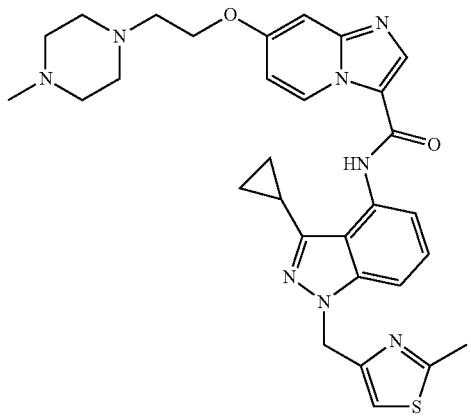

Prepared according to the method of Example 65, replacing 3-methyl-1-((6-methylpyridin-3-yl)methyl)-1H-indazol-4-amine with 3-cyclopropyl-1-((2-methylthiazol-4-yl)methyl)-1H-indazol-4-amine. MS (APCI) m/z=571 (M+H). 3-Cyclopropyl-1-((2-methylthiazol-4-yl)methyl)-1H-indazol-4-amine was prepared in manner analogous to that described in Preparation C and Example 75, Steps E-F, by substituting 2-(chloromethyl)-6-methylpyridine hydrochloride with 4-(chloromethyl)-2-methylthiazole hydrochloride in Preparation C.

Example 152

N-(3-ethyl-1-((2-isopropylthiazol-4-yl)methyl)-1H-indazol-4-yl)-7-(2-(4-methylpiperazin-1-yl)ethoxy)imidazo[1,2-a]pyridine-3-carboxamide

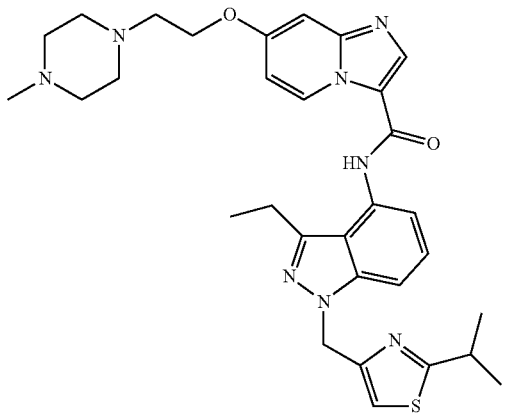 [SMILES: CCc1nn(Cc2csc(C(C)C)n2)c2cccc(NC(=O)c3cnc4cc(OCCN5CCN(C)CC5)ccn34)c12]

Prepared according to the method of Example 146, replacing 3-methyl-1-((6-methylpyridin-3-yl)methyl)-1H-indazol-4-amine with 3-ethyl-1-((2-isopropylthiazol-4-yl)methyl)-1H-indazol-4-amine. MS (APCI) m/z=587 (M+H). 3-Ethyl-1-((2-isopropylthiazol-4-yl)methyl)-1H-indazol-4-amine was prepared in manner analogous to that described in Example 146, steps A-E, substituting the appropriate thiazole derivative in step C.

Example 153

N-(3-cyclopropyl-1-((2-isopropylthiazol-4-yl)methyl)-1H-indazol-4-yl)-7-(2-(4-methylpiperazin-1-yl)ethoxy)imidazo[1,2-a]pyridine-3-carboxamide

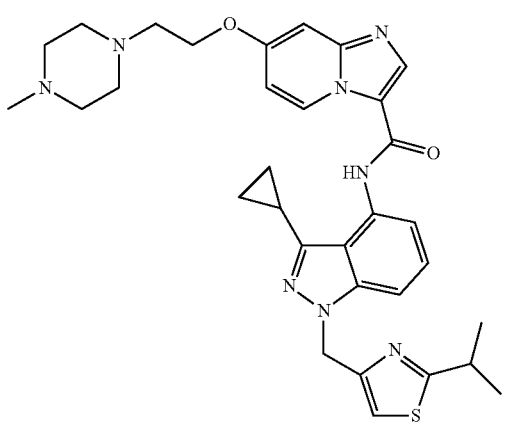 [SMILES: CC(C)c1nc(Cn2nc(C3CC3)c3c(NC(=O)c4cnc5cc(OCCN6CCN(C)CC6)ccn45)cccc32)cs1]

Prepared according to the method of Example 65, replacing 3-methyl-1-((6-methylpyridin-3-yl)methyl)-1H-indazol-4-amine with 3-cyclopropyl-1-((2-isopropylthiazol-4-yl)methyl)-1H-indazol-4-amine. MS (APCI) m/z=599 (M+H). 3-Cyclopropyl-1-((2-isopropylthiazol-4-yl)methyl)-1H-indazol-4-amine was prepared in a manner analogous to that described in Preparation C and Example 75, steps E-F, substituting 2-(chloromethyl)-6-methylpyridine hydrochloride with 4-(chloromethyl)-2-isopropylthiazole in Preparation C.

Example 154

N-(3-cyclopropyl-1-((5-fluoropyridin-2-yl)methyl)-1H-indazol-4-yl)-7-(2-(4-isopropylpiperazin-1-yl)ethoxy)imidazo[1,2-a]pyridine-3-carboxamide

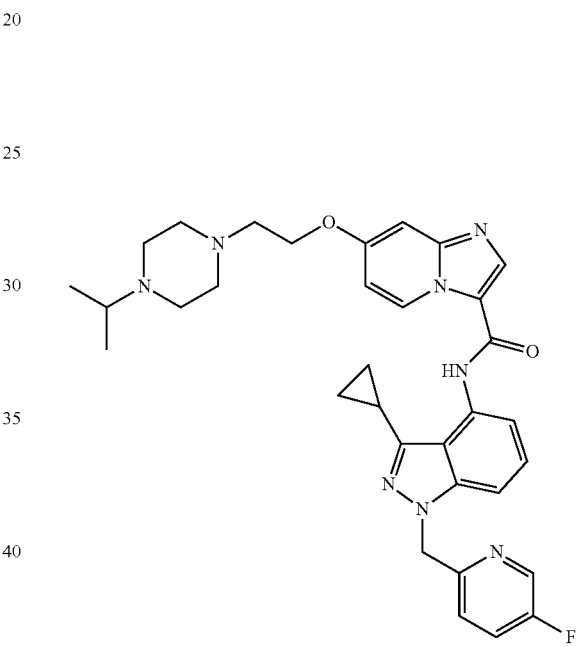

Prepared according to the method of Example 65, replacing 3-methyl-1-((6-methylpyridin-3-yl)methyl)-1H-indazol-4-amine and lithium 7-(2-(4-methylpiperazin-1-yl)ethoxy)imidazo[1,2-a]pyridine-3-carboxylate with 3-cyclopropyl-1-((5-fluoropyridin-2-yl)methyl)-1H-indazol-4-amine and lithium 7-(2-(4-isopropylpiperazin-1-yl)ethoxy)imidazo[1,2-a]pyridine-3-carboxylate respectively. 3-Cyclopropyl-1-((5-fluoropyridin-2-yl)methyl)-1H-indazol-4-amine was prepared in manner analogous to that described in Preparation C and Example 75, steps E-F, using 2-chloromethyl-5-fluoropyridine hydrochloride in Preparation C. 2-Chloromethyl-5-fluoropyridine hydrochloride, was prepared according to PCT Int. Appl., 2007002181. MS (APCI) m/z=597 (M+H).

Example 155

7-(2-acetamidoethylthio)-N-(3-ethyl-1-((6-methylpyridin-2-yl)methyl)-1H-indazol-4-yl)imidazo[1,2-a]pyridine-3-carboxamide

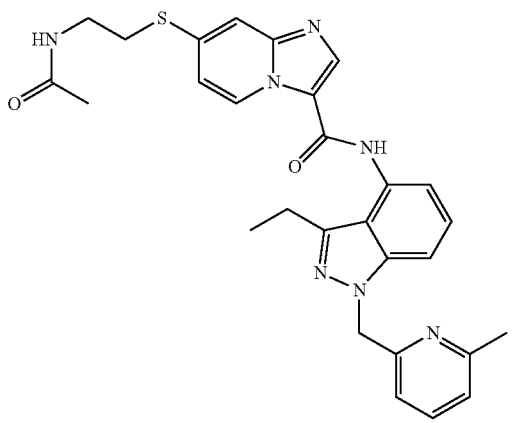 [SMILES: CCc1nn(Cc2cccc(C)n2)c2cccc(NC(=O)c3cnc4cc(SCCNC(C)=O)ccn34)c12]

N-(3-ethyl-1-((6-methylpyridin-2-yl)methyl)-1H-indazol-4-yl)-7-fluoroimidazo[1,2-a]pyridine-3-carboxamide (0.028 g, 0.065 mmol) (Example 74, Step A), N-(2-mercaptoethyl)acetamide (0.078 g, 0.65 mmol), and potassium tert-butoxide (0.022 g, 0.20 mmol) were added to a minimal amount of deoxygenated 1,4-dioxane in a sealed tube and heated for 18 hours at 95° C. The reaction mixture was cooled, concentrated under reduced pressure and purified by silica gel chromatography eluting with methanol (containing 6% ammonium hydroxide) and dichloromethane (1:9), to yield the product (20 mg) as a white powder. MS ESI (+) m/z 528 (M+1) detected.

Example 156

N-(3-cyclopropyl-1-((5-hydroxy-6-methylpyridin-2-yl)methyl)-1H-indazol-4-yl)-7-(2-(4-methylpiperazin-1-yl)ethoxy)imidazo[1,2-a]pyridine-3-carboxamide

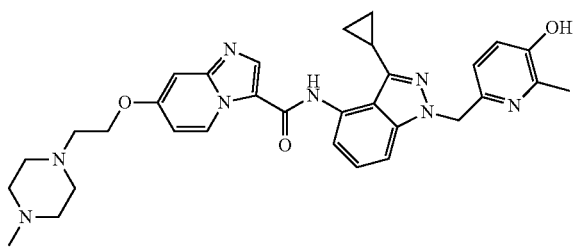 [SMILES: Cc1nc(Cn2nc(C3CC3)c3c(NC(=O)c4cnc5cc(OCCN6CCN(C)CC6)ccn45)cccc32)ccc1O]

Step A: Preparation of 1-((5-(benzyloxy)-6-methylpyridin-2-yl)methyl)-3-bromo-4-nitro-1H-indazole: To (5-(benzyloxy)-6-methylpyridin-2-yl)methanol (3.51 g, 15.3 mmol, Prepared as described in U.S. Pat. No. 3,952,101) in DCM (10 mL) was added sulfurous dichloride (10.9 g, 91.9 mmol). The reaction mixture was stirred for 3 hours, and then solvent was removed under reduced pressure. To the resulting solid was added 3-bromo-4-nitro-1H-indazole (3.71 g, 15.3 mmol), $K_2CO_3$ (6.35 g, 45.9 mmol) and anhydrous DMF (20 mL). The reaction mixture was stirred for 18 hours. The solvent was removed under reduced pressure. The residue was diluted with water (50 mL) and extracted with EtOAc. The combined organic extracts were dried ($Na_2SO_4$), and concentrated, and the residue was purified by silica gel flash chromatography (1:3 EtOAc/hexanes) to give desired product (87%).

Step B: Preparation of 1-((5-(benzyloxy)-6-methylpyridin-2-yl)methyl)-3-cyclopropyl-4-nitro-1H-indazole: A first flask was charged with 1,4-dioxane/$H_2O$ (50 mL/10 mL). The flask was cooled to 0° C. and vacuum was applied for 20 minutes. A second flask was charged with 1-((5-(benzyloxy)-6-methylpyridin-2-yl)methyl)-3-bromo-4-nitro-1H-indazole (6.07 g, 13.4 mmol), cyclopropylboronic acid (4.60 g, 53.6 mmol), diacetoxypalladium (0.150 g, 0.670 mmol), $K_2CO_3$ (5.55 g, 40.2 mmol) and sodium 2'-(dicyclohexylphosphino)-2,6-dimethoxybiphenyl-3-sulfonate (0.686 g, 1.34 mmol). The second flask was also evacuated with vacuum and back filled with $N_2$ for 3 times. The cold degassed dioxane/$H_2O$ was added to the second flask, which was evacuated with vacuum and back filled with argon for 5 times. The reaction mix was then heated to 80° C. for 3 hours. A sample ($^1$H NMR) taken from the flask showed complete reaction at this point. The reaction was cooled to ambient temperature, filtered and concentrated under reduced pressure. The residue was diluted with EtOAc (200 mL). The organic layer was washed with saturated $NaHCO_3$, dried ($Na_2SO_4$) and concentrated to give desired product, which was used in the next step without further purification.

Step C: Preparation of 6-((4-amino-3-cyclopropyl-1H-indazol-1-yl)methyl)-2-methylpyridin-3-ol: To 1-((5-(benzyloxy)-6-methylpyridin-2-yl)methyl)-3-cyclopropyl-4-nitro-1H-indazole (5.1 g, 12.3 mmol) in EtOH (100 mL) was carefully added Pd/C (10%, 1.5 g, 1.41 mmol). The reaction mixture was evacuated with $N_2$ and $H_2$ (three times each), and stirred under a $H_2$ balloon for 3 hours. The reaction mixture was then evacuated with $N_2$, filtered through Celite® and washed with MeOH. The filtrate was concentrated to give the desired product (86%) which was used in the next step without further purification.

Step D: Preparation of 1-((5-(tert-butyldimethylsilyloxy)-6-methylpyridin-2-yl)methyl)-3-cyclopropyl-1H-indazol-4-amine: To 6-((4-amino-3-cyclopropyl-1H-indazol-1-yl)methyl)-2-methylpyridin-3-ol (100 mg, 0.340 mmol) in DMF (5 mL) was added tert-butylchlorodimethylsilane (66.6 mg, 0.442 mmol) and 1H-imidazole (116 mg, 1.70 mmol). The reaction mixture was stirred for 18 hours at ambient temperature. The solvent was removed under reduced pressure, and the residue was purified by silica gel flash chromatography (1:4 EtOAc/hexanes) to give final product (97%).

Step E: Preparation of N-(3-cyclopropyl-1-((5-hydroxy-6-methylpyridin-2-yl)methyl)-1H-indazol-4-yl)-7-(2-(4-methylpiperazin-1-yl)ethoxy)imidazo[1,2-a]pyridine-3-carboxamide: To lithium 7-(2-(4-methylpiperazin-1-yl)ethoxy)imidazo[1,2-a]pyridine-3-carboxylate (101 mg, 0.318 mmol) was added NMP (5 mL, distilled over oven dried $MgSO_4$). A heat gun was used to dissolve the starting material. The reaction was cooled to 0° C. and 2,4,6-trichlorobenzoyl chloride (50.8 μL, 0.318 mmol) was added dropwise. The cold bath was removed once the addition was complete. The reaction mixture was stirred for one hour. 1-((5-(tert-Butyldimethylsilyloxy)-6-methylpyridin-2-yl)methyl)-3-cyclopropyl-1H-indazol-4-amine (100 mg, 0.245 mmol) was then added in one portion to the reaction mixture and the reaction was heated to 88° C. and stirred for 5 hours. NMP was removed by vacuum distillation until the reaction mixture became a thick oil. NaOH (3 equivalents relative to lithium salt starting material) in $H_2O$ (5 mL) was added to the thick oil. The mixture was stirred at 80° C. for 30 minutes. The mixture was cooled to ambient temperature and the pH of the dark solution was adjusted to about pH 12-13 with saturated NH$_4$Cl aqueous solution. The mixture was cooled to 0° C. and H$_2$O (10 mL) was added. Stirring was continued for 30 minutes, during which time a solid started to crash out. The mixture was filtered and the solid was washed with a saturated NaHCO$_3$ solution and H$_2$O. The solid was dissolved in DCM and dried (Na$_2$SO$_4$). The solution was filtered, concentrated and triturated with MTBE give the final product (49%). MS (ES+APCI) m/z=581.4 (M+H).

Example 157

7-(Benzyloxy)-N-(3-cyclopropyl-1-((6-methylpyridin-2-yl)methyl)-1H-indazol-4-yl)imidazo[1,2-a]pyridine-3-carboxamide

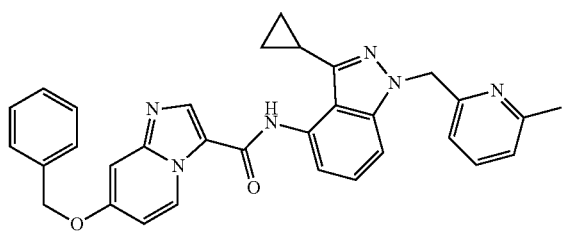 [SMILES: Cc1cccc(Cn2nc(C3CC3)c3c(NC(=O)c4cnc5cc(OCc6ccccc6)ccn45)cccc32)n1]

A mixture of 7-chloro-N-(3-cyclopropyl-1-((6-methylpyridin-2-yl)methyl)-1H-indazol-4-yl)imidazo[1,2-a]pyridine-3-carboxamide (1.0 g, 2.2 mmol; prepared as in Example 65, step C), benzyl alcohol (1.2 g, 11 mmol) and potassium hydroxide (0.61 g, 11 mmol) was dissolved in DMSO (7 mL). The reaction mixture was heated at 90° C. for 20 hours. The mixture was cooled to ambient temperature, transferred into water (100 mL) with stirring, and the resulting solid was collected by vacuum filtration and dried under vacuum to give the product (1.1 g). MS (ES+APCI) m/z=529.7 (M+H).

Example 158

N-(3-cyclopropyl-1-((6-methylpyridin-2-yl)methyl)-1H-indazol-4-yl)-7-hydroxyimidazo[1,2-a]pyridine-3-carboxamide

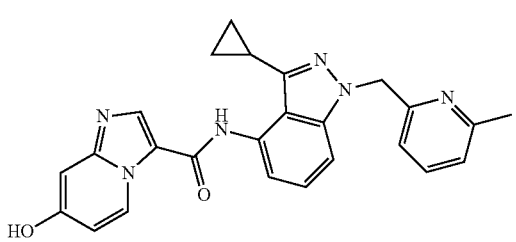 [SMILES: Cc1cccc(Cn2nc(C3CC3)c3c(NC(=O)c4cnc5cc(O)ccn45)cccc32)n1]

A mixture of 7-(benzyloxy)-N-(3-cyclopropyl-1-((6-methylpyridin-2-yl)methyl)-1H-indazol-4-yl)imidazo[1,2-a]pyridine-3-carboxamide (0.75 g, 1.4 mmol; prepared as in Example 157) and 10% Pd/C (Degussa type, 0.75 g, 0.35 mmol) was treated with THF (12 mL). The reaction vessel was heated at 55° C. with stirring while maintaining 100 psi of hydrogen in the headspace of the reaction vessel for 20 hours. The reaction mixture was cooled to ambient temperature and filtered to remove the catalyst. The filtrate was diluted with EtOAc (75 mL) and extracted with 2.5 N sodium hydroxide (2×50 mL). The pH of the combined aqueous extracts was adjusted to approximately 5 using 0.5 M monobasic potassium phosphate solution and 6 N HCl to induce precipitation. The resulting solid was collected by vacuum filtration and dried under vacuum to give the product (0.24 g). MS (ES+APCI) m/z=439.4 (M+H).

Example 159

N-(3-cyclopropyl-1-((6-methylpyridin-2-yl)methyl)-1H-indazol-4-yl)-7-(methylthio)imidazo[1,2-a]pyridine-3-carboxamide

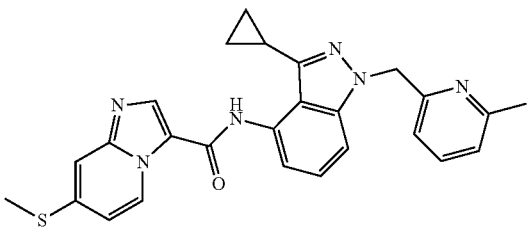

A mixture of 7-chloro-N-(3-cyclopropyl-1-((6-methylpyridin-2-yl)methyl)-1H-indazol-4-yl)imidazo[1,2-a]pyridine-3-carboxamide (200 mg, 0.44 mmol; prepared as in Example 65, step C) and sodium methanethiolate (61 mg, 0.88 mmol) was dissolved in DMSO (2 mL). The reaction mixture was heated at 55° C. for 4 hours. The mixture was cooled to ambient temperature, transferred into water (100 mL) with stirring, and the resulting solid was collected by vacuum filtration and dried under vacuum to give the product (0.17 g). MS (ES+APCI) m/z=468.9 (M+H).

Example 160

N-(3-cyclopropyl-1-((6-methylpyridin-2-yl)methyl)-
1H-indazol-4-yl)-7-(2-(2-(vinyloxy)ethoxy)ethoxy)
imidazo[1,2-a]pyridine-3-carboxamide

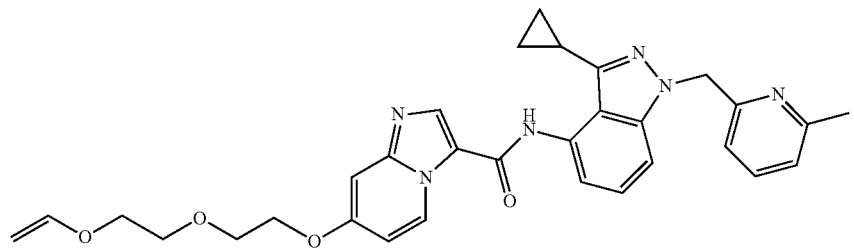 [SMILES: C=COCCOCCOc1ccn2c(C(=O)Nc3cccc4c3c(C3CC3)nn4Cc3cccc(C)n3)cnc2c1]

A mixture of 7-chloro-N-(3-cyclopropyl-1-((6-methylpyridin-2-yl)methyl)-1H-indazol-4-yl)imidazo[1,2-a]pyridine-3-carboxamide (1.0 g, 2.2 mmol; prepared as in Example 65, step C)), 2-(2-(vinyloxy)ethoxy)ethanol (1.2 g, 8.8 mmol) and potassium hydroxide (0.61 g, 11 mmol) was dissolved in DMSO (10 mL). The reaction mixture was heated at 95° C. for 20 hours. The mixture was cooled to ambient temperature, transferred into water (100 mL) and saturated aqueous NaCl (200 mL) and stirred at ambient temperature for 4 hours. The resulting solid was collected by vacuum filtration and dried under vacuum to give the product (0.90 g). MS (ES+APCI) m/z=552.9 (M+H).

Example 161

(3-cyclopropyl-1-((6-methylpyridin-2-yl)methyl)-
1H-indazol-4-yl)-7-(2-(2-hydroxyethoxy)ethoxy)
imidazo[1,2-a]pyridine-3-carboxamide

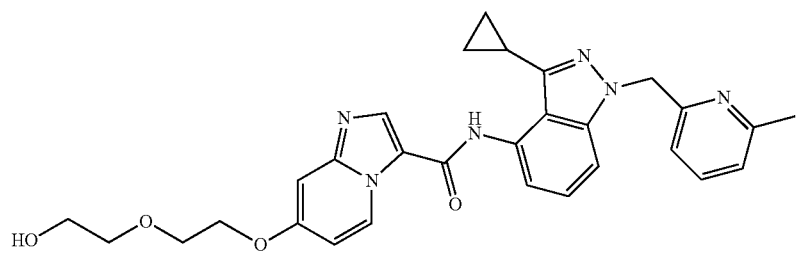 [SMILES: Cc1cccc(Cn2nc(C3CC3)c3c(NC(=O)c4cnc5cc(OCCOCCO)ccn45)cccc32)n1]

A solution of N-(3-cyclopropyl-1-((6-methylpyridin-2-yl)methyl)-1H-indazol-4-yl)-7-(2-(2-(vinyloxy)ethoxy)ethoxy)imidazo[1,2-a]pyridine-3-carboxamide (0.4 g, 0.72 mmol; prepared as in Example 160) in MeOH (5 mL) was treated with concentrated HCl (0.3 mL). The reaction mixture was stirred at ambient temperature for 90 minutes then diluted with MTBE (30 mL), EtOAc (30 mL) and MeOH (30 mL). The resulting mixture was dried over MgSO$_4$, filtered and concentrated to give the crude product which was contaminated with residual MgSO$_4$ (1.80 g). MS (ES+APCI) m/z=527.0 (M+H).

Example 162

7-bromo-N-(3-cyclopropyl-1-((6-methylpyridin-2-yl)methyl)-1H-indazol-4-yl)imidazo[1,2-a]pyridine-3-carboxamide

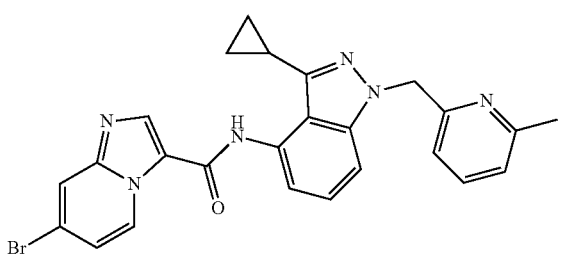 [SMILES: Cc1cccc(Cn2nc(C3CC3)c3c(NC(=O)c4cnc5cc(Br)ccn45)cccc32)n1]

Step A: Preparation of ethyl 7-bromoimidazo[1,2-a]pyridine-3-carboxylate: Potassium (E)-2-chloro-3-ethoxy-3-oxoprop-1-en-1-olate (4.4 g, 23 mmol; prepared as in Example 65, step B1) was suspended in toluene (40 mL) and a 4M solution of HCl in dioxane (2.0 mL, 8.1 mmol). The mixture was stirred at ambient temperature for 5 minutes. 4-Bromopyridin-2-amine (2.0 g, 12 mmol) was added to the mixture and heated to 40° C. for 22 hours. The mixture was cooled to ambient temperature and extracted with 2M HCl (3×75 mL). Solid $K_2CO_3$ was added to the combined aqueous extracts until $CO_2$ evolution ceased. The aqueous phase was extracted with MTBE (2×50 mL), dried over $MgSO_4$, filtered and concentrated to give the product (2.4 g). MS (ES+APCI) m/z=268.7 (M+H).

Step B: Preparation of 7-bromo-N-(3-cyclopropyl-1-((6-methylpyridin-2-yl)methyl)-1H-indazol-4-yl)imidazo[1,2-a]pyridine-3-carboxamide: A mixture of ethyl 7-bromoimidazo[1,2-a]pyridine-3-carboxylate (0.54 g, 2.0 mmol) and 3-cyclopropyl-1-((6-methylpyridin-2-yl)methyl)-1H-indazol-4-amine (0.56 g, 2.0 mmol; prepared as in Example 65, steps A1-A3) in THF (10 mL) was cooled to −13° C. using an ice/water/MeOH bath. A solution of 1.0M lithium bis(trimethylsilyl)amide (4.4 mL, 4.4 mmol) was added over 5 minutes keeping the internal temperature below −10° C. The mixture was stirred at −10° C. for 10 minutes, warmed to ambient temperature and concentrated to give an oily residue. The residue was dissolved using IPA (10 mL) and treated with a 10% aqueous ammonium chloride solution (20 mL) to give a slurry which was stirred overnight. The slurry was filtered to collect the solid which was dried under vacuum to give the product (0.89 g). MS (ES+APCI) m/z=501.0 (M+H).

What is claimed is:

1. A compound having the general formula I

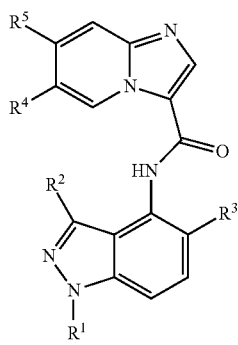

I or a pharmaceutically acceptable salt thereof, wherein:

$R^1$ is $hetAr^1CH_2$—, $hetAr^2CH_2$—, (3-6C cycloalkyl)-$CH_2$—, tetrahydropyranyl$CH_2$—, benzyl which is optionally substituted with (1-4C)alkoxy, or (N-1-3C alkyl)pyridinonyl-$CH_2$— which is optionally substituted with one or more substituents independently selected from (1-6C)alkyl;

$hetAr^1$ is pyridyl optionally substituted with one or more substituents independently selected from (1-6C)alkyl, (1-4C)alkoxy, halogen, $hetCyc^1$, $hetCyc^1$-$CH_2$—, amino(2-4C)alkoxy, [di(1-3C alkyl)amino](2-4C)alkoxy, dihydroxy(3-4C)alkoxy, $hetCyc^2O$—, $hetCyc^{2a}$(1-2C)alkoxy and OH;

$hetCyc^1$ is a 6-membered heterocycle having 1-2 ring N atoms and optionally substituted with $NH_2$;

$hetCyc^2$ and $hetCyc^{2a}$ are independently a 5-6 membered heterocycle having 1-2 ring N atoms and optionally substituted with one or more substituents independently selected from (1-6C)alkyl, OH, and halogen;

$hetAr^2$ is a 5-membered heteroaryl ring having 2-3 ring heteroatoms independently selected from N, S and O where at least one of said heteroatoms is N, wherein said ring is optionally substituted with one or more substituents independently selected from (1-6C)alkyl, (2-4C)hydroxyalkyl, (3-4C)dihydroxyalkyl, (3-6C cycloalkyl)$CH_2$—, $hetCyc^3$, $hetCyc^{3a}$(1-2C)alkyl, and benzyl optionally substituted with (1-4C)alkoxy;

$hetCyc^3$ and $hetCyc^{3a}$ are independently a 6-membered heterocyclic ring having 1-2 ring N atoms and optionally substituted with a halogen;

$R^2$ is (2-4C)alkyl, cyclopropyl, OMe, I or Br;

$R^3$ is H or Cl;

$R^4$ is H or CN;

$R^5$ is H, halogen, OH, $hetAr^3$, $hetAr^4$, N-(1-3C alkyl)pyridinone, $hetAr^5$, $hetCyc^4$, $hetCyc^5C(=O)$—, $hetCyc^6(1-4Calkyl)$-, $hetCyc^7(1-4C)alkoxy$, $(hetCyc^8)$-O—, $hetCyc^9(1-4C)alkoxy$, (1-3C alkoxy)(1-4C)alkoxy, hydroxy(1-4C)alkoxy, dihydroxy(2-4C)alkoxy, difluoroamino(1-4C)alkoxy, [di(1-3C alkyl)amino](1-4C)alkoxy, [(1-4C alkoxy)carbonylamide]difluoro(1-4C)alkoxy, (1-4C alkyl)C(=O)NH(2-4C)alkylthio-, (1-4Calkyl)OC(=O)—, (1-4C alkyl)C(=O)—, hydroxy(1-4C)alkyl, [hydroxy(2-4C)alkyl)amino]-(1-4C)alkyl, [(1-4C alkoxy)(1-4C alkyl)amino](1-4C)alkyl, [di(1-4C alkyl)amino](1-4C)alkyl, R'R"NC(=O)—, 1-6Calkylthio, benzyloxy, [hydroxy(1-4C)alkoxy](1-4C)alkoxy, or [(2-4Calkenyloxy)(1-4C)alkoxy](1-4C)alkoxy;

$hetAr^3$ is a 5-membered heteroaryl ring having 1-3 ring heteroatoms independently selected from N, O and S, wherein said ring is optionally substituted with one or more substituents independently selected from (1-6C)alkyl and [di(1-3C alkyl)amino]$CH_2$—;

$hetAr^4$ is a 6-membered heteroaryl ring having 1-2 ring N atoms and optionally substituted with one or more substituents independently selected from (1-6C)alkyl;

$hetAr^5$ is a 9-membered partially unsaturated bicyclic heterocyclic ring having 3 ring N atoms and optionally substituted with one or more substituents independently selected from (1-6C)alkyl;

$hetCyc^4$ is a 5-7 membered saturated or partially unsaturated heterocyclic ring having 1-2 ring heteroatoms selected from N and O and at least one of said heteroatoms is N, wherein said ring is optionally substituted with one or more substituents independently selected from (1-6C)alkyl, hydroxy(1-4C)alkyl, OH and oxo;

hetCyc⁵ is a 6 membered heterocyclic ring having 1-2 ring N atoms and optionally substituted with one or more substituents independently selected from (1-6C)alkyl;

hetCyc⁶ is a 4-6 membered heterocyclic ring having 1-2 ring N atoms and optionally substituted with one or more substituents independently selected from (1-6C)alkyl, (1-4C)alkoxy and halogen;

hetCyc⁷ is a 4-6 membered heterocycle having 1-2 ring heteroatoms independently selected from N, O and S, wherein one of said ring nitrogen atoms is optionally oxidized to N(o) and wherein said S ring atom is optionally oxidized to SO or $SO_2$, wherein hetCyc⁷ is optionally substituted with one or more substituents independently selected from (1-6C)alkyl, (1-4C)alkylOC(=O)—, (1-4C)alkoxy, OH and halogen;

hetCyc⁸ is a 4-6 membered heterocycle having one or two ring N atoms and optionally substituted with one or more substituents independently selected from (1-6C)alkyl and OH;

hetCyc⁹ is a bridged 8-membered heterocyclic ring having 2 ring atoms selected from N and O wherein at least one of said heteroatoms is N, wherein said ring is optionally substituted with (1-6C)alkyl;

R' is H or (1-4C)alkyl;

R" is (1-4C)alkyl, hetCyc¹⁰-, amino(1-4C)alkyl, or [di(1-4C alkyl)amino](1-4C alkyl); and hetCyc¹⁰ is a 5 membered heterocycle having a ring N atom and optionally substituted with one or more substituents independently selected from (1-6C)alkyl.

2. A compound of claim 1, wherein:

R¹ is hetAr¹$CH_2$—, hetAr²$CH_2$—, (3-6C cycloalkyl)-$CH_2$—, tetrahydropyranyl$CH_2$—, benzyl which is optionally substituted with (1-4C)alkoxy, or (N-1-3C alkyl)pyridinonyl-$CH_2$— which is optionally substituted with one or more substituents independently selected from (1-6C)alkyl;

hetAr¹ is pyridyl optionally substituted with one or more substituents independently selected from (1-6C)alkyl, (1-4C)alkoxy, halogen, hetCyc¹, hetCyc¹-$CH_2$—, amino(2-4C)alkoxy, [di(1-3C alkyl)amino](2-4C)alkoxy, dihydroxy(3-4C)alkoxy, hetCyc²O— and hetCyc²ᵃ(1-2C)alkoxy;

hetCyc¹ is a 6-membered heterocycle having 1-2 ring N atoms and optionally substituted with $NH_2$;

hetCyc² and hetCyc²ᵃ are independently a 5-6 membered heterocycle having 1-2 ring N atoms and optionally substituted with one or more substituents independently selected from (1-6C)alkyl, OH, and halogen;

hetAr² is a 5-membered heteroaryl ring having 2-3 ring heteroatoms independently selected from N, S and O where at least one of said heteroatoms is N, wherein said ring is optionally substituted with one or more substituents independently selected from (1-6C)alkyl, (2-4C)hydroxyalkyl, (3-4C)dihydroxyalkyl, (3-6C cycloalkyl)$CH_2$—, hetCyc³, hetCyc³ᵃ(1-2C)alkyl, and benzyl optionally substituted with (1-4C)alkoxy;

hetCyc³ and hetCyc³ᵃ are independently a 6-membered heterocyclic ring having 1-2 ring N atoms and optionally substituted with a halogen;

R² is (2-4C)alkyl, cyclopropyl, OMe, I or Br;

R³ is H or Cl;

R⁴ is H or CN;

R⁵ is H, F, OH, hetAr³, hetAr⁴, N-(1-3C alkyl)pyridinone, hetAr⁵, hetCyc⁴, hetCyc⁵C(=O)—, hetCyc⁶(1-4Calkyl)-, hetCyc⁷(1-4C)alkoxy, (hetCyc⁸)-O—, hetCyc⁹(1-4C)alkoxy, (1-3C alkoxy)(1-4C)alkoxy, hydroxy(1-4C)alkoxy, dihydroxy(2-4C)alkoxy, difluoroamino(1-4C)alkoxy, [di(1-3C alkyl)amino](1-4C)alkoxy, [(1-4C alkoxy)carbonylamide]difluoro (1-4C)alkoxy, (1-4C alkyl)C(=O)NH(2-4C)alkylthio-, (1-4Calkyl)OC(=O)—, (1-4C alkyl)C(=O)—, hydroxy(1-4C)alkyl, [hydroxy(2-4C)alkyl]amino]-(1-4C)alkyl, [(1-4C alkoxy)(1-4C alkyl)amino](1-4C)alkyl, [di(1-4C alkyl)amino](1-4C)alkyl, or R'R"NC(=O)—;

hetAr³ is a 5-membered heteroaryl ring having 1-3 ring heteroatoms independently selected from N, O and S, wherein said ring is optionally substituted with one or more substituents independently selected from (1-6C)alkyl and [di(1-3C alkyl)amino]$CH_2$—;

hetAr⁴ is a 6-membered heteroaryl ring having 1-2 ring N atoms and optionally substituted with one or more substituents independently selected from (1-6C)alkyl;

hetAr⁵ is a 9-membered partially unsaturated bicyclic heterocyclic ring having 3 ring N atoms and optionally substituted with one or more substituents independently selected from (1-6C)alkyl;

hetCyc⁴ is a 5-7 membered saturated or partially unsaturated heterocyclic ring having 1-2 ring heteroatoms selected from N and O and at least one of said heteroatoms is N, wherein said ring is optionally substituted with one or more substituents independently selected from (1-6C)alkyl, hydroxy(1-4C)alkyl, OH and oxo;

hetCyc⁵ is a 6 membered heterocyclic ring having 1-2 ring N atoms and optionally substituted with one or more substituents independently selected from (1-6C)alkyl;

hetCyc⁶ is a 4-6 membered heterocyclic ring having 1-2 ring N atoms and optionally substituted with one or more substituents independently selected from (1-6C)alkyl, (1-4C)alkoxy and halogen;

hetCyc⁷ is a 4-6 membered heterocycle having 1-2 ring heteroatoms independently selected from N, O and S, wherein one of said ring nitrogen atoms is optionally oxidized to N(0) and wherein said S ring atom is optionally oxidized to SO or $SO_2$, wherein hetCyc⁷ is optionally substituted with one or more substituents independently selected from (1-6C)alkyl, (1-4C)alkylCO(=O)—, (1-4C)alkoxy, OH and F;

hetCyc⁸ is a 4-6 membered heterocycle having one or two ring N atoms and optionally substituted with one or more substituents independently selected from (1-6C)alkyl and OH;

hetCyc⁹ is a bridged 8-membered heterocyclic ring having 2 ring atoms selected from N and O wherein at least one of said heteroatoms is N, wherein said ring is optionally substituted with (1-6C)alkyl;

R' is H or (1-4C)alkyl;

R" is (1-4C)alkyl, hetCyc¹⁰-, [amino(1-4C)alkyl)], or [di(1-4C alkyl)amino](1-4C alkyl); and hetCyc¹⁰ is a 5 membered heterocycle having a ring N atom and optionally substituted with one or more substituents independently selected from (1-6C)alkyl.

3. A compound according to claim 1, wherein R¹ is hetAr¹$CH_2$— or hetAr²$CH_2$—.

4. A compound according to claim 1, wherein R¹ is hetAr¹$CH_2$—.

5. A compound according to claim 1, wherein R¹ is hetAr²$CH_2$—.

6. A compound according to claim 1, wherein R¹ is (3-6C cycloalkyl)-$CH_2$—, tetrahydropyranyl$CH_2$—, or benzyl which is optionally substituted with (1-4C)alkoxy.

7. A compound according to claim 1, wherein R¹ is (N-1-3C alkyl)pyridinonyl-$CH_2$— optionally substituted with (1-6C)alkyl.

8. A compound according to claim 1, wherein $R^5$ is halogen.

9. A compound according to claim 1, wherein $R^5$ is selected from H, F and OH.

10. A compound according to a claim 1, wherein $R^5$ is selected from hetAr$^3$, hetAr$^4$, N-(1-3C alkyl)pyridinone and hetAr$^5$.

11. A compound according to claim 1, wherein $R^5$ is selected from hetCyc$^4$, hetCyc$^5$C(=O)—, hetCyc$^6$(1-4Calkyl)-, hetCyc$^7$(1-4C)alkoxy, (hetCyc$^8$)-O— and hetCyc$^9$(1-4C)alkoxy.

12. A compound according to claim 11, wherein $R^5$ is selected from hetCyc$^7$(1-4C)alkoxy, (hetCyc$^8$)-O— and hetCyc$^9$(1-4C)alkoxy.

13. A compound according to claim 12, wherein $R^5$ is hetCyc$^7$(1-4C)alkoxy.

14. A compound according to claim 1, wherein $R^5$ is selected from (1-3C alkoxy)(1-4C)alkoxy, hydroxy(1-4C)alkoxyl, dihydroxy(2-4C)alkoxy, difluoroamino(1-4C)alkoxy, [di(1-3C alkyl)amino](1-4C)alkoxy, [(1-4C alkoxy)carbonylamide]difluoro(1-4C)alkoxy and (1-4C alkyl)C(=O)NH(2-4C)alkylthio-.

15. A compound according to a claim 1, wherein $R^5$ is selected from (1-4Calkyl)OC(=O)— and (1-4C alkyl)C(=O)—.

16. A compound according to claim 1, wherein $R^5$ is selected from hydroxy(1-4C)alkyl, [(2-4C)hydroxyalkyl]amino-(1-4C)alkyl, [(1-4C alkoxy)(1-4C alkyl)]amino(1-4C)alkyl and [di(1-4C alkyl)amino](1-4C)alkyl.

17. A compound according to claim 1, wherein $R^5$ is R'R"NC(=O)—.

18. A compound according to claim 1, wherein $R^5$ is (1-6C)alkylthio.

19. A compound according to claim 1, wherein $R^5$ is selected from benzyloxy, [hydroxy(1-4C)alkoxy](1-4C)alkoxy and [(2-4Calkenyloxy)(1-4C)alkoxy](1-4C)alkoxy.

20. A compound according to claim 1, wherein $R^2$ is cyclopropyl or (2-4C)alkyl.

21. A compound according to claim 20, wherein $R^2$ is cyclopropyl.

22. A compound according to claim 20, wherein $R^2$ is (2-4C)alkyl.

23. A compound according to claim 22, wherein $R^2$ is ethyl.

24. A compound according to claim 1, wherein $R^2$ is OMe, I or Br.

25. A compound according to claim 1, wherein $R^3$ is H.

26. A compound according to claim 1, wherein $R^3$ is Cl.

27. A compound according to claim 1, wherein $R^4$ is H.

28. A compound according to claim 1, wherein $R^4$ is CN.

29. A pharmaceutical composition, which comprises a compound of Formula I as defined in claim 1, or a pharmaceutically acceptable salt thereof, and a pharmaceutically acceptable diluent or carrier.

30. A compound of Formula I as defined in claim 1, or a pharmaceutically acceptable salt thereof, for use in therapy.

31. A compound of claim 1, selected from:
N-(1-Benzyl-3-iodo-1H-indazol-4-yl)-7-(2-methoxyethoxy)imidazo[1,2-a]pyridine-3-carboxamide;
N-(1-Benzyl-3-ethyl-1H-indazol-4-yl)-7-(2-methoxyethoxy)imidazo[1,2-a]pyridine-3-carboxamide;
N-(1-Benzyl-3-cyclopropyl-1H-indazol-4-yl)-7-(2-methoxyethoxy)imidazo[1,2-a]pyridine-3-carboxamide;
N-(1-Benzyl-5-chloro-3-ethyl-1H-indazol-4-yl)-7-(2-methoxyethoxy)imidazo[1,2-a]pyridine-3-carboxamide;
N-(3-Ethyl-1-((6-methylpyridin-2-yl)methyl)-1H-indazol-4-yl)imidazo[1,2-a]pyridine-3-carboxamide;
N-(3-ethyl-1-((2-methoxy-6-methylpyridin-3-yl)methyl)-1H-indazol-4-yl)imidazo[1,2-a]pyridine-3-carboxamide;
N-(3-ethyl-1-((1-(2-(piperazin-1-yl)ethyl)-1H-pyrazol-3-yl)methyl)-1H-indazol-4-yl)imidazo[1,2-a]pyridine-3-carboxamide;
N-(1-((1-(2,3-dihydroxypropyl)-1H-pyrazol-5-yl)methyl)-3-ethyl-1H-indazol-4-yl)imidazo[1,2-a]pyridine-3-carboxamide;
N-(1-((6-(2-aminoethoxy)pyridin-2-yl)methyl)-3-ethyl-1H-indazol-4-yl)imidazo[1,2-a]pyridine-3-carboxamide;
N-(1-((6-(3-aminopropoxy)pyridin-2-yl)methyl)-3-ethyl-1H-indazol-4-yl)imidazo[1,2-a]pyridine-3-carboxamide;
N-(1-((6-(3-(dimethylamino)propoxy)pyridin-2-yl)methyl)-3-ethyl-1H-indazol-4-yl)imidazo[1,2-a]pyridine-3-carboxamide;
N-(3-ethyl-1-((6-methylpyridin-2-yl)methyl)-1H-indazol-4-yl)-7-(piperazine-1-carbonyl)imidazo[1,2-a]pyridine-3-carboxamide;
N-(3-ethyl-1-((6-methylpyridin-2-yl)methyl)-1H-indazol-4-yl)-7-(4-methylpiperazine-1-carbonyl)imidazo[1,2-a]pyridine-3-carboxamide;
N-(3-ethyl-1-((6-(piperazin-1-ylmethyl)pyridin-2-yl)methyl)-1H-indazol-4-yl)imidazo[1,2-a]pyridine-3-carboxamide;
N-(3-ethyl-1-((6-methoxypyridin-2-yl)methyl)-1H-indazol-4-yl)imidazo[1,2-a]pyridine-3-carboxamide;
N-(3-ethyl-1-((6-methylpyridin-2-yl)methyl)-1H-indazol-4-yl)-7-(2-morpholinoethoxy)imidazo[1,2-a]pyridine-3-carboxamide;
(S)—N-(3-ethyl-1-((6-(pyrrolidin-3-yloxy)pyridin-2-yl)methyl)-1H-indazol-4-yl)imidazo[1,2-a]pyridine-3-carboxamide;
N-(3-ethyl-1-((6-((3R,4R)-3-fluoropiperidin-4-yloxy)pyridin-2-yl)methyl)-1H-indazol-4-yl)imidazo[1,2-a]pyridine-3-carboxamide;
N-(3-ethyl-1-((6-(piperidin-4-yloxy)pyridin-2-yl)methyl)-1H-indazol-4-yl)imidazo[1,2-a]pyridine-3-carboxamide;
N-(3-ethyl-1-((1-(4-methoxybenzyl)-1H-pyrazol-4-yl)methyl)-1H-indazol-4-yl)imidazo[1,2-a]pyridine-3-carboxamide;
N-(3-ethyl-1-((1-(2-hydroxyethyl)-1H-pyrazol-4-yl)methyl)-1H-indazol-4-yl)imidazo[1,2-a]pyridine-3-carboxamide;
N-(3-ethyl-1-((1-((3R,4R)-3-fluoropiperidin-4-yl)-1H-pyrazol-4-yl)methyl)-1H-indazol-4-yl)imidazo[1,2-a]pyridine-3-carboxamide;
Ethyl 3-(3-ethyl-1-((6-methylpyridin-2-yl)methyl)-1H-indazol-4-ylcarbamoyl)imidazo[1,2-a]pyridine-7-carboxylate;
N-(3-ethyl-1-((6-ethylpyridin-2-yl)methyl)-1H-indazol-4-yl)imidazo[1,2-a]pyridine-3-carboxamide;
N-(3-ethyl-1-((1-methyl-6-oxo-1,6-dihydropyridin-2-yl)methyl)-1H-indazol-4-yl)imidazo[1,2-a]pyridine-3-carboxamide;
N-(3-ethyl-1-((1-ethyl-6-oxo-1,6-dihydropyridin-2-yl)methyl)-1H-indazol-4-yl)imidazo[1,2-a]pyridine-3-carboxamide;
N-(1-((6-ethoxypyridin-2-yl)methyl)-3-ethyl-1H-indazol-4-yl)imidazo[1,2-a]pyridine-3-carboxamide;
N-(3-ethyl-1-((6-methylpyridin-2-yl)methyl)-1H-indazol-4-yl)-7-(1,3,4-oxadiazol-2-yl)imidazo[1,2-a]pyridine-3-carboxamide;

N-(3-ethyl-1-((6-methylpyridin-2-yl)methyl)-1H-indazol-4-yl)-7-(5-methyl-1,3,4-oxadiazol-2-yl)imidazo[1,2-a]pyridine-3-carboxamide;
N-(3-ethyl-1-((6-methylpyridin-2-yl)methyl)-1H-indazol-4-yl)-7-(piperazin-1-ylmethyl)imidazo[1,2-a]pyridine-3-carboxamide;
N-(3-ethyl-1-((6-methylpyridin-2-yl)methyl)-1H-indazol-4-yl)-7-((4-methylpiperazin-1-yl)methyl)imidazo[1,2-a]pyridine-3-carboxamide;
N-(3-ethyl-1-((6-methylpyridin-2-yl)methyl)-1H-indazol-4-yl)-7-(((3S,4S)-4-hydroxypyrrolidin-3-yloxy)imidazo[1,2-a]pyridine-3-carboxamide;
N-(3-ethyl-1-((6-methylpyridin-2-yl)methyl)-1H-indazol-4-yl)-7-(((3R,4R)-4-hydroxypyrrolidin-3-yloxy)imidazo[1,2-a]pyridine-3-carboxamide;
N-(3-ethyl-1-((6-methylpyridin-2-yl)methyl)-1H-indazol-4-yl)-7-(((3S,4S)-4-hydroxy-1-methylpyrrolidin-3-yloxy)imidazo[1,2-a]pyridine-3-carboxamide;
N-(3-ethyl-1-((6-methylpyridin-2-yl)methyl)-1H-indazol-4-yl)-7-(((3R,4R)-4-hydroxy-1-methylpyrrolidin-3-yloxy)imidazo[1,2-a]pyridine-3-carboxamide;
N-(3-ethyl-1-((6-(((2R,3S)-3-hydroxypyrrolidin-2-yl)methoxy)pyridin-2-yl)methyl)-1H-indazol-4-yl)imidazo[1,2-a]pyridine-3-carboxamide;
4-(2-(3-(3-ethyl-1-((6-methylpyridin-2-yl)methyl)-1H-indazol-4-ylcarbamoyl)imidazo[1,2-a]pyridin-7-yloxy)ethyl)-1-methylpiperazine 1-oxide;
N-(3-ethyl-1-((6-methylpyridin-2-yl)methyl)-1H-indazol-4-yl)-7-(((2R,3S)-3-hydroxypyrrolidin-2-ylmethoxy)imidazo[1,2-a]pyridine-3-carboxamide;
N-(3-ethyl-1-((1-ethyl-1H-pyrazol-5-yl)methyl)-1H-indazol-4-yl)imidazo[1,2-a]pyridine-3-carboxamide;
N-(3-ethyl-1-((1-ethyl-1H-pyrazol-3-yl)methyl)-1H-indazol-4-yl)imidazo[1,2-a]pyridine-3-carboxamide;
N-(3-ethyl-1-((6-(((2R,3S)-3-hydroxy-1-methylpyrrolidin-2-yl)methoxy)pyridin-2-yl)methyl)-1H-indazol-4-yl)imidazo[1,2-a]pyridine-3-carboxamide;
N-(3-ethyl-1-((6-methylpyridin-2-yl)methyl)-1H-indazol-4-yl)-7-(((2R,3S)-3-hydroxy-1-methylpyrrolidin-2-yl)methoxy)imidazo[1,2-a]pyridine-3-carboxamide;
N-(3-ethyl-1-((6-(2-(piperazin-1-yl)ethoxy)pyridin-2-yl)methyl)-1H-indazol-4-yl)imidazo[1,2-a]pyridine-3-carboxamide;
N-(3-ethyl-1-((6-methylpyridin-2-yl)methyl)-1H-indazol-4-yl)-7-(1,3,4-thiadiazol-2-yl)imidazo[1,2-a]pyridine-3-carboxamide;
N-(3-ethyl-1-((6-methylpyridin-2-yl)methyl)-1H-indazol-4-yl)-7-(2-(4-methylpiperazin-1-yl)ethoxy)imidazo[1,2-a]pyridine-3-carboxamide;
N3-(3-ethyl-1-((6-methylpyridin-2-yl)methyl)-1H-indazol-4-yl)-N7-(pyrrolidin-3-yl)imidazo[1,2-a]pyridine-3,7-dicarboxamide;
N7-(2-aminoethyl)-N3-(3-ethyl-1-((6-methylpyridin-2-yl)methyl)-1H-indazol-4-yl)imidazo[1,2-a]pyridine-3,7-dicarboxamide;
N3-(3-ethyl-1-((6-methylpyridin-2-yl)methyl)-1H-indazol-4-yl)-N7-methylimidazo[1,2-a]pyridine-3,7-dicarboxamide;
N3-(3-ethyl-1-((6-methylpyridin-2-yl)methyl)-1H-indazol-4-yl)-N7,N7-dimethylimidazo[1,2-a]pyridine-3,7-dicarboxamide;
N3-(3-ethyl-1-((6-methylpyridin-2-yl)methyl)-1H-indazol-4-yl)-N7-(1-methylpyrrolidin-3-yl)imidazo[1,2-a]pyridine-3,7-dicarboxamide;
N-(2-(dimethylamino)ethyl)-N3-(3-ethyl-1-((6-methylpyridin-2-yl)methyl)-1H-indazol-4-yl)imidazo[1,2-a]pyridine-3,7-dicarboxamide;
7-(1,2-dimethyl-1H-imidazol-5-yl)-N-(3-ethyl-1-((6-methylpyridin-2-yl)methyl)-1H-indazol-4-yl)imidazo[1,2-a]pyridine-3-carboxamide;
N-(1-((1,6-dimethyl-2-oxo-1,2-dihydropyridin-3-yl)methyl)-3-ethyl-1H-indazol-4-yl)imidazo[1,2-a]pyridine-3-carboxamide;
N-(3-ethyl-1-((6-(2-(4-methylpiperazin-1-yl)ethoxy)pyridin-2-yl)methyl)-1H-indazol-4-yl)imidazo[1,2-a]pyridine-3-carboxamide;
N-(1-((1,5-dimethyl-1H-pyrazol-3-yl)methyl)-3-ethyl-1H-indazol-4-yl)imidazo[1,2-a]pyridine-3-carboxamide;
N-(1-((1,5-dimethyl-1H-pyrazol-3-yl)methyl)-3-ethyl-1H-indazol-4-yl)-7-(2-(4-methylpiperazin-1-yl)ethoxy)imidazo[1,2-a]pyridine-3-carboxamide;
N-(3-ethyl-1-((1-methyl-1H-pyrazol-3-yl)methyl)-1H-indazol-4-yl)imidazo[1,2-a]pyridine-3-carboxamide;
N-(3-ethyl-1-((1-methyl-1H-pyrazol-3-yl)methyl)-1H-indazol-4-yl)-7-(2-(4-methylpiperazin-1-yl)ethoxy)imidazo[1,2-a]pyridine-3-carboxamide;
N-(3-ethyl-1-((6-methylpyridin-2-yl)methyl)-1H-indazol-4-yl)-7-(5,6,7,8-tetrahydroimidazo[1,2-a]pyrazin-3-yl)imidazo[1,2-a]pyridine-3-carboxamide;
N-(3-ethyl-1-((6-methylpyridin-2-yl)methyl)-1H-indazol-4-yl)-7-(7-methyl-5,6,7,8-tetrahydroimidazo[1,2-a]pyrazin-3-yl)imidazo[1,2-a]pyridine-3-carboxamide;
N-(3-cyclopropyl-1-((1-ethyl-1H-pyrazol-3-yl)methyl)-1H-indazol-4-yl)-7-(2-(4-methylpiperazin-1-yl)ethoxy)imidazo[1,2-a]pyridine-3-carboxamide;
N-(3-cyclopropyl-1-((1-ethyl-1H-pyrazol-3-yl)methyl)-1H-indazol-4-yl)-7-(2-(4-isopropylpiperazin-1-yl)ethoxy)imidazo[1,2-a]pyridine-3-carboxamide;
N-(3-cyclopropyl-1-((1-isopropyl-1H-pyrazol-3-yl)methyl)-1H-indazol-4-yl)-7-(2-(4-methylpiperazin-1-yl)ethoxy)imidazo[1,2-a]pyridine-3-carboxamide;
N-(3-cyclopropyl-1-((1-isopropyl-1H-pyrazol-3-yl)methyl)-1H-indazol-4-yl)-7-(2-(4-isopropylpiperazin-1-yl)ethoxy)imidazo[1,2-a]pyridine-3-carboxamide;
N-(3-cyclopropyl-1-((6-methylpyridin-2-yl)methyl)-1H-indazol-4-yl)-7-(2-(4-methylpiperazin-1-yl)ethoxy)imidazo[1,2-a]pyridine-3-carboxamide;
7-chloro-N-(3-cyclopropyl-1-((6-methylpyridin-2-yl)methyl)-1H-indazol-4-yl)imidazo[1,2-a]pyridine-3-carboxamide;
N-(1-((6-(2,3-dihydroxypropoxy)pyridin-2-yl)methyl)-3-ethyl-1H-indazol-4-yl)imidazo[1,2-d]pyridine-3-carboxamide;
N-(3-ethyl-1-((6-(piperazin-1-yl)pyridin-2-yl)methyl)-1H-indazol-4-yl)imidazo[1,2-d]pyridine-3-carboxamide;
N-(1-((6-(4-aminopiperidin-1-yl)pyridin-2-yl)methyl)-3-ethyl-1H-indazol-4-yl)imidazo[1,2-a]pyridine-3-carboxamide;
N-(3-ethyl-1-((1-ethyl-1H-pyrazol-4-yl)methyl)-1H-indazol-4-yl)imidazo[1,2-a]pyridine-3-carboxamide;
N-(1-((1-(cyclopropylmethyl)-1H-pyrazol-4-yl)methyl)-3-ethyl-1H-indazol-4-yl)imidazo[1,2-a]pyridine-3-carboxamide;
4-(2-(3-(3-cyclopropyl-1-((6-methylpyridin-2-yl)methyl)-1H-indazol-4-ylcarbamoyl)imidazo[1,2-a]pyridin-7-yloxy)ethyl)-1-methylpiperazine 1-oxide;
N-(3-cyclopropyl-1-((6-methylpyridin-2-yl)methyl)-1H-indazol-4-yl)-7-(2-(piperazin-1-yl)ethoxy)imidazo[1,2-a]pyridine-3-carboxamide;
6-cyano-N-(3-ethyl-1-((6-methylpyridin-2-yl)methyl)-1H-indazol-4-yl)imidazo[1,2-a]pyridine-3-carboxamide;

N-(3-ethyl-1-((6-methylpyridin-2-yl)methyl)-1H-indazol-4-yl)-7-(2-(4-isopropylpiperazin-1-yl)ethoxy)imidazo[1,2-a]pyridine-3-carboxamide;

N-(3-cyclopropyl-1-((6-methylpyridin-2-yl)methyl)-1H-indazol-4-yl)-7-(2-(4-isopropylpiperazin-1-yl)ethoxy)imidazo[1,2-a]pyridine-3-carboxamide;

N-(3-cyclopropyl-1-((1-methyl-2-oxo-1,2-dihydropyridin-3-yl)methyl)-1H-indazol-4-yl)-7-(2-(4-methylpiperazin-1-yl)ethoxy)imidazo[1,2-a]pyridine-3-carboxamide;

7-(2-(azetidin-1-yl)ethoxy)-N-(3-cyclopropyl-1-((6-methylpyridin-2-yl)methyl)-1H-indazol-4-yl)imidazo[1,2-a]pyridine-3-carboxamide;

7-fluoro-N-(3-cyclopropyl-1-((6-methylpyridin-2-yl)methyl)-1H-indazol-4-yl)imidazo[1,2-a]pyridine-3-carboxamide;

N-(3-ethyl-1-((6-methylpyridin-2-yl)methyl)-1H-indazol-4-yl)-7-((1-methylpiperidin-4-yl)methoxy)imidazo[1,2-a]pyridine-3-carboxamide;

N-(3-ethyl-1-((6-methylpyridin-2-yl)methyl)-1H-indazol-4-yl)-7-(2-(4-ethylpiperazin-1-yl)ethoxy)imidazo[1,2-a]pyridine-3-carboxamide;

(R)—N-(3-ethyl-1-((6-methylpyridin-2-yl)methyl)-1H-indazol-4-yl)-7-(1-methylpyrrolidin-3-yloxy)imidazo[1,2-a]pyridine-3-carboxamide;

N-(3-ethyl-1-((6-methylpyridin-2-yl)methyl)-1H-indazol-4-yl)-7-(1-methylpiperidin-4-yloxy)imidazo[1,2-a]pyridine-3-carboxamide;

N-(3-ethyl-1-((6-methylpyridin-2-yl)methyl)-1H-indazol-4-yl)-7-(2-(pyrrolidin-1-yl)ethoxy)imidazo[1,2-a]pyridine-3-carboxamide;

N-(3-cyclopropyl-1-((6-methylpyridin-2-yl)methyl)-1H-indazol-4-yl)-7-(2-morpholinoethoxy)imidazo[1,2-a]pyridine-3-carboxamide;

(S)—N-(3-ethyl-1-((6-methylpyridin-2-yl)methyl)-1H-indazol-4-yl)-7-(1-methylpyrrolidin-3-yloxy)imidazo[1,2-a]pyridine-3-carboxamide;

tert-butyl 2-((3-(3-ethyl-1-((6-methylpyridin-2-yl)methyl)-1H-indazol-4-ylcarbamoyl)imidazo[1,2-a]pyridin-7-yloxy)methyl)morpholine-4-carboxylate;

tert-butyl 3-(3-(3-ethyl-1-((6-methylpyridin-2-yl)methyl)-1H-indazol-4-ylcarbamoyl)imidazo[1,2-a]pyridin-7-yloxy)-2,2-difluoropropylcarbamate;

N-(3-ethyl-1-((1-ethyl-1H-pyrazol-3-yl)methyl)-1H-indazol-4-yl)-7-(2-(4-isopropylpiperazin-1-yl)ethoxy)imidazo[1,2-a]pyridine-3-carboxamide;

N-(3-cyclopropyl-1-((6-methylpyridin-2-yl)methyl)-1H-indazol-4-yl)-7-(2-(pyrrolidin-1-yl)ethoxy)imidazo[1,2-a]pyridine-3-carboxamide;

(R)—N-(3-ethyl-1-((6-methylpyridin-2-yl)methyl)-1H-indazol-4-yl)-7-(2-(3-methoxypyrrolidin-1-yl)ethoxy)imidazo[1,2-a]pyridine-3-carboxamide;

N-(3-ethyl-1-((6-methylpyridin-2-yl)methyl)-1H-indazol-4-yl)-7-(2-(8-methyl-3,8-diazabicyclo[3.2.1]octan-3-yl)ethoxy)imidazo[1,2-a]pyridine-3-carboxamide;

(S)—N-(3-ethyl-1-((6-methylpyridin-2-yl)methyl)-1H-indazol-4-yl)-7-(2-(3-methoxypyrrolidin-1-yl)ethoxy)imidazo[1,2-a]pyridine-3-carboxamide;

N-(3-ethyl-1-((1-ethyl-1H-pyrazol-3-yl)methyl)-1H-indazol-4-yl)-7-(2-(pyrrolidin-1-yl)ethoxy)imidazo[1,2-a]pyridine-3-carboxamide;

N-(3-cyclopropyl-1-((6-methylpyridin-2-yl)methyl)-1H-indazol-4-yl)-7-(1-methylpiperidin-4-yloxy)imidazo[1,2-a]pyridine-3-carboxamide;

(S)—N-(3-ethyl-1-((6-methylpyridin-2-yl)methyl)-1H-indazol-4-yl)-7-(2-(3-fluoropyrrolidin-1-yl)ethoxy)imidazo[1,2-a]pyridine-3-carboxamide;

N-(3-cyclopropyl-1-((6-methylpyridin-2-yl)methyl)-1H-indazol-4-yl)-7-(2-thiomorpholine 1,1-dioxide ethoxy)imidazo[1,2-a]pyridine-3-carboxamide;

N-(3-ethyl-1-((1-ethyl-1H-pyrazol-3-yl)methyl)-1H-indazol-4-yl)-7-(1-methylpiperidin-4-yloxy)imidazo[1,2-a]pyridine-3-carboxamide;

N-(3-ethyl-1-((6-methylpyridin-2-yl)methyl)-1H-indazol-4-yl)-7-(2-(8-Oxa-3-azabicyclo[3.2.1]octane)ethoxy)imidazo[1,2-a]pyridine-3-carboxamide;

N-(3-cyclopropyl-1-((1-methyl-2-oxo-1,2-dihydropyridin-3-yl)methyl)-1H-indazol-4-yl)-7-(2-(pyrrolidin-1-yl)ethoxy)imidazo[1,2-a]pyridine-3-carboxamide;

N-(3-ethyl-1-((1-ethyl-1H-pyrazol-3-yl)methyl)-1H-indazol-4-yl)-7-(2-morpholinoethoxy)imidazo[1,2-a]pyridine-3-carboxamide;

N-(3-cyclopropyl-1-((1-methyl-2-oxo-1,2-dihydropyridin-3-yl)methyl)-1H-indazol-4-yl)-7-(2-morpholinoethoxy)imidazo[1,2-a]pyridine-3-carboxamide;

7-(2-(azetidin-1-yl)ethoxy)-N-(3-cyclopropyl-1-((1-methyl-2-oxo-1,2-dihydropyridin-3-yl)methyl)-1H-indazol-4-yl)imidazo[1,2-a]pyridine-3-carboxamide;

N-(3-ethyl-1-((6-methylpyridin-2-yl)methyl)-1H-indazol-4-yl)-7-(2-(piperazin-1-yl)ethoxy)imidazo[1,2-a]pyridine-3-carboxamide;

N-(3-ethyl-1-((6-methylpyridin-2-yl)methyl)-1H-indazol-4-yl)-7-(2-hydroxyethoxy)imidazo[1,2-a]pyridine-3-carboxamide;

7-(3-amino-2,2-difluoropropoxy)-N-(3-ethyl-1-((6-methylpyridin-2-yl)methyl)-1H-indazol-4-yl)imidazo[1,2-a]pyridine-3-carboxamide;

7-(azetidin-3-yloxy)-N-(3-ethyl-1-((6-methylpyridin-2-yl)methyl)-1H-indazol-4-yl)imidazo[1,2-a]pyridine-3-carboxamide;

N-(3-ethyl-1-((6-methylpyridin-2-yl)methyl)-1H-indazol-4-yl)-7-(morpholin-2-ylmethoxy)imidazo[1,2-a]pyridine-3-carboxamide;

(R)—N-(3-ethyl-1-((6-methylpyridin-2-yl)methyl)-1H-indazol-4-yl)-7-(2-(3-fluoropyrrolidin-1-yl)ethoxy)imidazo[1,2-a]pyridine-3-carboxamide;

N-(3-ethyl-1-((6-methylpyridin-2-yl)methyl)-1H-indazol-4-yl)-7-(piperazin-1-yl)imidazo[1,2-a]pyridine-3-carboxamide;

N-(3-ethyl-1-((6-methylpyridin-2-yl)methyl)-1H-indazol-4-yl)-7-morpholinoimidazo[1,2-a]pyridine-3-carboxamide;

(R)—N-(3-ethyl-1-((6-methylpyridin-2-yl)methyl)-1H-indazol-4-yl)-7-(3-hydroxypyrrolidin-1-yl)imidazo[1,2-a]pyridine-3-carboxamide;

N-(3-ethyl-1-((6-methylpyridin-2-yl)methyl)-1H-indazol-4-yl)-7-(4-(2-hydroxyethyl)piperazin-1-yl)imidazo[1,2-a]pyridine-3-carboxamide;

N-(3-ethyl-1-((6-methylpyridin-2-yl)methyl)-1H-indazol-4-yl)-7-(4-hydroxypiperidin-1-yl)imidazo[1,2-a]pyridine-3-carboxamide;

(S)—N-(3-ethyl-1-((6-methylpyridin-2-yl)methyl)-1H-indazol-4-yl)-7-(3-hydroxypyrrolidin-1-yl)imidazo[1,2-a]pyridine-3-carboxamide;

N-(3-ethyl-1-((6-methylpyridin-2-yl)methyl)-1H-indazol-4-yl)-7-(4-ethylpiperazin-1-yl)imidazo[1,2-a]pyridine-3-carboxamide;

N-(3-ethyl-1-((6-methylpyridin-2-yl)methyl)-1H-indazol-4-yl)-7-(3-oxopiperazin-1-yl)imidazo[1,2-a]pyridine-3-carboxamide;

7-(1,4-diazepan-1-yl)-N-(3-ethyl-1-((6-methylpyridin-2-yl)methyl)-1H-indazol-4-yl)imidazo[1,2-a]pyridine-3-carboxamide;

N-(3-ethyl-1-((1-ethyl-1H-pyrazol-3-yl)methyl)-1H-indazol-4-yl)-7-(1H-1,2,4-triazol-1-yl)imidazo[1,2-a]pyridine-3-carboxamide;

N-(3-ethyl-1-((1-ethyl-1H-pyrazol-3-yl)methyl)-1H-indazol-4-yl)-7-fluoroimidazo[1,2-a]pyridine-3-carboxamide;

N-(3-ethyl-1-((6-methylpyridin-2-yl)methyl)-1H-indazol-4-yl)-7-(1H-1,2,4-triazol-1-yl)imidazo[1,2-a]pyridine-3-carboxamide;

N-(3-ethyl-1-((6-methylpyridin-2-yl)methyl)-1H-indazol-4-yl)-7-(3-methyl-1H-1,2,4-triazol-1-yl)imidazo[1,2-a]pyridine-3-carboxamide;

N-(3-ethyl-1-((6-methylpyridin-2-yl)methyl)-1H-indazol-4-yl)-7-(5-methyl-1H-1,2,4-triazol-1-yl)imidazo[1,2-a]pyridine-3-carboxamide;

N-(3-ethyl-1-((6-methylpyridin-2-yl)methyl)-1H-indazol-4-yl)-7-(3-methyl-4H-1,2,4-triazol-4-yl)imidazo[1,2-a]pyridine-3-carboxamide;

7-(2,3-dihydroxypropoxy)-N-(3-ethyl-1-((6-methylpyridin-2-yl)methyl)-1H-indazol-4-yl)imidazo[1,2-a]pyridine-3-carboxamide;

N-(3-ethyl-1-((1-ethyl-1H-pyrazol-3-yl)methyl)-1H-indazol-4-yl)-7-(1-methyl-1H-pyrazol-4-yl)imidazo[1,2-a]pyridine-3-carboxamide;

N-(3-ethyl-1-((1-ethyl-1H-pyrazol-3-yl)methyl)-1H-indazol-4-yl)-7-(1-methyl-1H-pyrazol-4-yl)imidazo[1,2-a]pyridine-3-carboxamide;

N-(1-((1,5-dimethyl-1H-pyrazol-3-yl)methyl)-3-ethyl-1H-indazol-4-yl)-7-(5-((dimethylamino)methyl)furan-2-yl)imidazo[1,2-a]pyridine-3-carboxamide;

(R)—N-(3-ethyl-1-((6-methylpyridin-2-yl)methyl)-1H-indazol-4-yl)-7-(2-(3-fluoropyrrolidin-1-yl)ethyl)imidazo[1,2-a]pyridine-3-carboxamide;

N-(3-ethyl-1-((6-methylpyridin-2-yl)methyl)-1H-indazol-4-yl)-7-(2-(4-methylpiperazin-1-yl)ethyl)imidazo[1,2-a]pyridine-3-carboxamide;

N-(3-ethyl-1-((6-methylpyridin-2-yl)methyl)-1H-indazol-4-yl)-7-(2-(3-fluoroazetidin-1-yl)ethyl)imidazo[1,2-a]pyridine-3-carboxamide;

7-(2-(dimethylamino)ethyl)-N-(3-ethyl-1-((6-methylpyridin-2-yl)methyl)-1H-indazol-4-yl)imidazo[1,2-a]pyridine-3-carboxamide;

N-(3-ethyl-1-((6-methylpyridin-2-yl)methyl)-1H-indazol-4-yl)-7-(2-(3-methoxyazetidin-1-yl)ethyl)imidazo[1,2-a]pyridine-3-carboxamide;

7-((Dimethylamino)methyl)-N-(3-ethyl-1-((6-methylpyridin-2-yl)methyl)-1H-indazol-4-yl)imidazo[1,2-a]pyridine-3-carboxamide;

7-((dimethylamino)methyl)-N-(3-ethyl-1-((1-ethyl-1H-pyrazol-3-yl)methyl)-1H-indazol-4-yl)imidazo[1,2-a]pyridine-3-carboxamide;

N-(3-iodo-1-((2-methylthiazol-5-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((5-methyl-1,3,4-thiadiazol-2-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((2-methyloxazol-4-yl)methyl)-1H-indazol-4-yl)-7-(2-(4-methylpiperazin-1-yl)ethoxy)imidazo[1,2-a]pyridine-3-carboxamide;

N-(3-ethyl-1-((6-methylpyridin-2-yl)methyl)-1H-indazol-4-yl)-7-(pyrimidin-5-yl)imidazo[1,2-a]pyridine-3-carboxamide;

N-(3-ethyl-1-((6-methylpyridin-2-yl)methyl)-1H-indazol-4-yl)-7-(6-methylpyridin-3-yl)imidazo[1,2-a]pyridine-3-carboxamide;

N-(3-ethyl-1-((6-methylpyridin-2-yl)methyl)-1H-indazol-4-yl)-7-(3-(4-methylpiperazin-1-yl)propyl)imidazo[1,2-a]pyridine-3-carboxamide;

N-(3-methoxy-1-((6-methylpyridin-3-yl)methyl)-1H-indazol-4-yl)-7-(2-methoxyethoxy)imidazo[1,2-a]pyridine-3-carboxamide;

N-(3-bromo-1-((6-methylpyridin-3-yl)methyl)-1H-indazol-4-yl)-7-(2-methoxyethoxy)imidazo[1,2-a]pyridine-3-carboxamide;

N-(3-methoxy-1-((6-methylpyridin-2-yl)methyl)-1H-indazol-4-yl)-7-(2-(4-methylpiperazin-1-yl)ethoxy)imidazo[1,2-a]pyridine-3-carboxamide;

N-(3-ethyl-1-(thiazol-2-ylmethyl)-1H-indazol-4-yl)imidazo[1,2-a]pyridine-3-carboxamide;

N-(3-ethyl-1-((6-methylpyridin-3-yl)methyl)-1H-indazol-4-yl)imidazo[1,2-a]pyridine-3-carboxamide;

N-(3-ethyl-1-((6-methylpyridin-3-yl)methyl)-1H-indazol-4-yl)-7-(2-(4-methylpiperazin-1-yl)ethoxy)imidazo[1,2-a]pyridine-3-carboxamide;

N-(3-ethyl-1-(thiazol-2-ylmethyl)-1H-indazol-4-yl)-7-(2-(4-methylpiperazin-1-yl)ethoxy)imidazo[1,2-a]pyridine-3-carboxamide;

N-(3-ethyl-1-((4-methylthiazol-2-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((6-methylpyridin-3-yl)methyl)-1H-indazol-4-yl)-7-(2-(4-methylpiperazin-1-yl)ethoxy)imidazo[1,2-a]pyridine-3-carboxamide;

N-(3-ethyl-1-((2-methylthiazol-4-yl)methyl)-1H-indazol-4-yl)-7-(2-(4-methylpiperazin-1-yl)ethoxy)imidazo[1,2-a]pyridine-3-carboxamide;

N-(3-ethyl-1-((5-fluoropyridin-2-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((5-fluoropyridin-2-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((2-methylthiazol-4-yl)methyl)-1H-indazol-4-yl)-7-(2-(4-methylpiperazin-1-yl)ethoxy)imidazo[1,2-a]pyridine-3-carboxamide;

N-(3-ethyl-1-((2-isopropylthiazol-4-yl)methyl)-1H-indazol-4-yl)-7-(2-(4-methylpiperazin-1-yl)ethoxy)imidazo[1,2-a]pyridine-3-carboxamide;

N-(3-cyclopropyl-1((2-isopropylthiazol-4-yl)methyl)-1H-indazol-4-yl)-7-(2-(4-methylpiperazin-1-yl)ethoxy)imidazo[1,2-a]pyridine-3-carboxamide;

N-(3-cyclopropyl-1-((5-fluoropyridin-2-yl)methyl)-1H-indazol-4-yl)-7-(2-(4-isopropylpiperazin-1-yl)ethoxy)imidazo[1,2-a]pyridine-3-carboxamide;

7-(2-acetamidoethylthio)-N-(3-ethyl-1-((6-methylpyridin-2-yl)methyl)-1H-indazol-4-yl)imidazo[1,2-a]pyridine-3-carboxamide;

N-(3-cyclopropyl-1-((5-hydroxy-6-methylpyridin-2-yl)methyl)-1H-indazol-4-yl)-7-(2-(4-methylpiperazin-1-yl)ethoxy)imidazo[1,2-a]pyridine-3-carboxamide;

7-(Benzyloxy)-N-(3-cyclopropyl-1-((6-methylpyridin-2-yl)methyl)-1H-indazol-4-yl)imidazo[1,2-a]pyridine-3-carboxamide;

N-(3-cyclopropyl-1-((6-methylpyridin-2-yl)methyl)-1H-indazol-4-yl)-7-hydroxyimidazo[1,2-a]pyridine-3-carboxamide;

N-(3-cyclopropyl-1-((6-methylpyridin-2-yl)methyl)-1H-indazol-4-yl)-7-(methylthio)imidazo[1,2-a]pyridine-3-carboxamide;

N-(3-cyclopropyl-1-((6-methylpyridin-2-yl)methyl)-1H-indazol-4-yl)-7-(2-(2-(vinyloxy)ethoxy)ethoxy)imidazo[1,2-a]pyridine-3-carboxamide;

N-(3-cyclopropyl-1-((6-methylpyridin-2-yl)methyl)-1H-indazol-4-yl)-7-(2-(2-hydroxyethoxy)ethoxy)imidazo[1,2-a]pyridine-3-carboxamide;

7-bromo-N-(3-cyclopropyl-1-((6-methylpyridin-2-yl)methyl)-1H-indazol-4-yl)imidazo[1,2-a]pyridine-3-carboxamide; and pharmaceutically acceptable salts thereof.

32. A compound of claim 31, which is N-(3-ethyl-1-((6-methylpyridin-2-yl)methyl)-1H-indazol-4-yl)-7-(2-(4-methylpiperazin-1-yl)ethoxy)imidazo[1,2-a]pyridine-3-carboxamide, or a pharmaceutically acceptable salt thereof.

33. A compound according to claim 31, which is N-(3-cyclopropyl-1-((6-methylpyridin-2-yl)methyl)-1H-indazol-4-yl)-7-(2-(4-methylpiperazin-1-yl)ethoxy)imidazo[1,2-a]pyridine-3-carboxamide, or a pharmaceutically acceptable salt thereof.

34. A compound according to claim 31, which is 4-(2-(3-(3-cyclopropyl-1-((6-methylpyridin-2-yl)methyl)-1H-indazol-4-ylcarbamoyl)imidazo[1,2-a]pyridin-7-yloxy)ethyl)-1-methylpiperazine 1-oxide, or a pharmaceutically acceptable salt thereof.

35. A compound according to claim 31, which is N-(3-cyclopropyl-1-((6-methylpyridin-2-yl)methyl)-1H-indazol-4-yl)-7-(2-(piperazin-1-yl)ethoxy)imidazo[1,2-a]pyridine-3-carboxamide, or a pharmaceutically acceptable salt thereof.

36. A compound according to claim 31, which is N-(3-cyclopropyl-1-((6-methylpyridin-2-yl)methyl)-1H-indazol-4-yl)-7-(2-(4-isopropylpiperazin-1-yl)ethoxy)imidazo[1,2-a]pyridine-3-carboxamide, or a pharmaceutically acceptable salt thereof.

37. A compound according to claim 31, which is N-(3-ethyl-1-((5-fluoropyridin-2-yl)methyl)-1H-indazol-4-yl)-7-(2-(4-methylpiperazin-1-yl)ethoxy)imidazo[1,2-a]pyridine-3-carboxamide, or a pharmaceutically acceptable salt thereof.

38. A compound according to claim 4, wherein $R^5$ is hetCyc$^7$(1-4C)alkoxy.

39. A compound according to claim 38, wherein $R^2$ is cyclopropyl.

40. A compound according to claim 39, wherein $R^3$ is hydrogen.

41. A compound according to claim 40, wherein $R^4$ is hydrogen.

* * * * *

UNITED STATES PATENT AND TRADEMARK OFFICE
CERTIFICATE OF CORRECTION

Page 1 of 1

PATENT NO. : 8,841,455 B2
APPLICATION NO. : 13/517938
DATED : September 23, 2014
INVENTOR(S) : Boys et al.

It is certified that error appears in the above-identified patent and that said Letters Patent is hereby corrected as shown below:

In the Claims

In column 209, line 11:
Please replace "N(o)" with --N(O)--.

In column 210, line 37:
Please replace "N(0)" with --N(O)--.

In column 214, lines 48 through 50:
Please replace "N-(3-ethyl-1-((6-piperazin-1-yl)pyridin-2-yl)methyl)-1H-indazol-4-yl)imidazo[1,2-d]pyridine-3-carboxamide" with --N-(3-ethyl-1-((6-piperazin-1-yl)pyridin-2-yl)methyl)-1H-indazol-4-yl)imidazo[1,2-a]pyridine-3-carboxamide--.

Signed and Sealed this
Third Day of February, 2015

Michelle K. Lee
*Deputy Director of the United States Patent and Trademark Office*